United States Patent [19]
Kojima et al.

[11] Patent Number: 6,005,116
[45] Date of Patent: Dec. 21, 1999

[54] ISOXAZOLE COMPOUNDS USEFUL FOR THE PROPHYLAXIS OR TREATMENT OF NERVOUS DISEASES

[75] Inventors: Koichi Kojima, Yokohama; Junichi Sakai, Koshigaya; Naozumi Samata; Masao Kozuka, both of Tokyo; Kenji Yoshimi, Yokohama; Tsugio Kaneko, Tokyo, all of Japan

[73] Assignee: Sankyo Company, Limited, Tokyo, Japan

[21] Appl. No.: 09/148,905

[22] Filed: Aug. 26, 1998

Related U.S. Application Data

[63] Continuation of application No. PCT/JP97/00583, Feb. 27, 1997.

[30] Foreign Application Priority Data

Feb. 27, 1996 [JP] Japan ................................. 8-039819

[51] Int. Cl.$^6$ ...................... C07D 261/12; C07D 261/10; C07D 413/04; C07D 417/104; A61K 31/42; A61K 31/425
[52] U.S. Cl. ........................ 548/243; 514/236.8
[58] Field of Search .......................... 548/243; 514/236.8

[56] References Cited

U.S. PATENT DOCUMENTS

| | | | |
|---|---|---|---|
| 4,888,044 | 12/1989 | Sumitomo et al. | 548/243 X |
| 5,116,839 | 5/1992 | Iwata et al. | 514/236.8 |
| 5,321,037 | 6/1994 | Nagano et al. | 514/379 |
| 5,547,967 | 8/1996 | Kearbach et al. | 514/361 |
| 5,643,923 | 7/1997 | Nagano et al. | 514/305 |

FOREIGN PATENT DOCUMENTS

| | | |
|---|---|---|
| 0 335 723 | 10/1989 | European Pat. Off. |
| 0 405 905 | 1/1991 | European Pat. Off. |
| 43-14704 | 6/1968 | Japan |
| 59-216881 | 12/1984 | Japan |
| 3-74374 | 3/1991 | Japan |

OTHER PUBLICATIONS

Mitsunobu et al "Preparation of Esters of Carboxylic and Phosphoric Acid via Quaternary Phosphonium Salts", Bulletin of the Chemical Society of Japan, vol. 40, No. 10, pp. 2380–2382 (1967).

Chemical Abstracts, vol. 74, 1971, p. 462, Abstract No. 125521e, Tomita et al "Isoxazoles. I. Synthesis of 3–hydroxylisoxazoles" (1970).

Tomita et al "Isoxazoles. I. Syntheses of 3–Hydroxyisoxazoles", Ann. Sankyo Res. Lab., vol. 22, pp. 215–220 (1970).

Sato et al "Synthesis of 3–Hydroxyisoxazoles from β–Ketoesters and Hydroxylamine", Agric. Biol. Chem., vol. 50, No. 7, pp. 1831–1837 (1986).

Micetich et al "Studies in isoxazole. III. The preparation and lithiation of 3, 5–disubstituted isoxazoles", Canadian Jouranl of Chemistry, vol. 48, pp. 1371–1376 (1970).

Mattingly "Mono–Protected Diamines. N$^\alpha$–tert–Butoxycarbonyl α, ω–Alkanediamine Hydrochlorides from Amino Alcohols", Synthesis, pp. 366–368 (1990).

Doherty et al "New Inhibitors of Human Renin That Contain Novel Replacements at the $P_2$ Site", J. Med. Chem. vol. 34, No. 4, pp. 1258–1271 (1991).

Kinemuchi et al "Substracte Selectivity of Type A and B Monoamine Oxidase in Rat Brain ", Journal of Neurochemistry, vol. 35, pp. 109–115 (1980).

Wurtman et al "A sensitive and specific assay for the estimation of monoamine oxidase", Biochem. Pharmacol. 12, pp. 1439–1441 (1963).

*Primary Examiner*—Floyd D. Higel
*Attorney, Agent, or Firm*—Frishauf, Holtz, Goodman, Langer & Chick, P.C.

[57] ABSTRACT

Isoxazole compounds having the following general formula:

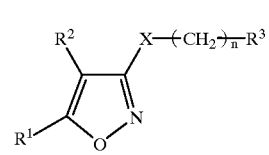

(I)

wherein $R^1$ represents an optionally substituted aryl group or aromatic heterocyclic group; $R^2$ represents a hydrogen atom, a halogen atom, an optionally substituted alkyl group, an alkenyl group, an alkynyl group, a cycloalkyl group, a cycloalkenyl group, an alkoxy group, a cyano group, a carboxyl group, an alkanoyl group, an alkoxycarbonyl group or an optionally substituted carbamoyl group; $R^3$ represents an optionally substituted amino group or a saturated heterocyclic group; X represents an oxygen atom or a sulfur atom; and n is an integer of from 2 to 6. These compounds have excellent monoamine oxidase inhibitory activity and are useful as a therapeutic agent or a preventive agent against nervous diseases such as depression.

43 Claims, No Drawings

ISOXAZOLE COMPOUNDS USEFUL FOR THE PROPHYLAXIS OR TREATMENT OF NERVOUS DISEASES

This application is a continuation application of International Application PCT/JP97/00583 filed Feb. 27, 1997.

The present invention relates to isoxazole derivatives and pharmaceutically acceptable salts thereof, which have excellent inhibition activities against type A-monoamine oxidase;

compositions containing the compounds for treating or preventing nervous diseases (particularly for depression), including depression, Parkinson's disease, Alzheimer's dementia (cognitive disorder owing to Alzheimer's disease) or cerebrovascular dementia (cognitive disorder owing to cerebrovascular dementia);

use of the compounds for producing pharmaceutical preparations for treating or preventing the above-mentioned diseases; and a method for treating or preventing the above diseases by administering a pharmaceutically effective amount of the compounds to warm-blood animals.

BACKGROUND ART

Depression is a disease which shows a typical condition of suppressed mood among mood disorders, and one of its causes is considered to be functional disorders in the central serotonergic and noradrenergic nervous systems. Serotonin and noradrenaline are decomposed and metabolized by monoamine oxidases (mainly by type A-monoamine oxidase) to lose their biological activities. Type A-monoamine oxidase inhibitors are considered to be useful as antidepressants and such inhibitors have been studied and developed intensively. Recently, Moclobernide has been supplied clinically as a selective type A-monoamine oxidase inhibitor.

DISCLOSURE OF THE INVENTION

The present inventors made intensive studies for years on the synthesis of isoxazole derivatives and their pharmacological activities with the aim of developing an excellent therapeutic agent for depression and found that isoxazole derivatives having a specific structure exhibit potent type A-monoamine oxidase inhibitory activities and have therapeutic or preventing effects (particularly therapeutic effect) on nervous diseases (particularly for depression) including depression, Parkinson's disease, Alzheimer's dementia (cognitive disorder owing to Alzheimer's disease) or cerebrovascular dementia (cognitive disorder owing to cerebrovascular dementia).

The present invention provides isoxazole derivatives and pharmaceutically acceptable salts thereof, which have excellent inhibition activities to type A-monoamine oxidase;

compositions containing the compounds for treating or preventing nervous diseases (particularly for depression) including depression, Parkinson's disease, Alzheimer's dementia (cognitive disorder owing to Alzheimer's disease) or cerebrovascular dementia (cognitive disorder owing to cerebrovascular dementia);

use of the compounds for producing pharmaceutical preparations for treating or preventing the above-mentioned diseases; and a method for treating or preventing the above diseases by administering a pharmaceutically effective amount of the compounds to warm-blood animals.

The isoxazole derivatives of the present invention have the general formula (I):

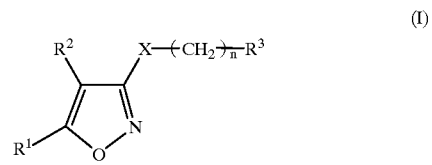

wherein $R^1$ represents a $C_6$–$C_{14}$ aryl group optionally having from 1 to 3 substituents which may be the same as or different from each other and selected from the following substituent group, or a 5- or 6-membered aromatic heterocyclic group optionally having from 1 to 3 substituents and having one or two hetero atoms which may be the same as or different from each other and selected from the group consisting of nitrogen, oxygen and sulfur atoms [the substituent group is a halogen; a $C_1$–$C_6$ alkyl; a $C_1$–$C_6$ alkyl substituted with a halogen or a $C_1$–$C_6$ alkoxy; a $C_1$–$C_6$ alkoxy; a $C_6$–$C_{14}$ aryl, a $C_7$–$C_{18}$ aralkyl, a $C_6$–$C_{14}$ aryloxy or a $C_7$–$C_8$ aralkyloxy optionally having from 1 to 3 substituents which may be the same as or different from each other and selected from the following group (the substituent group is a halogen, a $C_1$–$C_6$ alkyl or a $C_1$–$C_6$ alkoxy); a cyano; a nitro; a hydroxyl group; a $C_1$–$C_7$ alkanoyl; a $C_1$–$C_7$ alkanoyloxy; a $C_2$–$C_7$ alkoxycarbonyl; an amino; a carbamoyl; a mono ($C_1$–$C_6$ alkyl)carbamoyl; a di($C_1$–$C_6$ alkyl)carbamoyl or a mono $C_7$–$C_{15}$ arylcarbonylamino group optionally having from 1 to 3 substituents (the substituent group is a halogen, a $C_1$–$C_6$ alkyl or a $C_1$–$C_6$ alkoxy)], $R^2$ represents a hydrogen atom; a halogen atom; a $C_1$–$C_6$ alkyl; a $C_1$–$C_6$ alkyl substituted with a halogen or a $C_1$–$C_6$ alkoxy; a $C_2$–$C_6$ alkenyl; a $C_2$–$C_6$ alkynyl; a $C_3$–$C_{10}$ cycloalkyl; a $C_3$–$C_{10}$ cycloalkenyl; a $C_1$–$C_6$ alkoxy; a cyano; a carboxyl; a $C_1$–$C_7$ alkanoyl; a $C_2$–$C_7$ alkoxycarbonyl; a carbamoyl; a mono ($C_1$–$C_6$ alkyl) carbamoyl or a di($C_1$–$C_6$ alkyl)carbamoyl group, $R^3$ represents an amino, a mono $C_1$–$C_6$ alkylamino, a di($C_1$–$C_6$ alkyl)amino, a mono $C_1$–$C_7$ alkanoylamino, a mono $C_2$–$C_7$ alkoxycarbonylamino, a mono $C_7$–$C_{15}$ arylcarbonylamino optionally having from 1 to 3 substituents which may be the same as or different from each other and selected from the following group (the substituent group is a halogen, a $C_1$–$C_6$ alkyl or a $C_1$–$C_6$ alkoxy group) or a 5- or 6-membered saturated heterocyclic group (attached thorough a ring nitrogen atom), which contains one nitrogen atom and optionally may contain further one nitrogen atom or oxygen atom.

X represents an oxygen or a sulfur atom, and n represents an integer of 2 to 6.

Further, the active ingredient of the monoamine oxidase inhibitor of the present invention is the isoxazole derivative of general formula (I).

In the formula (I), "the halogen atom" in the definition of $R^2$ and the definition of the substituent included in $R^1$ may be, for example, a fluorine, chlorine, bromine or iodine atom, preferably the fluorine or chlorine atom, more preferably the chlorine atom.

In the formula (I), "the $C_1$–$C_6$ alkyl group" in the definition of $R^2$ and in the definition of the substituent included in $R^1$ may be, for example, a straight or branched alkyl group having from 1 to 6 carbon atoms such as a methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group. The substituent included in $R^1$ is preferably the $C_1$–$C_4$ alkyl group, more preferably the methyl or ethyl group, and most preferably the methyl group. Further, $R^2$ is preferably the $C_1$–$C_4$ alkyl group, more preferably the ethyl, propyl, isopropyl, isobutyl or t-butyl group, most preferably the isopropyl group.

In the formula (I), "the $C_2$–$C_6$ alkenyl group" in the definition of $R^2$ may be, for example, a straight or branched alkenyl group having from 2 to 6 carbon atoms with one or two double bonds such as a vinyl, 1-propenyl, allyl, 1-methyl-1-propenyl, 1-methyl-2-propenyl, 2-methyl-1-propenyl, isopropenyl, allenyl, 1-butenyl, 2-butenyl, 3-butenyl, 2-pentenyl, isoprenyl, 5-hexenyl or 1,4-hexadienyl group, preferably the vinyl, 1-propenyl, allyl, 1-methyl-1-propenyl, isopropenyl, 2-butenyl or 3-butenyl group, more preferably the allyl, isopropenyl or 2-butenyl groups, most preferably the allyl group.

In the formula (I), "the $C_2$–$C_6$ alkynyl group" in the definition of $R^2$ may be, for example, a straight or branched alkynyl group having from 2 to 6 carbon atoms such as an ethynyl, 1-propynyl, propargyl, 1-methyl-2-propynyl, 2-methyl-2-propynyl, 2-ethyl-2-propynyl, 2-butynyl, 1-methyl-2-butynyl, 2-methyl-2-butynyl, 3-butynyl, 2-pentynyl, 5-hexynyl or 2-methyl-4-pentynyl group, preferably the ethynyl, propargyl, 2-butynyl or 3-butynyl group, more preferably the propargyl group.

In the formula (I), "the $C_3$–$C_{10}$ cycloalkyl group" in the definition of $R^2$ may be, for example, a 3- to 10-membered saturated cyclic hydrocarbon group which may form a condensed ring, such as a cyclopropyl, cyclobutyl, cyclopentyl, cyclohexyl, cycloheptyl, norbornyl or adamantyl group, preferably the cyclopropyl, cyclopentyl or cyclohexyl group, more preferably the cyclopropyl group.

In the formula (I), "the $C_3$–$C_{10}$ cycloalkenyl group" in the definition of $R^2$ may be, for example, a 3- to 1O-membered unsaturated cyclic hydrocarbon group which may form a condensed ring having one double bond, such as a 2-cyclopropenyl, 2-cyclobutenyl, 1-cyclopentenyl, 2-cyclopentenyl, 3-cyclopentenyl, 1-cyclohexenyl, 2-cyclohexenyl, 3-cyclohexenyl, 2-cycloheptenyl, 3-norbornenyl or 3-adamantenyl group, preferably the 2-cyclopentenyl, 3-cyclopentenyl, 2-cyclohexenyl or 3-cyclohexenyl group, more preferably the 2-cyclopentenyl group.

In the formula (I), "$C_1$–$C_6$ alkyl group substituted with a halogen or a $C_1$–$C_6$ alkoxy" in the definition of $R^2$ and in the definition of the substituent included in $R^1$ represents a group in which 1 to 5 "halogen atoms" mentioned above are bonded to the above-mentioned "$C_1$–$C_6$ alkyl group" or a group in which "the $C_1$–$C_6$alkoxy" mentioned below is bonded to th above-mentioned $C_1$–$C_6$ alkyl group. The group in which the halogen is bonded to the $C_1$–$C_6$ alkyl group may be, for example, a fluoromethyl, difluoromethyl, trifluoromethyl, 2-fluoroethyl, 2-chloroethyl, 2,2,2-trifluoroethyl, 3-fluoropropyl, 3-chloropropyl, 3-bromopropyl, 4-fluoroburyl or 6-iodohexyl group. The group in which $C_1$–$C_6$ alkoxy is bonded to the $C_1$–$C_6$ alkyl group may be, for example, a methoxymethyl, ethoxymethyl, propoxymethyl, butoxymethyl, methoxyethyl, ethoxyethyl, propoxyethyl, butoxyethyl, propoxypropyl, butoxy-butyl or hexyloxyhexyl group. The substituent included in $R^1$ is preferably a $C_1$–$C_6$ alkyl group substituted with 1 to 3 halogens or a $C_1$–$C_4$ alkoxy, more preferably the fluoromethyl, difluoromethyl, trifluoromethyl, 2-fluoroethyl, 2-chloroethyl, 2,2,2-trifluoroethyl, methoxymethyl or methoxyethyl groups, still more preferably the trifluoromethyl, 2,2,2-trifluoroethyl or methoxymethyl group, most preferably the trifluoromethyl group. Further, $R^2$ is preferably the fluoromethyl, difluoromethyl, trifluoromethyl, 2-fluoroethyl, 1-chloroethyl, 2-chloroethyl, 2,2,2-trifuoroethyl, methoxymethyl or methoxyethyl group, more preferably the trifluoromethyl, 2-fluoroethyl, 1-chloroethyl or 2-chloroethyl group, most preferably the 1-chloroethyl group.

In the formula (I), "the $C_1$–$C_6$ alkoxy group" in the definition of the substituent included in $R^1$ and $R^2$ and in the definition of $R^2$ represents a group in which the above-mentioned "$C_1$–$C_6$ alkyl group" is bonded to an oxygen atom and such group may be, for example, a methoxy, ethoxy, propoxy, isopropoxy, butoxy, isobutoxy, s-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy group, preferably the $C_1$–$C_4$ alkoxy group, more preferably the methoxy or ethyoxy group, most preferably the methoxy group.

In the formula (I), the "$C_6$–$C_{14}$ aryl group optionally having from 1 to 3 substituents which may be the same as or different from each other and selected from the following group (the substituent group is a halogen, a $C_1$–$C_6$ alkyl or a $C_1$–$C_6$ alkoxy)" in the definition of the substituent included in $R^1$ represents an aromatic hydrocarbon group having from 6 to 14 carbon atoms optionally having from 1 to 3 substituents which may be the same as or different from each other and selected from the substituent group, and such group may be, for example, a phenyl, fluorophenyl, chlorophenyl, dichlorophenyl, methylphenyl, trimethylphenyl, methoxyphenyl, indenyl, methylindenyl, naphthyl, dichloronaphthyl, phenanthrenyl, hexylphenanthrenyl, anthracenyl, dimethylanthracenyl or hexyloxyanthracenyl group, preferably the phenyl group optionally having one or two substituents which may be the same as or different from each other and selected from the group consisting of fluorine, chlorine, methyl and methoxy, more preferably the phenyl, 4-fluorophenyl, 4-chlorophenyl, 2,4-dichlorophenyl, 4-methylphenyl or 4-methoxyphenyl group, most preferably the phenyl group.

In the formula (I), "the $C_7$–$C_{18}$ aralkyl group optionally having from 1 to 3 substituents which may be the same as or different from each other and selected from the following group (the substituent group is a halogen, a $C_1$–$C_6$ alkyl or a $C_1$–$C_6$ alkoxy)" in the definition of the substituent included in $R^1$ represents a group in which one or two phenyl groups or one naphthyl group optionally having from 1 to 3 substituents which may be the same as or different from each other and selected from the substituent group is bonded to the above-mentioned "$C_1$–$C_6$ alkyl", and such group may be, for example, a benzyl, fluorobenzyl, difluorobenzyl, trifluorobenzyl, chlorobenzyl, dichlorobenzyl, trichlorobenzyl, bromobenzyl, methylbenzyl, dimethylbenzyl, trimethylbenzyl, ethylbenzyl, propylbenzyl, methoxybenzyl, dimethoxybenzyl, ethoxybenzyl, hexyloxybenzyl, diphenylmethyl, naphthylmethyl, fluoronaphthylmethyl, difluoronaphthylmethyl, chloronaphthylmethyl, dichloronaphthylmethyl, methylnaphthylmethyl, dimethylnaphthylmethyl, ethylnaphthylmethyl, phenethyl, fluorophenethyl, difluorophenethyl, chlorophenethyl, dichlorophenethyl, methylphenethyl, trimethylphenethyl, naphthylethyl, fluoronaphthylethyl, chloronaphthylethyl, phenylpropyl, fluorophenylpropyl, chlorophenylpropyl, dichlorophenylpropyl, methylphenylpropyl, dimethylphenylpropyl, trimethylphenylpropyl, naphthylpropyl, iodonaphthylpropyl, hexylnaphthylpropyl, methoxynaphthylpropyl, hexyloxynaphthylpropyl, phenylbutyl, fluorophenylbutyl, difluorophenylbutyl, chlorophenylbutyl, dichlorophenylbutyl, trimethylphenylbutyl or naphthylbutyl group, preferably the benzyl group or phenethyl group optionally having from 1 to 3 substituents which may be the same as or different from each other and selected from the group consisting of halogen, $C_1$–$C_4$ alkyl and $C_1$–$C_4$ alkoxy, more preferably, the benzyl group optionally having one substituent selected from the group consisting of fluorine, chlorine, $C_1$–$C_4$ alkyl and $C_1$–$C_4$ alkoxy, still more preferably the benzyl, fluorobenzyl, chlorobenzyl, difluorobenzyl, dichlorobenzyl, methylbenzyl, dimethylbenzyl or methoxybenzyl group, most preferably the benzyl group.

In the formula (I), "the $C_6$–$C_{14}$ aryloxy group optionally having from 1 to 3 substituents which may be the same as or different from each other and selected from the following group (the substituent group is a halogen, a $C_1$–$C_6$ alkyl or a $C_1$–$C_6$ alkoxy)" in the definition of the substituent included in $R^1$ represents a group in which the "$C_6$–$C_{14}$ aryl group optionally having from 1 to 3 substituents which may be the same as or different from each other and selected from the following group (the substituent group is halogen, $C_1$–$C_6$ alkyl or $C_1$–$C_6$ alkoxy)" is bonded to an oxygen atom, and such group may be, for example, a phenoxy, fluorophenoxy, chlorophenoxy, dichlorophenoxy, methylphenoxy, trimethylphenoxy, methoxyphenoxy, indenyloxy, methylindenyloxy, naphthyloxy, dichloronaphthyloxy, phenanthrenyloxy, hexylphenanthrenyloxy, anthracenyloxy, dimethylanthracenyloxy or hexyloxyanthracenyloxy group; preferably the phenoxy group optionally having one or two substituents which may be the same as or different from each other and selected from the group consisting of fluorine, chlorine, methyl and methoxy, more preferably the phenoxy, 4-fluorophenoxy, 4-chlorophenoxy, 2,4-dichlorophenoxy, 4-methylphenoxy or 4methoxyphenoxy group; most preferably the phenoxy group.

In the formula (I), "the $C_7$–$C_{18}$ aralkyloxy group optionally having from 1 to 3 substituents which may be the same as or different from each other and selected from the following group (the substituent group is halogen, $C_1$–$C_6$ alkyl or $C_1$–$C_6$ alkoxy)" in the definition of the substituent included in $R^1$ represents a group in which the "$C_7$–$C_{18}$ aralkyl group optionally having from 1 to 3 substituents which may be the same as or different from each other and selected from the following group (the substituent group is halogen, $C_1$–$C_6$ alkyl or $C_1$–$C_6$ alkoxy)" is bonded to an oxygen atom, and such group may be, for example, a benzyloxy, fluorobenzyloxy, difluorobenzyloxy, trifluorobenzyloxy, chlorobenzyloxy, dichlorobenzyloxy, trichlorobenzyloxy, bromobenzyloxy, methylbenzyloxy, dimethylbenzyloxy, trimethylbenzyloxy, ethylbenzyloxy, propylbenzyloxy, methoxybenzyloxy, dimethoxybenzyloxy, ethoxybenzyloxy, hexyloxybenzyloxy, diphenylmethoxy, naphthylmethoxy, fluoronaphthylmethoxy, difluoronaphthylmethoxy, chloronaphthylmethoxy, dichloronaphthylmethoxy, methylnaphthylmethoxy, dimethylnaphthylmethoxy, ethylnaphthylmethoxy, phenylethoxy, fluorophenylethoxy, difluorophenylethoxy, chlorophenylethoxy, dichlorophenylethoxy, methylphenylethoxy, trimethylphenylethoxy, naphthylethoxy, fluoronaphthylethoxy, chloronaphthylethoxy, phenylpropoxy, fluorophenylpropoxy, chlorophenylpropoxy, dichlorophenylpropoxy, methylphenylpropoxy, dimethylphenylpropoxy, trimethylphenylpropoxy, naphthylpropoxy, iodonaphthylpropoxy, hexylnaphthylpropoxy, methoxynaphthylpropoxy, hexyloxynaphthylpropoxy, phenylbutoxy, fluorophenylbutoxy, difluorophenylbutoxy, chlorophenylbutoxy, dichlorophenylbutoxy, trimethylphenylbutoxy or naphthylbutoxy group; preferably the benzyloxy and phenylethoxy groups optionally having from 1 to 3 substituents which may be the same as or different from each other and selected from the group consisting of halogen, $C_1$–$C_4$ alkyl and $C_1$–$C_4$ alkoxy, more preferably the benzyloxy group optionally having one substituent selected from the group consisting of fluorine, chlorine, $C_1$–$C_4$ alkyl and $C_1$–$C_4$ alkoxy, still more preferably the benzyloxy, 4-fluorobenzyloxy, 4-chlorobenzyloxy, 2,4-difluorobenzyloxy, 2,4-dichlorobenzyloxy, 4-methylbenzvloxy, 2,4-dimethylbenzyloxy or 4-methoxybenzyloxy group, most preferably the benzyloxy group.

In the formula (I), "the $C_1$–$C_7$ alkanoyl group" in the definition of the substituent included in $R^1$ and in the definition of $R^2$ represents a group in which a hydrogen atom or the above-mentioned "$C_1$–$C_6$ alkyl" is bonded to a carbonyl group, and such group may be, for example, a formyl, acetyl, propionyl, butyryl, isobutyryl, valeryl, isovaleryl, pivaloyl, hexanoyl or heptanoyl group, preferably the formyl or acetyl group, most preferably the acetyl group.

In the formula (I), "the $C_1$–$C_7$ alkanoyloxy group" in the definition of the substituent included in $R^1$ represents a group in which the above-mentioned "the $C_1$–$C_7$ alkanoyl group" is bonded to an oxygen atom, and such group may be, for example, a formyloxy, acetoxy, propionvloxy, butyryloxy, isobutyryloxy, valeryloxy, isovaleryloxy, pivaloyloxy, hexanoyloxy or heptanoyloxy group, preferably the formyloxy or acetoxy group, more preferably the acetoxy group.

In the formula (I), "the $C_2$–$C_7$ alkoxycarbonyl group" in the definition of the substituent included in $R^1$ and in the definition of $R^2$ represents a group in which the above-mentioned "$C_1$–$C_6$ alkoxy group" is bonded to a carbonyl group, and such group may be, for example, a methoxycarbonyl, ethoxycarbonyl, propoxycarbonyl, isopropoxycarbonyl, butoxycarbonyl, isobutoxycarbonyl, s-butoxycarbonyl, t-butoxycarbonyl, pentyloxycarbonyl, isopentyloxycarbonyl, 2-methylbutoxycarbonyl, neopentyloxycarbonyl, 1-ethylpropoxycarbonyl, hexyloxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxvcarbonyl, 1,1-dimethylbutoxycarbonyl, 1,2-dimethylbutoxycarbonyl, 1,1-dimethylbutoxycarbonyl, 2,3-dimethylbutoxycarbonyl or 2-ethylbutoxycarbonyl group, preferably a $C_2$–$C_5$ alkoxycarbonyl group, more preferably the methoxycarbonyl or ethoxycarbonyl group, most preferably the methoxycarbonyl group.

In the formula (I), "the mono $C_1$–$C_6$ alkylamino group" in the definition of $R^3$ represents a group in which the above-mentioned "$C_1$–$C_6$ alkyl group" is bonded to an amino group, and such group may be, for example, a methylamino, ethylamino, propylamino, isopropylamino, butylamino, isobutylamino, s-butylamino, t-butylamino, pentylamino or hexylamino group, preferably a mono $C_1$–$C_4$ alkylamino group, more preferably the methylamino or ethylamino groups, most preferably the methylamino group.

In the formula (I), "the di($C_1$–$C_6$ alkyl)amino" in the definition of $R^3$ may be, for example, a N,N-dimethylamino, N-ethyl-N-methylamino, N-methyl-N-propylamino, N-isopropyl-N-methylamino, N-butyl-N-methylamino, N-isobutyl-N-methylamino, N-s-butyl-N-methylamino, N-t-butyl-N-methylamino, N,N-diethylamino, N-ethyl-N-propylamino, N-ethyl-N-isobutylamino, N,N-dipropylamino, N,N-dibutylamino, N,N-dipentylamino or N,N-dihexylamino group, preferably the di($C_1$–$C_4$ alkyl) amino group, more preferably the N,N-dimethylamino or N,N-diethylamino group, most preferably the N,N-dimethylamino group.

In the formula (I), "the $C_1$–$C_7$ alkanoylamino group" in the definition of $R^3$ represents a group in which the above-mentioned "$C_1$–$C_7$ alkanoyl group" is bonded to an amino group, and such group may be, for example, a formylamino, acetylamino, propionylamino, butyrylamino, isobutyrylamino, valerylamino, isovalerylamino, pivaloylamino, hexanoylamino or heptanoylamino group, preferably the formylamino or acetylamino group, particularly preferably the acetylamino group.

In the formula (I), "the $C_2$–$C_7$ alkoxycarbonylamino group" in the definition of $R^3$ represents a group in which the above-mentioned "$C_1$–$C_7$ alkoxycarbonyl group" is bonded to an amino group, and such group may be, for example, a methoxycarbonylamino, ethoxycarbonylamino, propoxycarbonylamino, isopropoxycarbonylamino, butoxycarbonylamino, isobutoxycarbonylamino, s-butoxycarbonylamino, t-butoxycarbonylamino, pentyloxycarbonylamino, isopentyloxycarbonylamino, 2-methylbutoxycarbonylamino, neopentyloxycarbonylamino, 1-ethylpropoxycarbonylamino, hexyloxycarbonylamino, 4methylpentyloxycarbonylamino, 3-methylpentyloxycarbonylamino, 2-methylpentyloxycarbonylamino, 1-methylpentyloxycarbonylamino, 3,3dimethylbutoxycarbonylamino, 2,2-dimethylbutoxycarbonylamino, 1,1-dimethylbutoxycarbonylamino, 1,2-dimethylbutoxycarbonylamino, 1,3-dimethylbutoxycarbonylamino, 2,3-dimethylbutoxycarbonylamino or 2-ethylbutoxycarbonylamino group, preferably the $C_2$–$C_5$ alkoxycarbonylamino group, more preferably the methoxycarbonylamino or ethoxycarbonylamino group, most preferably the methoxycarbonylamino group.

In the formula (I), "the mono($C_1$–$C_6$ alkyl)carbamoyl group" in the definition of the substituent included in $R^1$ and in the definition of $R^2$ may be, for example, a methylcarbamoyl, ethylcarbamoyl, propylcarbamoyl, isopropylcarbamoyl, butylcarbamoyl, isobutylcarbamoyl, s-butylcarbamoyl, t-butylcarbamoyl, pentylcarbamoyl or hexylcarbamoyl group; preferably the mono($C_1$–$C_4$ alkyl) carbamoyl group; more preferably the methylcarbamoyl or ethylcarbamoyl group.

In the formula (I), "the di($C_1$–$C_6$ alkyl)carbamoyl group" in the definition of the substituent included in $R^1$ and in the definition of $R^2$ may be, for example, a N,N-dimethylcarbamoyl, N-ethyl-N-methylcarbamoyl, N,N-diethylcarbamoyl, N,N-dipropylcarbamoyl, N,N-diisopropylcarbamoyl, N,N-dibutylcarbamoyl, N,N-diisobutylcarbamoyl, N,N-di-s-butylcarbamoyl, N,N-di-t-butylcarbamoyl, N,N-dipentylcarbamoyl or N,N-dihexylcarbamoyl group, preferably the di($C_1$–$C_4$ alkyl) carbamoyl group, more preferably the N,N-dimethylcarbamoyl or N,N-diethylcarbamoyl group, most preferably the N,N-dimethylcarbamoyl group.

In the formula (I), "the mono $C_7$–$C_{15}$ arylcarbonylamino group optionally having from 1 to 3 substituents which may be the same as or different from each other and selected from the following group (the substituent group is halogen, $C_1$–$C_6$ alkyl or $C_1$–$C_6$ alkoxy)" in the definition of the substituent included in $R^1$ and in the definition of $R^3$ represents a group in which the above-mentioned "$C_6$–$C_{14}$ aryl group optionally having from 1 to 3 substituents which may be the same as or different from each other and selected from the following group (the substituent group is halogen, $C_1$–$C_6$ alkyl or $C_1$–$C_6$ alkoxy)" is bonded to a carbonylamino group, and such group may be, for example, a benzoylamino, fluorobenzoylamino, chlorobenzoylamino, dichlorobenzoylamino, toluoylamino, trimethylbenzoylamino, anisoylamino, indenoylamino, methylindenoylamino, naphthoylamino, dichloronaphthoylamino, phenanthrenoylamino, hexylphenanthrenoylamino, anthracenoylamino, dimethylanthracenoylamino or hexyloxyanthracenoylamino group; preferably the benzoylamino group optionally having one or two substituents which may be the same as or different from each other and selected from the group consisting of fluorine, chlorine, methyl and methoxy; more preferably the benzoylamino, 4-fluorobenzoylamino, 4-chlorobenzoylamino, 2,4-dichlorobenzoylamino, 4-toluoylamino or 4-anisoylamino group; most preferably the benzoylamino group.

In the formula (I), "the 5- or 6-membered saturated heterocyclic group (provided that the group is attached through a ring nitrogen atom) containing one nitrogen atom and optionally containing one nitrogen atom or oxygen atom" in the definition of $R^3$ may be, for example, a pyrrolidinyl, imidazolidinyl, pyrazolidinyl, piperidyl, piperazinyl or morpholinyl group, preferably the piperidyl or morpholinyl group.

In the formula (I), "the $C_6$–$C_{14}$ aryl group optionally having from 1 to 3 substituents which may be the same as or different from each other and selected from the following substituent group" in the definition of $R^1$ may be, for example, a phenyl, indenyl, naphthyl, phenanthrenyl or anthracenyl group which may be substituted with the following substituent; preferably a $C_6$–$C_{14}$ aryl group optionally having from 1 to 3 substituents which may be the same as or different from each other and selected from the following substituent group [the substituent group is halogen; $C_1$–$C_6$ alkyl; $C_1$–$C_6$ alkyl substituted with halogen or $C_1$–$C_6$ alkoxy; $C_1$–$C_6$ alkoxy; $C_6$–$C_{14}$ aryl optionally having from 1 to 3 substituents which may be the same as or different from each other and selected from the following group (the substituent group is halogen, $C_1$–$C_6$ alkyl or $C_1$–$C_6$ alkoxy); a benzyl, fluorobenzyl, chlorobenzyl, difluorobenzyl, dichlorobenzyl, methylbenzyl, dimethylbenzyl, methoxybenzyl; phenoxy, 4-fluorophenoxy, 4-chlorophenoxy, 2,4-dichlorophenoxy, 4-methylphenoxy, 4-methoxyphenoxy; benzyloxy, 4-fluorobenzyloxy, 4-chlorobenzyloxy, 2,4-difluorobenzyloxy, 2,4-dichlorobenzyloxy, 4-methylbenzyloxy, 2,4-dimethylbenzyloxy, 4-methoxybenzyloxy; cyano; nitro; a hydroxyl group; acetoxy; $C_2$–$C_7$ alkoxycarbonyl; amino; carbamoyl; mono-($C_1$–$C_6$ alkyl)carbamoyl; di($C_1$–$C_6$ alkyl)

carbamoyl; benzoylamino, 4-fluorobenzoylamino, 4-chlorobenzoylamino, 2,4-dichlorobenzoylamino, 4-toluoylamino or 4-anisoylamino group]; more preferably a $C_6$–$C_{14}$ aryl group optionally having from 1 to 3 substituents which may be the same as or different from each other and selected from the following substituent group [the substituent group is a halogen; a $C_1$–$C_6$ alkyl; a $C_1$–$C_6$ alkyl substituted with a halogen or a $C_1$–$C_6$ alkoxy; a $C_1$–$C_6$ alkoxy; a $C_6$–$C_{14}$ aryl optionally having from 1 to 3 substituents which may be the same as or different from each other and selected from the following group (the substituent group is a halogen, a $C_1$–$C_6$ alkyl or a $C_1$–$C_6$ alkoxy); cyano; $C_2$–$C_7$ alkoxycarbonyl; carbamoyl; mono-($C_1$–$C_6$ alkyl)carbamoyl; or di($C_1$–$C_6$ alkyl)carbamoyl group]; more preferably the $C_6$–$C_{14}$ aryl group optionally having from 1 to 3 substituents which may be the same as or different from each other and selected from the following substituent group [the substituent group is the halogen, $C_1$–$C_4$ alkyl, fluoromethyl, difluoromethyl, trifluoromethyl, 2-fluoroethyl, 2,2,2-trifluoroethyl, methoxymethyl, methoxyethyl, $C_1$–$C_4$ alkoxy, phenyl, 4-fluorophenyl, 4-chlorophenyl, 2,4-dichlorophenyl, 4-methylphenyl, 4-methoxyphenyl, cyano, methoxycarbonyl, ethoxycarbonyl, carbamoyl, methylcarbamoyl, ethylcarbamoyl, N,N-dimethylcarbamoyl or N,N-diethylcarbamoyl group]; still more preferably the phenyl group optionally having from 1 to 3 substituents which may be the same as or different from each other and selected from the following substituent group [the substituent group is the halogen, methyl, ethyl, trifluoromethyl, methoxy, phenyl, cyano, methoxycarbonyl, carbamoyl, methylcarbamoyl, ethylcarbamoyl or N,N-dimethylcarbamoyl group], further still more preferably the phenyl group optionally having one or two substituents which may be the same as or different from each other and selected from the following substituent group [the substituent group is the fluorine, chlorine, methyl, ethyl, trifluoromethyl and methoxy group]; particularly preferably the phenyl, fluorophenyl, chlorophenyl, difluorophenyl, dichlorophenyl or methylphenyl group; most preferably the phenyl, 2-chlorophenyl, 4-chlorophenyl, 2,4-difluorophenyl or 2,4-dichlorophenyl group.

Incidentally, the number of substituents on the aryl group is preferably 1 to 3, more preferably 1 or 2, most preferably 2.

In the formula (I), "the 5- or 6-membered aromatic heterocyclic group optionally having from 1 to 3 substituents and having one or two hetero atoms which may be the same as or different from each other and selected from the group consisting of nitrogen, oxygen and sulfur atoms" in the definition of $R^1$ may be, for example, a pyrrolyl, imidazolyl, pyrazolyl, furyl, thienyl, oxazolyl, isoxazolyl, thiazolyl, isothiazolyl, pyridyl, pyrazinyl, pyrimidinyl or pyridazinyl group which are optionally substituted with the following substituent, preferably 5- or 6-membered aromatic heterocyclic group optionally having from 1 to 3 substituents which may be the same as or different from each other and having one or two hetero atoms which may be the same as or different from each other and selected from the group consisting of nitrogen, oxygen and sulfur atoms [the substituent group is halogen; $C_1$–$C_6$ alkyl; $C_1$–$C_6$ alkyl substituted with halogen or $C_1$–$C_6$ alkoxy; $C_1$–$C_6$ alkoxy; $C_6$–$C_{14}$ aryl optionally having from 1 to 3 substituents which may be the same as or different from each other and selected from the following group (the substituent group is halogen, $C_1$–$C_6$ alkyl or $C_1$–$C_6$ alkoxy); benzyl, fluorobenzyl, chlorobenzyl, difluorobenzyl, dichlorobenzyl, methylbenzyl, dimethylbenzyl, methoxybenzyl; phenoxy, 4-fluorophenoxy, 4-chlorophenoxy, 2,4-dichlorophenoxy, 4-methylphenoxy, 4-methoxyphenoxy; benzyloxy, 4-fluorobenzyloxy, 4-chlorobenzyloxy, 2,4-difluorobenzyloxy, 2,4-dichlorobenzyloxy, 4-methylbenzyloxy, 2,4-dimethylbenzyloxy, 4-methoxybenzyloxy; cyano; nitro; hydroxyl; acetoxy; $C_2$–$C_7$ alkoxycarbonyl; amino; carbamoyl; mono-($C_1$–$C_6$ alkyl)carbamoyl; di($C_1$–$C_6$ alkyl) carbamoyl; benzoylamino, 4-fluorobenzoylamino, 4-chlorobenzoylamino, 2,4-dichlorobenzoylamino, 4-toluoylamino and 4-anisoylamino group]; preferably the 5- or 6-membered aromatic heterocyclic group optionally having from 1 to 3 substituents which may be the same as or different from each other and selected from the following substituent group and having one or two hetero atoms which may be the same as or different from each other and selected from the group consisting of nitrogen, oxygen and sulfur atoms [the substituent group is the halogen; $C_1$–$C_6$ alkyl; $C_1$–$C_6$ alkyl substituted with halogen or $C_1$–$C_6$ alkoxy; $C_1$–$C_6$ alkoxy; $C_6$–$C_{14}$ aryl optionally having from 1 to 3 substituents which may be the same as or different from each other and selected from the following substituent group and having one or two hetero atoms which may be the same as or different from each other and selected from the group consisting of nitrogen, oxygen and sulfur atoms (the substituent group is a halogen; a $C_1$–$C_6$ alkyl or a $C_1$–$C_6$ alkoxy); cyano; $C_2$–$C_7$ alkoxycarbonyl; carbamoyl; mono-($C_1$–$C_6$ alkyl)carbamoyl; or di($C_1$–$C_6$ alkyl)carbamoyl group]; more preferably the 5- or 6-membered aromatic heterocyclic group optionally having one or two substituents which may be the same as or different from each other and selected from the following substituent group [the substituent group is the halogen, $C_1$–$C_4$ alkyl, fluoromethyl, difluoromethyl, trifluoromethyl, 2-fluoroethyl, 2,2,2-trifluoroethyl, methoxymethyl, methoxyethyl, $C_1$–$C_4$ alkoxy, phenyl, 4-fluorophenyl, 4-chlorophenyl, 2,4-dichlorophenyl, 4-methylphenyl, 4-methoxyphenyl, cyano, methoxycarbonyl, ethoxycarbonyl, carbamoyl, methylcarbamoyl, ethylcarbamoyl, N,N-dimethylcarbamoyl or N,N-diethylcarbamoyl group], still more preferably furyl, thienyl or pyridyl group optionally having one or two substituents which may be the same as or different from each other and selected from the following substituent group [the substituent group is the halogen, methyl, ethyl, trifluoromethyl, methoxy, phenyl, cyano, methoxycarbonyl, carbamoyl, methylcarbamoyl, ethylcarbamoyl and N,N-dimethylcarbamoyl group], further still more preferably the furyl, thienyl or pyridyl group optionally having one substituent selected from the following substituent group [the substituent group is the fluorine, chlorine, methyl, ethyl, trifluoromethyl and methoxy group], particularly preferably the 2-furyl, 3-furyl, 2-thienyl or 3-thienyl group, most preferably the 2-furyl or 2-thienyl group.

Incidentally, the number of substituents on the aromatic heterocyclic group is preferably from 1 to 3, more preferably one or two, most preferably one.

Moreover, with respect to the bond of the aromatic heterocyclic group and the isoxazole ring, the bond is preferably formed on a carbon atom on the aromatic heterocycle.

In the formula (I), X is preferably an oxygen atom.

In the formula (I), n is preferably an integer from 2 to 4, more preferably 2.

The compound (I) of the present invention can be converted to an acid addition salt by a conventional method. For example, the salt can be obtained by treating the compound (I) with a corresponding acid in a solvent (for example, ethers, esters or alcohols, particularly ethers) at room temperature for 5 to 30 minutes and collecting the precipitated crystals by filtration or removing the solvent by evaporation. Such a salt includes mineral acid salt such as hydrofluoride, hydrochloride, hydrobromide, hydroiodide, nitrate, perchlorate, sulfate and phosphate; sulfonic acid salt such as methanesulfonate, trifluoromethanesulfonate, ethanesulfonate, benzenesulfonate and p-toluenesulfonate; carboxylic acid salt such as fumarate, succinate, citrate, tartrate, oxalate and maleate; and amino acid salt such as glutamate and aspartate, preferably the mineral acid salt (more preferably the hydrochloride).

The compound (I) of the present invention sometimes has an asymmetric carbon atom in the molecule, and stereoisomers of the R-configuration and the S-configuration sometimes exist. Each of the stereoisomers or a mixture containing the isomers in an optional proportion are all included in the present invention.

The compound (I) and salt thereof occasionally absorbs moisture when they are left to stand in the atmosphere and they occasionally form hydrates when they are recrystallized. Such products containing water are also included in the present invention.

Examples of preferable compounds of formula (I) include:

(1) compounds in which $R^1$ is the $C_6$–$C_{14}$ aryl group optionally having from 1 to 3 substituents which may be the same as or different from each other and selected from the following substituent group, or a 5- or 6-membered aromatic heterocyclic group optionally having from 1 to 3 substituents and having one or two hetero atoms which may be the same as or different from each other and selected from the group consisting of nitrogen, oxygen and sulfur atoms [the substituent group is the halogen; $C_1$–$C_6$ alkyl; $C_1$–$C_6$ alkyl substituted with halogen or $C_1$–$C_6$ alkoxy; $C_1$–$C_6$ alkoxy; $C_6$–$C_{14}$ aryl optionally having from 1 to 3 substituents which may be the same as or different from each other and selected from the following group (the substituent group is halogen, $C_1$–$C_6$ alkyl or $C_1$–$C_6$ alkoxy); benzyl, fluorobenzyl, chlorobenzyl, difluorobenzyl, dichlorobenzyl, methylbenzyl, dimethylbenzyl, methoxybenzyl; phenoxy, 4-fluorophenoxy, 4-chlorophenoxy, 2,4-dichlorophenoxy, 4-methylphenoxy, 4-methoxyphenoxy; benzyloxy, 4-fluorobenzyloxy, 4-chlorobenzyloxy, 2,4-difluorobenzyloxy, 2,4-dichlorobenzyloxy, 4-methylbenzyloxy, 2,4-dimethylbenzyloxy, 4-methoxybenzyloxy; cyano; nitro; a hydroxyl group; acetoxy; $C_2$–$C_7$ alkoxycarbonyl; amino; carbamoyl; mono-($C_1$–$C_6$ alkyl)carbamoyl; di($C_1$–$C_6$ alkyl) carbamoyl; benzoylamino, 4-fluorobenzoylamino, 4-chlorobenzoylamino, 2,4-dichlorobenzoylamino, 4-toluoylamino and 4-anisoylamino group], (2) compounds in which $R^1$ is the $C_6$–$C_{14}$ aryl group optionally having from I to 3 substituents which may be the same as or different from each other and selected from the following substituent group, or a 5- or 6-membered aromatic heterocyclic group optionally having from 1 to 3 substituents and having one or two hetero atoms which may be the same as or different from each other and selected from the group consisting of nitrogen, oxygen and sulfur atoms [the substituent group is the halogen; $C_1$–$C_6$ alkyl; $C_1$–$C_6$ alkyl substituted with halogen or $C_1$–$C_6$ alkoxy; $C_1$–$C_6$ alkoxy; $C_6$–$C_{14}$ aryl optionally having from 1 to 3 substituents which may be the same as or different selected from the following group (the substituent group is halogen, $C_1$–$C_6$ alkyl or $C_1$–$C_6$ alkoxy); cyano; $C_2$–$C_7$ alkoxycarbonyl; carbamoyl; mono-($C_1$–$C_6$ alkyl)carbamoyl; and di($C_1$–$C_6$ alkyl)carbamoyl group], (3) compounds in which $R^1$ is the $C_6$–$C_{14}$ aryl group optionally having from 1 to 3 substituents which may be the same as or different each other and selected from the following substituent group, or a 5- or 6-membered aromatic heterocyclic group optionally having one or two substituents and having one or two hetero atoms which may be the same as or different from each other and selected from the group consisting of nitrogen, oxygen and sulfur atoms [the substituent group is the halogen, $C_1$–$C_4$ alkyl, fluoromethyl, difluoromethyl, trifluoromethyl, 2-fluoroethyl, 2,2,2-trifluoroethyl, methoxymethyl, methoxyethyl, $C_1$–$C_4$ alkoxy, phenyl, 4-fluorophenyl, 4-chlorophenyl, 2,4-dichlorophenyl, 4methylphenyl, 4-methoxyphenyl, cyano, methoxycarbonyl, ethoxycarbonyl, carbamoyl, methylcarbamoyl, ethylcarbamoyl, N,N-dimethylcarbamoyl and N,N-diethylcarbamoyl group], (4) compounds in which $R^1$ is the phenyl group optionally having from 1 to 3 substituents which may be the same as or different from each other and selected from the following substituent group, or the furyl, thienyl or pyridyl group optionally having one or two substituents [the substituent group is the halogen, methyl, ethyl, trifluoromethyl, methoxy, phenyl, cyano, methoxycarbonyl, carbamoyl, methylcarbamoyl, ethylcarbamoyl and N,N-dimethylcarbamoyl group], (5) compounds in which $R^1$ is the phenyl group optionally having one or two substituents which may be the same as or different from each other and selected from the following substituent group, or the furyl, thienyl or pyridyl group optionally having one substituent [the substituent group is fluorine, chlorine, methyl, ethyl, trifluoromethyl and methoxy group], (6) compounds in which $R^1$ is the phenyl, fluorophenyl, chlorophenyl, difluorophenyl, dichlorophenyl, methylphenyl, 2-furyl, 3-furyl, 2-thienyl or 3-thienyl group, (7) compounds in which $R^1$ is the phenyl, 2-chlorophenyl, 4-chlorophenyl, 2,4-difluorophenyl, 2,4-dichlorophenyl, 2-furyl or 2-thienyl group, (8) compounds in which $R^2$ is the hydrogen, halogen, $C_1$–$C_6$ alkyl, fluoromethyl, difluoromethyl, trifluoromethyl, 2-fluoroethyl, 1-chloroethyl, 2-chloroethyl, 2,2,2-trifluoroethyl, methoxymethyl, methoxyethyl, $C_2$–$C_6$ alkenyl, $C_2$–$C_6$ alkynyl, cyclopropyl, cyclopentyl, cyclohexyl, 2-cyclopentenyl, 3-cyclopentenyl, 2-cyclohexenyl, 3-cyclohexenyl, methoxy, ethoxy, cyano, carboxyl, formyl, acetyl, methoxycarbonyl, ethoxycarbonyl, carbamoyl, methylcarbamoyl, ethylcarbamoyl or N,N-dimethylcarbamoyl group, (9) compounds in which $R^2$ is the hydrogen, halogen, $C_1$–$C_6$ alkyl, $C_2$–$C_6$ alkenyl or $C_2$–$C_6$ alkynyl group,

(10) compounds in which $R^2$ is the hydrogen, halogen, $C_1$–$C_4$ alkyl, allyl, isopropenyl, 2-butenyl or propargyl group,

(11) compounds in which $R^2$ is the hydrogen, chlorine, ethyl, propyl, isopropyl, isobutyl or t-butyl group,

(12) compounds in which $R^2$ is the hydrogen or isopropyl group,

(13) compounds in which $R^3$ is the amino, mono $C_1$–$C_6$ alkylamino, di($C_1$–$C_6$ alkyl)amino or 5- or 6-membered saturated heterocyclic group (provided that the group is attached thorough a ring nitrogen atom), having one nitrogen atom and further optionally having one nitrogen atom or oxygen atom

(14) compounds in which $R^3$ is the amino, methylamino, ethylamino, N,N-dimethylamino, piperidyl or morpholinyl group,
(15) compounds in which $R^3$ is the amino group,
(16) compounds in which X is the oxygen atom, and
(17) compounds in which n is 2.

The order of preference of $R^1$ increases in the ascending orders of (1) to (7), that of $R^2$ increases in the ascending orders of (8) to (12), and that of $R^3$ increases in the ascending orders of (13) to (15).

Further, compounds of formula (I) include combinations of from two to five selected from the group consisting of (1)–(7), (8)–(12), (13)–(15), (16) and (17) and preferable examples of such combinations are shown below,

(18) compounds in which $R^1$ is the $C_6$–$C_{14}$ aryl group optionally having from 1 to 3 substituents which may be the same as or different from each other and selected from the following substituent group, or the 5- or 6-membered aromatic heterocyclic group optionally having from 1 to 3 substituents and having one or two hetero atoms which may be the same as or different from each other and selected from the group consisting of nitrogen, oxygen and sulfur atoms [the substituent group is the halogen; $C_1$–$C_6$ alkyl; $C_1$–$C_6$ alkyl substituted with halogen or $C_1$–$C_6$ alkoxy; $C_1$–$C_6$ alkoxy; $C_6$–$C_{14}$ aryl optionally having from 1 to 3 substituents which may be the same as or different from each other and selected from the following group (the substituent group is halogen, $C_1$–$C_6$ alkyl or $C_1$–$C_6$ alkoxy); cyano; $C_2$–$C_7$ alkoxycarbonyl; carbamoyl; mono-($C_1$–$C_6$ alkyl)carbamoyl; and di($C_1$–$C_6$ alkyl)carbamoyl group],
$R^2$ is the hydrogen, halogen, $C_1$–$C_6$ alkyl, $C_2$–$C_6$ alkenyl or $C_2$–$C_6$ alkynyl group, and
$R^3$ is the amino, mono $C_1$–$C_6$ alkylamino, di($C_1$–$C_6$ alkyl)amino group or the 5- or 6-membered saturated heterocyclic group (provided that the group attached thorough a ring nitrogen atom) containing one nitrogen atom and further one nitrogen or oxygen atom,

(19) compounds in which $R^1$ is the $C_6$–$C_{14}$ aryl group optionally having from 1 to 3 substituents which may be the same as or different from each other and selected from the following substituent group, or the 5- or 6-membered aromatic heterocyclic group optionally having from 1 to 3 substituents and having one or two hetero atoms which may be the same as or different from each other and selected from the group consisting of nitrogen, oxygen and sulfur atoms [the substituent group is the halogen; $C_1$–$C_6$ alkyl; $C_1$–$C_6$ alkyl substituted with halogen or $C_1$–$C_6$ alkoxy; $C_1$–$C_6$ alkoxy; $C_6$–$C_{14}$ aryl optionally having from 1 to 3 substituents which may be the same as or different from each other and selected from the following group (the substituent group is halogen, $C_1$–$C_6$ alkyl or $C_1$–$C_6$ alkoxy); cyano; $C_2$–$C_7$ alkoxycarbonyl; carbamoyl; mono($C_1$–$C_6$ alkyl)carbamoyl; and di($C_1$–$C_6$ alkyl)carbamoyl group],
$R^2$ is the hydrogen, halogen, $C_1$–$C_6$ alkyl, $C_2$–$C_6$ alkenyl or $C_2$–$C_6$ alkynyl group,
$R^3$ is the amino group,
X is the oxygen atom, and
n is 2,

(20) compounds in which $R^1$ is the $C_6$–$C_{14}$ aryl group optionally having from 1 to 3 substituents which may be the same as or different from each other and selected from the following substituent group, or the 5- or 6-membered aromatic heterocyclic group optionally having one or two substituents and having one or two hetero atoms which may be the same as or different from each other and selected from the group consisting of nitrogen, oxygen and sulfur atoms [the substituent group is the halogen, $C_1$–$C_4$ alkyl, fluoromethyl, difluoromethyl, trifluoromethyl, 2-fluoroethyl, 2,2,2-trifluoroethyl, methoxymethyl, methoxyethyl, $C_1$–$C_4$ alkoxy, phenyl, 4-fluorophenyl, 4-chlorophenyl, 2,4-dichlorophenyl, 4-methylphenyl, 4-methoxyphenyl, cyano, methoxycarbonyl, ethoxycarbonyl, carbamoyl, methylcarbamoyl, ethylcarbamoyl, N,N-dimethylcarbamoyl and N,N-diethylcarbamoyl group],
$R^2$ is the hydrogen, halogen, $C_1$–$C_4$ alkyl, allyl, isopropenyl, 2-butenyl or propargyl group,
$R^3$ is the amino group,
X is the oxygen atom, and
n is 2,

(21) compounds in which $R^1$ is the phenyl group optionally having from 1 to 3 substituents which may be the same as or different from each other and selected from the following substituent group, or the furyl, thienyl or pyridyl group optionally having one or two substituents [the substituent group is the halogen, methyl, ethyl, trifluoromethyl, methoxy, phenyl, cyano, methoxycarbonyl, carbamoyl, methylcarbamoyl, ethylcarbamoyl and N,N-dimethylcarbamoyl group],
$R^2$ is the hydrogen, halogen, $C_1$–$C_4$ alkyl, allyl, isopropenyl, 2-butenyl or propargyl group,
$R^3$ is the amino group,
X is the oxygen atom, and
n is 2,

(22) compounds in which $R^1$ is the phenyl group optionally having one or two substituents which may be the same as or different from each other and selected from the following substituent group, or the furyl, thienyl or pyridyl group optionally having one substituent [the substituent group is the fluorine, chlorine, methyl, ethyl, trifluoromethyl and methoxy group],
$R^2$ is the hydrogen, chlorine, ethyl, propyl, isopropyl, isobutyl or t-butyl group,
$R^3$ is the amino group,
X is the oxygen atom, and
n is 2,

(23) compounds in which $R^1$ is the fluorophenyl, chlorophenyl, difluorophenyl, dichlorophenyl, methylphenyl, 2-furyl, 3-furyl, 2-thienyl or 3-thienyl group,
$R^2$ is the hydrogen, chlorine, ethyl, propyl, isopropyl, isobutyl or t-butyl group,
$R^3$ is the amino group,
X is the oxygen atom, and
n is 2,

(24) compounds in which $R^1$ is the phenyl, 2-chlorophenyl, 4-chlorophenyl, 2,4-difluorophenyl, 2,4-dichlorophenyl, 2-furyl or 2-thienyl group,
$R^2$ is the hydrogen atom or the isopropyl group,
$R^3$ is the amino group,
X is the oxygen atom, and
n is 2.

With respect to the compounds described above, the order of preference of the compounds increases in the ascending orders of (18) to (24).

The representative compounds of the present invention are illustrated in the following Table, but the present invention is not limited to them.

In the Table the following abbreviations are used.

| | |
|---|---|
| Ac | Acetyl |
| All | Allyl |
| Bn | Benzyl |
| Bu | Butyl |
| $Bu^i$ | Isobutyl |
| $Bu^s$ | s-Butyl |
| $Bu^t$ | t-Butyl |
| Bun(2) | 2-Butenyl |
| Bz | Benzoyl |
| Et | Ethyl |
| Fur(2) | 2-Furyl |
| Hex | Hexyl |
| Imid(2) | 2-Imidazolyl |
| Inde(1) | 1-Indenyl |
| Isothiz(3) | 3-Isothiazolyl |
| Isox(3) | 3-Isoxazolyl |
| Me | Methyl |
| Moc | Methoxycarbonyl |
| Mor(4) | 4-Morpholinyl |
| Np(1) | 1-Naphthyl |
| Np(2) | 2-Naphthyl |
| Oxa(2) | 2-Oxazolyl |
| $Pen^c(2)$ | 2-Cyclopentenyl |
| Ph | Phenyl |
| Pip(1) | 1-Piperidyl |
| Piz(1) | 1-Piperazinyl |
| Pn | Pentyl |
| $Pn^c$ | Cyclopentyl |
| $Pn^i$ | Isopentyl |
| Pr | Propyl |
| $Pr^c$ | Cyclopropyl |
| $Pr^i$ | Isopropyl |
| $Pre^i$ | Isopropenyl |
| Prg | Propargyl |
| Pym(2) | 2-Pyrimidinyl |
| Pyr(2) | 2-Pyridyl |
| Pyr(3) | 3-Pyridyl |
| Pyr(4) | 4-Pyridyl |
| Pyrd(1) | 1-Pyrrolidinyl |
| Pyrr(3) | 3-Pyrrolyl |
| Pyz(2) | 2-Pyrazinyl |
| Pyza(1) | 1-Pyrazolyl |
| Pyzn(3) | 3-Pyridazinyl |
| Thi(2) | 2-Thienyl |
| Thi(3) | 3-Thienyl |
| Thiz(2) | 2-Thiazolyl |

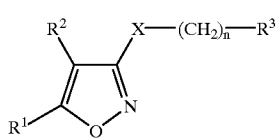

(I)

TABLE 1

| Compd. No. | $R^1$ | $R^2$ | $R^3$ | X | n |
|---|---|---|---|---|---|
| 1 | Ph | H | $NH_2$ | O | 2 |
| 2 | Ph | H | $NH_2$ | O | 3 |
| 3 | Ph | H | $NH_2$ | O | 4 |
| 4 | Ph | F | $NH_2$ | O | 2 |
| 5 | Ph | Cl | $NH_2$ | O | 2 |
| 6 | Ph | Me | $NH_2$ | O | 2 |
| 7 | Ph | Et | $NH_2$ | O | 2 |
| 8 | Ph | Pr | $NH_2$ | O | 2 |
| 9 | Ph | $Pr^i$ | $NH_2$ | O | 2 |
| 10 | Ph | Bu | $NH_2$ | O | 2 |
| 11 | Ph | $Bu^i$ | $NH_2$ | O | 2 |
| 12 | Ph | $Bu^s$ | $NH_2$ | O | 2 |
| 13 | Ph | $Bu^t$ | $NH_2$ | O | 2 |
| 14 | Ph | $CF_3$ | $NH_2$ | O | 2 |
| 15 | Ph | H | $NH_2$ | S | 2 |
| 16 | Ph | H | $NH_2$ | S | 3 |

TABLE 1-continued

| Compd. No. | $R^1$ | $R^2$ | $R^3$ | X | n |
|---|---|---|---|---|---|
| 17 | Ph | H | $NH_2$ | S | 4 |
| 18 | Ph | F | $NH_2$ | S | 2 |
| 19 | Ph | Cl | $NH_2$ | S | 2 |
| 20 | Ph | Me | $NH_2$ | S | 2 |
| 21 | Ph | Et | $NH_2$ | S | 2 |
| 22 | Ph | Pr | $NH_2$ | S | 2 |
| 23 | Ph | $Pr^i$ | $NH_2$ | S | 2 |
| 24 | Ph | Bu | $NH_2$ | S | 2 |
| 25 | Ph | H | NHMe | O | 2 |
| 26 | Ph | H | NHEt | O | 2 |
| 27 | Ph | H | $N(Me)_2$ | O | 2 |
| 28 | Ph | H | Pip(1) | O | 2 |
| 29 | Ph | H | Mor(4) | O | 2 |
| 30 | 2-F—Ph | H | $NH_2$ | O | 2 |
| 31 | 2-F—Ph | F | $NH_2$ | O | 2 |
| 32 | 2-F—Ph | Cl | $NH_2$ | O | 2 |
| 33 | 2-F—Ph | Me | $NH_2$ | O | 2 |
| 34 | 2-F—Ph | Et | $NH_2$ | O | 2 |
| 35 | 2-F—Ph | Pr | $NH_2$ | O | 2 |
| 36 | 2-F—Ph | $Pr^i$ | $NH_2$ | O | 2 |
| 37 | 2-F—Ph | Bu | $NH_2$ | O | 2 |
| 38 | 2-F—Ph | $Bu^i$ | $NH_2$ | O | 2 |
| 39 | 2-F—Ph | $Bu^s$ | $NH_2$ | O | 2 |
| 40 | 2-F—Ph | $Bu^t$ | $NH_2$ | O | 2 |
| 41 | 2-F—Ph | H | $NH_2$ | S | 2 |
| 42 | 2-F—Ph | F | $NH_2$ | S | 2 |
| 43 | 2-F—Ph | Cl | $NH_2$ | S | 2 |
| 44 | 2-F—Ph | Me | $NH_2$ | S | 2 |
| 45 | 2-F—Ph | Et | $NH_2$ | S | 2 |
| 46 | 2-F—Ph | Pr | $NH_2$ | S | 2 |
| 47 | 2-F—Ph | $Pr^i$ | $NH_2$ | S | 2 |
| 48 | 3-F—Ph | H | $NH_2$ | O | 2 |
| 49 | 3-F—Ph | F | $NH_2$ | O | 2 |
| 50 | 3-F—Ph | Cl | $NH_2$ | O | 2 |
| 51 | 3-F—Ph | Me | $NH_2$ | O | 2 |
| 52 | 3-F—Ph | Et | $NH_2$ | O | 2 |
| 53 | 3-F—Ph | Pr | $NH_2$ | O | 2 |
| 54 | 3-F—Ph | $Pr^i$ | $NH_2$ | O | 2 |
| 55 | 3-F—Ph | Bu | $NH_2$ | O | 2 |
| 56 | 3-F—Ph | $Bu^i$ | $NH_2$ | O | 2 |
| 57 | 3-F—Ph | $Bu^s$ | $NH_2$ | O | 2 |
| 58 | 3-F—Ph | $Bu^t$ | $NH_2$ | O | 2 |
| 59 | 3-F—Ph | H | $NH_2$ | S | 2 |
| 60 | 3-F—Ph | F | $NH_2$ | S | 2 |
| 61 | 3-F—Ph | Cl | $NH_2$ | S | 2 |
| 62 | 3-F—Ph | Me | $NH_2$ | S | 2 |
| 63 | 3-F—Ph | Et | $NH_2$ | S | 2 |
| 64 | 3-F—Ph | Pr | $NH_2$ | S | 2 |
| 65 | 3-F—Ph | $Pr^i$ | $NH_2$ | S | 2 |
| 66 | 4-F—Ph | H | $NH_2$ | O | 2 |
| 67 | 4-F—Ph | H | $NH_2$ | O | 3 |
| 68 | 4-F—Ph | H | $NH_2$ | O | 4 |
| 69 | 4-F—Ph | F | $NH_2$ | O | 2 |
| 70 | 4-F—Ph | Cl | $NH_2$ | O | 2 |
| 71 | 4-F—Ph | Me | $NH_2$ | O | 2 |
| 72 | 4-F—Ph | Et | $NH_2$ | O | 2 |
| 73 | 4-F—Ph | Pr | $NH_2$ | O | 2 |
| 74 | 4-F—Ph | $Pr^i$ | $NH_2$ | O | 2 |
| 75 | 4-F—Ph | Bu | $NH_2$ | O | 2 |
| 76 | 4-F—Ph | Bui | $NH_2$ | O | 2 |
| 77 | 4-F—Ph | $Bu^s$ | $NH_2$ | O | 2 |
| 78 | 4-F—Ph | $Bu^t$ | $NH_2$ | O | 2 |
| 79 | 4-F—Ph | H | $NH_2$ | S | 2 |
| 80 | 4-F—Ph | H | $NH_2$ | S | 3 |
| 81 | 4-F—Ph | H | $NH_2$ | S | 4 |
| 82 | 4-F—Ph | F | $NH_2$ | S | 2 |
| 83 | 4-F—Ph | Cl | $NH_2$ | S | 2 |
| 84 | 4-F—Ph | Me | $NH_2$ | S | 2 |
| 85 | 4-F—Ph | Et | $NH_2$ | S | 2 |
| 86 | 4-F—Ph | Pr | $NH_2$ | S | 2 |
| 87 | 4-F—Ph | $Pr^i$ | $NH_2$ | S | 2 |
| 88 | 4-F—Ph | H | NHMe | O | 2 |
| 89 | 4-F—Ph | H | NHEt | O | 2 |
| 90 | 4-F—Ph | H | $N(Me)_2$ | O | 2 |
| 91 | 4-F—Ph | H | Pip(1) | O | 2 |
| 92 | 4-F—Ph | H | Mor(4) | O | 2 |

TABLE 1-continued

| Compd. No. | R¹ | R² | R³ | X | n |
|---|---|---|---|---|---|
| 93 | 2,4-diF—Ph | H | NH$_2$ | O | 2 |
| 94 | 2,4-diF—Ph | F | NH$_2$ | O | 2 |
| 95 | 2,4-diF—Ph | Cl | NH$_2$ | O | 2 |
| 96 | 2,4-diF—Ph | Me | NH$_2$ | O | 2 |
| 97 | 2,4-diF—Ph | Et | NH$_2$ | O | 2 |
| 98 | 2,4-diF—Ph | Pr | NH$_2$ | O | 2 |
| 99 | 2,4-diF—Ph | Pr$^i$ | NH$_2$ | O | 2 |
| 100 | 2,4-diF—Ph | Bu | NH$_2$ | O | 2 |
| 101 | 2,4-diF—Ph | Bu$^i$ | NH$_2$ | O | 2 |
| 102 | 2,4-diF—Ph | Bu$^s$ | NH$_2$ | O | 2 |
| 103 | 2,4-diF—Ph | Bu$^t$ | NH$_2$ | O | 2 |
| 104 | 2,4-diF—Ph | H | NH$_2$ | S | 2 |
| 105 | 2,4-diF—Ph | F | NH$_2$ | S | 2 |
| 106 | 2,4-diF—Ph | Cl | NH$_2$ | S | 2 |
| 107 | 2,4-diF—Ph | Me | NH$_2$ | S | 2 |
| 108 | 2,4-diF—Ph | Et | NH$_2$ | S | 2 |
| 109 | 2,4-diF—Ph | Pr | NH$_2$ | S | 2 |
| 110 | 2,4-diF—Ph | Pr$^i$ | NH$_2$ | S | 2 |
| 111 | 2-Cl—Ph | H | NH$_2$ | O | 2 |
| 112 | 2-Cl—Ph | F | NH$_2$ | O | 2 |
| 113 | 2-Cl—Ph | Cl | NH$_2$ | O | 2 |
| 114 | 2-Cl—Ph | Me | NH$_2$ | O | 2 |
| 115 | 2-Cl—Ph | Et | NH$_2$ | O | 2 |
| 116 | 2-Cl—Ph | Pr | NH$_2$ | O. | 2 |
| 117 | 2-Cl—Ph | Pr$^i$ | NH$_2$ | O | 2 |
| 118 | 2-Cl—Ph | H | NH$_2$ | S | 2 |
| 119 | 2-Cl—Ph | F | NH$_2$ | S | 2 |
| 120 | 2-Cl—Ph | Cl | NH$_2$ | S | 2 |
| 121 | 2-Cl—Ph | Me | NH$_2$ | S | 2 |
| 122 | 2-Cl—Ph | Et | NH$_2$ | S | 2 |
| 123 | 2-Cl—Ph | Pr | NH$_2$ | S | 2 |
| 124 | 2-Cl—Ph | Pr$^i$ | NH$_2$ | S | 2 |
| 125 | 3-Cl—Ph | H | NH$_2$ | O | 2 |
| 126 | 3-Cl—Ph | F | NH$_2$ | O | 2 |
| 127 | 3-Cl—Ph | Cl | NH$_2$ | O | 2 |
| 128 | 3-Cl—Ph | Me | NH$_2$ | O | 2 |
| 129 | 3-Cl—Ph | Et | NH$_2$ | O | 2 |
| 130 | 3-Cl—Ph | Pr | NH$_2$ | O | 2 |
| 131 | 3-Cl—Ph | Pr$^i$ | NH$_2$ | O | 2 |
| 132 | 3-Cl—Ph | Bu | NH$_2$ | O | 2 |
| 133 | 3-Cl—Ph | Bu$^i$ | NH$_2$ | O | 2 |
| 134 | 3-Cl—Ph | Bu$^s$ | NH$_2$ | O | 2 |
| 135 | 3-Cl—Ph | Bu$^t$ | NH$_2$ | O | 2 |
| 136 | 3-Cl—Ph | H | NH$_2$ | S | 2 |
| 137 | 3-Cl—Ph | F | NH$_2$ | S | 2 |
| 138 | 3-Cl—Ph | Cl | NH$_2$ | S | 2 |
| 139 | 3-Cl—Ph | Me | NH$_2$ | S | 2 |
| 140 | 3-Cl—Ph | Et | NH$_2$ | S | 2 |
| 141 | 3-Cl—Ph | Pr | NH$_2$ | S | 2 |
| 142 | 3-Cl—Ph | Pr$^i$ | NH$_2$ | S | 2 |
| 143 | 4-Cl—Ph | H | NH$_2$ | O | 2 |
| 144 | 4-Cl—Ph | H | NH$_2$ | O | 3 |
| 145 | 4-Cl—Ph | H | NH$_2$ | O | 4 |
| 146 | 4-Cl—Ph | F | NH$_2$ | O | 2 |
| 147 | 4-Cl—Ph | Cl | NH$_2$ | O | 2 |
| 148 | 4-Cl—Ph | Me | NH$_2$ | O | 2 |
| 149 | 4-Cl—Ph | Et | NH$_2$ | O | 2 |
| 150 | 4-Cl—Ph | Pr | NH$_2$ | O | 2 |
| 151 | 4-Cl—Ph | Pr$^i$ | NH$_2$ | O | 2 |
| 152 | 4-Cl—Ph | Bu | NH$_2$ | O | 2 |
| 153 | 4-Cl—Ph | Bu$^i$ | NH$_2$ | O | 2 |
| 154 | 4-Cl—Ph | Bu$^s$ | NH$_2$ | O | 2 |
| 155 | 4-Cl—Ph | Bu$^t$ | NH$_2$ | O | 2 |
| 156 | 4-Cl—Ph | H | NH$_2$ | S | 2 |
| 157 | 4-Cl—Ph | H | NH$_2$ | S | 3 |
| 158 | 4-Cl—Ph | H | NH$_2$ | S | 4 |
| 159 | 4-Cl—Ph | F | NH$_2$ | S | 2 |
| 160 | 4-Cl—Ph | Cl | NH$_2$ | S | 2 |
| 161 | 4-Cl—Ph | Me | NH$_2$ | S | 2 |
| 162 | 4-Cl—Ph | Et | NH$_2$ | S | 2 |
| 163 | 4-Cl—Ph | Pr | NH$_2$ | S | 2 |
| 164 | 4-Cl—Ph | Pr$^i$ | NH$_2$ | S | 2 |
| 165 | 4-Cl—Ph | H | NHMe | O | 2 |
| 166 | 4-Cl—Ph | H | NHEt | O | 2 |
| 167 | 4-Cl—Ph | H | N(Me)$_2$ | O | 2 |
| 168 | 4-Cl—Ph | H | Pip(1) | O | 2 |
| 169 | 4-Cl—Ph | H | Mor(4) | O | 2 |
| 170 | 2,4-diCl—Ph | H | NH$_2$ | O | 2 |
| 171 | 2,4-diCl—Ph | F | NH$_2$ | O | 2 |
| 172 | 2,4-diCl—Ph | Cl | NH$_2$ | O | 2 |
| 173 | 2,4-diCl—Ph | Me | NH$_2$ | O | 2 |
| 174 | 2,4-diCl—Ph | Et | NH$_2$ | O | 2 |
| 175 | 2,4-diCl—Ph | Pr | NH$_2$ | O | 2 |
| 176 | 2,4-diCl—Ph | Pr$^i$ | NH$_2$ | O | 2 |
| 177 | 2,4-diCl—Ph | Bu | NH$_2$ | O | 2 |
| 178 | 2,4-diCl—Ph | Bu$^i$ | NH$_2$ | O | 2 |
| 179 | 2,4-diCl—Ph | Bu5 | NH$_2$ | O | 2 |
| 180 | 2,4-diCl—Ph | Bu$^t$ | NH$_2$ | O | 2 |
| 181 | 2,4-diCl—Ph | H | NH$_2$ | S | 2 |
| 182 | 2,4-diCl—Ph | F | NH$_2$ | S | 2 |
| 183 | 2,4-diCl—Ph | Cl | NH$_2$ | S | 2 |
| 184 | 2,4-diCl—Ph | Me | NH$_2$ | S | 2 |
| 185 | 2,4-diCl—Ph | Et | NH$_2$ | S | 2 |
| 186 | 2,4-diCl—Ph | Pr | NH$_2$ | S | 2 |
| 187 | 2,4-diCl—Ph | Pr$^i$ | NH$_2$ | S | 2 |
| 188 | 2,6-diCl—Ph | H | NH$_2$ | O | 2 |
| 189 | 2,6-diCl—Ph | F | NH$_2$ | O | 2 |
| 190 | 2,6-diCl—Ph | Cl | NH$_2$ | O | 2 |
| 191 | 2,6-diCl—Ph | Me | NH$_2$ | O | 2 |
| 192 | 2,6-diCl—Ph | Et | NH$_2$ | O | 2 |
| 193 | 2,6-diCl—Ph | Pr | NH$_2$ | O | 2 |
| 194 | 2,6-diCl—Ph | Pr$^i$ | NH$_2$ | O | 2 |
| 195 | 2,6-diCl—Ph | Bu | NH$_2$ | O | 2 |
| 196 | 2,6-diCl—Ph | Bu$^i$ | NH$_2$ | O | 2 |
| 197 | 2,6-diCl—Ph | Bu5 | NH$_2$ | O | 2 |
| 198 | 2,6-diCl—Ph | Bu$^t$ | NH$_2$ | O | 2 |
| 199 | 2,6-diCl—Ph | H | NH$_2$ | S | 2 |
| 200 | 2,6-diCl—Ph | F | NH$_2$ | S | 2 |
| 201 | 2,6-diCl—Ph | Cl | NH$_2$ | S | 2 |
| 202 | 2,6-diCl—Ph | Me | NH$_2$ | S | 2 |
| 203 | 2,6-diCl—Ph | Et | NH$_2$ | S | 2 |
| 204 | 2,6-diCl—Ph | Pr | NH$_2$ | S | 2 |
| 205 | 2,6-diCl—Ph | Pr$^i$ | NH$_2$ | S | 2 |
| 206 | 3,5-diCl—Ph | H | NH$_2$ | O | 2 |
| 207 | 3,5-diCl—Ph | F | NH$_2$ | O | 2 |
| 208 | 3,5-diCl—Ph | Cl | NH$_2$ | O | 2 |
| 209 | 3,5-diCl—Ph | Me | NH$_2$ | O | 2 |
| 210 | 3,5-diCl—Ph | Et | NH$_2$ | O | 2. |
| 211 | 3,5-diCl—Ph | Pr | NH$_2$ | O | 2 |
| 212 | 3,5-diCl—Ph | Pr$^i$ | NH$_2$ | O | 2 |
| 213 | 3,5-diCl—Ph | Bu | NH$_2$ | O | 2 |
| 214 | 3,5-diCl—Ph | Bu$^i$ | NH$_2$ | O | 2 |
| 215 | 3,5-diCl—Ph | Bu$^s$ | NH$_2$ | O | 2 |
| 216 | 3,5-diCl—Ph | Bu$^t$ | NH$_2$ | O | 2 |
| 217 | 3,5-diCl—Ph | H | NH$_2$ | S | 2 |
| 218 | 3,5-diCl—Ph | F | NH$_2$ | S | 2 |
| 219 | 3,5-diCl—Ph | Cl | NH$_2$ | S | 2 |
| 220 | 3,5-diCl—Ph | Me | NH$_2$ | S | 2 |
| 221 | 3,5-diCl—Ph | Et | NH$_2$ | S | 2 |
| 222 | 3,5-diCl—Ph | Pr | NH$_2$ | S | 2 |
| 223 | 3,5-diCl—Ph | Pr$^i$ | NH$_2$ | S | 2 |
| 224 | 2-Me—Ph | H | NH$_2$ | O | 2 |
| 225 | 2-Me—Ph | F | NH$_2$ | O | 2 |
| 226 | 2-Me—Ph | Cl | NH$_2$ | O | 2 |
| 227 | 2-Me—Ph | Me | NH$_2$ | O | 2 |
| 228 | 2-Me—Ph | Et | NH$_2$ | O | 2 |
| 229 | 2-Me—Ph | Pr | NH$_2$ | O | 2 |
| 230 | 2-Me—Ph | Pr$^i$ | NH$_2$ | O | 2 |
| 231 | 2-Me—Ph | Bu | NH$_2$ | O | 2 |
| 232 | 2-Me—Ph | Bu$^i$ | NH$_2$ | O | 2 |
| 233 | 2-Me—Ph | Bu5 | NH$_2$ | O | 2 |
| 234 | 2-Me—Ph | Bu$^t$ | NH$_2$ | O | 2 |
| 235 | 2-Me—Ph | H | NH$_2$ | S | 2 |
| 236 | 2-Me—Ph | F | NH$_2$ | S | 2 |
| 237 | 2-Me—Ph | Cl | NH$_2$ | S | 2 |
| 238 | 2-Me—Ph | Me | NH$_2$ | S | 2 |
| 239 | 2-Me—Ph | Et | NH$_2$ | S | 2 |
| 240 | 2-Me—Ph | Pr | NH$_2$ | S | 2 |
| 241 | 2-Me—Ph | Pr$^i$ | NH$_2$ | S | 2 |
| 242 | 3-Me—Ph | H | NH$_2$ | O | 2 |
| 243 | 3-Me—Ph | F | NH$_2$ | O | 2 |
| 244 | 3-Me—Ph | Cl | NH$_2$ | O | 2 |

TABLE 1-continued

| Compd. No. | R¹ | R² | R³ | X | n |
|---|---|---|---|---|---|
| 245 | 3-Me—Ph | Me | $NH_2$ | O | 2 |
| 246 | 3-Me—Ph | Et | $NH_2$ | O | 2 |
| 247 | 3-Me—Ph | Pr | $NH_2$ | O | 2 |
| 248 | 3-Me—Ph | $Pr^i$ | $NH_2$ | O | 2 |
| 249 | 3-Me—Ph | Bu | $NH_2$ | O | 2 |
| 250 | 3-Me—Ph | $Bu^i$ | $NH_2$ | O | 2 |
| 251 | 3-Me—Ph | $Bu^s$ | $NH_2$ | O | 2 |
| 252 | 3-Me—Ph | $Bu^t$ | $NH_2$ | O | 2 |
| 253 | 3-Me—Ph | H | $NH_2$ | S | 2 |
| 254 | 3-Me—Ph | F | $NH_2$ | S | 2 |
| 255 | 3-Me—Ph | Cl | $NH_2$ | S | 2 |
| 256 | 3-Me—Ph | Me | $NH_2$ | S | 2 |
| 257 | 3-Me—Ph | Et | $NH_2$ | S | 2 |
| 258 | 3-Me—Ph | Pr | $NH_2$ | S | 2 |
| 259 | 3-Me—Ph | $Pr^i$ | $NH_2$ | S | 2 |
| 260 | 4-Me—Ph | H | $NH_2$ | O | 2 |
| 261 | 4-Me—Ph | F | $NH_2$ | O | 2 |
| 262 | 4-Me—Ph | Cl | $NH_2$ | O | 2 |
| 263 | 4-Me—Ph | Me | $NH_2$ | O | 2 |
| 264 | 4-Me—Ph | Et | $NH_2$ | O | 2 |
| 265 | 4-Me—Ph | Pr | $NH_2$ | O | 2 |
| 266 | 4-Me—Ph | $Pr^i$ | $NH_2$ | O | 2 |
| 267 | 4-Me—Ph | Bu | $NH_2$ | O | 2 |
| 268 | 4-Me—Ph | $Bu^i$ | $NH_2$ | O | 2 |
| 269 | 4-Me—Ph | $Bu^s$ | $NH_2$ | O | 2 |
| 270 | 4-Me—Ph | $Bu^t$ | $NH_2$ | O | 2 |
| 271 | 4-Me—Ph | H | $NH_2$ | S | 2 |
| 272 | 4-Me—Ph | F | $NH_2$ | S | 2 |
| 273 | 4-Me—Ph | Cl | $NH_2$ | S | 2 |
| 274 | 4-Me—Ph | Me | $NH_2$ | S | 2 |
| 275 | 4-Me—Ph | Et | $NH_2$ | S | 2 |
| 276 | 4-Me—Ph | Pr | $NH_2$ | S | 2 |
| 277 | 4-Me—Ph | $Pr^i$ | $NH_2$ | S | 2 |
| 278 | 4-Et—Ph | H | $NH_2$ | O | 2 |
| 279 | 4-Et—Ph | F | $NH_2$ | O | 2 |
| 280 | 4-Et—Ph | Cl | $NH_2$ | O | 2 |
| 281 | 4-Et—Ph | Me | $NH_2$ | O | 2 |
| 282 | 4-Et—Ph | Et | $NH_2$ | O | 2 |
| 283 | 4-Et—Ph | Pr | $NH_2$ | O | 2 |
| 284 | 4-Et—Ph | $Pr^i$ | $NH_2$ | O | 2 |
| 285 | 4-Et—Ph | Bu | $NH_2$ | O | 2 |
| 286 | 4-Et—Ph | $Bu^i$ | $NH_2$ | O | 2 |
| 287 | 4-Et—Ph | $Bu^s$ | $NH_2$ | O | 2 |
| 288 | 4-Et—Ph | $Bu^t$ | $NH_2$ | O | 2 |
| 289 | 4-Et—Ph | H | $NH_2$ | S | 2 |
| 290 | 4-Et—Ph | F | $NH_2$ | S | 2 |
| 291 | 4-Et—Ph | Cl | $NH_2$ | S | 2 |
| 292 | 4-Et—Ph | Me | $NH_2$ | S | 2 |
| 293 | 4-Et—Ph | Et | $NH_2$ | S | 2 |
| 294 | 4-Et—Ph | Pr | $NH_2$ | S | 2 |
| 295 | 4-Et—Ph | $Pr^i$ | $NH_2$ | S | 2 |
| 296 | 2-$CF_3$—Ph | H | $NH_2$ | O | 2 |
| 297 | 2-$CF_3$—Ph | F | $NH_2$ | O | 2 |
| 298 | 2-$CF_3$—Ph | Cl | $NH_2$ | O | 2 |
| 299 | 2-$CF_3$—Ph | Me | $NH_2$ | O | 2 |
| 300 | 2-$CF_3$—Ph | Et | $NH_2$ | O | 2 |
| 301 | 2-$CF_3$—Ph | Pr | $NH_2$ | O | 2 |
| 302 | 2-$CF_3$—Ph | $Pr^i$ | $NH_2$ | O | 2 |
| 303 | 2-$CF_3$—Ph | Bu | $NH_2$ | O | 2 |
| 304 | 2-$CF_3$—Ph | $Bu^i$ | $NH_2$ | O | 2 |
| 305 | 2-$CF_3$—Ph | $Bu^s$ | $NH_2$ | O | 2 |
| 306 | 2-$CF_3$—Ph | $Bu^t$ | $NH_2$ | O | 2 |
| 307 | 2-$CF_3$—Ph | H | $NH_2$ | S | 2 |
| 308 | 2-$CF_3$—Ph | F | $NH_2$ | S | 2 |
| 309 | 2-$CF_3$—Ph | Cl | $NH_2$ | S | 2 |
| 310 | 2-$CF_3$—Ph | Me | $NH_2$ | S | 2 |
| 311 | 2-$CF_3$—Ph | Et | $NH_2$ | S | 2 |
| 312 | 2-$CF_3$—Ph | Pr | $NH_2$ | S | 2 |
| 313 | 2-$CF_3$—Ph | $Pr^i$ | $NH_2$ | S | 2 |
| 314 | 3-$CF_3$—Ph | H | $NH_2$ | O | 2 |
| 315 | 3-$CF_3$—Ph | F | $NH_2$ | O | 2 |
| 316 | 3-$CF_3$—Ph | Cl | $NH_2$ | O | 2 |
| 317 | 3-$CF_3$—Ph | Me | $NH_2$ | O | 2 |
| 318 | 3-$CF_3$—Ph | Et | $NH_2$ | O | 2 |
| 319 | 3-$CF_3$—Ph | Pr | $NH_2$ | O | 2 |
| 320 | 3-$CF_3$—Ph | $Pr^i$ | $NH_2$ | O | 2 |
| 321 | 3-$CF_3$—Ph | Bu | $NH_2$ | O | 2 |
| 322 | 3-$CF_3$—Ph | $Bu^i$ | $NH_2$ | O | 2 |
| 323 | 3-$CF_3$—Ph | $Bu^s$ | $NH_2$ | O | 2 |
| 324 | 3-$CF_3$—Ph | $Bu^t$ | $NH_2$ | O | 2 |
| 325 | 3-$CF_3$—Ph | H | $NH_2$ | S | 2 |
| 326 | 3-$CF_3$—Ph | F | $NH_2$ | S | 2 |
| 327 | 3-$CF_3$—Ph | Cl | $NH_2$ | S | 2 |
| 328 | 3-$CF_3$—Ph | Me | $NH_2$ | S | 2 |
| 329 | 3-$CF_3$—Ph | Et | $NH_2$ | S | 2 |
| 330 | 3-$CF_3$—Ph | Pr | $NH_2$ | S | 2 |
| 331 | 3-$CF_3$—Ph | $Pr^i$ | $NH_2$ | S | 2 |
| 332 | 4-$CF_3$—Ph | H | $NH_2$ | O | 2 |
| 333 | 4-$CF_3$—Ph | F | $NH_2$ | O | 2 |
| 334 | 4-$CF_3$—Ph | Cl | $NH_2$ | O | 2 |
| 335 | 4-$CF_3$—Ph | Me | $NH_2$ | O | 2 |
| 336 | 4-$CF_3$—Ph | Et | $NH_2$ | O | 2 |
| 337 | 4-$CF_3$—Ph | Pr | $NH_2$ | O | 2 |
| 338 | 4-$CF_3$—Ph | $Pr^i$ | $NH_2$ | O | 2 |
| 339 | 4-$CF_3$—Ph | Bu | $NH_2$ | O | 2 |
| 340 | 4-$CF_3$—Ph | $Bu^i$ | $NH_2$ | O | 2 |
| 341 | 4-$CF_3$—Ph | $Bu^s$ | $NH_2$ | O | 2 |
| 342 | 4-$CF_3$—Ph | $Bu^t$ | $NH_2$ | O | 2 |
| 343 | 4-$CF_3$—Ph | H | $NH_2$ | S | 2 |
| 344 | 4-$CF_3$—Ph | F | $NH_2$ | S | 2 |
| 345 | 4-$CF_3$—Ph | Cl | $NH_2$ | S | 2 |
| 346 | 4-$CF_3$—Ph | Me | $NH_2$ | S | 2 |
| 347 | 4-$CF_3$—Ph | Et | $NH_2$ | S | 2 |
| 348 | 4-$CF_3$—Ph | Pr | $NH_2$ | S | 2 |
| 349 | 4-$CF_3$—Ph | $Pr^i$ | $NH_2$ | S | 2 |
| 350 | 4-MeO—Ph | H | $NH_2$ | O | 2 |
| 351 | 4-MeO—Ph | F | $NH_2$ | O | 2 |
| 352 | 4-MeO—Ph | Cl | $NH_2$ | O | 2 |
| 353 | 4-MeO—Ph | Me | $NH_2$ | O | 2 |
| 354 | 4-MeO—Ph | Et | $NH_2$ | O | 2 |
| 355 | 4-MeO—Ph | Pr | $NH_2$ | O | 2 |
| 356 | 4-MeO—Ph | $Pr^i$ | $NH_2$ | O | 2 |
| 357 | 2-MeO—Ph | H | $NH_2$ | O | 2 |
| 358 | 2-MeO—Ph | F | $NH_2$ | O | 2 |
| 359 | 2-MeO—Ph | Cl | $NH_2$ | O | 2 |
| 360 | 2-MeO—Ph | Me | $NH_2$ | O | 2 |
| 361 | 2-MeO—Ph | Et | $NH_2$ | O | 2 |
| 362 | 2-MeO—Ph | $Pr^i$ | $NH_2$ | O | 2 |
| 363 | 3-MeO—Ph | H | $NH_2$ | O | 2 |
| 364 | 3-MeO—Ph | Cl | $NH_2$ | O | 2 |
| 365 | 3-MeO—Ph | Me | $NH_2$ | O | 2 |
| 366 | 3-MeO—Ph | Et | $NH_2$ | O | 2 |
| 367 | 3-MeO—Ph | $Pr^i$ | $NH_2$ | O | 2 |
| 368 | 4-Ph—Ph | H | $NH_2$ | O | 2 |
| 369 | 4-Ph—Ph | F | $NH_2$ | O | 2 |
| 370 | 4-Ph—Ph | Cl | $NH_2$ | O | 2 |
| 371 | 4-Ph—Ph | Me | $NH_2$ | O | 2 |
| 372 | 4-Ph—Ph | Et | $NH_2$ | O | 2 |
| 373 | 4-Ph—Ph | Pr | $NH_2$ | O | 2 |
| 374 | 4-Ph—Ph | $Pr^i$ | $NH_2$ | O | 2 |
| 375 | 4-Ph—Ph | Bu | $NH_2$ | O | 2 |
| 376 | 4-Ph—Ph | $Bu^i$ | $NH_2$ | O | 2 |
| 377 | 4-Ph—Ph | $Bu^s$ | $NH_2$ | O | 2 |
| 378 | 4-Ph—Ph | $Bu^t$ | $NH_2$ | O | 2 |
| 379 | 2-Ph—Ph | H | $NH_2$ | S | 2 |
| 380 | 3-Ph—Ph | F | $NH_2$ | S | 2 |
| 381 | 4-Ph—Ph | Cl | $NH_2$ | S | 2 |
| 382 | 2-Ph—Ph | Me | $NH_2$ | S | 2 |
| 383 | 2-Ph—Ph | Et | $NH_2$ | S | 2 |
| 384 | 2-Ph—Ph | Pr | $NH_2$ | S | 2 |
| 385 | 3-Ph—Ph | $Pr^i$ | $NH_2$ | S | 2 |
| 386 | 4-CN—Ph | H | $NH_2$ | O | 2 |
| 387 | 4-CN—Ph | F | $NH_2$ | O | 2 |
| 388 | 4-CN—Ph | Cl | $NH_2$ | O | 2 |
| 389 | 4-CN—Ph | Me | $NH_2$ | O | 2 |
| 390 | 4-CN—Ph | Et | $NH_2$ | O | 2 |
| 391 | 4-CN—Ph | Pr | $NH_2$ | O | .2 |
| 392 | 4-CN—Ph | $Pr^i$ | $NH_2$ | O | 2 |
| 393 | 4-CN—Ph | Bu | $NH_2$ | O | 2 |
| 394 | 4-CN—Ph | $Bu^i$ | $NH_2$ | O | 2 |
| 395 | 4-CN—Ph | $Bu^s$ | $NH_2$ | O | 2 |
| 396 | 4-CN—Ph | $Bu^t$ | $NH_2$ | O | 2 |

TABLE 1-continued

| Compd. No. | R$^1$ | R$^2$ | R$^3$ | X | n |
|---|---|---|---|---|---|
| 397 | 4-MeOCO—Ph | H | NH$_2$ | O | 2 |
| 398 | 4-MeOCO—Ph | F | NH$_2$ | O | 2 |
| 399 | 4-MeOCO—Ph | Cl | NH$_2$ | O | 2 |
| 400 | 4-MeOCO—Ph | Me | NH$_2$ | O | 2 |
| 401 | 4-MeOCO—Ph | Et | NH$_2$ | O | 2 |
| 402 | 4-MeOCO—Ph | Pr | NH$_2$ | O | 2 |
| 403 | 4-MeOCO—Ph | Pr$^i$ | NH$_2$ | O | 2 |
| 404 | 4-MeOCO—Ph | Bu | NH$_2$ | O | 2 |
| 405 | 4-MeOCO—Ph | Bu$^i$ | NH$_2$ | O | 2 |
| 406 | 4-MeOCO—Ph | Bu$^s$ | NH$_2$ | O | 2 |
| 407 | 4-MeOCO—Ph | Bu$^t$ | NH$_2$ | O | 2 |
| 408 | 2-MeOCO—Ph | H | NH$_2$ | S | 2 |
| 409 | 3-MeOCO—Ph | F | NH$_2$ | S | 2 |
| 410 | 4-MeOCO—Ph | Cl | NH$_2$ | S | 2 |
| 411 | 2-MeOCO—Ph | Me | NH$_2$ | S | 2 |
| 412 | 2-MeOCO—Ph | Et | NH$_2$ | S | 2 |
| 413 | 2-MeOCO—Ph | Pr | NH$_2$ | S | 2 |
| 414 | 3-MeOCO—Ph | Pr$^i$ | NH$_2$ | S | 2 |
| 415 | 4-H$_2$NCO—Ph | H | NH$_2$ | O | 2 |
| 416 | 4-H$_2$NCO—Ph | F | NH$_2$ | O | 2 |
| 417 | 4-H$_2$NCO—Ph | Cl | NH$_2$ | O | 2 |
| 418 | 4-H$_2$NCO—Ph | Me | NH$_2$ | 0 | 2 |
| 419 | 4-H$_2$NCO—Ph | Et | NH$_2$ | O | 2 |
| 420 | 4-H$_2$NCO—Ph | Pr | NH$_2$ | O | 2 |
| 421 | 4-H$_2$NCO—Ph | Pr$^i$ | NH$_2$ | 0 | 2 |
| 422 | 4-H$_2$NCO—Ph | Bu | NH$_2$ | O | 2 |
| 423 | 4-H$_2$NCO—Ph | Bu$^i$ | NH$_2$ | O | 2 |
| 424 | 4-H$_2$NCO—Ph | Bu$^s$ | NH$_2$ | O | 2 |
| 425 | 4-H$_2$NCO—Ph | Bu$^t$ | NH$_2$ | O | 2 |
| 426 | 2-H$_2$NCO—Ph | H | NH$_2$ | S | 2 |
| 427 | 3-H$_2$NCO—Ph | F | NH$_2$ | S | 2 |
| 428 | 4-H$_2$NCO—Ph | Cl | NH$_2$ | S | 2 |
| 429 | 2-H$_2$NCO—Ph | Me | NH$_2$ | S | 2 |
| 430 | 2-H$_2$NCO—Ph | Et | NH$_2$ | S | 2 |
| 431 | 2-H$_2$NCO—Ph | Pr | NH$_2$ | S | 2 |
| 432 | 3-H$_2$NCO—Ph | Pr$^i$ | NH$_2$ | S | 2 |
| 433 | 4-MeNHCO—Ph | H | NH$_2$ | O | 2 |
| 434 | 4-MeNHCO—Ph | F | NH$_2$ | O | 2 |
| 435 | 4-MeNHCO—Ph | Cl | NH$_2$ | O | 2 |
| 436 | 4-MeNHCO—Ph | Me | NH$_2$ | O | 2 |
| 437 | 4-MeNHCO—Ph | Et | NH$_2$ | O | 2 |
| 438 | 4-MeNHCO—Ph | pr | NH$_2$ | O | 2 |
| 439 | 4-MeNHCO—Ph | Pr$^i$ | NH$_2$ | O | 2 |
| 440 | 4-MeNHCO—Ph | Bu | NH$_2$ | O | 2 |
| 441 | 4-MeNHCO—Ph | Bu$^i$ | NH$_2$ | O | 2 |
| 442 | 4-MeNHCO—Ph | Bu$^s$ | NH$_2$ | O | 2 |
| 443 | 4-MeNHCO—Ph | Bu$^t$ | NH$_2$ | O | 2 |
| 444 | 2-MeNHCO—Ph | H | NH$_2$ | S | 2 |
| 445 | 3-MeNHCO—Ph | F | NH$_2$ | S | 2 |
| 446 | 4-MeNHCO—Ph | Cl | NH$_2$ | S | 2 |
| 447 | 2-MeNHCO—Ph | Me | NH$_2$ | S | 2 |
| 448 | 2-MeNHCO—Ph | Et | NH$_2$ | S | 2 |
| 449 | 2-MeNHCO—Ph | Pr | NH$_2$ | S | 2 |
| 450 | 3-MeNHCO—Ph | Pr$^i$ | NH$_2$ | S | 2 |
| 451 | 4-(Me)$_2$NCO—Ph | H | NH$_2$ | O | 2 |
| 452 | 4-(Me)$_2$NCO—Ph | F | NH$_2$ | O | 2 |
| 453 | 4-(Me)$_2$NCO—Ph | Cl | NH$_2$ | O | 2 |
| 454 | 4-(Me)$_2$NCO—Ph | Me | NH$_2$ | O | 2 |
| 455 | 4-(Me)$_2$NCO—Ph | Et | NH$_2$ | O | 2 |
| 456 | 4-(Me)$_2$NCO—Ph | Pr | NH$_2$ | O | 2 |
| 457 | 4-(Me)$_2$NCO—Ph | Pr$^i$ | NH$_2$ | O | 2 |
| 458 | 4-(Me)$_2$NCO—Ph | Bu | NH$_2$ | O | 2 |
| 459 | 4-(Me)$_2$NCO—Ph | Bu$^i$ | NH$_2$ | O | 2 |
| 460 | 4-(Me)$_2$NCO—Ph | Bu$^s$ | NH$_2$ | O | 2 |
| 461 | 4-(Me)$_2$NCO—Ph | Bu$^t$ | NH$_2$ | O | 2 |
| 462 | 2-(Me)$_2$NCO—Ph | H | NH$_2$ | S | 2 |
| 463 | 3-(Me)$_2$NCO—Ph | F | NH$_2$ | S | 2 |
| 464 | 4-(Me)$_2$NCO—Ph | Cl | NH$_2$ | S | 2 |
| 465 | 2-(Me)$_2$NCO—Ph | Me | NH$_2$ | S | 2 |
| 466 | 2-(Me)$_2$NCO—Ph | Et | NH$_2$ | S | 2 |
| 467 | 2-(Me)$_2$NCO—Ph | Pr | NH$_2$ | S | 2 |
| 468 | 3-(Me)$_2$NCO—Ph | Pr$^i$ | NH$_2$ | S | 2 |
| 469 | Inde(1) | H | NH$_2$ | O | 2 |
| 470 | Inde(1) | Cl | NH$_2$ | O | 2 |
| 471 | Inde(1) | Me | NH$_2$ | O | 2 |
| 472 | Inde(1) | Et | NH$_2$ | O | 2 |
| 473 | Inde(1) | Pr | NH$_2$ | O | 2 |
| 474 | Inde(1) | Pr$^i$ | NH$_2$ | O | 2 |
| 475 | Np(1) | H | NH$_2$ | O | 2 |
| 476 | Np(1) | Cl | NH$_2$ | O | 2 |
| 477 | Np(1) | Me | NH$_2$ | O | 2 |
| 478 | Np(1) | Et | NH$_2$ | O | 2 |
| 479 | Np(1) | Pr | NH$_2$ | O | 2 |
| 480 | Np(1) | Pr$^i$ | NH$_2$ | O | 2 |
| 481 | Np(2) | H | NH$_2$ | O | 2 |
| 482 | Np(2) | Cl | NH$_2$ | O | 2 |
| 483 | Np(2) | Me | NH$_2$ | O | 2 |
| 484 | Np(2) | Et | NH$_2$ | O | 2 |
| 485 | Np(2) | Pr | NH$_2$ | O | 2 |
| 486 | Np(2) | Pr$^i$ | NH$_2$ | O | 2 |
| 487 | Pyrr(3) | H | NH$_2$ | O | 2 |
| 488 | Pyrr(3) | Cl | NH$_2$ | O | 2 |
| 489 | Pyrr(3) | Me | NH$_2$ | O | 2 |
| 490 | Pyrr(3) | Et | NH$_2$ | O | 2 |
| 491 | Pyrr(3) | Pr | NH$_2$ | O | 2 |
| 492 | Pyrr(3) | Pr$^i$ | NH$_2$ | O | 2 |
| 493 | Imid(2) | H | NH$_2$ | O | 2 |
| 494 | Irnid(2) | Cl | NH$_2$ | O | 2 |
| 495 | Imid(2) | Me | NH$_2$ | d | 2 |
| 496 | Imid(2) | Et | NH$_2$ | O | 2 |
| 497 | Imid(2) | Pr | NH$_2$ | O | 2 |
| 498 | Imid(2) | Pr$^i$ | NH$_2$ | O | 2 |
| 499 | Pyza(1) | H | NH$_2$ | O | 2 |
| 500 | Pyza(1) | Cl | NH$_2$ | O | 2 |
| 501 | Pyza(1) | Me | NH$_2$ | O | 2 |
| 502 | Pyza(1) | Et | NH$_2$ | O | 2 |
| 503 | Pyza(1) | Pr | NH$_2$ | O | 2 |
| 504 | Pyza(1) | Pr$^i$ | NH$_2$ | O | 2 |
| 505 | Fur(2) | H | NH$_2$ | O | 2 |
| 506 | Fur(2) | Cl | NH$_2$ | O | 2 |
| 507 | Fur(2) | Me | NH$_2$ | O | 2 |
| 508 | Fur(2) | Et | NH$_2$ | O | 2 |
| 509 | Fur(2) | Pr | NH$_2$ | O | 2 |
| 510 | Fur(2) | Pr$^i$ | NH$_2$ | O | 2 |
| 511 | Oxa(2) | H | NH$_2$ | O | 2 |
| 512 | Oxa(2) | Cl | NH$_2$ | O | 2 |
| 513 | Oxa(2) | Me | NH$_2$ | O | 2 |
| 514 | Oxa(2) | Et | NH$_2$ | O | 2 |
| 515 | Oxa(2) | Pr | NH$_2$ | O | 2 |
| 516 | Oxa(2) | Pr$^i$ | NH$_2$ | O | 2 |
| 517 | Isox(3) | H | NH$_2$ | O | 2 |
| 518 | Isox(3) | Cl | NH$_2$ | O | 2 |
| 519 | Isox(3) | Me | NH$_2$ | O | 2 |
| 520 | Isox(3) | Et | NH$_2$ | O | 2 |
| 521 | Isox(3) Pr | | NH$_2$ | O | 2 |
| 522 | Isox(3) | Pr$^i$ | NH$_2$ | O | 2 |
| 523 | Thiz(2) | H | NH$_2$ | O | 2 |
| 524 | Thiz(2) | Cl | NH$_2$ | O | 2 |
| 525 | Thiz(2) | Me | NH$_2$ | O | 2 |
| 526 | Thiz(2) | Et | NH$_2$ | O | 2 |
| 527 | Thiz(2) | Pr | NH$_2$ | O | 2 |
| 528 | Thiz(2) | Pr$^i$ | NH$_2$ | O | 2 |
| 529 | Isothiz(3) | H | NH$_2$ | O | 2 |
| 530 | Isothiz(3) | cI | NH$_2$ | O | 2 |
| 531 | Isothiz(3) | Me | NH$_2$ | O | 2 |
| 532 | Isothiz(3) | Et | NH$_2$ | O | 2 |
| 533 | Isothiz(3) | Pr | NH$_2$ | O | 2 |
| 534 | Isothiz(3) | Pr$^i$ | NH$_2$ | O | 2 |
| 535 | Thi(2) | H NH$_2$ | | O | 2 |
| 536 | Thi(2) | H | NH$_2$ | O | 3 |
| 537 | Thi(2) | H | NH$_2$ | O | 4 |
| 538 | Thi(2) | F | NH$_2$ | O | 2 |
| 539 | Thi(2) | Cl | NH$_2$ | O | 2 |
| 540 | Thi(2) | Me | NH$_2$ | O | 2 |
| 541 | Thi(2) | Et | NH$_2$ | O | 2 |
| 542 | Thi(2) | Pr | NH$_2$ | O | 2 |
| 543 | Thi(2) | Pr$^i$ | NH$_2$ | O | 2 |
| 544 | Thi(2) | Bu | NH$_2$ | O | 2 |
| 545 | Thi(2) | Bu$^i$ | NH$_2$ | O | 2 |
| 546 | Thi(2) | Bu$^s$ | NH$_2$ | O | 2 |
| 547 | Thi(2) | Bu$^t$ | NH$_2$ | O | 2 |
| 548 | Thi(2) | H | NH$_2$ | S | 2 |

TABLE 1-continued

| Compd. No. | R¹ | R² | R³ | X | n |
|---|---|---|---|---|---|
| 549 | Thi(2) | H | NH₂ | S | 3 |
| 550 | Thi(2) | H | NH₂ | S | 4 |
| 551 | Thi(2) | F | NH₂ | S | 2 |
| 552 | Thi(2) | Cl | NH₂ | S | 2 |
| 553 | Thi(2) | Me | NH₂ | S | 2 |
| 554 | Thi(2) | Et | NH₂ | S | 2 |
| 555 | Thi(2) | Pr | NH₂ | S | 2 |
| 556 | Thi(2) | Prⁱ | NH₂ | S | 2 |
| 557 | Thi(2) | H | NHMe | O | 2 |
| 558 | Thi(2) | H | NHEt | O | 2 |
| 559 | Thi(2) | H | N(Me)₂ | O | 2 |
| 560 | Thi(2) | H | Pip(1) | O | 2 |
| 561 | Thi(2) | H | Mor(4) | O | 2 |
| 562 | 3-F—Thi(2) | H | NH₂ | O | 2 |
| 563 | 3-F—Thi(2) | Cl | NH₂ | O | 2 |
| 564 | 3-F—Thi(2) | Me | NH₂ | O | 2 |
| 565 | 3-F—Thi(2) | Et | NH₂ | O | 2 |
| 566 | 3-F—Thi(2) | Pr | NH₂ | O | 2 |
| 567 | 3-F—Thi(2) | Prⁱ | NH₂ | O | 2 |
| 568 | 4-F—Thi(2) | H | NH₂ | O | 2 |
| 569 | 4-F—Thi(2) | Cl | NH₂ | O | 2 |
| 570 | 4-F—Thi(2) | Me | NH₂ | O | 2 |
| 571 | 4-F—Thi(2) | Et | NH₂ | O | 2 |
| 572 | 4-F—Thi(2) | Pr | NH₂ | O | 2 |
| 573 | 4-F—Thi(2) | Prⁱ | NH₂ | O | 2 |
| 574 | 5-F—Thi(2) | H | NH₂ | O | 2 |
| 575 | 5-F—Thi(2) | Cl | NH₂ | O | 2 |
| 576 | 5-F—Thi(2) | Me | NH₂ | O | 2 |
| 577 | 5-F—Thi(2) | Et | NH₂ | O | 2 |
| 578 | 5-F—Thi(2) | Pr | NH₂ | O | 2 |
| 579 | 5-F—Thi(2) | Prⁱ | NH₂ | O | 2 |
| 580 | 3-Cl—Thi(2) | H | NH₂ | O | 2 |
| 581 | 3-Cl—Thi(2) | Cl | NH₂ | O | 2 |
| 582 | 3-Cl—Thi(2) | Me | NH₂ | O | 2 |
| 583 | 3-Cl—Thi(2) | Et | NH₂ | O | 2 |
| 584 | 3-Cl—Thi(2) | Pr | NH₂ | O | 2 |
| 585 | 3-Cl—Thi(2) | Prⁱ | NH₂ | O | 2 |
| 586 | 4-Cl—Thi(2) | H | NH₂ | O | 2 |
| 587 | 4-Cl—Thi(2) | Cl | NH₂ | O | 2 |
| 588 | 4-Cl—Thi(2) | Me | NH₂ | O | 2 |
| 589 | 4-Cl—Thi(2) | Et | NH₂ | O | 2 |
| 590 | 4-Cl—Thi(2) | Pr | NH₂ | O | 2 |
| 591 | 4-Cl—Thi(2) | Prⁱ | NH₂ | O | 2 |
| 592 | 5-Cl—Thi(2) | H | NH₂ | O | 2 |
| 593 | 5-Cl—Thi(2) | Cl | NH₂ | O | 2 |
| 594 | 5-Cl—Thi(2) | Me | NH₂ | O | 2 |
| 595 | 5-Cl—Thi(2) | Et | NH₂ | O | 2 |
| 596 | 5-Cl—Thi(2) | Pr | NH₂ | O | 2 |
| 597 | 5-Cl—Thi(2) | Prⁱ | NH₂ | .O | 2 |
| 598 | 3-Br—Thi(2) | H | NH₂ | O | 2 |
| 599 | 3-Br—Thi(2) | Cl | NH₂ | O | 2 |
| 600 | 3-Br—Thi(2) | Me | NH₂ | O | 2 |
| 601 | 3-Br—Thi(2) | Et | NH₂ | O | 2 |
| 602 | 3-Br—Thi(2) | Pr | NH₂ | O | 2 |
| 603 | 3-Br—Thi(2) | Prⁱ | NH₂ | O | 2 |
| 604 | 3-Me—Thi(2) | H | NH₂ | O | 2 |
| 605 | 3-Me—Thi(2) | Cl | NH₂ | O | 2 |
| 606 | 3-Me—Thi(2) | Me | NH₂ | O | 2 |
| 607 | 3-Me—Thi(2) | Et | NH₂ | O | 2 |
| 608 | 3-Me—Thi(2) | Pr | NH₂ | O | 2 |
| 609 | 3-Me—Thi(2) | Prⁱ | NH₂ | O | 2 |
| 610 | 4-Me—Thi(2) | H | NH₂ | O | 2 |
| 611 | 4-Me—Thi(2) | Cl | NH₂ | O | 2 |
| 612 | 4-Me—Thi(2) | Me | NH₂ | O | 2 |
| 613 | 4-Me—Thi(2) | Et | NH₂ | O | 2 |
| 614 | 4-Me—Thi(2) | Pr | NH₂ | O | 2 |
| 615 | 4-Me—Thi(2) | Prⁱ | NH₂ | O | 2 |
| 616 | 4-Et—Thi(2) | H | NH₂ | O | 2 |
| 617 | 4-Et—Thi(2) | Cl | NH₂ | O | 2 |
| 618 | 4-Et—Thi(2) | Me | NH₂ | O | 2 |
| 619 | 4-Et—Thi(2) | Et | NH₂ | O | 2 |
| 620 | 4-Et—Thi(2) | Pr | NH₂ | O | 2 |
| 621 | 4-Et—Thi(2) | Prⁱ | NH₂ | O | 2 |
| 622 | 4-CF₃—Thi(2) | H | NH₂ | O | 2 |
| 623 | 4-CF₃—Thi(2) | Cl | NH₂ | O | 2 |
| 624 | 4-CF₃—Thi(2) | Me | NH₂ | O | 2 |
| 625 | 4-CF₃—Thi(2) | Et | NH₂ | O | 2 |
| 626 | 4-CF₃—Thi(2) | Pr | NH₂ | O | 2 |
| 627 | 4-CF₃—Thi(2) | Prⁱ | NH₂ | O | 2 |
| 628 | 4-MeO—Thi(2) | H | NH₂ | O | 2 |
| 629 | 4-MeO—Thi(2) | Cl | NH₂ | O | 2 |
| 630 | 4-MeO—Thi(2) | Me | NH₂ | O | 2 |
| 631 | 4-MeO—Thi(2) | Et | NH₂ | O | 2 |
| 632 | 4-MeO—Thi(2) | Pr | NH₂ | O | 2 |
| 633 | 4-MeO—Thi(2) | Prⁱ | NH₂ | O | 2 |
| 634 | 3-Ph—Thi(2) | H | NH₂ | O | 2 |
| 635 | 3-Ph—Thi(2) | Cl | NH₂ | O | 2 |
| 636 | 3-Ph—Thi(2) | Me | NH₂ | O | 2 |
| 637 | 3-Ph—Thi(2) | Et | NH₂ | O | 2 |
| 638 | 3-Ph—Thi(2) | Pr | NH₂ | O | 2 |
| 639 | 3-Ph—Thi(2) | Prⁱ | NH₂ | O | 2 |
| 640 | 4-Ph—Thi(2) | H | NH₂ | O | 2 |
| 641 | 4-Ph—Thi(2) | Cl | NH₂ | O | 2 |
| 642 | 4-Ph—Thi(2) | Me | NH₂ | O | 2 |
| 643 | 4-Ph—Thi(2) | Et | NH₂ | O | 2 |
| 644 | 4-Ph—Thi(2) | Pr | NH₂ | O | 2 |
| 645 | 4-Ph—Thi(2) | Prⁱ | NH₂ | O | 2 |
| 646 | 5-Ph—Thi(2) | H | NH₂ | O | 2 |
| 647 | 5-Ph—Thi(2) | Cl | NH₂ | O | 2 |
| 648 | 5-Ph—Thi(2) | Me | NH₂ | O | 2 |
| 649 | 5-Ph—Thi(2) | Et | NH₂ | O | 2 |
| 650 | 5-Ph—Thi(2) | Pr | NH₂ | O | 2 |
| 651 | 5-Ph—Thi(2) | Prⁱ | NH₂ | O | 2 |
| 652 | 3-MeOCO—Thi(2) | H | NH₂ | O | 2 |
| 653 | 3-MeOCO—Thi(2) | Cl | NH₂ | O | 2 |
| 654 | 3-MeOCO—Thi(2) | Me | NH₂ | O | 2 |
| 655 | 3-MeOCO—Thi(2) | Et | NH₂ | O | 2 |
| 656 | 3-MeOCO—Thi(2) | Pr | NH₂ | O | 2 |
| 657 | 3-MeOCO—Thi(2) | Prⁱ | NH₂ | O | 2 |
| 658 | 4-MeOCO—Thi(2) | H | NH₂ | O | 2 |
| 659 | 4-MeOCO—Thi(2) | Cl | NH₂ | O | 2 |
| 660 | 4-MeOCO—Thi(2) | Me | NH₂ | o | 2 |
| 661 | 4-MeOCO—Thi(2) | Et | NH₂ | O | 2 |
| 662 | 4-MeOCO—Thi(2) | Pr | NH₂ | O | 2 |
| 663 | 4-MeOCO—Thi(2) | Prⁱ | NH₂ | O | 2 |
| 664 | 5-MeOCO—Thi(2) | H | NH₂ | O | 2 |
| 665 | 5-MeOCO—Thi(2) | Cl | NH₂ | O | 2 |
| 666 | 5-MeOCO—Thi(2) | Me | NH₂ | O | 2 |
| 667 | 5-MeOCO—Thi(2) | Et | NH₂ | O | 2 |
| 668 | 5-MeOCO—Thi(2) | Pr | NH₂ | O | 2 |
| 669 | 5-MeOCO—Th(2) | Prⁱ | NH₂ | O | 2 |
| 670 | 3-H₂NCO—Thi(2) | H | NH₂ | O | 2 |
| 671 | 3-H₂NCO—Thi(2) | Cl | NH₂ | O | 2 |
| 672 | 3-H₂NCO—Th(2) | Me | NH₂ | O | 2 |
| 673 | 3-H₂NCO—Thi(2) | Et | NH₂ | 0 | 2 |
| 674 | 3-H₂NCO—Thi(2) | Pr | NH₂ | 0 | 2 |
| 675 | 3-H₂NCO—Thi(2) | Prⁱ | NH₂ | 0 | 2 |
| 676 | 4-H₂NCO—Thi(2) | H | NH₂ | 0 | 2 |
| 677 | 4-H₂NCO—Thi(2) | Cl | NH₂ | 0 | 2 |
| 678 | 4-H₂NCO—Thi(2) | Me | NH₂ | 0 | 2 |
| 679 | 4-H₂NCO—Thi(2) | Et | NH₂ | 0 | 2 |
| 680 | 4-H₂NCO—Thi(2) | Pr | NH₂ | 0 | 2 |
| 681 | 4-H₂NCO—Thi(2) | Prⁱ | NH₂ | 0 | 2 |
| 682 | 5-H₂NCO—Thi(2) | H | NH₂ | O | 2 |
| 683 | 5-H₂NCO—Thi(2) | Cl | NH₂ | O | 2 |
| 684 | 5-H₂NCO—Thi(2) | Me | NH₂ | O | 2 |
| 685 | 5-H₂NCO—Thi(2) | Et | NH₂ | O | 2 |
| 686 | 5-H₂NCO—Thi(2) | Pr | NH₂ | O | 2 |
| 687 | 5-H₂NCO—Thi(2) | Prⁱ | NH₂ | O | 2 |
| 688 | 3-MeNHCO—Thi(2) | H | NH₂ | O | 2 |
| 689 | 3-MeNHCO—Thi(2) | Cl | NH₂ | O | 2 |
| 690 | 3-MeNHCO—Thi(2) | Me | NH₂ | O | 2 |
| 691 | 3-MeNHCO—Thi(2) | Et | NH₂ | O | 2 |
| 692 | 3-MeNHCO—Thi(2) | Pr | NH₂ | O | 2 |
| 693 | 3-MeNHCO—Thi(2) | Prⁱ | NH₂ | O | 2 |
| 694 | 4-MeNHCO—Th(2) | H | NH₂ | O | 2 |
| 695 | 4-MeNHCO—Thi(2) | Cl | NH₂ | O | 2 |
| 696 | 4-MeNHCO—Thi(2) | Me | NH₂ | O | 2 |
| 697 | 4-MeNHCO—Th(2) | Et | NH₂ | O | 2 |
| 698 | 4-MeNHCO—Thi(2) | Pr | NH₂ | O | 2 |
| 699 | 4-MeNHCO—Th(2) | Prⁱ | NH₂ | O | 2 |
| 700 | 5-MeNHCO—Thi(2) | H | NH₂ | O | 2 |

TABLE 1-continued

| Compd. No. | R¹ | R² | R³ | X | n |
|---|---|---|---|---|---|
| 701 | 5-MeNHCO—Thi(2) | Cl | $NH_2$ | O | 2 |
| 702 | 5-MeNHCO—Thi(2) | Me | $NH_2$ | O | 2 |
| 703 | 5-MeNHCO—Thi(2) | Et | $NH_2$ | O | 2 |
| 704 | 5-MeNHCO—Th(2) | Pr | $NH_2$ | O | .2 |
| 705 | 5-MeNHCO—Th(2) | $Pr^i$ | $NH_2$ | O | 2 |
| 706 | 3-$(Me)_2$NCO—Thi(2) | H | $NH_2$ | O | 2 |
| 707 | 3-$(Me)_2$NCO—Thi(2) | Cl | $NH_2$ | O | 2 |
| 708 | 3-$(Me)_2$NCO—Thi(2) | Me | $NH_2$ | O | 2 |
| 709 | 3-$(Me)_2$NCO—Thi(2) | Et | $NH_2$ | O | 2 |
| 710 | 3-$(Me)_2$NCO—Thi(2) | Pr | $NH_2$ | O | 2 |
| 711 | 3-$(Me)_2$NCO—Thi(2) | $Pr^i$ | $NH_2$ | O | 2 |
| 712 | 4-$(Me)_2$NCO—Thi(2) | H | $NH_2$ | O | 2 |
| 713 | 4-$(Me)_2$NCO—Thi(2) | Cl | $NH_2$ | O | 2 |
| 714 | 4-$(Me)_2$NCO—Thi(2) | Me | $NH_2$ | O | 2 |
| 715 | 4-$(Me)_2$NCO—Thi(2) | Et | $NH_2$ | O | 2 |
| 716 | 4-$(Me)_2$NCO—Thi(2) | Pr | $NH_2$ | O | 2 |
| 717 | 4-$(Me)_2$NCO—Thi(2) | $Pr^i$ | $NH_2$ | O | 2 |
| 718 | 5-$(Me)_2$NCO—Thi(2) | H | $NH_2$ | O | 2 |
| 719 | 5-$(Me)_2$NCO—Thi(2) | Cl | $NH_2$ | O | 2 |
| 720 | 5-$(Me)_2$NCO—Thi(2) | Me | $NH_2$ | O | 2 |
| 721 | 5-$(Me)_2$NCO—Thi(2) | Et | $NH_2$ | O | 2 |
| 722 | 5-$(Me)_2$NCO—Thi(2) | Pr | $NH_2$ | O | 2 |
| 723 | 5-$(Me)_2$NCO—Thi(2) | $Pr^i$ | $NH_2$ | O | 2 |
| 724 | Thi(3) | H | $NH_2$ | O | 2 |
| 725 | Thi(3) | H | $NH_2$ | O | 3 |
| 726 | Thi(3) | H | $NH_2$ | O | 4 |
| 727 | Thi(3) | H | $NH_2$ | O | 5 |
| 728 | Thi(3) | F | $NH_2$ | O | 2 |
| 729 | Thi(3) | Cl | $NH_2$ | O | 2 |
| 730 | Thi(3) | Me | $NH_2$ | O | 2 |
| 731 | Thi(3) | Et | $NH_2$ | O | 2 |
| 732 | Thi(3) | Pr | $NH_2$ | O | 2 |
| 733 | Thi(3) | $Pr^i$ | $NH_2$ | O | 2 |
| 734 | Thi(3) | Bu | $NH_2$ | O | 2 |
| 735 | Thi(3) | $Bu^i$ | $NH_2$ | O | 2 |
| 736 | Thi(3) | $Bu^s$ | $NH_2$ | O | 2 |
| 737 | Thi(3) | $Bu^t$ | $NH_2$ | O | 2 |
| 738 | Thi(3) | H | $NH_2$ | S | 2 |
| 739 | Thi(3) | H | $NH_2$ | S | 3 |
| 740 | Thi(3) | H | $NH_2$ | S | 4 |
| 741 | Thi(3) | F | $NH_2$ | S | 2 |
| 742 | Thi(3) | Cl | $NH_2$ | S | 2 |
| 743 | Thi(3) | Me | $NH_2$ | S | 2 |
| 744 | Thi(3) | Et | $NH_2$ | S | 2 |
| 745 | Thi(3) | Pr | $NH_2$ | S | 2 |
| 746 | Thi(3) | $Pr^i$ | $NH_2$ | S | 2 |
| 747 | Thi(3) | H | NHMe | O | 2 |
| 748 | Thi(3) | H | NHEt | O | 2 |
| 749 | Thi(3) | H | N(Me)$_2$ | O | 2 |
| 750 | Thi(3) | H | Pip(1) | O | 2 |
| 751 | Thi(3) | H | Mor(4) | O | 2 |
| 752 | 2-F—Thi(3) | H | $NH_2$ | O | 2 |
| 753 | 2-F—Thi(3) | Cl | $NH_2$ | O | 2 |
| 754 | 2-F—Thi(3) | Me | $NH_2$ | O | 2 |
| 755 | 2-F—Thi(3) | Et | $NH_2$ | O | 2 |
| 756 | 2-F—Thi(3) | Pr | $NH_2$ | O | 2 |
| 757 | 2-F—Thi(3) | $Pr^i$ | $NH_2$ | O | 2 |
| 758 | 2-F—Thi(3) | H | $NH_2$ | S | 2 |
| 759 | 2-F—Thi(3) | Cl | $NH_2$ | S | 2 |
| 760 | 2-F—Thi(3) | Me | $NH_2$ | S | 2 |
| 761 | 2-F—Thi(3) | Et | $NH_2$ | S | 2 |
| 762 | 2-F—Thi(3) | Pr | $NH_2$ | S | 2 |
| 763 | 2-F—Thi(3) | $Pr^i$ | $NH_2$ | S | 2 |
| 764 | 4-F—Thi(3) | H | $NH_2$ | O | 2 |
| 765 | 4-F—Thi(3) | Cl | $NH_2$ | O | 2 |
| 766 | 4-F—Thi(3) | Me | $NH_2$ | O | 2 |
| 767 | 4-F—Thi(3) | Et | $NH_2$ | O | 2 |
| 768 | 4-F—Thi(3) | Pr | $NH_2$ | O | 2 |
| 769 | 4-F—Thi(3) | $Pr^i$ | $NH_2$ | O | 2 |
| 770 | 4-F—Thi(3) | H | $NH_2$ | S | 2 |
| 771 | 4-F—Thi(3) | Cl | $NH_2$ | S | 2 |
| 772 | 4-F—Thi(3) | Me | $NH_2$ | S | 2 |
| 773 | 4-F—Thi(3) | Et | $NH_2$ | S | 2 |
| 774 | 4-F—Thi(3) | Pr | $NH_2$ | S | 2 |
| 775 | 4-F—Thi(3) | $Pr^i$ | $NH_2$ | S | 2 |
| 776 | 5-F—Thi(3) | H | $NH_2$ | O | 2 |
| 777 | 5-F—Thi(3) | Cl | $NH_2$ | O | 2 |
| 778 | 5-F—Thi(3) | Me | $NH_2$ | O | 2 |
| 779 | 5-F—Thi(3) | Et | $NH_2$ | O | 2 |
| 780 | 5-F—Thi(3) | Pr | $NH_2$ | O | 2 |
| 781 | 5-F—Thi(3) | $Pr^i$ | $NH_2$ | O | 2 |
| 782 | 5-F—Thi(3) | H | $NH_2$ | S | 2 |
| 783 | 5-F—Thi(3) | Cl | $NH_2$ | S | 2 |
| 784 | 5-F—Thi(3) | Me | $NH_2$ | S | 2 |
| 785 | 5-F—Thi(3) | Et | $NH_2$ | S | 2 |
| 786 | 5-F—Thi(3) | Pr | $NH_2$ | S | 2 |
| 787 | 5-F—Thi(3) | $Pr^i$ | $NH_2$ | S | 2 |
| 788 | 2-Cl—Thi(3) | H | $NH_2$ | O | 2 |
| 789 | 2-Cl—Thi(3) | Cl | $NH_2$ | O | 2 |
| 790 | 2-Cl—Thi(3) | Me | $NH_2$ | O | 2 |
| 791 | 2-Cl—Thi(3) | Et | $NH_2$ | O | 2 |
| 792 | 2-Cl—Thi(3) | Pr | $NH_2$ | O | 2 |
| 793 | 2-Cl—Thi(3) | $Pr^i$ | $NH_2$ | O | 2 |
| 794 | 4-Cl—Thi(3) | H | $NH_2$ | O | 2 |
| 795 | 4-Cl—Thi(3) | Cl | $NH_2$ | O | 2 |
| 796 | 4-Cl—Thi(3) | Me | $NH_2$ | O | 2 |
| 797 | 4-Cl—Thi(3) | Et | $NH_2$ | O | 2 |
| 798 | 4-Cl—Thi(3) | Pr | $NH_2$ | O | 2 |
| 799 | 4-Cl—Thi(3) | $Pr^i$ | $NH_2$ | O | 2 |
| 800 | 5-Cl—Thi(3) | H | $NH_2$ | O | 2 |
| 801 | 5-Cl—Thi(3) | Cl | $NH_2$ | O | 2 |
| 802 | 5-Cl—Thi(3) | Me | $NH_2$ | O | 2 |
| 803 | 5-Cl—Thi(3) | Et | $NH_2$ | O | 2 |
| 804 | 5-Cl—Thi(3) | Pr | $NH_2$ | O | 2 |
| 805 | 5-Cl—Thi(3) | $Pr^i$ | $NH_2$ | O | 2 |
| 806 | 4-Me—Thi(3) | H | $NH_2$ | O | 2 |
| 807 | 4-Me—Thi(3) | Cl | $NH_2$ | O | 2 |
| 808 | 4-Me—Thi(3) | Me | $NH_2$ | O | 2 |
| 809 | 4-Me—Thi(3) | Et | $NH_2$ | O | 2 |
| 810 | 4-Me—Thi(3) | Pr | $NH_2$ | O | 2 |
| 811 | 4-Me—Thi(3) | $Pr^i$ | $NH_2$ | O | 2 |
| 812 | 4-Et—Thi(3) | H | $NH_2$ | O | 2 |
| 813 | 4-Et—Thi(3) | Cl | $NH_2$ | O | 2 |
| 814 | 4-Et—Thi(3) | Me | $NH_2$ | O | 2 |
| 815 | 4-Et—Thi(3) | Et | $NH_2$ | O | 2 |
| 816 | 4-Et—Thi(3) | Pr | $NH_2$ | O | 2 |
| 817 | 4-Et—Thi(3) | $Pr^i$ | $NH_2$ | O | 2 |
| 818 | 4-$CF_3$—Thi(3) | H | $NH_2$ | O | 2 |
| 819 | 4-$CF_3$—Thi(3) | Cl | $NH_2$ | O | 2 |
| 820 | 4-$CF_3$—Thi(3) | Me | $NH_2$ | O | 2 |
| 821 | 4-$CF_3$—Thi(3) | Et | $NH_2$ | O | 2 |
| 822 | 4-$CF_3$—Thi(3) | Pr | $NH_2$ | O | 2 |
| 823 | 4-$CF_3$—Thi(3) | $Pr^i$ | $NH_2$ | O | 2 |
| 824 | 4-MeO—Thi(3) | H | $NH_2$ | O | 2 |
| 825 | 4-MeO—Thi(3) | Cl | $NH_2$ | O | 2 |
| 826 | 4-MeO—Thi(3) | Me | $NH_2$ | O | 2 |
| 827 | 4-MeO—Thi(3) | Et | $NH_2$ | O | 2 |
| 828 | 4-MeO—Th(3) | Pr | $NH_2$ | O | 2 |
| 829 | 4-MeO—Thi(3) | $Pr^i$ | $NH_2$ | O | 2 |
| 830 | 2-Ph—Thi(3) | H | $NH_2$ | O | 2 |
| 831 | 2-Ph—Thi(3) | Cl | $NH_2$ | O | 2 |
| 832 | 2-Ph—Thi(3) | Me | $NH_2$ | O | 2 |
| 833 | 2-Ph—Thi(3) | Et | $NH_2$ | O | 2 |
| 834 | 2-Ph—Thi(3) | Pr | $NH_2$ | O | 2 |
| 835 | 2-Ph—Thi(3) | $Pr^i$ | $NH_2$ | O | 2 |
| 836 | 4-Ph—Th(3) | H | $NH_2$ | O | 2 |
| 837 | 4-Ph—Thi(3) | Cl | $NH_2$ | O | 2 |
| 838 | 4-Ph—Thi(3) | Me | $NH_2$ | O | 2 |
| 839 | 4-Ph—Thi(3) | Et | $NH_2$ | O | 2 |
| 840 | 4-Ph—Thi(3) | Pr | $NH_2$ | O | 2 |
| 841 | 4-Ph—Thi(3) | $Pr^i$ | $NH_2$ | O | 2 |
| 842 | 5-Ph—Thi(3) | H | $NH_2$ | O | 2 |
| 843 | 5-Ph—Thi(3) | Cl | $NH_2$ | O | 2 |
| 844 | 5-Ph—Thi(3) | Me | $NH_2$ | O | 2 |
| 845 | 5-Ph—Thi(3) | Et | $NH_2$ | O | 2 |
| 846 | 5-Ph—Thi(3) | Pr | $NH_2$ | O | 2 |
| 847 | 5-Ph—Thi(3) | $Pr^i$ | $NH_2$ | O | 2 |
| 848 | 2-MeOCO—Th(3) | H | $NH_2$ | O | 2 |
| 849 | 2-MeOCO—Thi(3) | Cl | $NH_2$ | O | 2 |
| 850 | 2-MeOCO—Thi(3) | Me | $NH_2$ | O | 2 |
| 851 | 2-MeOCO—Thi(3) | Et | $NH_2$ | O | 2 |
| 852 | 2-MeOCO—Thi(3) | Pr | $NH_2$ | O | 2 |

TABLE 1-continued

| Compd. No. | R¹ | R² | R³ | X | n |
|---|---|---|---|---|---|
| 853 | 2-MeOCO—Thi(3) | Pr$^i$ | NH$_2$ | O | 2 |
| 854 | 4-MeOCO—Th(3) | H | NH$_2$ | O | 2 |
| 855 | 4-MeOCO—Thi(3) | Cl | NH$_2$ | O | 2 |
| 856 | 4-MeOCO—Thi(3) | Me | NH$_2$ | O | 2 |
| 857 | 4-MeOCO—Thi(3) | Et | NH$_2$ | O | 2 |
| 858 | 4-MeOCO—Thi(3) | Pr | NH$_2$ | O | 2 |
| 859 | 4-MeOCO—Thi(3) | Pr$^i$ | NH$_2$ | O | 2 |
| 860 | 5-MeOCO—Thi(3) | H | NH$_2$ | O | 2 |
| 861 | 5-MeOCO—Thi(3) | Cl | NH$_2$ | O | 2 |
| 862 | 5-MeOCO—Th(3) | Me | NH$_2$ | O | 2 |
| 863 | 5-MeOCO—Thi(3) | Et | NH$_2$ | O | 2 |
| 864 | 5-MeOCO—Thi(3) | Pr | NH$_2$ | O | 2 |
| 865 | 5-MeOCO—Thi(3) | Pr$^i$ | NH$_2$ | O | 2 |
| 866 | 2-H$_2$NCO—Thi(3) | H | NH$_2$ | O | 2 |
| 867 | 2-H$_2$NC&—Thi(3) | Cl | NH$_2$ | O | 2 |
| 868 | 2-H$_2$NCO—Thi(3) | Me | NH$_2$ | O | 2 |
| 869 | 2-H$_2$NCO—Thi(3) | Et | NH$_2$ | O | 2 |
| 870 | 2-H$_2$NCO—Th(3) | Pr | NH$_2$ | O | 2 |
| 871 | 2-H$_2$NCO—Thi(3) | Pr$^i$ | NH$_2$ | O | 2 |
| 872 | 4-H$_2$NCO—Thi(3) | H | NH$_2$ | O | 2 |
| 873 | 4-H$_2$NCO—Thi(3) | Cl | NH$_2$ | O | 2 |
| 874 | 4-H$_2$NCO—Thi(3) | Me | NH$_2$ | O | 2 |
| 875 | 4-H$_2$NCO—Thi(3) | Et | NH$_2$ | O | 2 |
| 876 | 4-H$_2$NCO—Thi(3) | Pr | NH$_2$ | O | 2 |
| 877 | 4-H$_2$NCO—Th(3) | Pr$^i$ | NH$_2$ | O | 2 |
| 878 | 5-H$_2$NCO—Thi(3) | H | NH$_2$ | O | 2 |
| 879 | 5-H$_2$NCO—Thi(3) | Cl | NH$_2$ | O | 2 |
| 880 | 5-H$_2$NCO—Thi(3) | Me | NH$_2$ | O | 2 |
| 881 | 5-H$_2$NCO—Thi(3) | Et | NH$_2$ | O | 2 |
| 882 | 5-H$_2$NCO—Thi(3) | Pr | NH$_2$ | O | 2 |
| 883 | 5-H$_2$NCO—Thi(3) | Pr$^i$ | NH$_2$ | O | 2 |
| 884 | 2-MeNHCO—Thi(3) | H | NH$_2$ | O | 2 |
| 885 | 2-MeNHCO—Thi(3) | Cl | NH$_2$ | O | 2 |
| 886 | 2-MeNHCO—Thi(3) | Me | NH$_2$ | O | 2 |
| 887 | 2-MeNHCO—Th(3) | Et | NH$_2$ | O | 2 |
| 888 | 2-MeNHCO—Thi(3) | Pr | NH$_2$ | O | 2 |
| 889 | 2-MeNHCO—Thi(3) | Pr$^i$ | NH$_2$ | O | 2 |
| 890 | 4-MeNHCO—Thi(3) | H | NH$_2$ | O | 2 |
| 891 | 4-MeNHCO—Th(3) | Cl | NH$_2$ | O | 2 |
| 892 | 4-MeNHCO—Thi(3) | Me | NH$_2$ | O | 2 |
| 893 | 4-MeNHCO—Thi(3) | Et | NH$_2$ | O | 2 |
| 894 | 4-MeNHCO—Thi(3) | Pr | NH$_2$ | O | 2 |
| 895 | 4-MeNHCO—Thi(3) | Pr$^i$ | NH$_2$ | O | 2 |
| 896 | 5-MeNHCO—Thi(3) | H | NH$_2$ | O | 2 |
| 897 | 5-MeNHCO—Thi(3) | Cl | NH$_2$ | O | 2 |
| 898 | 5-MeNHCO—Th(3) | Me | NH$_2$ | O | 2 |
| 899 | 5-MeNHCO—Th(3) | Et | NH$_2$ | O | 2 |
| 900 | 5-MeNHCO—Thi(3) | Pr | NH$_2$ | O | 2 |
| 901 | 5-MeNHCO—Thi(3) | Pr$^i$ | NH$_2$ | O | 2 |
| 902 | 2-(Me)$_2$NCO—Thi(3) | H | NH$_2$ | O | 2 |
| 903 | 2-(Me)$_2$NCO—Thi(3) | Cl | NH$_2$ | O | 2 |
| 904 | 2-(Me)$_2$NCO—Thi(3) | Me | NH$_2$ | O | 2 |
| 905 | 2-(Me)$_2$NCO—Thi(3) | Et | NH$_2$ | O | 2 |
| 906 | 2-(Me)$_2$NCO—Thi(3) | Pr | NH$_2$ | O | 2 |
| 907 | 2-(Me)$_2$NCO—Thi(3) | Pr$^i$ | NH$_2$ | O | 2 |
| 908 | 4-(Me)$_2$NCO—Thi(3) | H | NH$_2$ | O | 2 |
| 909 | 4-(Me)$_2$NCO—Thi(3) | Cl | NH$_2$ | O | 2 |
| 910 | 4-(Me)$_2$NCO—Thi(3) | Me | NH$_2$ | O | 2 |
| 911 | 4-(Me)$_2$NCO—Thi(3) | Et | NH$_2$ | O | 2 |
| 912 | 4-(Me)$_2$NCO—Thi(3) | Pr | NH$_2$ | O | 2 |
| 913 | 4-(Me)$_2$NCO—Thi(3) | Pr$^i$ | NH$_2$ | O | 2 |
| 914 | 5-(Me)$_2$NCO—Thi(3) | H | NH$_2$ | O | 2 |
| 915 | 5-(Me)$_2$NCO—Thi(3) | Cl | NH$_2$ | O | 2 |
| 916 | 5-(Me)$_2$NCO—Thi(3) | Me | NH$_2$ | 02 | |
| 917 | 5-(Me)$_2$NCO—Thi(3) | Et | NH$_2$ | O | 2 |
| 918 | 5-(Me)$_2$NCO—Thi(3) | Pr | NH$_2$ | O | 2 |
| 919 | 5-(Me)$_2$NCO—Thi(3) | Pr$^i$ | NH$_2$ | O | 2 |
| 920 | Pyr(2) | H | NH$_2$ | O | 2 |
| 921 | Pyr(2) | H | NH$_2$ | O | 2 |
| 922 | Pyr(2) | H | NH$_2$ | O | 3 |
| 923 | Pyr(2) | H | NH$_2$ | O | 4 |
| 924 | Pyr(2) | F | NH$_2$ | O | 2 |
| 925 | Pyr(2) | Cl | NH$_2$ | O | 2 |
| 926 | Pyr(2) | Me | NH$_2$ | O | 2 |
| 927 | Pyr(2) | Et | NH$_2$ | O | 2 |
| 928 | Pyr(2) | Pr | NH$_2$ | O | 2 |
| 929 | Pyr(2) | Pr$^i$ | NH$_2$ | O | 2 |
| 930 | Pyr(2) | Bu | NH$_2$ | O | 2 |
| 931 | Pyr(2) | Bu$^i$ | NH$_2$ | O | 2 |
| 932 | Pyr(2) | Bu$^s$ | NH$_2$ | O | 2 |
| 933 | Pyr(2) | Bu$^t$ | NH$_2$ | O | 2 |
| 934 | Pyr(2) | H | NH$_2$ | S | 2 |
| 935 | Pyr(2) | H | NH$_2$ | S | 3 |
| 936 | Pyr(2) | H | NH$_2$ | S | 4 |
| 937 | Pyr(2) | F | NH$_2$ | S | 2 |
| 938 | Pyr(2) | Cl | NH$_2$ | S | 2 |
| 939 | Pyr(2) | Me | NH$_2$ | S | 2 |
| 940 | Pyr(2) | Et | NH$_2$ | S | 2 |
| 941 | Pyr(2) | Pr | NH$_2$ | S | 2 |
| 942 | Pyr(2) | Pr$^i$ | NH$_2$ | S | 2 |
| 943 | Pyr(2) | H | NHMe | O | 2 |
| 944 | Pyr(2) | H | NHEt | O | 2 |
| 945 | Pyr(2) | H | N(Me)$_2$ | O | 2 |
| 946 | Pyr(2) | H | Pip(1) | O | 2 |
| 947 | Pyr(2) | H | Mor(4) | O | 2 |
| 948 | 3-F—Pyr(2) | H | NH$_2$ | O | 2 |
| 949 | 3-F—Pyr(2) | Cl | NH$_2$ | O | 2 |
| 950 | 3-F—Pyr(2) | Me | NH$_2$ | O | 2 |
| 951 | 3-F—Pyr(2) | Et | NH$_2$ | O | 2 |
| 952 | 3-F—Pyr(2) | Pr | NH$_2$ | O | 2 |
| 953 | 3-F—Pyr(2) | Pr$^i$ | NH$_2$ | O | 2 |
| 954 | 4-F—Pyr(2) | H | NH$_2$ | O | 2 |
| 955 | 4-F—Pyr(2) | Cl | NH$_2$ | O | 2 |
| 956 | 4-F—Pyr(2) | Me | NH$_2$ | O | 2 |
| 957 | 4-F—Pyr(2) | Et | NH$_2$ | O | 2 |
| 958 | 4-F—Pyr(2) | Pr | NH$_2$ | O | 2 |
| 959 | 4-F—Pyr(2) | Pr$^i$ | NH$_2$ | O | 2 |
| 960 | 3-Cl—Pyr(2) | H | NH$_2$ | O | 2 |
| 961 | 3-Cl—Pyr(2) | Cl | NH$_2$ | O | 2 |
| 962 | 3-Cl—Pyr(2) | Me | NH$_2$ | O | 2 |
| 963 | 3-Cl—Pyr(2) | Et | NH$_2$ | O | 2 |
| 964 | 3-Cl—Pyr(2) | Pr | NH$_2$ | O | 2 |
| 965 | 3-Cl—Pyr(2) | Pr$^i$ | NH$_2$ | O | 2 |
| 966 | 4-Cl—Pyr(2) | H | NH$_2$ | O | 2 |
| 967 | 4-Cl—Pyr(2) | Cl | NH$_2$ | O | 2 |
| 968 | 4-Cl—Pyr(2) | Me | NH$_2$ | O | 2 |
| 969 | 4-Cl—Pyr(2) | Et | NH$_2$ | O | 2 |
| 970 | 4-Cl—Pyr(2) | Pr | NH$_2$ | O | 2 |
| 971 | 4-Cl—Pyr(2) | Pr$^i$ | NH$_2$ | O | 2 |
| 972 | 4-Me—Pyr(2) | H | NH$_2$ | O | 2 |
| 973 | 4-Me—Pyr(2) | Cl | NH$_2$ | O | 2 |
| 974 | 4-Me—Pyr(2) | Me | NH$_2$ | O | 2 |
| 975 | 4-Me—Pyr(2) | Et | NH$_2$ | O | 2 |
| 976 | 4-Me—Pyr(2) | Pr | NH$_2$ | O | 2 |
| 977 | 4-Me—Pyr(2) | Pr$^i$ | NH$_2$ | O | 2 |
| 978 | 4-Et—Pyr(2) | H | NH$_2$ | O | 2 |
| 979 | 4-Et—Pyr(2) | Cl | NH$_2$ | O | 2 |
| 980 | 4-Et—Pyr(2) | Me | NH$_2$ | O | 2 |
| 981 | 4-Et—Pyr(2) | Et | NH$_2$ | O | 2 |
| 982 | 4-Et—Pyr(2) | Pr | NH$_2$ | O | 2 |
| 983 | 4-Et—Pyr(2) | Pr$^i$ | NH$_2$ | O | 2 |
| 984 | 4-CF$_3$—Pyr(2) | H | NH$_2$ | O | 2 |
| 985 | 4-CF$_3$—Pyr(2) | Cl | NH$_2$ | O | 2 |
| 986 | 4-CF$_3$—Pyr(2) | Me | NH$_2$ | O | 2 |
| 987 | 4-CF$_3$—Pyr(2) | Et | NH$_2$ | O | 2 |
| 988 | 4-CF$_3$—Pyr(2) | Pr | NH$_2$ | O | 2 |
| 989 | 4-CF$_3$—Pyr(2) | Pr$^i$ | NH$_2$ | O | 2 |
| 990 | 4-MeO—Pyr(2) | H | NH$_2$ | O | 2 |
| 991 | 4-MeO—Pyr(2) | Cl | NH$_2$ | O | 2 |
| 992 | 4-MeO—Pyr(2) | Me | NH$_2$ | O | 2 |
| 993 | 4-MeO—Pyr(2) | Et | NH$_2$ | O | 2 |
| 994 | 4-MeO—Pyr(2) | Pr | NH$_2$ | O | 2 |
| 995 | 4-MeO—Pyr(2) | Pr$^i$ | NH$_2$ | O | 2 |
| 996 | 3-Ph—Pyr(2) | H | NH$_2$ | O | 2 |
| 997 | 3-Ph—Pyr(2) | Cl | NH$_2$ | O | 2 |
| 998 | 3-Ph—Pyr(2) | Me | NH$_2$ | O | 2 |
| 999 | 3-Ph—Pyr(2) | Et | NH$_2$ | O | 2 |
| 1000 | 3-Ph—Pyr(2) | Pr | NH$_2$ | O | 2 |
| 1001 | 3-Ph—Pyr(2) | Pr$^i$ | NH$_2$ | O | 2 |
| 1002 | 4-Ph—Pyr(2) | H | NH$_2$ | O | 2 |
| 1003 | 4-Ph—Pyr(2) | Cl | NH$_2$ | O | 2 |
| 1004 | 4-Ph—Pyr(2) | Me | NH$_2$ | O | 2 |

TABLE 1-continued

| Compd. No. | R¹ | R² | R³ | X | n |
|---|---|---|---|---|---|
| 1005 | 4-Ph—Pyr(2) | Et | NH₂ | O | 2 |
| 1006 | 4-Ph—Pyr(2) | Pr | NH₂ | O | 2 |
| 1007 | 4-Ph—Pyr(2) | Pr$^i$ | NH₂ | O | 2 |
| 1008 | 3-MeOCO—Pyr(2) | H | NH₂ | O | 2 |
| 1009 | 3-MeOCO—Pyr(2) | Cl | NH₂ | O | 2 |
| 1010 | 3-MeOCO—Pyr(2) | Me | NH₂ | O | 2 |
| 1011 | 3-MeOCO—Pyr(2) | Et | NH₂ | O | 2 |
| 1012 | 3-MeOCO—Pyr(2) | ? r | NH₂ | O | 2 |
| 1013 | 3-MeOCO—Pyr(2) | Pr$^i$ | NH₂ | O | 2 |
| 1014 | 4-MeOCO—Pyr(2) | H | NH₂ | O | 2 |
| 1015 | 4-MeOCO—Py?(2) | Cl | NH₂ | O | 2 |
| 1016 | 4-MeOCO—Pyr(2) | Me | NH₂ | O | 2 |
| 1017 | 4-MeOCO—Pyr(2) | Et | NH₂ | O | 2 |
| 1018 | 4-MeOCO—Pyr(2) | Pr | NH₂ | O | 2 |
| 1019 | 4-MeOCO—Pyr(2) | Pr$^i$ | NH₂ | O | 2 |
| 1020 | 3-H₂NCO—Pyr(2) | H | NH₂ | O | 2 |
| 1021 | 3-H₂NCO—Pyr(2) | Cl | NH₂ | O | 2 |
| 1022 | 3-H₂NCO—Pyr(2) | Me | NH₂ | O | 2 |
| 1023 | 3-H₂NCO—Pyr(2) | Et | NH₂ | O | 2 |
| 1024 | 3-H₂NCO—Pyr(2) | Pr | NH₂ | O | 2 |
| 1025 | 3-H₂NCO—Pyr(2) | Pr$^i$ | NH₂ | O | 2 |
| 1026 | 4-H₂NCO—Pyr(2) | H | NH₂ | O | 2 |
| 1027 | 4-H₂NCO—Pyr(2) | Cl | NH₂ | O | 2 |
| 1028 | 4-H₂NCO—Pyr(2) | Me | NH₂ | O | 2 |
| 1029 | 4-H₂NCO—Pyr(2) | Et | NH₂ | O | 2 |
| 1030 | 4-H₂NCO—Pyr(2) | Pr | NH₂ | O | 2 |
| 1031 | 4-H₂NCO—Pyr(2) | Pr$^i$ | NH₂ | O | 2 |
| 1032 | 3-MeNHCO—Pyr(2) | H | NH₂ | O | 2 |
| 1033 | 3-MeNHCO—Pyr(2) | Cl | NH₂ | O | 2 |
| 1034 | 34-MeNHCO—Pyr(2) | Me | NH₂ | O | 2 |
| 1035 | 3-MeNHCO—Pyr(2) | Et | NH₂ | 0 2 | |
| 1036 | 3-MeNHCO—Pyr(2) | Pr | NH₂ | O | 2 |
| 1037 | 3-MeNHCO—Pyr(2) | Pr$^i$ | NH₂ | O | 2 |
| 1038 | 4-MeNHCO—Pyr(2) | H | NH₂ | O | 2 |
| 1039 | 4-MeNHCO—Pyr(2) | Cl | NH₂ | O | 2 |
| 1040 | 4-MeNHCO—Pyr(2) | Me | NH₂ | O | 2 |
| 1041 | 4-MeNHCO—Pyr(2) | Et | NH₂ | O | 2 |
| 1042 | 4-MeNHCO—Pyr(2) | Pr | NH₂ | O | 2 |
| 1043 | 4-MeNHCO—Pyr(2) | Pr$^i$ | NH₂ | O | 2 |
| 1044 | 3-(Me)₂NCO—Pyr(2) | H | NH₂ | O | 2 |
| 1045 | 3-(Me)₂NCO—Pyr(2) | Cl | NH₂ | O | 2 |
| 1046 | 3-(Me)₂NCO—PYr(2) | Me | NH₂ | O | 2 |
| 1047 | 3-(Me)₂NCO—Pyr(2) | Et | NH₂ | O | 2 |
| 1048 | 3-(Me)₂NCO—Pyr(2) | Pr | NH₂ | O | 2 |
| 1049 | 3-(Me)₂NCO—Pyr(2) | Pr$^i$ | NH₂ | O | 2 |
| 1050 | 4-(Me)₂NCO—Pyr(2) | H | NH₂ | O | 2 |
| 1051 | 4-(Me)₂NCO—Pyr(2) | Cl | NH₂ | O | 2 |
| 1052 | 4-(Me)₂NCO—Pyr(2) | Me | NH₂ | O | 2 |
| 1053 | 4-(Me)₂NCO—Pyr(2) | Et | NH₂ | O | 2 |
| 1054 | 4-(Me)₂NCO—Pyr(2) | Pr | NH₂ | O | 2 |
| 1055 | 4-(Me)₂NCO—Pyr(2) | Pr$^i$ | NH₂ | O | 2 |
| 1056 | Pyr(3) | H | NH₂ | O | 2 |
| 1057 | Pyr(3) | H | NH₂ | O | 2 |
| 1058 | Pyr(3) | H | NH₂ | O | 3 |
| 1059 | Pyr(3) | H | NH₂ | O | 4 |
| 1060 | Pyr(3) | F | NH₂ | O | 2 |
| 1061 | Pyr(3) | Cl | NH₂ | O | 2 |
| 1062 | Pyr(3) | Me | NH₂ | O | 2 |
| 1063 | Pyr(3) | Et | NH₂ | O | 2 |
| 1064 | Pyr(3) | Pr | NH₂ | O | 2 |
| 1065 | Pyr(3) | Pr$^i$ | NH₂ | O | 2 |
| 1066 | Pyr(3) | Bu | NH₂ | O | 2 |
| 1067 | Pyr(3) | Bu$^i$ | NH₂ | O | 2 |
| 1068 | Pyr(3) | Bu$^s$ | NH₂ | O | 2 |
| 1069 | Pyr(3) | Bu$^t$ | NH₂ | O | 2 |
| 1070 | Pyr(3) | H | NH₂ | S | 2 |
| 1071 | Pyr(3) | H | NH₂ | S | 3 |
| 1072 | Pyr(3) | H | NH₂ | S | 4 |
| 1073 | Pyr(3) | F | NH₂ | S | 2 |
| 1074 | Pyr(3) | Cl | NH₂ | S | 2 |
| 1075 | Pyr(3) | Me | NH₂ | S | 2 |
| 1076 | Pyr(3) | Et | NH₂ | S | 2 |
| 1077 | Pyr(3) | Pr | NH₂ | S | 2 |
| 1078 | Pyr(3) | Pr$^i$ | NH₂ | S | 2 |
| 1079 | Pyr(3) | H | NHMe | O | 2 |
| 1080 | Pyr(3) | H | NHEt | O | 2 |
| 1081 | Pyr(3) | H | N(Me)₂ | O | 2 |
| 1082 | Pyr(3) | H | Pip(1) | O | 2 |
| 1083 | Pyr(3) | H | Mor(4) | O | 2 |
| 1084 | 2-F—Pyr(3) | H | NH₂ | O | 2 |
| 1085 | 2-F—Pyr(3) | Cl | NH₂ | O | 2 |
| 1086 | 2-F—Pyr(3) | Me | NH₂ | O | 2 |
| 1087 | 2-F—Pyr(3) | Et | NH₂ | O | 2 |
| 1088 | 2-F—Pyr(3) | Pr | NH₂ | O | 2 |
| 1089 | 2-F—Pyr(3) | Pr$^i$ | NH₂ | 02 | |
| 1090 | 4-F—Pyr(3) | H | NH₂ | | 2 |
| 1091 | 4-F—Pyr(3) | Cl | NH₂ | O | 2 |
| 1092 | 4-F—Pyr(3) | Me | NH₂ | O | 2 |
| 1093 | 4-F—Pyr(3) | Et | NH₂ | O | 2 |
| 1094 | 4-F—Pyr(3) | Pr | NH₂ | O | 2 |
| 1095 | 4-F—Pyr(3) | Pr$^i$ | NH₂ | O | 2 |
| 1096 | 2-Cl—Pyr(3) | H | NH₂ | O | 2 |
| 1097 | 2-Cl—Pyr(3) | Cl | NH₂ | O | 2 |
| 1098 | 2-Cl—Pyr(3) | Me | NH₂ | O | 2 |
| 1099 | 2-Cl—Pyr(3) | Et | NH₂ | O | 2 |
| 1100 | 2-Cl—Pyr(3) | Pr | NH₂ | O | 2 |
| 1101 | 2-Cl—Pyr(3) | Pr$^i$ | NH₂ | O | 2 |
| 1102 | 4-Cl—Pyr(3) | H | NH₂ | O | 2 |
| 1103 | 4-Cl—Pyr(3) | Cl | NH₂ | O | 2 |
| 1104 | 4-Cl—Pyr(3) | Me | NH₂ | O | 2 |
| 1105 | 4-Cl—Pyr(3) | Et | NH₂ | O | 2 |
| 1106 | 4-Cl—Pyr(3) | Pr | NH₂ | O | 2 |
| 1107 | 4-Cl—Pyr(3) | Pr$^i$ | NH₂ | O | 2 |
| 1108 | 4-Me—Pyr(3) | H | NH₂ | O | 2 |
| 1109 | 4-Me—Pyr(3) | Cl | NH₂ | O | 2 |
| 1110 | 4-Me—Pyr(3) | Me | NH₂ | O | 2 |
| 1111 | 4-Me—Pyr(3) | Et | NH₂ | O | 2 |
| 1112 | 4-Me—Pyr(3) | Pr | NH₂ | O | 2 |
| 1113 | 4-Me—Pyr(3) | Pr$^i$ | NH₂ | O | 2 |
| 1114 | 4-Et—Pyr(3) | H | NH₂ | O | 2 |
| 1115 | 4-Et—Pyr(3) | Cl | NH₂ | O | 2 |
| 1116 | 4-Et—Pyr(3) | Me | NH₂ | O | 2 |
| 1117 | 4-Et—Pyr(3) | Et | NH₂ | O | 2 |
| 1118 | 4-Et—Pyr(3) | Pr | NH₂ | O | 2 |
| 1119 | 4-Et—Pyr(3) | Pr$^i$ | NH₂ | O | 2 |
| 1120 | 4-CF₃—Pyr(3) | H | NH₂ | O | 2 |
| 1121 | 4-CF₃—Pyr(3) | Cl | NH₂ | O | 2 |
| 1122 | 4-CF₃—Pyr(3) | Me | NH₂ | O | 2 |
| 1123 | 4-CF₃—Pyr(3) | Et | NH₂ | O | 2 |
| 1124 | 4-CF₃—Pyr(3) | Pr | NH₂ | O | 2 |
| 1125 | 4-CF₃—Pyr(3) | pri | NH₂ | O | 2 |
| 1126 | 4-MeO—Pyr(3) | H | NH₂ | O | 2 |
| 1127 | 4-MeO—Pyr(3) | Cl | NH₂ | O | 2 |
| 1128 | 4-MeO—Pyr(3) | Me | NH₂ | O | 2 |
| 1129 | 4-MeO—Pyr(3) | Et | NH₂ | O | 2 |
| 1130 | 4-MeO—Pyr(3) | Pr | NH₂ | O | 2 |
| 1131 | 4-MeO—Pyr(3) | Pr$^i$ | NH₂ | O | 2 |
| 1132 | 2-PhPyr(3) | H | NH₂ | O | 2 |
| 1133 | 2-Ph—Pyr(3) | Cl | NH₂ | O | 2 |
| 1134 | 2-Ph—Pyr(3) | Me | NH₂ | O | 2 |
| 1135 | 2-Ph—Pyr(3) | Et | NH₂ | O | 2 |
| 1136 | 2-Ph—Pyr(3) | Pr | NH₂ | O | 2 |
| 1137 | 2-Ph—Pyr(3) | Pr$^i$ | NH₂ | O | 2 |
| 1138 | 4-Ph—Pyr(3) | H | NH₂ | O | 2 |
| 1139 | 4-Ph—Pyr(3) | Cl | NH₂ | O | 2 |
| 1140 | 4-Ph—Pyr(3) | Me | NH₂ | O | 2 |
| 1141 | 4-Ph—Pyr(3) | Et | NH₂ | O | 2 |
| 1142 | 4-Ph—Pyr(3) | Pr | NH₂ | O | 2 |
| 1143 | 4-Ph—Pyr(3) | Pr$^i$ | NH₂ | O | 2 |
| 1144 | 2-MeOCO—Pyr(3) | H | NH₂ | O | 2 |
| 1145 | 2-MeOCO—Pyr(3) | Cl | NH₂ | O | 2 |
| 1146 | 2-MeOCO—Pyr(3) | Me | NH₂ | O | 2 |
| 1147 | 2-MeOCO—Pyr(3) | Et | NH₂ | O | 2 |
| 1148 | 2-MeOCO—Pyr(3) | Pr | NH₂ | O | 2 |
| 1149 | 2-MeOCO—Pyr(3) | Pr$^i$ | NH₂ | O | 2 |
| 1150 | 4-MeOCO—Pyr(3) | H | NH₂ | O | 2 |
| 1151 | 4-MeOCO—Pyr(3) | Cl | NH₂ | O | 2 |
| 1152 | 4-MeOCO—Pyr(3) | Me | NH₂ | O | 2 |
| 1153 | 4-MeOCO—Pyr(3) | Et | NH₂ | O | 2 |
| 1154 | 4-MeOCO—Pyr(3) | Pr | NH₂ | O | 2 |
| 1155 | 4-MeOCO—Pyr(3) | Pr$^i$ | NH₂ | O | 2 |
| 1156 | 2-H₂NCO—Pyr(3) | H | NH₂ | O | 2 |

TABLE 1-continued

| Compd. No. | R¹ | R² | R³ | X | n |
|---|---|---|---|---|---|
| 1157 | 2-H₂NCO—Pyr(3) | Cl | NH₂ | O | 2 |
| 1158 | 2-H₂NCO—Pyr(3) | Me | NH₂ | O | 2 |
| 1159 | 2-H₂NCO—Pyr(3) | Et | NH₂ | O | 2 |
| 1160 | 2-H₂NCO—Pyr(3) | Pr | NH₂ | O | 2 |
| 1161 | 2-H₂NCO—Pyr(3) | Prⁱ | NH₂ | O | 2 |
| 1162 | 4-H₂NCO—Pyr(3) | H | NH₂ | O | 2 |
| 1163 | 4-H₂NCO—Pyr(3) | Cl | NH₂ | O | 2 |
| 1164 | 4-H₂NCO—Pyr(3) | Me | NH₂ | O | 2 |
| 1165 | 4-H₂NCO—Pyr(3) | Et | NH₂ | O | 2 |
| 1166 | 4-H₂NCO—Pyr(3) | Pr | NH₂ | O | 2 |
| 1167 | 4-H₂NCO—Pyr(3) | Prⁱ | NH₂ | O | 2 |
| 1168 | 2-MeNHCO—Pyr(3) | H | NH₂ | O | 2 |
| 1169 | 2-MeNHCO—Pyr(3) | Cl | NH₂ | O | 2 |
| 1170 | 2-MeNHCO—Pyr(3) | Me | NH₂ | O | 2 |
| 1171 | 2-MeNHCO—Pyr(3) | Et | NH₂ | O | 2 |
| 1172 | 2-MeNHCO—.Pyr(3) | Pr | NH₂ | O | 2 |
| 1173 | 2-MeNHCO—Pyr(3) | Prⁱ | NH₂ | O | 2 |
| 1174 | 4-MeNHCO—Pyr(3) | H | NH₂ | O | 2 |
| 1175 | 4-MeNHCO—Pyr(3) | Cl | NH₂ | O | 2 |
| 1176 | 4-MeNHCO—Pyr(3) | Me | NH₂ | O | 2 |
| 1177 | 4-MeNHCO—Pyr(3) | Et | NH₂ | O | 2 |
| 1178 | 4-MeNHCO—Pyr(3) | Pr | NH₂ | O | 2 |
| 1179 | 4-MeNHCO—Pyr(3) | Prⁱ | NH₂ | O | 2 |
| 1180 | 2-(Me)₂NCO—Pyr(3) | H | NH₂ | O | 2 |
| 1181 | 2-(Me)₂NCO—Pyr(3) | Cl | NH₂ | O | 2 |
| 1182 | 2-(Me)₂NCO—Pyr(3) | Me | NH₂ | O | 2 |
| 1183 | 2-(Me)₂NCO—Pyr(3) | Et | NH₂ | O | 2 |
| 1184 | 2-(Me)₂NCO—Pyr(3) | Pr | NH₂ | O | 2 |
| 1185 | 2-(Me)₂NCO—Pyr(3) | Prⁱ | NH₂ | O | 2 |
| 1186 | 4-(Me)₂NCO—Pyr(3) | H | NH₂ | O | 2 |
| 1187 | 4-(Me)₂NCO—Pyr(3) | Cl | NH₂ | O | 2 |
| 1188 | 4-(Me)₂NCO—Pyr(3) | Me | NH₂ | O | 2 |
| 1189 | 4-(Me)₂NCO—Pyr(3) | Et | NH₂ | O | 2 |
| 1190 | 4-(Me)₂NCO—Pyr(3) | Pr | NH₂ | O | 2 |
| 1191 | 4-(Me)₂NCO—Pyr(3) | Prⁱ | NH₂ | O | 2 |
| 1192 | Pyr(4) | H | NH₂ | O | 2 |
| 1193 | Pyr(4) | H | NH₂ | O | 2 |
| 1194 | Pyr(4) | H | NH₂ | O | 3 |
| 1195 | Pyr(4) | H | NH₂ | O | 4 |
| 1196 | Pyr(4) | F | NH₂ | O | 2 |
| 1197 | Pyr(4) | Cl | NH₂ | O | 2 |
| 1198 | Pyr(4) | Me | NH₂ | O | 2 |
| 1199 | Pyr(4) | Et | NH₂ | O | 2 |
| 1200 | Pyr(4) | Pr | NH₂ | O | 2 |
| 1201 | Pyr(4) | Prⁱ | NH₂ | O | 2 |
| 1202 | Pyr(4) | Bu | NH₂ | O | 2 |
| 1203 | Pyr(4) | Buⁱ | NH₂ | O | 2 |
| 1204 | Pyr(4) | Buˢ | NH₂ | O | 2 |
| 1206 | Pyr(4) | Buᵗ | NH₂ | O | 2 |
| 1207 | Pyr(4) | H | NH₂ | S | 2 |
| 1208 | Pyr(4) | H | NH₂ | S | 3 |
| 1209 | Pyr(4) | H | NH₂ | S | 4 |
| 1210 | Pyr(4) | F | NH₂ | S | 2 |
| 1211 | Pyr(4) | Cl | NH₂ | S | 2 |
| 1212 | Pyr(4) | Me | NH₂ | S | 2 |
| 1213 | Pyr(4) | Et | NH₂ | S | 2 |
| 1214 | Pyr(4) | Pr | NH₂ | S | 2 |
| 1215 | Pyr(4) | Prⁱ | NH₂ | S | 2 |
| 1216 | Pyr(4) | H | NHMe | O | 2 |
| 1217 | Pyr(4) | H | NHEt | O | 2 |
| 1218 | Pyr(4) | H | N(Me)₂ | O | 2 |
| 1219 | Pyr(4) | H | Pip(l) | O | 2 |
| 1220 | Pyr(4) | H | Mor(4) | O | 2 |
| 1221 | 2-F—Pyr(4) | H | NH₂ | O | 2 |
| 1222 | 2-F—Pyr(4) | Cl | NH₂ | O | 2 |
| 1223 | 2-F—Pyr(4) | Me | NH₂ | O | 2 |
| 1224 | 2-F—Pyr(4) | Et | NH₂ | O | 2 |
| 1225 | 2-F—Pyr(4) | Pr | NH₂ | O | 2 |
| 1226 | 2-F—Pyr(4) | Prⁱ | NH₂ | O | 2 |
| 1227 | 3-F—Pyr(4) | H | NH₂ | O | 2 |
| 1228 | 3-F—Pyr(4) | Cl | NH₂ | O | 2 |
| 1229 | 3-F—Pyr(4) | Me | NH₂ | O | 2 |
| 1230 | 3-F—Pyr(4) | Et | NH₂ | O | 2 |
| 1231 | 3-F—Pyr(4) | Pr | NH₂ | O | 2 |
| 1232 | 3-F—Pyr(4) | Prⁱ | NH₂ | O | 2 |
| 1233 | 2-Cl—Pyr(4) | H | NH₂ | O | 2 |
| 1234 | 2-Cl—Pyr(4) | Cl | NH₂ | O | 2 |
| 1235 | 2-Cl—Pyr(4) | Me | NH₂ | O | 2 |
| 1236 | 2-Cl—Pyr(4) | Et | NH₂ | O | 2 |
| 1237 | 2-Cl—Pyr(4) | Pr | NH₂ | O | 2 |
| 1235 | 2-Cl—Pyr(4) | Prⁱ | NH₂ | O | 2 |
| 1239 | 3-Cl—Pyr(4) | H | NH₂ | O | 2 |
| 1240 | 3-Cl—Pyr(4) | Cl | NH₂ | O | 2 |
| 1241 | 3-Cl—Pyr(4) | Me | NH₂ | O | 2 |
| 1242 | 3-Cl—Pyr(4) | Et | NH₂ | O | 2 |
| 1243 | 3-Cl—Pyr(4) | Pr | NH₂ | O | 2 |
| 1244 | 3-Cl—Pyr(4) | Prⁱ | NH₂ | O | 2 |
| 1245 | 3-Me—Pyr(4) | H | NH₂ | O | 2 |
| 1246 | 3-Me—Pyr(4) | Cl | NH₂ | O | 2 |
| 1247 | 3-Me—Pyr(4) | Me | NH₂ | O | 2 |
| 1248 | 3-Me—Pyr(4) | Et | NH₂ | O | 2 |
| 1249 | 3-Me—Pyr(4) | Pr | NH₂ | O | 2 |
| 1250 | 3-Me—Pyr(4) | Prⁱ | NH₂ | O | 2 |
| 1251 | 3-Et—Pyr(4) | H | NH₂ | O | 2 |
| 1252 | 3-Et—Pyr(4) | Cl | NH₂ | O | 2 |
| 1253 | 3-Et—Pyr(4) | Me | NH₂ | o | 2 |
| 1254 | 3-Et—Pyr(4) | Et | NH₂ | O | 2 |
| 1255 | 3-Et—Pyr(4) | Pr | NH₂ | O | 2 |
| 1256 | 3-Et—Pyr(4) | Prⁱ | NH₂ | O | 2 |
| 1257 | 3-CF₃—Pyr(4) | H | NH₂ | O | 2 |
| 1258 | 3-CF₃—Pyr(4) | Cl | NH₂ | O | 2 |
| 1259 | 3-CF₃—Pyr(4) | Me | NH₂ | O | 2 |
| 1260 | 3-CF₃—Pyr(4) | Et | NH₂ | O | 2 |
| 1261 | 3-CF₃—Pyr(4) | Pr | NH₂ | O | 2 |
| 1262 | 3-CF₃—Pyr(4) | Prⁱ | NH₂ | O | 2 |
| 1263 | 3-MeO—Pyr(4) | H | NH₂ | O | 2 |
| 1264 | 3-MeO—Pyr(4) | Cl | NH₂ | O | 2 |
| 1265 | 3-MeO—Pyr(4) | Me | NH₂ | O | 2 |
| 1266 | 3-MeO—Pyr(4) | Et | NH₂ | O | 2 |
| 1267 | 3-MeO—Pyr(4) | Pr | NH₂ | O | 2 |
| 1268 | 3-MeO—Pyr(4) | Prⁱ | NH₂ | O | 2 |
| 1269 | 2-Ph—Pyr(4) | H | NH₂ | O | 2 |
| 1270 | 2-Ph—Pyr(4) | Cl | NH₂ | O | 2 |
| 1271 | 2-Ph—Pyr(4) | Me | NH₂ | O | 2 |
| 1272 | 2-Ph—Pyr(4) | Et | NH₂ | O | 2 |
| 1273 | 2-Ph—Pyr(4) | Pr | NH₂ | O | 2 |
| 1274 | 2-Ph—Pyr(4) | Prⁱ | NH₂ | O | 2 |
| 1275 | 3-Ph—Pyr(4) | H | NH₂ | O | 2 |
| 1276 | 3-Ph—Pyr(4) | Cl | NH₂ | O | 2 |
| 1277 | 3-Ph—Pyr(4) | Me | NH₂ | O | 2 |
| 1278 | 3-Ph—Pyr(4) | Et | NH₂ | O | 2 |
| 1279 | 3-Ph—Pyr(4) | Pr | NH₂ | O | 2 |
| 1280 | 3-Ph—Pyr(4) | Prⁱ | NH₂ | O | 2 |
| 1281 | 2-MeOCO—Pyr(4) | H | NH₂ | O | 2 |
| 1282 | 2-MeOCO—Pyr(4) | Cl | NH₂ | O | 2 |
| 1283 | 2-MeOCO—Pyr(4) | Me | NH₂ | O | 2 |
| 1284 | 2-MeOCO—Pyr(4) | Et | NH₂ | O | 2 |
| 1285 | 2-MeOCO—Pyr(4) | Pr | NH₂ | O | 2 |
| 1286 | 2-MeOCO—Pyr(4) | Prⁱ | NH₂ | O | 2 |
| 1287 | 3-MeOCO—Pyr(4) | H | NH₂ | O | 2 |
| 1288 | 3-MeOCO—Pyr(4) | Cl | NH₂ | O | 2 |
| 1289 | 3-MeOCO—Pyr(4) | Me | NH₂ | O | 2 |
| 1290 | 3-MeOCO—Pyr(4) | Et | NH₂ | O | 2 |
| 1291 | 3-MeOCO—Pyr(4) | Pr | NH₂ | O | 2 |
| 1292 | 3-MeOCO—Pyr(4) | Prⁱ | NH₂ | O | 2 |
| 1293 | 2-H₂NCO—Pyr(4) | H | NH₂ | O | 2 |
| 1294 | 2-H₂NCO—Pyr(4) | Cl | NH₂ | O | 2 |
| 1295 | 2-H₂NCO—Pyr(4) | Me | NH₂ | O | 2 |
| 1296 | 2-H₂NCO—Pyr(4) | Et | NH₂ | O | 2 |
| 1297 | 2-H₂NCO—Pyr(4) | Pr | NH₂ | O | 2 |
| 1298 | 2-H₂NCO—Pyr(4) | Prⁱ | NH₂ | O | 2 |
| 1299 | 2-H₂NCO—Pyr(4) | | NH₂ | O | 2 |
| 1300 | 3-H₂NCO—Pyr(4) | | | | |
| 1301 | 3-H₂NCO—Pyr(4) | Cl | NH₂ | O | 2 |
| 1302 | 3-H₂NCO—Pyr(4) | Me | NH₂ | O | 2 |
| 1303 | 3-H₂NCO—Pyr(4) | Et | NH₂ | O | 2 |
| 1304 | 3-H₂NCO—Pyr(4) | Pr | NH₂ | O | 2 |
| 1305 | 2-MeNHCO—Pyr(4) | Prⁱ | NH₂ | O | 2 |
| 1306 | 2-MeNHCO—Pyr(4) | H | NH₂ | O | 2 |
| 1307 | 2-MeNHCO—Pyr(4) | Cl | NH₂ | O | 2 |
| 1308 | 2-MeNHCO—Pyr(4) | Me | NH₂ | O | 2 |
| 1309 | 2-MeNHCO—Pyr(4) | Et | NH₂ | O | 2 |
| | | Pr | NH₂ | O | 2 |

TABLE 1-continued

| Compd. No. | R¹ | R² | R³ | X | n |
|---|---|---|---|---|---|
| 1310 | 2-MeNHCO—Pyr(4) | Pr$^i$ | NH$_2$ | O | 2 |
| 1311 | 3-MeNHCO—Pyr(4) | H | NH$_2$ | O | 2 |
| 1312 | 3-MeNHCO—Pyr(4) | Cl | NH$_2$ | O | 2 |
| 1313 | 3-MeNHCO—Pyr(4) | Me | NH$_2$ | O | 2 |
| 1314 | 3-MeNHCO—Pyr(4) | Et | NH$_2$ | O | 2 |
| 1315 | 3-MeNHCO—Pyr(4) | Pr | NH$_2$ | O | 2 |
| 1316 | 3-MeNHCO—Pyr(4) | Pr$^i$ | NH$_2$ | O | 2 |
| 1317 | 2-(Me)$_2$NCO—Pyr(4) | H | NH$_2$ | O | 2 |
| 1318 | 2-(Me)$_2$NCO—Pyr(4) | Cl | NH$_2$ | O | 2 |
| 1319 | 2-(Me)$_2$NCO—Pyr(4) | Me | NH$_2$ | O | 2 |
| 1320 | 2-(Me)$_2$NCO—Pyr(4) | Et | NH$_2$ | O | 2 |
| 1321 | 2-(Me)$_2$NCO—Pyr(4) | Pr | NH$_2$ | O | 2 |
| 1322 | 2-(Me)$_2$NCO—Pyr(4) | Pr$^i$ | NH$_2$ | O | 2 |
| 1323 | 3-(Me)$_2$NCO—Pyr(4) | H | NH$_2$ | O | 2 |
| 1324 | 3-(Me)$_2$NCO—Pyr(4) | Cl | NH$_2$ | O | 2 |
| 1325 | 3-(Me)$_2$NCO—Pyr(4) | Me | NH$_2$ | O | 2 |
| 1326 | 3-(Me)$_2$NCO—Pyr(4) | Et | NH$_2$ | O | 2 |
| 1327 | 3-(Me)$_2$NCO—Pyr(4) | Pr | NH$_2$ | O | 2 |
| 1328 | 3-(Me)$_2$NCO—Pyr(4) | Pr$^i$ | NH$_2$ | O | 2 |
| 1329 | Pyrazinyl(2) | H | NH$_2$ | O | 2 |
| 1330 | Pyrazinyl(2) | Cl | NH$_2$ | O | 2 |
| 1331 | Pyrazinyl(2) | Me | NH$_2$ | O | 2 |
| 1332 | Pyrazinyl(2) | Et | NH$_2$ | O | 2 |
| 133 | Pyrazinyl(2) | Pr | NH$_2$ | O | 2 |
| 1334 | Pyrazinyl(2) | Pr$^i$ | NH$_2$ | O | 2 |
| 1335 | Pyrimidinyl(2) | H | NH$_2$ | O | 2 |
| 1336 | Pyrimidinyl(2) | Cl | NH$_2$ | O | 2 |
| 1337 | Pyrimidinyl(2) | Me | NH$_2$ | O | 2 |
| 1338 | Pyrimidinyl(2) | Et | NH$_2$ | O | 2 |
| 1339 | Pyrimidinyl(2) | Pr | NH$_2$ | O | 2 |
| 1340 | Pyrimidinyl(2) | Pr$^i$ | NH$_2$ | O | 2 |
| 1341 | Pyridazinyl(3) | H | NH$_2$ | O | 2 |
| 1342 | Pyridazinyl(3) | Cl | NH$_2$ | O | 2 |
| 1343 | Pyridazinyl(3) | Me | NH$_2$ | O | 2 |
| 1344 | Pyridazinyl(3) | Et | NH$_2$ | O | 2 |
| 1345 | Pyridazinyl(3) | Pr | NH$_2$ | O | 2 |
| 1346 | Pyridazinyl(3) | Pr$^i$ | NH$_2$ | O | 2 |
| 1347 | Ph | H | NHAc | O | 2 |
| 1348 | Ph | H | NHMoc | O | 2 |
| 1349 | Ph | H | NHBz | O | 2 |
| 1350 | Ph | H | Pyrd(1) | O | 2 |
| 1351 | Ph | H | Piz(1) | O | 2 |
| 1352 | Ph | Cl | NHAc | O | 2 |
| 1353 | Ph | Cl | NHMoc | O | 2 |
| 1354 | Ph | Cl | NHBz | O | 2 |
| 1355 | Ph | Cl | Pyrd(1) | O | 2 |
| 1356 | Ph | Cl | Piz(1) | O | 2 |
| 1357 | Ph | Br | NH$_2$ | O | 2 |
| 1358 | Ph | Br | NH$_2$ | S | 2 |
| 1359 | Ph | I | NH$_2$ | O | 2 |
| 1360 | Ph | I | NH$_2$ | S | 2 |
| 1361 | Ph | Et | NHAc | O | 2 |
| 1362 | Ph | Et | NHMoc | O | 2 |
| 1363 | Ph | Et | NHBz | O | 2 |
| 1364 | Ph | Et | Pyrd(1) | O | 2 |
| 1365 | Ph | Et | Piz(1) | O | 2 |
| 1366 | Ph | Pr | NHAc | O | 2 |
| 1367 | Ph | Pr | NHMoc | O | 2 |
| 1368 | Ph | Pr | NHBz | O | 2 |
| 1369 | Ph | Pr | Pyrd(1) | O | 2 |
| 1370 | Ph | Pr | Piz(1) | O | 2 |
| 1371 | Ph | Pr$^i$ | NHAc | O | 2 |
| 1372 | Ph | Pr$^i$ | NHMoC | O | 2 |
| 1373 | Ph | Pr$^i$ | NHBz | O | 2 |
| 1374 | Ph | Pr$^i$ | Pyrd(1) | O | 2 |
| 1375 | Ph | Pr$^i$ | Piz(1) | O | 2 |
| 1376 | Ph | Bu$^i$ | NHAc | O | 2 |
| 1377 | Ph | Bu$^i$ | NHMoc | O | 2 |
| 1378 | Ph | Bu$^i$ | NHBz | O | 2 |
| 1379 | Ph | Bu$^i$ | Pyrd(1) | O | 2 |
| 1380 | Ph | Bu$^i$ | Piz(1) | O | 2 |
| 1381 | Ph | Bu$^t$ | NHAc | O | 2 |
| 1382 | Ph | Bu$^t$ | NHMoc | O | 2 |
| 1383 | Ph | Bu$^t$ | NHBz | O | 2 |
| 1384 | Ph | Bu$^t$ | Pyrd(1) | O | 2 |
| 1385 | Ph | Bu$^t$ | Piz(l) | O | 2 |
| 1386 | Ph | Pn | NH$_2$ | O | 2 |
| 1387 | Ph | Pn | NH$_2$ | S | 2 |
| 1388 | Ph | Hex | NH$_2$ | O | 2 |
| 1389 | Ph | Hex | NH$_2$ | S | 2 |
| 1390 | Ph | 1-Cl—Et | NH$_2$ | O | 2 |
| 1391 | Ph | 1-Cl—Et | NH$_2$ | S | 2 |
| 1392 | Ph | All | NH$_2$ | O | 2 |
| 1393 | Ph | All | NH$_2$ | S | 2 |
| 1394 | Ph | Pre$^i$ | NH$_2$ | O | 2 |
| 1395 | Ph | Pre$^i$ | NH$_2$ | S | 2 |
| 1396 | Ph | Bun(2) | NH$_2$ | O | 2 |
| 1397 | Ph | Bun(2) | NH$_2$ | S | 2 |
| 1398 | Ph | Prg | NH$_2$ | O | 2 |
| 1399 | Ph | Prg | NH$_2$ | S | 2 |
| 1400 | Ph | Pr$^c$ | NH$_2$ | O | 2 |
| 1401 | Ph | Pr$^c$ | NH$_2$ | S | 2 |
| 1402 | Ph | Pn$^c$ | NH$_2$ | O | 2 |
| 1403 | Ph | Pn$^c$ | NH$_2$ | S | 2 |
| 1404 | Ph | Pen$^c$(2) | NH$_2$ | O | 2 |
| 1405 | Ph | Pen$^c$(2) | NH$_2$ | S | 2 |
| 1406 | Ph | CN | NH$_2$ | O | 2 |
| 1407 | Ph | CN | NH$_2$ | S | 2 |
| 1408 | Ph | COOH | NH$_2$ | O | 2 |
| 1409 | Ph | COOH | NH$_2$ | S | 2 |
| 1410 | Ph | Ac | NH$_2$ | O | 2 |
| 1411 | Ph | Ac | NH$_2$ | S | 2 |
| 1412 | Ph | COOMe | NH$_2$ | O | 2 |
| 1413 | Ph | COOMe | NH$_2$ | S | 2 |
| 1414 | Ph | CONH$_2$ | NH$_2$ | O | 2 |
| 1415 | Ph | CONH$_2$ | NH$_2$ | S | 2 |
| 1416 | Ph | CONHMe | NH$_2$ | O | 2 |
| 1417 | Ph | CONHMe | NH$_2$ | S | 2 |
| 1418 | 2,4-diF—Ph | Br | NH$_2$ | O | 2 |
| 1419 | 2,4-diF—Ph | I | NH$_2$ | O | 2 |
| 1420 | 2,4-diF—Ph | Pn | NH$_2$ | O | 2 |
| 1421 | 2,4-diF—Ph | Hex | NH$_2$ | O | 2 |
| 1422 | 2,4-diF—Ph | 1-Cl—Et | NH$_2$ | O | 2 |
| 1423 | 2,4-diF—Ph | All | NH$_2$ | O | 2 |
| 1424 | 2,4-diF—Ph | Pre$^i$ | NH$_2$ | O | 2 |
| 1425 | 2,4-diF—Ph | Bun(2) | NH$_2$ | O | 2 |
| 1426 | 2,4-diF—Ph | Prg | NH$_2$ | O | 2 |
| 1427 | 2,4-diF—Ph | Pr$^c$ | NH$_2$ | O | 2 |
| 1428 | 2,4-diF—Ph | Pn$^c$ | NH$_2$ | O | 2 |
| 1429 | 2,4-diF—Ph | Pen$^c$(2) | NH$_2$ | O | 2 |
| 1430 | 2,4-diF—Ph | CN | NH$_2$ | O | 2 |
| 1431 | 2,4-diF—Ph | COOH | NH$_2$ | O | 2 |
| 1432 | 2,4-diF—Ph | Ac | NH$_2$ | O | 2 |
| 1433 | 2,4-diF—Ph | COOMe | NH$_2$ | O | 2 |
| 1434 | 2,4-diF—Ph | CONH$_2$ | NH$_2$ | O | 2 |
| 1435 | 2,4-diF—Ph | CONHMe | NH$_2$ | O | 2 |
| 1436 | 2,4-diF—Ph | Br | NH$_2$ | S | 2 |
| 1437 | 2,4-diF—Ph | I | NH$_2$ | S | 2 |
| 1438 | 2,4-diF—Ph | Pn | NH$_2$ | S | 2 |
| 1439 | 2,4-diF—Ph | Hex | NH$_2$ | S | 2 |
| 1440 | 2,4-diF—Ph | 1-Cl—Et | NH$_2$ | S | 2 |
| 1441 | 2,4-diF—Ph | All | NH$_2$ | S | 2 |
| 1442 | 2,4-diF—Ph | Pre$^i$ | NH$_2$ | S | 2 |
| 1443 | 2,4-diF—Ph | Bun(2) | NH$_2$ | S | 2 |
| 1444 | 2,4-diF—Ph | Prg | NH$_2$ | S | 2 |
| 1445 | 2,4-diF—Ph | Pr$^c$ | NH$_2$ | S | 2 |
| 1446 | 2,4-diF—Ph | Pn$^c$ | NH$_2$ | S | 2 |
| 1447 | 2,4-diF—Ph | Pen$^c$(2) | NH$_2$ | S | 2 |
| 1448 | 2,4-diF—Ph | CN | NH$_2$ | S | 2 |
| 1449 | 2,4-diF—Ph | COOH | NH$_2$ | S | 2 |
| 1450 | 2,4-diF—Ph | Ac | NH$_2$ | S | 2 |
| 1451 | 2,4-diF—Ph | COOMe | NH$_2$ | S | 2 |
| 1452 | 2,4-diF—Ph | CONH$_2$ | NH$_2$ | S | 2 |
| 1453 | 2,4-diF—Ph | CONHMe | NH$_2$ | S | 2 |
| 1454 | 2-Cl—Ph | Br | NH$_2$ | O | 2 |
| 1455 | 2-Cl—Ph | I | NH$_2$ | O | 2 |
| 1456 | 2-Cl—Ph | Pn | NH$_2$ | O | 2 |
| 1457 | 2-Cl—Ph | Hex | NH$_2$ | O | 2 |
| 1458 | 2-Cl—Ph | 1-Cl—Et | NH$_2$ | O | 2 |
| 1459 | 2-Cl—Ph | All | NH$_2$ | O | 2 |
| 1460 | 2-Cl—Ph | Bun(2) | NH$_2$ | O | 2 |
| 1461 | 2-Cl—Ph | Pre$^i$ | NH$_2$ | O | 2 |

TABLE 1-continued

| Compd. No. | R¹ | R² | R³ | X | n |
|---|---|---|---|---|---|
| 1462 | 2-Cl—Ph | Prg | NH₂ | O | 2 |
| 1463 | 2-Cl—Ph | Pr^c | NH₂ | O | 2 |
| 1464 | 2-Cl—Ph | Pn^c | NH₂ | O | 2 |
| 1465 | 2-Cl—Ph | Pen^c(2) | NH₂ | O | 2 |
| 1466 | 2-Cl—Ph | CN | NH₂ | O | 2 |
| 1467 | 2-Cl—Ph | COOH | NH₂ | O | 2 |
| 1468 | 2-Cl—Ph | Ac | NH₂ | O | 2 |
| 1469 | 2-Cl—Ph | COOMe | NH₂ | O | 2 |
| 1470 | 2-Cl—Ph | CONH₂ | NH₂ | O | 2 |
| 1471 | 2-Cl—Ph | CONHMe | NH₂ | O | 2 |
| 1472 | 2-Cl—Ph | Br | NH₂ | S | 2 |
| 1473 | 2-Cl—Ph | I | NH₂ | S | 2 |
| 1474 | 2-Cl—Ph | Pn | NH₂ | S | 2 |
| 1475 | 2-Cl—Ph | Hex | NH₂ | S | 2 |
| 1476 | 2-Cl—Ph | 1-Cl—Et | NH₂ | S | 2 |
| 1477 | 2-Cl—Ph | All | NH₂ | S | 2 |
| 1478 | 2-Cl—Ph | Bun(2) | NH₂ | S | 2 |
| 1479 | 2-Cl—Ph | Pre^i | NH₂ | S | 2 |
| 1480 | 2-Cl—Ph | Prg | NH₂ | S | 2 |
| 1481 | 2-Cl—Ph | Pr^c | NH₂ | S | 2 |
| 1482 | 2-Cl—Ph | Pn^c | NH₂ | S | 2 |
| 1483 | 2-Cl—Ph | Pen^c(2) | NH₂ | S | 2 |
| 1484 | 2-Cl—Ph | CN | NH₂ | S | 2 |
| 1485 | 2-Cl—Ph | COOH | NH₂ | S | 2 |
| 1486 | 2-Cl—Ph | Ac | NH₂ | S | 2 |
| 1487 | 2-Cl—Ph | COOMe | NH₂ | S | 2 |
| 1488 | 2-Cl—Ph | CONH₂ | NH₂ | S | 2 |
| 1489 | 2-Cl—Ph | CONHMe | NH₂ | S | 2 |
| 1490 | 4-Cl—Ph | Br | NH₂ | O | 2 |
| 1491 | 4-Cl—Ph | I | NH₂ | O | 2 |
| 1492 | 4-Cl—Ph | Pn | NH₂ | O | 2 |
| 1493 | 4-Cl—Ph | Hex | NH₂ | O | 2 |
| 1494 | 4-Cl—Ph | 1-Cl—Et | NH₂ | O | 2 |
| 1495 | 4-Cl—Ph | All | NH₂ | O | 2 |
| 1496 | 4-Cl—Ph | Bun(2) | NH₂ | O | 2 |
| 1497 | 4-Cl—Ph | Pre^i | NH₂ | O | 2 |
| 1498 | 4-Cl—Ph | Prg | NH₂ | O | 2 |
| 1499 | 4-Cl—Ph | Pr^c | NH₂ | O | 2 |
| 1500 | 4-Cl—Ph | Pn^c | NH₂ | O | 2 |
| 1501 | 4-Cl—Ph | Pen^c(2) | NH₂ | O | 2 |
| 1502 | 4-Cl—Ph | CN | NH₂ | O | 2 |
| 1503 | 4-Cl—Ph | COOH | NH₂ | O | 2 |
| 1504 | 4-Cl—Ph | Ac | NH₂ | O | 2 |
| 1505 | 4-Cl—Ph | COOMe | NH₂ | O | 2 |
| 1506 | 4-Cl—Ph | CONH₂ | NH₂ | O | 2 |
| 1507 | 4-Cl—Ph | CONHMe | NH₂ | O | 2 |
| 1508 | 4-Cl—Ph | Br | NH₂ | S | 2 |
| 1509 | 4-Cl—Ph | I | NH₂ | S | 2 |
| 1510 | 4-Cl—Ph | Pn | NH₂ | S | 2 |
| 1511 | 4-Cl—Ph | Hex | NH₂ | S | 2 |
| 1512 | 4-Cl—Ph | 1-Cl—Et | NH₂ | S | 2 |
| 1513 | 4-Cl—Ph | All | NH₂ | S | 2 |
| 1514 | 4-Cl—Ph | Bun(2) | NH₂ | S | 2 |
| 1515 | 4-Cl—Ph | Pre^i | NH₂ | S | 2 |
| 1516 | 4-Cl—Ph | Prg | NH₂ | S | 2 |
| 1517 | 4-Cl—Ph | Pr^c | NH₂ | S | 2 |
| 1518 | 4-Cl—Ph | Pn^c | NH₂ | S | 2 |
| 1519 | 4-Cl—Ph | Pen^c(2) | NH₂ | S | 2 |
| 1520 | 4-Cl—Ph | CN | NH₂ | S | 2 |
| 1521 | 4-Cl—Ph | COOH | NH₂ | S | 2 |
| 1522 | 4-Cl—Ph | Ac | NH₂ | S | 2 |
| 1523 | 4-Cl—Ph | COOMe | NH₂ | S | 2 |
| 1524 | 4-Cl—Ph | CONH₂ | NH₂ | S | 2 |
| 1525 | 4-Cl—Ph | CONHMe | NH₂ | S | 2 |
| 1526 | 2,3-diCl—Ph | H | NH₂ | O | 2 |
| 1527 | 2,3-diCl—Ph | Cl | NH₂ | O | 2 |
| 1528 | 2,3-diCl—Ph | Et | NH₂ | O | 2 |
| 1529 | 2,3-diCl—Ph | Pr | NH₂ | O | 2 |
| 1530 | 2,3-diCl—Ph | Pr^i | NH₂ | O | 2 |
| 1531 | 2,3-diCl—Ph | Bu^i | NH₂ | O | 2 |
| 1532 | 2,3-diCl—Ph | Bu^t | NH₂ | O | 2 |
| 1533 | 2,3-diCl—Ph | H | NH₂ | S | 2 |
| 1534 | 2,3-diCl—Ph | Cl | NH₂ | S | 2 |
| 1535 | 2,3-diCl—Ph | Et | NH₂ | S | 2 |
| 1536 | 2,3-diCl—Ph | Pr | NH₂ | S | 2 |
| 1537 | 2,3-diCl—Ph | Pr^i | NH₂ | S | 2 |
| 1538 | 2,3-diCl—Ph | Bu^i | NH₂ | S | 2 |
| 1539 | 2,3-diCl—Ph | Bu^t | NH₂ | S | 2 |
| 1540 | 2,4-diCl—Ph | Br | NH₂ | O | 2 |
| 1541 | 2,4-diCl—Ph | I | NH₂ | O | 2 |
| 1542 | 2,4-diCl—Ph | Pn | NH₂ | O | 2 |
| 1543 | 2,4-diCl—Ph | Hex | NH₂ | O | 2 |
| 1544 | 2,4-diCl—Ph | 1-Cl—Et | NH₂ | O | 2 |
| 1545 | 2,4-diCl—Ph | All | NH₂ | O | 2 |
| 1546 | 2,4-diCl—Ph | Bun(2) | NH₂ | O | 2 |
| 1547 | 2,4-diCl—Ph | Pre^i | NH₂ | O | 2 |
| 1548 | 2,4-diCl—Ph | Prg | NH₂ | O | 2 |
| 1549 | 2,4-diCl—Ph | Pr^c | NH₂ | O | 2 |
| 1550 | 2,4-diCl—Ph | Pn^c | NH₂ | O | 2 |
| 1551 | 2,4-diCl—Ph | Pen^c(2) | NH₂ | O | 2 |
| 1552 | 2,4-diCl—Ph | CN | NH₂ | O | 2 |
| 1553 | 2,4-diCl—Ph | COOH | NH₂ | O | 2 |
| 1554 | 2,4-diCl—Ph | Ac | NH₂ | O | 2 |
| 1555 | 2,4-diCl—Ph | COOMe | NH₂ | O | 2 |
| 1556 | 2,4-diCl—Ph | CONH₂ | NH₂ | O | 2 |
| 1557 | 2,4-diCl—Ph | CONHMe | NH₂ | O | 2 |
| 1558 | 2,4-diCl—Ph | Br | NH₂ | S | 2 |
| 1559 | 2,4-diCl—Ph | I | NH₂ | S | 2 |
| 1560 | 2,4-diCl—Ph | Pn | NH₂ | S | 2 |
| 1561 | 2,4-diCl—Ph | Hex | NH₂ | S | 2 |
| 1562 | 2,4-diCl—Ph | 1-Cl—Et | NH₂ | S | 2 |
| 1563 | 2,4-diCl—Ph | All | NH₂ | S | 2 |
| 1564 | 2,4-diCl—Ph | Bun(2) | NH₂ | S | 2 |
| 1565 | 2,4-diCl—Ph | Pre^i | NH₂ | S | 2 |
| 1566 | 2,4-diCl—Ph | Prg | NH₂ | S | 2 |
| 1567 | 2,4-diCl—Ph | Pr^c | NH₂ | S | 2 |
| 1568 | 2,4-diCl—Ph | Pn^c | NH₂ | S | 2 |
| 1569 | 2,4-diCl—Ph | Pen^c(2) | NH₂ | S | 2 |
| 1570 | 2,4-diCl—Ph | CN | NH₂ | S | 2 |
| 1571 | 2,4-diCl—Ph | COOH | NH₂ | S | 2 |
| 1572 | 2,4-diCl—Ph | Ac | NH₂ | S | 2 |
| 1573 | 2,4-diCl—Ph | COOMe | NH₂ | S | 2 |
| 1574 | 2,4-diCl—Ph | CONH₂ | NH₂ | S | 2 |
| 1575 | 2,4-diCl—Ph | CONHMe | NH₂ | S | 2 |
| 1576 | 2,4-diCl—3-Me—Ph | H | NH₂ | O | 2 |
| 1577 | 2,4-diCl—3-Me—Ph | Cl | NH₂ | O | 2 |
| 1578 | 2,4-diCl—3-Me—Ph | Et | NH₂ | O | 2 |
| 1579 | 2,4-diCl—3-Me—Ph | Pr | NH₂ | O | 2 |
| 1580 | 2,4-diCl—3-Me—Ph | Pr^i | NH₂ | O | 2 |
| 1581 | 2,4-diCl—3-Me—Ph | Bu^i | NH₂ | O | 2 |
| 1582 | 2,4-diCl—3-Me—Ph | Bu^t | NH₂ | O | 2 |
| 1583 | 2,4-diCl—3-Me—Ph | H | NH₂ | S | 2 |
| 1584 | 2,4-diCl—3-Me—Ph | Cl | NH₂ | S | 2 |
| 1585 | 2,4-diCl—3-Me—Ph | Et | NH₂ | S | 2 |
| 1586 | 2,4-diCl—3-Me—Ph | Pr | NH₂ | S | 2 |
| 1587 | 2,4-diCl—3-Me—Ph | Pr^i | NH₂ | S | 2 |
| 1588 | 2,4-diCl—3-Me—Ph | Bu^i | NH₂ | S | 2 |
| 1589 | 2,4-diCl—3-Me—Ph | Bu^t | NH₂ | S | 2 |
| 1590 | 2,4-diCl—3-Et—Ph | H | NH₂ | O | 2 |
| 1591 | 2,4-diCl—3-Et—Ph | Cl | NH₂ | O | 2 |
| 1592 | 2,4-diCl—3-Et—Ph | Et | NH₂ | O | 2 |
| 1593 | 2,4-diCl—3-Et—Ph | Pr | NH₂ | O | 2 |
| 1594 | 2,4-diCl—3-Et—Ph | Pr^i | NH₂ | O | 2 |
| 1595 | 2,4-diCl—3-Et—Ph | Bu^i | NH₂ | O | 2 |
| 1596 | 2,4-diCl—3-Et—Ph | Bu^t | NH₂ | O | 2 |
| 1597 | 2,4-diCl—3-Et—Ph | H | NH₂ | S | 2 |
| 1598 | 2,4-diCl—3-Et—Ph | Cl | NH₂ | S | 2 |
| 1599 | 2,4-diCl—3-Et—Ph | Et | NH₂ | S | 2 |
| 1600 | 2,4-diCl—3-Et—Ph | Pr | NH₂ | S | 2 |
| 1601 | 2,4-diCl—3-Et—Ph | Pr^i | NH₂ |   | 2 |
| 1602 | 2,4-diCl—3-Et—Ph | Bu^i | NH₂ | S | 2 |
| 1603 | 2,4-diCl—3-Et—Ph | Bu^t | NH₂ | S | 2 |
| 1604 | 3,4-diCl—Ph | H | NH₂ | O | 2 |
| 1605 | 3,4-diCl—Ph | Cl | NH₂ | O | 2 |
| 1606 | 3,4-diCl—Ph | Et | NH₂ | O | 2 |
| 1607 | 3,4-diCl—Ph | Pr | NH₂ | O | 2 |
| 1608 | 3,4-diCl—Ph | Pr^i | NH₂ | O | 2 |
| 1609 | 3,4-diCl—Ph | Bu^i | NH₂ | O | 2 |

TABLE 1-continued

| Compd. No. | R¹ | R² | R³ | X | n |
|---|---|---|---|---|---|
| 1610 | 3,4-diCl—Ph | BUt | NH$_2$ | O | 2 |
| 1611 | 3,4-diCl—Ph | H | NH$_2$ | S | 2 |
| 1612 | 3,4-diCl—Ph | Cl | NH$_2$ | S | 2 |
| 1613 | 3,4-diCl—Ph | Et | NH$_2$ | S | 2 |
| 1614 | 3,4-diCl—Ph | Pr | NH$_2$ | S | 2 |
| 1615 | 3,4-diCl—Ph | Pr$^i$ | NH$_2$ | S | 2 |
| 1616 | 3,4-diCl—Ph | Bu$^i$ | NH$_2$ | S | 2 |
| 1617 | 3,4-diCl—Ph | BUt | NH$_2$ | S | 2 |
| 1618 | 4-Pr$^i$—Ph | H | NH$_2$ | O | 2 |
| 1619 | 4-Pr$^i$—Ph | Cl | NH$_2$ | O | 2 |
| 1620 | 4-Pr$^i$—Ph | Et | NH$_2$ | O | 2 |
| 1621 | 4-Pr$^i$—Ph | Pr | NH$_2$ | O | 2 |
| 1622 | 4-Pr$^i$—Ph | Pr$^i$ | NH$_2$ | O | 2 |
| 1623 | 4-Pr$^i$—Ph | Bu$^i$ | NH$_2$ | O | 2 |
| 1624 | 4-Pr$^i$—Ph | Bu$^t$ | NH$_2$ | O | 2 |
| 1625 | 4-Pr$^i$—Ph | H | NH$_2$ | S | 2 |
| 1626 | 4-Pr$^i$—Ph | Cl | NH$_2$ | S | 2 |
| 1627 | 4-Pr$^i$—Ph | Et | NH$_2$ | S | 2 |
| 1628 | 4-Pr$^i$—Ph | Pr | NH$_2$ | S | 2 |
| 1629 | 4-Pr$^i$—Ph | Pr$^i$ | NH$_2$ | S | 2 |
| 1630 | 4-Pr$^i$—Ph | Bu$^i$ | NH$_2$ | S | 2 |
| 1631 | 4-Pr$^i$—Ph | Bu$^t$ | NH$_2$ | S | 2 |
| 1632 | 4-PhO—Ph | H | NH$_2$ | O | 2 |
| 1633 | 4-PhO—Ph | Cl | NH$_2$ | O | 2 |
| 1634 | 4-PhO—Ph | Et | NH$_2$ | O | 2 |
| 1635 | 4-PhO—Ph | Pr | NH$_2$ | O | 2 |
| 1636 | 4-PhO—Ph | Pr$^i$ | NH$_2$ | O | 2 |
| 1637 | 4-PhO—Ph | Bu$^i$ | NH$_2$ | O | 2 |
| 1638 | 4-PhO—Ph | Bu$^t$ | NH$_2$ | O | 2 |
| 1639 | 4-PhO—Ph | H | NH$_2$ | S | 2 |
| 1640 | 4-PhO—Ph | Cl | NH$_2$ | S | 2 |
| 1641 | 4-PhO—Ph | Et | NH$_2$ | S | 2 |
| 1642 | 4-PhO—Ph | Pr | NH$_2$ | S | 2 |
| 1643 | 4-PhO—Ph | Pr$^i$ | NH$_2$ | S | 2 |
| 1644 | 4-PhO—Ph | Bu$^i$ | NH$_2$ | S | 2 |
| 1645 | 4-PhO—Ph | Bu$^t$ | NH$_2$ | S | 2 |
| 1646 | 4-BnO—Ph | H | NH$_2$ | O | 2 |
| 1647 | 4-BnO—Ph | Cl | NH$_2$ | O | 2 |
| 1648 | 4-BnO—Ph | Et | NH$_2$ | O | 2 |
| 1649 | 4-BnO—Ph | Pr | NH$_2$ | O | 2 |
| 1650 | 4-BnO—Ph | Pr$^i$ | NH$_2$ | O | 2 |
| 1651 | 4-BnO—Ph | Bu$^i$ | NH$_2$ | O | 2 |
| 1652 | 4-BnO—Ph | Bu$^t$ | NH$_2$ | O | 2 |
| 1653 | 4-BnO—Ph | H | NH$_2$ | S | 2 |
| 1654 | 4-BnO—Ph | Cl | NH$_2$ | S | 2 |
| 1655 | 4-BnO—Ph | Et | NH$_2$ | S | 2 |
| 1656 | 4-BnO—Ph | Pr | NH$_2$ | S | 2 |
| 1657 | 4-BnO—Ph | Pr$^i$ | NH$_2$ | S | 2 |
| 1658 | 4-BnO—Ph | Bu$^i$ | NH$_2$ | S | 2 |
| 1659 | 4-BnO—Ph | Bu$^t$ | NH$_2$ | S | 2 |
| 1660 | 4-NO$_2$—Ph | H | NH$_2$ | O | 2 |
| 1661 | 4-NO$_2$—Ph | Cl | NH$_2$ | O | 2 |
| 1662 | 4-NO$_2$—Ph | Et | NH$_2$ | O | 2 |
| 1663 | 4-NO$_2$—Ph | Pr | NH$_2$ | O | 2 |
| 1664 | 4-NO$_2$—Ph | Pr$^i$ | NH$_2$ | O | 2 |
| 1665 | 4-NO$_2$—Ph | Bu$^i$ | NH$_2$ | O | 2 |
| 1666 | 4-NO$_2$—Ph | Bu$^t$ | NH$_2$ | O | 2 |
| 1667 | 4-NO$_2$—Ph | H | NH$_2$ | S | 2 |
| 1668 | 4-NO$_2$—Ph | Cl | NH$_2$ | S | 2 |
| 1669 | 4-NO$_2$—Ph | Et | NH$_2$ | S | 2 |
| 1670 | 4-NO$_2$—Ph | Pr | NH$_2$ | S | 2 |
| 1671 | 4-NO$_2$—Ph | Pr$^i$ | NH$_2$ | S | 2 |
| 1672 | 4-NO$_2$—Ph | Bu$^i$ | NH$_2$ | S | 2 |
| 1673 | 4-NO$_2$—Ph | Bu$^t$ | NH$_2$ | S | 2 |
| 1674 | 4-OH—Ph | H | NH$_2$ | O | 2 |
| 1675 | 4-OH—Ph | Cl | NH$_2$ | O | 2 |
| 1676 | 4-OH—Ph | Et | NH$_2$ | O | 2 |
| 1677 | 4-OH—Ph | Pr | NH$_2$ | O | 2 |
| 1678 | 4-OH—Ph | Pr$^i$ | NH$_2$ | O | 2 |
| 1679 | 4-OH—Ph | Bu$^i$ | NH$_2$ | O | 2 |
| 1680 | 4-OH—Ph | Bu$^t$ | NH$_2$ | O | 2 |
| 1681 | 4-OH—Ph | H | NH$_2$ | S | 2 |
| 1682 | 4-OH—Ph | Cl | NH$_2$ | S | 2 |
| 1683 | 4-OH—Ph | Et | NH$_2$ | S | 2 |
| 1684 | 4-OH—Ph | Pr | NH$_2$ | S | 2 |
| 1685 | 4-OH—Ph | Pr$^i$ | NH$_2$ | S | 2 |
| 1686 | 4-OH—Ph | Bu$^i$ | NH$_2$ | S | 2 |
| 1687 | 4-OH—Ph | Bu$^t$ | NH$_2$ | S | 2 |
| 1688 | 4-AcO—Ph | H | NH$_2$ | O | 2 |
| 1689 | 4-AcO—Ph | Cl | NH$_2$ | O | 2 |
| 1690 | 4-AcO—Ph | Et | NH$_2$ | O | 2 |
| 1691 | 4-AcO—Ph | Pr | NH$_2$ | O | 2 |
| 1692 | 4-AcO—Ph | Pr$^i$ | NH$_2$ | O | 2 |
| 1693 | 4-AcO—Ph | Bu$^i$ | NH$_2$ | O | 2 |
| 1694 | 4-AcO—Ph | Bu$^t$ | NH$_2$ | O | 2 |
| 1695 | 4-AcO—Ph | H | NH$_2$ | S | 2 |
| 1696 | 4-AcO—Ph | Cl | NH$_2$ | S | 2 |
| 1697 | 4-AcO—Ph | Et | NH$_2$ | S | 2 |
| 1698 | 4-AcO—Ph | Pr | NH$_2$ | S | 2 |
| 1699 | 4-AcO—Ph | Pr$^i$ | NH$_2$ | S | 2 |
| 1700 | 4-AcO—Ph | Bu$^i$ | NH$_2$ | S | 2 |
| 1701 | 4-AcO—Ph | BUt | NH$_2$ | S | 2 |
| 1702 | 4-NH$_2$—Ph | H | NH$_2$ | O | 2 |
| 1703 | 4-NH$_2$—Ph | Cl | NH$_2$ | O | 2 |
| 1704 | 4-NH$_2$—Ph | Et | NH$_2$ | O | 2 |
| 1705 | 4-NH$_2$—Ph | Pr | NH$_2$ | O | 2 |
| 1706 | 4-NH$_2$—Ph | Pr$^i$ | NH$_2$ | O | 2 |
| 1707 | 4-NH$_2$—Ph | Bu$^i$ | NH$_2$ | O | 2 |
| 1708 | 4-NH$_2$—Ph | Bu$^t$ | NH$_2$ | O | 2 |
| 1709 | 4-NH$_2$—Ph | H | NH$_2$ | S | 2 |
| 1710 | 4-NH$_2$—Ph | Cl | NH$_2$ | S | 2 |
| 1711 | 4-NH$_2$—Ph | Et | NH$_2$ | S | 2 |
| 1712 | 4-NH$_2$—Ph | Pr | NH$_2$ | S | 2 |
| 1713 | 4-NH$_2$—Ph | Pr$^i$ | NH$_2$ | S | 2 |
| 1714 | 4-NH$_2$—Ph | Bu$^i$ | NH$_2$ | S | 2 |
| 1715 | 4-NH$_2$—Ph | Bu$^t$ | NH$_2$ | S | 2 |
| 1716 | 4-BzHN—Ph | H | NH$_2$ | O | 2 |
| 1717 | 4-BzHN—Ph | Cl | NH$_2$ | O | 2 |
| 1718 | 4-BzHN—Ph | Et | NH$_2$ | O | 2 |
| 1719 | 4-BzHN—Ph | Pr | NH$_2$ | O | 2 |
| 1720 | 4-BzHN—Ph | Pr$^i$ | NH$_2$ | O | 2 |
| 1721 | 4-BzHN—Ph | Bu$^i$ | NH$_2$ | O | 2 |
| 1722 | 4-BzHN—Ph | Bu$^t$ | NH$_2$ | O | 2 |
| 1723 | 4-BzHN—Ph | H | NH$_2$ | S | 2 |
| 1724 | 4-BzHN—Ph | Cl | NH$_2$ | S | 2 |
| 1725 | 4-BzHN—Ph | Et | NH$_2$ | S | 2 |
| 1726 | 4-BzHN—Ph | Pr | NH$_2$ | S | 2 |
| 1727 | 4-BzHN—Ph | Pr$^i$ | NH$_2$ | S | 2 |
| 1728 | 4-BzHN—Ph | Bu$^i$ | NH$_2$ | S | 2 |
| 1729 | 4-BzHN—Ph | Bu$^t$ | NH$_2$ | S | 2 |
| 1730 | Fur(2) | Br | NH$_2$ | O | 2 |
| 1731 | Fur(2) | I | NH$_2$ | O | 2 |
| 1732 | Fur(2) | Pn | NH$_2$ | O | 2 |
| 1733 | Fur(2) | Hex | NH$_2$ | O | 2 |
| 1734 | Fur(2) | 1-Cl—Et | NH$_2$ | O | 2 |
| 1735 | Fur(2) | All | NH$_2$ | O | 2 |
| 1736 | Fur(2) | Pre$^i$ | NH$_2$ | O | 2 |
| 1737 | Fur(2) | Bun(2) | NH$_2$ | O | 2 |
| 1738 | Fur(2) | Prg | NH$_2$ | O | 2 |
| 1739 | Fur(2) | Pr$^c$ | NH$_2$ | O | 2 |
| 1740 | Fur(2) | Pn$^c$ | NH$_2$ | O | 2 |
| 1741 | Fur(2) | Pen$^c$(2) | NH$_2$ | O | 2 |
| 1742 | Fur(2) | CN | NH$_2$ | O | 2 |
| 1743 | Fur(2) | COOH | NH$_2$ | O | 2 |
| 1744 | Fur(2) | Ac | NH$_2$ | O | 2 |
| 1745 | Fur(2) | COOMe | NH$_2$ | O | 2 |
| 1746 | Fur(2) | CONH$_2$ | NH$_2$ | O | 2 |
| 1747 | Fur(2) | CONHMe | NH$_2$ | O | 2 |
| 1748 | Fur(2) | Br | NH$_2$ | S | 2 |
| 1749 | Fur(2) | I | NH$_2$ | S | 2 |
| 1750 | Fur(2) | Pn | NH$_2$ | S | 2 |
| 1751 | Fur(2) | Hex | NH$_2$ | S | 2 |
| 1752 | Fur(2) | 1-Cl—Et | NH$_2$ | S | 2 |
| 1753 | Fur(2) | All | NH$_2$ | S | 2 |
| 1754 | Fur(2) | Pre$^i$ | NH$_2$ | S | 2 |
| 1755 | Fur(2) | Bun(2) | NH$_2$ | S | 2 |
| 1756 | Fur(2) | Prg | NH$_2$ | S | 2 |
| 1757 | Fur(2) | Pr$^c$ | NH$_2$ | S | 2 |
| 1758 | Fur(2) | Pn$^c$ | NH$_2$ | S | 2 |
| 1759 | Fur(2) | Pen$^c$(2) | NH$_2$ | S | 2 |
| 1760 | Fur(2) | CN | NH$_2$ | S | 2 |
| 1761 | Fur(2) | COOH | NH$_2$ | S | 2 |

TABLE 1-continued

| Compd. No. | R¹ | R² | R³ | X | n |
|---|---|---|---|---|---|
| 1762 | Fur(2) | Ac | NH₂ | S | 2 |
| 1763 | Fur(2) | COOMe | NH₂ | S | 2 |
| 1764 | Fur(2) | CONH₂ | NH₂ | S | 2 |
| 1765 | Fur(2) | CONHMe | NH₂ | S | 2 |
| 1766 | Thi(2) | Br | NH₂ | O | 2 |
| 1767 | Thi(2) | I | NH₂ | O | 2 |
| 1768 | Thi(2) | Pn | NH₂ | O | 2 |
| 1769 | Thi(2) | Hex | NH₂ | O | 2 |
| 1770 | Thi(2) | 1-Cl—Et | NH₂ | O | 2 |
| 1771 | Thi(2) | All | NH₂ | O | 2 |
| 1772 | Thi(2) | Preⁱ | NH₂ | O | 2 |
| 1773 | Thi(2) | Bun(2) | NH₂ | O | 2 |
| 1774 | Thi(2) | Prg | NH₂ | O | 2 |
| 1775 | Thi(2) | Prᶜ | NH₂ | O | 2 |
| 1776 | Thi(2) | Pnᶜ | NH₂ | O | 2 |
| 1777 | Thi(2) | Penᶜ(2) | NH₂ | O | 2 |
| 1778 | Thi(2) | CN | NH₂ | O | 2 |
| 1779 | Thi(2) | COOH | NH₂ | O | 2 |
| 1780 | Thi(2) | Ac | NH₂ | O | 2 |
| 1781 | Thi(2) | COOMe | NH₂ | O | 2 |
| 1782 | Thi(2) | CONH₂ | NH₂ | O | 2 |
| 1783 | Thi(2) | CONHMe | NH₂ | O | 2 |
| 1784 | Thi(2) | Br | NH₂ | S | 2 |
| 1785 | Thi(2) | I | NH₂ | S | 2 |
| 1786 | Thi(2) | Pn | NH₂ | S | 2 |
| 1787 | Thi(2) | Hex | NH₂ | S | 2 |
| 1788 | Thi(2) | 1-Cl—Et | NH₂ | S | 2 |
| 1789 | Thi(2) | All | NH₂ | S | 2 |
| 1790 | Thi(2) | Preⁱ | NH₂ | S | 2 |
| 1791 | Thi(2) | Bun(2) | NH₂ | S | 2 |
| 1792 | Thi(2) | Prg | NH₂ | S | 2 |
| 1793 | Thi(2) | Prᶜ | NH₂ | S | 2 |
| 1794 | Thi(2) | Pnᶜ | NH₂ | S | 2 |
| 1795 | Thi(2) | Penᶜ(2) | NH₂ | S | 2 |
| 1796 | Thi(2) | CN | NH₂ | S | 2 |
| 1797 | Thi(2) | COOH | NH₂ | S | 2 |
| 1798 | Thi(2) | Ac | NH₂ | S | 2 |
| 1799 | Thi(2) | COOMe | NH₂ | S | 2 |
| 1800 | Thi(2) | CONH₂ | NH₂ | S | 2 |
| 1801 | Thi(2) | CONHMe | NH₂ | S | 2 |
| 1802 | Ph | 1-Cl—Pr | NH₂ | O | 2 |
| 1803 | Ph | 1-Cl—Pr | NH₂ | S | 2 |
| 1804 | Ph | 1-Cl—Buⁱ | NH₂ | O | 2 |
| 1805 | Ph | 1-Cl—Buⁱ | NH₂ | S | 2 |
| 1806 | Ph | 1-Cl—Pnⁱ | NH₂ | O | 2 |
| 1807 | Ph | 1-Cl—Pnⁱ | NH₂ | S | 2 |
| 1808 | 2,4-diMe—Ph | H | NH₂ | O | 2 |
| 1809 | 2,4-diMe—Ph | Prⁱ | NH₂ | O | 2 |
| 1810 | 3,5-diMe—Ph | H | NH₂ | O | 2 |
| 1811 | 3,5-diMe—Ph | Prⁱ | NH₂ | O | 2 |

Of the isoxazole derivatives illustrated in the Table invention, preferred compounds are 1, 4, 5, 6, 7, 8, 9, 10, 11, 12, 13, 14, 15, 25, 27, 28, 29, 30, 32, 36, 48, 50, 54, 66, 70, 74, 93, 95, 99, 111, 112, 113, 114, 115, 116, 117, 125, 127, 131, 143, 146, 147, 148, 149, 150, 151, 152, 153, 154, 155, 170, 171, 172, 173, 174, 175, 176, 177, 178, 179, 180, 188, 190, 194, 206, 208, 212, 224, 226, 230, 242, 244, 248, 260, 262, 263, 264, 266, 278, 296, 298, 314, 316, 332, 334, 350, 357, 363, 368, 379, 386, 397, 408, 469, 475, 481, 505, 510, 511, 517, 523, 535, 538, 539, 540, 541, 542, 543, 544, 545, 546, 562, 568, 574, 580, 586, 592, 598, 604, 610, 616, 622, 628, 724, 728, 729, 730, 731, 732, 733, 752, 764, 776, 788, 794, 800, 806, 812, 818, 824, 1056, 1061, 1347, 1348, 1349, 1350, 1351, 1357, 1359, 1386, 1388, 1390, 1392, 1394, 1396, 1398, 1400, 1402, 1404, 1406, 1408, 1410, 1412, 1414, 1416, 1459, 1495, 1499, 1500, 1526, 1545, 1549, 1550, 1576, 1590, 1604, 1618, 1632, 1646, 1660, 1674, 1688, 1702, 1716, 1809 or 1811, more preferred compounds are 1, 4, 5, 6, 7, 8, 9, 11, 13, 14, 15, 30, 32, 36, 48, 50, 54, 66, 70, 74, 93, 95, 99, 111, 113, 117, 125, 127, 131, 143, 147, 149, 150, 151, 170, 172, 176, 188, 190, 194, 206, 208, 212, 224, 226, 230, 242, 244, 248, 260, 262, 263, 264, 266, 278, 296, 298, 314, 316, 332, 334, 350, 357, 363, 368, 379, 386, 397, 408, 469, 475, 481, 505, 510, 511, 517, 523, 535, 538, 539, 540, 541, 542, 543, 544, 545, 546, 562, 568, 574, 580, 586, 592, 598, 604, 610, 616, 622, 628, 724, 728, 729, 730, 731, 732, 733, 752, 764, 776, 788, 794, 800, 806, 812, 818, 824, 1056, 1061, 1392, 1394, 1398, 1809 or 1811, still more preferred compounds are 1, 4, 5, 6, 7, 8, 9, 11, 13, 14, 15, 30, 48, 66, 74, 93, 111, 117, 125, 143, 149, 150, 151, 170, 176, 188, 206, 224, 242, 260, 296, 314, 332, 350, 368, 386, 408, 469, 475, 481, 505, 510, 511, 517, 523, 535, 538, 539, 543, 568, 586, 598, 604, 622, 724, 733, 1392, 1394 or 1398, and particularly preferred compounds are 1, 4, 5, 6, 7, 8, 9, 11, 13, 66, 93, 111, 117, 125, 143, 149, 150, 151, 170, 176, 224, 260, 332, 386, 510, 535, 539, 543, 604, 1392, 1394 or 1398.

The most preferred compounds are:

Compound list No. 1: 3-(2-aminoethoxy)-5-phenylisoxazole,

Compound list No. 5: 3-(2-aminoethoxy)-4-chloro-5-phenylisoxazole,

Compound list No. 7: 3-(2-aminoethoxy)-4-ethyl-5-phenylisoxazole,

Compound list No. 8: 3-(2-aminoethoxy)-5-phenyl-4-propylisoxazole,

Compound list No. 9: 3-(2-aminoethoxy)-4-isopropyl-5-phenylisoxazole,

Compound list No. 11: 3-(2-aminoethoxy)-4-isobutyl-5-phenylisoxazole,

Compound list No. 117: 3-(2-aminoethoxy)-5-(2-chlorophenyl)-4-isopropylisoxazole, Compound list No. 143: 3-(2-aminoethoxy)-5-(4-chlorophenyl)isoxazole, Compound list No. 151: 3-(2-aminoethoxy)-5-(4-chlorophenyl)-4-isopropylisoxazole, Compound list No. 176: 3-(2-aminoethoxy)-5-(2,4-dichlorophenyl)-4-isopropylisoxazole, Compound list No. 510: 3-(2-aminoethoxy)-5-(2-furyl)-4-isopropylisoxazole, Compound list No. 535: 3-(2-aminoethoxy)-5-(2-thienyl)isoxazole, Compound list No. 539: 3-(2-aminoethoxy)-4-chloro-5-(2-thienyl)isoxazole, Compound list No. 543: 3-(2-aminoethoxy)-4-isopropyl-5-(2-thienyl)isoxazole, or Compound list No. 1392: 4-allyl-3-(2-aminoethoxy)-5-phenylisoxazole.

Methods for preparing the compounds of the present invention are illustrated below.

Method A

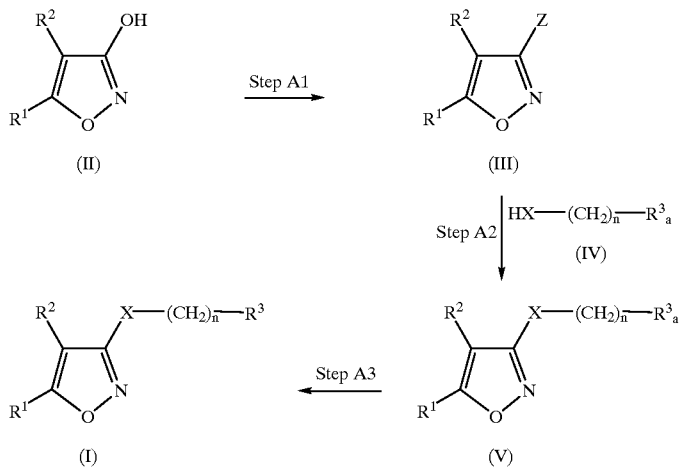

Method B

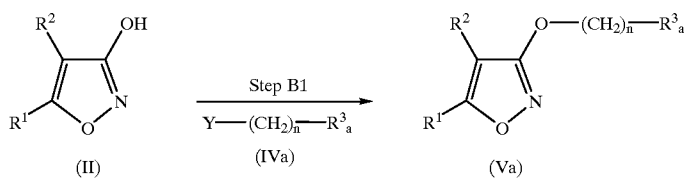

Method C

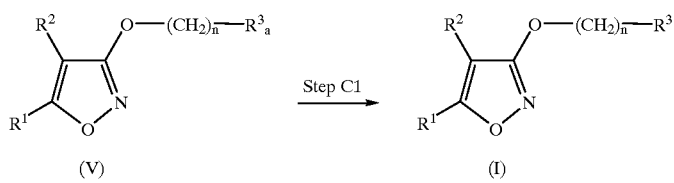

Wherein $R^1$, $R^2$, $R^3$, $1$ X and n have the same meanings as defined above, $R^3_a$ has the same meanings as defined for $R^3$ with the proviso that the amino group in $R^3$ is protected, Y represents a hydroxyl group or a leaving group, and Z represents a halogen atom.

The protecting group of the amino group or the mono $C_1$–$C_6$ alkylamino group of $R^3_a$ can be used without particular limitation so long as it is a group generally used as a protecting group for an amino group, and may be, for example, a $C_1$–$C_6$ alkanoyl group such as the formyl, acetyl, propionyl, butyryl, isobutyryl, pentanoyl, pivaloyl, valeryl, isovaleryl or hexanoyl groups; a $C_1$–$C_4$ alkanoyl group substituted with halogen or $C_1$–$C_4$ alkoxy, such as the chloroacetyl, dichloroacetyl, trichloroacetyl, trifluoroacetyl, 3-fluoropropionyl, 4,4-dichlorobutyryl, methoxyacetyl, butoxyacetyl, ethoxypropionyl or propoxybutyryl groups; an unsaturated $C_1$–$C_4$ alkanoyl group such as the acryloyl, propioloyl, methacryloyl, crotonoyl or isocrotonoyl groups; a $C_6$–$C_{10}$ arylcarbonyl group optionally substituted with halogen, $C_1$–$C_4$ alkyl, $C_1$–$C_4$ alkoxy, $C_1$–$C_4$ alkoxycarbonyl, $C_6$–$C_{10}$ aryl or nitro such as the benzoyl, α-naphthoyl, β-naphthoyl, 2-fluorobenzoyl, 2-bromobenzoyl, 2,4dichlorobenzoyl, 6-chloro-α-naphthoyl, 4-toluoyl, 4-propylbenzoyl, 4-t-butylbenzoyl, 2,4,6-trimethylbenzoyl, 6-ethyl-α-naphthoyl, 4-anisoyl, 4-propoxybenzoyl, 4-t-butoxybenzoyl, 6-ethoxy-α-naphthoyl, 2-ethoxycarbonylbenzoyl, 4-t-butoxycarbonylbenzoyl, 6-methoxycarbonyl-α-naphthoyl, 4-phenylbenzoyl, 4-phenyl-α-naphthoyl, 6-α-naphthylbenzoyl, 4-nitrobenzoyl, 2-nitrobenzoyl group or 6-nitro-α-naphthoyl groups; a $C_1$–$C_4$ alkoxycarbonyl group optionally substituted with halogen or tri-$C_1$–$C_4$ alkylsilyl such as the methoxycarbonyl, ethoxycarbonyl, propoxycarbonyl, isopropoxycarbonyl, butoxycarbonyl, isobutoxycarbonyl, s-butoxycarbonyl, t-butoxycarbonyl, chloromethoxycarbonyl, 2,2,2-trichloroethoxycarbonyl, 2-fluoropropoxycarbonyl, 2-bromo-t-butoxycarbonyl, 2,2-dibromo-t-butoxycarbonyl, triethylsilylrnethoxycarbonyl, 2-trimethylsilylethoxycarbonyl, 4-tripropylsilylbutoxycarbonyl or t-butyl-dimethylsilylpropoxycarbonyl groups; a $C_2$–$C_5$ alkenyloxycarbonyl group such as the vinyloxycarbonyl, allyloxycarbonyl, 1,3-butadienyloxycarbonyl or 2-pentenyloxycarbonyl groups; an aryldicarbonyl group such as a phthaloyl group; an aralkyl group such as the benzyl, phenethyl, 3-phenylpropyl, 4-phenylbutyl, α-naphthylmethyl, β-naphthylmethyl, diphenylmethyl, triphenylmethyl, or α-naphthyldiphenylmethyl group or 9-anthrylmethyl groups; or a $C_7$–$C_{15}$ aralkyloxycarbonyl group optionally substituted with methoxy or nitro such as the benzyloxycarbonyl, (1-phenyl)benzyloxycarbonyl, α-naphthylmethoxycarbonyl, β-naphthylmethoxycarbonyl, 9-anthrylmethoxycarbonyl, p-methoxybenzyloxycarbonyl or p-nitrobenzyloxycarbonyl groups, preferably, the $C_1$–$C_4$ alkanoyl; trifluoroacetyl; methoxyacetyl; benzoyl group; α-naphthoyl; P-naphthoyl; anisoyl; nitrobenzoyl; the $C_1$–$C_4$ alkoxycarbonyl; methoxycarbonyl; ethoxycarbonyl; t-butoxycarbonyl; 2,2,2-trichloroethoxycarbonyl; triethylsilylmethoxycarbonyl; 2-trimethylsilylethoxycarbonyl; vinyloxycarbonyl group; allyloxycarbonyl; phthaloyl; benzyl; benzyloxycarbonyl; or nitrobenzyloxycarbonyl groups, more preferably the formyl, acetyl, benzoyl, 4-anisoyl, 4-nitrobenzoyl, methoxycarbonyl, ethoxycarbonyl, butoxycarbonyl, t-butoxycarbonyl, phthaloyl, benzyl, benzyloxycarbonyl or p-nitrobenzyloxycarbonyl groups, most preferably the t-butoxycarbonyl group.

The leaving group of Y is not particularly limited so long as it is a usual leaving group as a nucleophilic residual group, and may be, for example, a halogen atom such as the chlorine, bromine or iodine atoms; a $C_1$–$C_4$ alkanesulfonyloxy group such as the methanesulfonyloxy, ethanesulfonyloxy, propanesulfonyloxy or butanesulfonyloxy groups; a halogeno $C_1$–$C_4$ alkanesulfonyloxy group such as the trifluoromethanesulfonyloxy, 2,2,2-trichloroethanesulfonyloxy, 3,3,3-tribromopropanesulfonyloxy or 4,4,4-trifluorobutanesulfonyloxy groups; or a $C_6$–$C_{10}$ arylsulfonyloxy group optionally having from one to three $C_1$–$C_4$ alkyls such as the benzenesulfonyloxy, α-naphthylsulfonyloxy, β-naphthylsulfonyloxy, p-toluenesulfonyloxy, 4-t-butylbenzenesulfonyloxy, mesitylenesulfonyloxy or 6-ethyl-α-naphthylsulfonyloxy groups, and preferably the chlorine, bromine or iodine atoms; the methanesulfonyloxy, ethanesulfonyloxy, trifluoromethanesulfonyloxy, 2,2,2-trichloroethanesulfonyloxy, benzenesulfonyloxy, toluenesulfonyloxy or mesitylenesulfonyloxy groups, more preferably the chlorine, bromine or iodine atoms, the methanesulfonyloxy, trifluoromethanesulfonyloxy, benzenesulfonyloxy, p-toluenesulfonyloxy or mesitylenesulfonyloxy groups.

The halogen atom of Z may be, for example, fluorine, chlorine, bromine or iodine atoms, and preferably the chlorine atom.

Method A is a method for synthesizing the compound of general formula (I).

In step A1 a compound of formula (III) is prepared by reacting a compound (II) with a halogenating agent in an inert solvent or in the absence of a solvent (preferably in an inert solvent) in the presence or absence of a base (preferably in the presence of a base).

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; or ethers such as diethyl ether, diisopropyl ether, tetrahydrofuran, dioxane, dimethoxyethane or diethylene glycol dimethyl ether, preferably halogenated hydrocarbons (particularly methylene chloride) or ethers (particularly tetrahydrofuran or dioxane).

The base to be employed here may be, for example, alkali metal carbonates such as sodium carbonate, potassium carbonate or lithium carbonate; alkali metal hydrogencarbonates such as sodium hydrogencarbonate, potassium hydrogencarbonate or lithium hydrogencarbonate; or organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), preferably alkali metal carbonates or organic amines, more preferably organic amines (particularly triethylamine or pyridine).

The halogenating agent to be employed here may be, for example, phosphorus oxychloride, phosphorus oxybromide, phosphorus oxyiodide or phosphorus pentachloride, or a mixture thereof, preferably phosphorus oxychloride, phosphorus pentachloride or a mixture thereof.

The reaction temperature may be varied depending on the nature of the starting material and reagent, and is usually from 0° C. to 150° C., preferably from 10° C. to 100° C.

The reaction time may be varied depending on the nature of the starting material, reagent and reaction temperature and is usually from 30 minutes to 10 hours, preferably from 1 to 5 hours.

After the completion of the reaction, the target compound of this step is isolated from the reaction mixture according to a conventional method. For example, the target compound is obtained by removing the solvent by evaporation, adding water to the reaction mixture, adding a hydrophobic solvent (for example, benzene, ether, ethyl acetate, etc.) to the resulting mixture to extract the target compound, washing the extracted organic layer with water, drying it over anhydrous magnesium sulfate and removing the solvent by evaporation. The target compound thus obtained may be further purified, if necessary, according to a conventional method, for example, recrystallization, reprecipitation or chromatography.

In step A2 a compound of formula (V) is prepared by reacting the compound (III) with a compound of the general formula (IV) in an inert solvent in the presence of a base.

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; amides such as formamide, dimethylformamide, dimethylacetamide or hexamethylphosphoric triamide; or sulfoxides such as dimethyl sulfoxide or sulfolane, preferably the ethers, amides or sulfoxides, more preferably the ethers (particularly diethyl ether, tetrahydrofuran or dioxane) or the amides (particularly dimethylformamide).

The base to be employed here may be, for example, alkali metal carbonates such as sodium carbonate, potassium carbonate or lithium carbonate; alkali metal hydrogencarbonates such as sodium hydrogencarbonate, potassium hydrogencarbonate or lithium hydrogencarbonate; alkali metal hydrides such as lithium hydride, sodium hydride or potassium hydride; alkali metal hydroxides such as sodium hydroxide, potassium hydroxide or lithium hydroxide; organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene (DBN), 1,4-diazabicyclo-[2.2.2]octane (DABCO) or 1,8-diazabicyclo[5.4.0]undec-7-ene (DBU); alkyllithiums such as methyllithium, ethyllithium or butyllithium; or lithium alkylamides such as lithium diisopropylamide or lithium dicyclohexylamide, preferably the alkali metal carbonates, alkali metal hydrides or organic amines, more preferably the alkali metal carbonates (particularly sodium carbonate or potassium carbonate) or the alkali metal hydrides (particularly sodium hydride).

Incidentally, in order to effectively carry out the reaction, crown ethers such as dibenzo-18-crown-6 can be also added to the reaction mixture.

The reaction temperature may be varied depending on the nature of the starting material and reagent, and is usually from −10° C. to 150° C., preferably from 0° C. to 80° C.

The reaction time may be varied depending on the nature of the starting material, reagent and reaction temperature and is usually from 30 minutes to 30 hours, preferably from 1 to 10 hours.

After the completion of the reaction, the target compound of this step is isolated from the reaction mixture according to a conventional method. For example, the target compound is obtained by appropriately neutralizing the reaction mixture, removing the insolubles by filtration, if necessary, in the case where the insolubles exist, removing the solvent by evaporation, adding water to the reaction mixture, adding a hydrophobic solvent (for example, benzene, ether, ethyl acetate, etc.) to the resulting mixture to extract the target compound, washing the extracted organic layer with water, drying the organic layer containing the desired product over anhydrous magnesium sulfate and removing the solvent by evaporation. The target compound thus obtained may be further purified, if necessary, according to a conventional method, for example, recrystallization, reprecipitation or chromatography.

In step A3 a compound of general formula (I) is prepared by removing the protecting group of the amino group or the alkylamino group, if necessary.

Removal of the protecting group of the amino group varies depending on the kind thereof and is generally carried out as follows according to a conventional method in organic chemistry.

In the case where the protecting group of the amino group is a $C_1$–$C_6$ alkanoyl group (preferably formyl or acetyl groups); a $C_6$–$C_{10}$ arylcarbonyl group (preferably a benzoyl group); a $C_1$–$C_4$ alkoxycarbonyl group optionally substituted with halogen or a tri-$C_1$–$C_4$ alkylsilyl group (preferably the methoxycarbonyl, ethoxycarbonyl, t-butoxycarbonyl, 2-trimethylsilylethoxycarbonyl, 2-bromo-t-butoxycarbonyl or 2,2-dibromo-t-butoxycarbonyl groups); a $C_2$–$C_5$ alkenyloxycarbonyl group (preferably a vinyloxycarbonyl group); or a $C_7$–$C_{15}$ aralkyloxycarbonyl group optionally substituted with methoxy or nitro (preferably the benzyloxycarbonyl, (1-phenyl) benzyloxycarbonyl, 9-anthrylmethoxycarbonyl, p-methoxybenzyloxycarbonyl or p-nitrobenzyloxycarbonyl groups), it can be removed by treating it with an acid in an inert solvent or an aqueous solvent. Further, in this case, the target compound can be also obtained as a salt. The acid to be employed here may be, for example, an acid such as hydrochloric acid, sulfuric acid, phosphoric acid, hydrobromic acid or trifluoroacetic acid, preferably hydrochloric acid, sulfuric acid, hydrobromic acid or trifluoroacetic acid.

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; esters such as methyl acetate or ethyl acetate; alcohols such as methanol, ethanol, propanol, isopropanol or butanol; amides such as formamide, dimethylformamide, dimethylacetamide or hexamethylphosphoric triamide; sulfoxides such as dimethyl sulfoxide or sulfolane; aliphatic acids such as formic acid or acetic acid; water; or an aqueous mixture of the above-mentioned solvent, preferably the halogenated hydrocarbons, ethers, alcohols, aliphatic acids or an aqueous mixture of the above-mentioned solvent, more preferably the halogenated hydrocarbons (particularly methylene chloride), ethers (particularly tetrahydrofuran or dioxane), aliphatic acids (particularly acetic acid), water; or an aqueous mixture of the above-mentioned solvent.

The reaction temperature may be varied depending on the nature of the starting material, solvent or acid used and is usually from −10° C. to 150° C., preferably from 0° C. to 60° C.

The reaction time may be varied depending on the nature of the starting material, solvent or acid used, and is usually from 5 minutes to 20 hours, preferably from 10 minutes to 5 hours.

After the completion of the reaction, the target compound of this step is isolated from the reaction mixture according to a conventional method. For example, the target compound is obtained by collecting the precipitated target compound in the reaction mixture by filtration or appropriately neutralizing the reaction mixture, removing the solvent by evaporation, adding water to the reaction mixture, adding a hydrophobic solvent (for example, benzene, ether, ethyl acetate, etc.) to the resulting mixture to extract the target compound, washing the extracted organic layer with water, drying the organic layer containing the target compound over anhydrous magnesium sulfate and removing the solvent by evaporation. The target compound thus obtained can be further purified, if necessary, by a conventional method, for example, recrystallization, reprecipitation or chromatography.

In the case where the protecting group of the amino group is an alkanoyl, arylcarbonyl, alkoxycarbonyl, alkenyloxycarbonyl, aryldicarbonyl, aralkyl or aralkyloxycarbonyl, it can be removed by treating it with a base in an inert solvent or an aqueous solvent.

The base to be employed here may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; or an alkali metal mercaptan such as methyl mercaptan sodium or ethyl mercaptan sodium, preferably the alkali metal carbonates (particularly the sodium carbonate or potassium carbonate), the alkali metal hydroxides (particularly the sodium hydroxide or potassium hydroxide), the alkali metal alkoxides (particularly the sodium methoxide, sodium ethoxide or potassium t-butoxide) or organic amines (particularly hydrazine or methylamine).

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; ethers such as diethyl ether, diisopropyl ether, tetrahydrofuran, dioxane, dimethoxyethane or diethylene glycol dimethyl ether; alcohols such as methanol, ethanol, propanol, isopropanol or butanol; amides such as dimethylacetamide or hexamethylphosphoric triamide; sulfoxides such as dimethyl sulfoxide or sulfolane; or an aqueous mixture of the above-mentioned solvent, preferably the halogenated hydrocarbons, ethers, alcohols, or an aqueous mixture of the above-mentioned solvent, more preferably the ethers (particularly the tetrahydrofuran or dioxane), the alcohols (particularly the methanol or ethanol) or an aqueous mixture of the above-mentioned solvent.

The reaction temperature may be varied depending on the nature of the starting material, solvent or base used and is usually from −10° C. to 150° C., preferably from 0° C. to 50° C.

The reaction time may be varied depending on the nature of the starting material, solvent or base used, and is usually from 30 minutes to 20 hours, preferably from 1 to 5 hours.

After completion of the reaction, the target compound of this step is isolated from the reaction mixture according to a conventional method. For example, the target compound is obtained by separating the precipitated target compound from the reaction mixture by filtration or removing the solvent by evaporation, adding water to the reaction mixture, separating the precipitate from the mixture by filtration, or adding a hydrophobic solvent (for example, benzene, ether, ethyl acetate, etc.) to the resulting mixture to extract the target compound, washing the extracted organic layer containing the target compound with water, drying it over anhydrous magnesium sulfate and removing the solvent by evaporation. The target compound thus obtained may be further purified, if necessary, according to a conventional method, for example, recrystallization, reprecipitation or chromatography.

Further, in the case where the protecting group of the amino group is a tert-butoxycarbonyl group, it can be removed by treating it with a silyl compound or an acid particularly in an inert solvent.

The silyl compound to be employed here may be, for example, trimethylsilyl chloride, trimethylsilyl iodide or trimethylsilyl trifluoromethanesulfonate.

The acid employed here may be, for example, aluminum chloride, hydrochloric acid or trifluoroacetic acid.

The solvent to be employed here is not particularly limited so long as it does not interfere with the reaction and can dissolve a certain amount of the starting material. Examples of suitable solvents may be halogenated hydrocarbons such as methylene chloride, chloroform or carbon tetrachloride; ethers such as diethyl ether, tetrahydrofuran or dioxane; and nitrites such as acetonitrile, preferably the halogenated hydrocarbons (particularly methylene chloride or chloroform) or the nitrites (particularly acetonitrile).

The reaction temperature may be varied depending on the nature of the starting material, reagent or solvent and is usually from −20° C. to 100° C., preferably from 0° C. to 50° C.

The reaction time may be varied depending on the nature of the starting material, reagent, solvent or reaction temperature, and is usually from 10 minutes to 10 hours, preferably from 30 minutes to 3 hours.

After the completion of the reaction, the target compound of this step is isolated from the reaction mixture according to a conventional method. For example, the target compound is obtained by separating the precipitated desired compound in the reaction mixture by filtration, or adding water to the reaction mixture, making the aqueous layer alkaline to separate the precipitated substance from the mixture by filtration or adding a hydrophobic solvent (for example, benzene, ether, ethyl acetate, etc.) to the resulting mixture to extract the desired compound, washing the organic layer containing the desired compound with water, drying it over anhydrous magnesium sulfate and removing the solvent by evaporation. The target compound thus obtained can be further purified, if necessary, by a usual method, for example, recrystallization, reprecipitation or chromatography.

Further, in the case where the protecting group of the amino group is an allyloxycarbonyl group, it can be removed using palladium and triphenylphosphine or nickel tetracarbonyl under similar reaction condition such as solvent, reaction temperature, reaction time and the like to those of the removal reaction of the aralkyl group, etc. by catalytic reduction reagent.

In the case where the protecting group of the amino group is an aralkyl group or a $C_7$–$C_{11}$ aralkyloxycarbonyl group, the protecting group can be removed easily by contacting it with a reductant (preferably a catalytic hydrogenation reaction in the presence of a catalyst) in an inert solvent or by a removal reaction using an oxidant.

In the case of the removal reaction of the protecting group by a catalytic hydrogenation reaction in a catalytic reduction, the solvent to be employed here is not particularly limited so long as it does not interfere with the present reaction. Examples of suitable solvents may be aliphatic hydrocarbons such as hexane or cyclohexane; aromatic hydrocarbons such as toluene, benzene or xylene; ethers such as diethyl ether, tetrahydrofuran or dioxane; esters such as ethyl acetate or propyl acetate; alcohols such as methanol, ethanol or isopropanol; aliphatic acids such as formic acid or acetic acid; or an aqueous mixture of the above solvent, preferably the aliphatic hydrocarbons, aromatic hydrocarbons, ethers, esters, alcohols, aliphatic acids or an aqueous mixture of the above solvent, more preferably the alcohols (particularly the methanol or ethanol), the aliphatic acids (particularly the formic acid or acetic acid) or an aqueous mixture of the above solvent.

The catalyst to be employed here is not particularly limited so long as it is used for usual catalytic reduction reaction. Examples of suitable catalysts may be palladium black, palladium-carbon, Raney nickel, rhodium-aluminum oxide or palladium-barium sulfate, preferably the palladium-carbon or Raney nickel.

The pressure of hydrogen is not particularly limited, and is usually between 1 and 10 atmospheric pressure, preferably it is 1 atmospheric pressures.

The reaction temperature may be varied depending on the nature of the starting material, solvent or reductant used and is usually from 0° C. to 100° C., preferably from 10° C. to 50° C.

The reaction time may be varied depending on the nature of the starting material, solvent, reductant or reaction temperature, and is usually from 15 minutes to 10 hours, preferably from 30 minutes to 3 hours.

After the completion of the reaction, the target compound of this step is isolated from the reaction mixture according to a conventional method. For example, the target compound is obtained by removing the catalyst by filtration, removing the solvent by evaporation, adding water to the reaction mixture, making the aqueous layer alkaline to separate the precipitate from the mixture by filtration or adding a hydrophobic solvent (for example, benzene, ether, ethyl acetate, etc.) to the resulting mixture to extract the desired compound, washing the organic layer containing the desired compound with water, drying it over anhydrous magnesium sulfate and removing the solvent by evaporation. The target compound thus obtained can be further purified, if necessary, by a conventional method, for example, recrystallization, reprecipitation or chromatography.

In a removal reaction of protecting group by oxidation the solvent to be employed is not particularly limited so long as it does not interfere with the present reaction. Examples of suitable solvents may be ketones such as acetone; halogenated hydrocarbons such as methylene chloride, chloroform or carbon tetrachloride; nitrites such as acetonitrile; ethers such as diethyl ether, tetrahydrofuran or dioxane; amides such as dimethylformamide, dimethylacetamide or hexamethylphosphoric triamide; sulfoxides such as dimethyl sulfoxide or an aqueous mixture of the above solvent, preferably the ketones, halogenated hydrocarbons, nitrites, ethers, amides, sulfoxides or an aqueous mixture of the above solvent, more preferably the ketones (particularly the acetone), the halogenated hydrocarbons (particularly the methylene chloride), the nitrites (particularly the acetonitrile), the amides (particularly the hexamethylphosphoric triamide), the sulfoxides (particularly the dimethyl sulfoxide) or an aqueous mixture of the above solvent.

The oxidant to be employed here may be, for example, potassium persulfate, sodium persulfate, ammonium cerium nitrate (CAN) or 2,3-dichloro-5,6-dicyano-p-benzoquinone (DDQ), preferably ammonium cerium nitrate (CAN) or 2,3-dichloro-5,6-dicyano-p-benzoquinone (DDQ).

The reaction temperature may be varied depending on the nature of the starting material, solvent or oxidant used and is usually from 0° C. to 150° C., preferably from 10° C. to 50° C.

The reaction time may be varied depending on the nature of the starting material, solvent and oxidant used and is usually from 15 minutes to 24 hours, preferably from 30 minutes to 5 hours.

After the completion of the reaction, the target compound of this step is isolated from the reaction mixture according to a conventional method. For example, the target compound is obtained by removing the oxidant by filtration, removing the solvent by evaporation, adding water to the reaction mixture, making the aqueous layer alkaline to separate the precipitate by filtration or adding a hydrophobic solvent (for example, benzene, ether, ethyl acetate, etc.) to the resulting mixture to extract the desired compound, washing the organic layer containing the desired compound with water, drying it over anhydrous magnesium sulfate and removing the solvent by evaporation. The target compound thus obtained can be further purified, if necessary, by a conventional method, for example, recrystallization, reprecipitation or chromatography.

Further, in the case where the protecting group of the amino group is removed using an acid, the desired compound is usually obtained in the form of a salt, but the amino group of the desired compound can be made to a free base by removing the acid used according to a conventional method in organic chemistry.

Method B is an alternative method for synthesizing the compound (Va) in which X is an oxygen atom in the intermediate compound (V) of Process A.

In step B1 a compound of formula (Va) is prepared by reacting the compound of formula (II) with the compound of formula (IVa).

In the case where Y is a hydroxyl group, the reaction is carried out by dehydration-condensation between the compound (II) and the corresponding compound (IVa) in an inert solvent in the presence of phosphine-compound and azo-compound as conducted based on the Mitsunobu reaction reported in $Bull.$ $Chem.$ $Soc.$ $Jap.,$ 40, 2380 (1967).

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; or ethers such as diethyl ether, diisopropyl ether, tetrahydrofuran, dioxane, dimethoxyethane or diethylene glycol dimethyl ether, preferably the aliphatic hydrocarbons, aromatic hydrocarbons or ethers, more preferably the ethers (particularly the diethyl ether or tetrahydrofuran).

The phosphine-compound to be employed here may be, for example, a tri-$C_1$–$C_6$ alkylphosphine such as trimethylphosphine, triethylphosphine, tripropylphosphine, tributylphosphine, tripentylphosphine or trihexylphosphine; a tri-$C_6$–$C_{10}$ arylphosphine such as triphenylphosphine, triindenylphosphine or trinaphthylphosphine; or a tri-$C_6$–$C_{10}$ arylphosphine optionally having $C_1$–$C_4$ alkyl as a sub stituent such as tolyldiphenylphosphine, tritolylphosphine, trimesitylphosphine, tributylphenylphosphine or tri-6-ethyl-2-naphthylphosphine, preferably the tri-$C_1$–$C_6$ alkylphosphines (particularly trimethylphosphine, triethylphosphine, tripropylphosphine or tributylphosphine) or tri-$C_6$–$C_{10}$ arylphosphine (particularly triphenylphosphine, triindenylphosphine or trinaphthylphosphine), more preferably the tri-$C_6$–$C_{10}$ arylphosphines (particularly triphenylphosphine).

The azo-compound to be employed here is not particularly limited so long as it is a known azodicarboxylic acid derivative, and may be, for example, a di-$C_1$–$C_4$ alkyl azodicarboxylate such as dimethyl azodicarboxylate, diethyl azodicarboxylate, dipropyl azodicarboxylate or dibutyl azodicarboxylate, preferably dimethyl azodicarboxylate or diethyl azodicarboxylate.

The reaction temperature may be varied depending on the nature of the starting material and reagent, and is usually from –10° C. to 100° C., preferably from 0° C. to 50° C.

The reaction time may be varied depending on the nature of the starting material, reagent and reaction temperature, and is usually from 15 minutes to 48 hours, preferably from 30 minutes to 24 hours.

After the completion of the reaction, the target compound of this step is isolated from the reaction mixture according to a conventional method. For example, the target compound is obtained by filtering off the insolubles in the case where they exist, removing the solvent by evaporation, or adding water to the residue obtained by removing the solvent by evaporation, adding a hydrophobic solvent (for example, benzene, ether, ethyl acetate, etc.) to the resulting mixture to effect extraction, washing the extract with water, drying over anhydrous magnesium sulfate and removing the solvent by evaporation. The target compound thus obtained can be further purified, if necessary, by a conventional method, for example, recrystallization, reprecipitation or chromatography.

In the case where Y is a leaving group, the compound (Va) can be prepared by reacting the compound (II) with the corresponding compound (IVa) in the presence of a base in an inert solvent.

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; amides such as formamide, dimethylformamide, dimethylacetamide or hexamethylphosphoric triamide; or sulfoxides such as dimethyl sulfoxide or sulfolane, preferably the amides and sulfoxides, more preferably the amides (particularly dimethylformamide, dimethylacetamide or hexamethylphosphoric triamide).

The base to be employed here may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; an alkali metal mercaptan such as methylmercaptan sodium on ethylmercaptan sodium; an organic amine such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2]-octane (DABCO) or 1,8-diazabicyclo[5.4.0]undec-7-ene (DBU); an alkyllithium such as methyllithium, ethyllithium or butyllithium; or a lithium alkylamide such as lithium diisopropylamide or lithium dicyclohexylamide, preferably the alkali metal carbonates, alkali metal hydrides or alkali metal hydroxides, more preferably the alkali metal hydrides (particularly sodium hydroxide).

A crown ether such as dibenzo-18-crown-6 may be added to enhance the reaction.

The reaction temperature may be varied depending on the nature of the starting material, the reagent, etc., and is usually from −10° C. to 100° C., preferably from 0° C. to 50° C.

The reaction time may be varied depending on the nature of the starting material, the reagent and the reaction temperature, and is usually from 30 minutes to 20 hours, preferably from 1 to 5 hours.

After the completion of the reaction, the target compound of this step is isolated from the reaction mixture according to a conventional method. For example, the target compound is obtained by appropriately neutralizing the reaction mixture, removing the insolubles by filtration in the case where they exist, removing the solvent by evaporation, adding water to the reaction mixture, adding a hydrophobic solvent (for example, benzene, ether, ethyl acetate, etc.) to the resulting mixture to effect extraction, washing the organic layer including the target compound with water, drying it over anhydrous magnesium sulfate and removing the solvent by evaporation. The target compound thus obtained can be further purified, if necessary, by a conventional method, for example, recrystallization, reprecipitation or chromatography.

Method C is an alternative method for synthesizing a compound (I) of method A.

Step C1 is carried out, if necessary, and includes reaction (a): the reaction in which an alkyl group, an alkoxy group or a carboxyl group is introduced to an isoxazole ring or an aromatic ring included in $R^1$, reaction (b): the reaction in which a hydroxyalkyl group is introduced to an isoxazole ring or an aromatic ring included in $R^1$, reaction (c): the reaction in which a hydroxyl group contained in the hydroxylalkyl group produced by the reaction (b) is converted to a halogen atom, reaction (d): the reaction in which a hydroxyl group contained in the hydroxylalkyl group produced by the reaction (b) is subjected to a 1,2-elimination reaction (β elimination), reaction (e): the reaction in which the hydroxylalkyl group produced by the reaction (b) is converted to a carbonyl group, reaction (f): the reaction in which a carboxyl group is esterified, reaction (g): the reaction in which an alkoxycarbonyl group is converted to a carbamoyl group, reaction (h): the reaction in which a carboxyl group is converted to a carbamoyl group, reaction (i): the reaction in which a carbamoyl group is converted to a cyano group, reaction (j): the reaction in which an alkoxy group on the aromatic ring is converted to a hydroxyl group, reaction (k): the reaction in which a hydroxyl group or an amino group is subjected to an acylation reaction, reaction (l): the reaction in which a hydroxyl group or an amino group is subjected to an aralkylation reaction, reaction (m): the reaction in which a nitro group is converted to an amino group, and reaction (n): the reaction in which the protecting group of the amino group included in $R^3_a$ is removed.

These reaction are carried out by appropriately in any order.

Reaction (a):

The reaction in which an alkyl group, an alkoxy group or a carboxyl group is introduced to an isoxazole ring or an aromatic ring in RI is carried out according to a conventional method in organic chemistry. For example, the reaction is carried out by reacting a halo $C_1$–$C_6$ alkane, di-$C_1$–$C_6$ alkylcarbonate or carbon dioxide (preferably a halo $C_1$–$C_6$ alkane or carbon dioxide) in the presence of a base in an inert solvent.

The halo $C_1$–$C_6$ alkane to be employed here may be, for example, methyl chloride, methyl bromide, methyl iodide, ethyl chloride, ethyl iodide, propyl bromide, butyl iodide, pentyl iodide or hexyl iodide, preferably methyl bromide or methyl iodide, more preferably methyl iodide.

The di-$C_1$–$C_6$ alkylcarbonate may be, for example, dimethyl carbonate, diethyl carbonate, dipropyl carbonate, diisopropyl carbonate, dibutyl carbonate, di-sec-butyl carbonate, di-tert-butyl carbonate, dipentyl carbonate or dihexyl carbonate, preferably dimethyl carbonate or diethyl carbonate.

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; diamines such as N,N,N',N'-tetramethylethylenediamine; amides such as formamide, dimethylformamide, dimethylacetamide or hexamethylphosphoric triamide or hexamethylphosphorous triamide; or sulfoxides such as dimethyl sulfoxide or sulfolane, preferably the ethers, amides or sulfoxides, more preferably the ethers (particularly tetrahydrofuran).

The base to be employed here may be, for example, an alkali metal hydride such as lithium hydride, sodium hydride or potassium hydride; an alkyllithium such as methyllithium, ethyllithium, butyllithium or sec-butyllithium; or a lithium alkylamide such as lithium diisopropylamide, lithium dicyclohexylamide, lithium bis(trimethylsilyl)amide, potassium bis(trimethylsilyl)amide or sodium bis(trimethylsilyl)amide, preferably the alkyllithiums (particularly butyllithium) or lithium alkylamides (particularly lithium diisopropylamide).

The reaction temperature may be varied depending on the nature of the starting material, the reagent, etc., and is usually from −100° C. to 30° C., preferably from −70° C. to 0° C.

The reaction time may be varied depending on the nature of the starting material, the reagent and the reaction temperature, and is usually from 5 minutes to 10 hours, preferably from 10 minutes to 5 hours.

After the completion of the reaction, the target compound of this step is isolated from the reaction mixture according to a conventional method. For example, the target compound is obtained by removing the solvent by evaporation, or adding water to the residue obtained by removing the solvent by evaporation, making the aqueous layer acidic, if desired, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (b):

The reaction in which a hydroxylalkyl group is introduced on an isoxazole ring or an aromatic ring in $R^1$ is carried out according to a conventional method in organic chemistry. For example, the reaction is carried out by reacting the compounds with aldehydes or ketones in the presence of a base in an inert solvent.

The aldehydes may be, for example, a straight or branched alkanal having from 2 to 6 carbon atoms such as acetaldehyde, propionaldehyde, butylaldehyde, isobutylaldehyde, valeraldehyde, isovaleraldehyde or hexaldehyde, preferably a $C_2$–$C_4$ alkanal, more preferably acetaldehyde.

The ketones may be, for example, a straight or branched alkanone having from 3 to 6 carbon atoms such as acetone, 2-butanone, 2-pentanone, 3-pentanone, 3-methyl-2-butanone, 2-hexanone, 3-hexanone, 3-methyl-2-pentanone, 4-methyl-2-pentanone or 3,3-dimethyl-2-butanone, preferably the acetone, 2-butanone or 3-butanone, more preferably acetone.

The solvent to be employed here is not particularly limited so long as it does not interfere with the reaction and can dissolve a certain amount of the starting material. Examples of suitable solvent may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; diamines such as N,N,N',N'-tetramethylethylenediamine; amides such as formamide, dimethylformamide, dimethylacetamide, hexamethylphosphoric triamide or hexamethylphosphorous triamide; or sulfoxides such as dimethyl sulfoxide or sulfolane, preferably the ethers, amides or sulfoxides, more preferably the ethers (particularly tetrahydrofuran).

The base to be employed here may be, for example, an alkali metal hydride such as lithium hydride, sodium hydride or potassium hydride; an alkyllithium such as methyllithium, ethyllithium, butyllithium or sec-butyllithium; or a lithium alkylamide such as lithium diisopropylamide, lithium dicyclohexylamide, lithium bis(trimethylsilyl)amide, potassium bis(trimethylsilyl)amide or sodium bis(trimethylsilyl)amide, preferably the alkyllithiums (particularly butyllithium) or lithium alkylamides (particularly lithium diisopropylamide).

The reaction temperature may be varied depending on the nature of the starting material, the reagent, etc., and is usually from −100° C. to 30° C., preferably from −70° C. to 0° C.

The reaction time may be varied depending on the nature of the starting material, the reagent and the reaction temperature, and is usually from 5 minutes to 10 hours, preferably from 10 minutes to 5 hours.

After the completion of the reaction, the target compound of this step is isolated from the reaction mixture according to a conventional method. For example, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (c):

The reaction in which a hydroxyl group in a hydroxyalkyl group produced by the reaction (b) is converted to a halogen atom is carried out according to a conventional method in organic chemistry. For example, the reaction is carried out by reacting a hydroxyl group with a hydrohalogenic acid in an inert solvent.

The hydrohalogenic acid to be employed may be, for example, hydrofluoric acid, hydrochloric acid, hydrobromic acid or hydroiodic acid, preferably hydrochloric acid.

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; esters such as methyl acetate or ethyl acetate; water, or an aqueous mixture of the above-mentioned solvent, preferably the ethers (particularly dioxane) or a mixture of ethers and water.

The reaction temperature may be varied depending on the nature of the starting material and reagent, and is usually from −50° C. to 80° C., preferably from 0° C. to 50° C.

The reaction time may be varied depending on the nature of the starting material, reagent and reaction temperature, and is usually from 5 minutes to 10 hours, preferably from 10 minutes to 5 hours.

After the completion of the reaction, the target compound of this step is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (d):

The reaction in which a hydroxyl group in the hydroxyalkyl group produced by the reaction (b) is subjected to 1,2-elimination reaction (β elimination) is carried out according to a conventional method in organic chemistry. For example, the reaction is carried out by reacting the hydroxyl group with an acid in an inert solvent.

The acid to be employed here may be, for example, a mineral acid such as hydrofluoric acid, hydrochloric acid, hydrobromic acid, hydroiodic acid, nitric acid, perchloric acid, sulfuric acid or phosphoric acid; a sulfonic acid such as methanesulfonic acid, trifluoromethanesulfonic acid, ethanesulfonic acid, benzenesulfonic acid or p-toluenesulfonic acid; or a carboxylic acid such as trifluoroacetic acid, fumaric acid, succinic acid, citric acid, tartaric acid, oxalic acid or maleic acid, preferably the mineral acids (particularly hydrochloric acid).

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; or esters such as methyl acetate or ethyl acetate, preferably the ethers or esters, more preferably the ethers (particularly dioxane).

The reaction temperature may be varied depending on the nature of the starting material and reagent, and is usually from 0° C. to 150° C., preferably from 50° C. to 130° C.

The reaction time may be varied depending on the nature of the starting material, reagent and reaction temperature, and is usually from 5 minutes to 10 hours, preferably from 10 minutes to 5 hours.

After the completion of the reaction, the target compound of this step is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (e):

The reaction in which the hydroxyalkyl group produced by the reaction (b) is converted to a carbonyl group is carried out according to a conventional method in organic chemistry. For example, the reaction is carried out by reacting the hydroxyalkyl group with an oxidant in an inert solvent.

The oxidant to be employed here is not particularly limited so long as it is used for an oxidation reaction, and may be, for example, an inorganic metal oxidant such as manganese oxides, e.g. potassium permanganate or manganese dioxide; a ruthenium oxide, e.g. ruthenium tetroxide; a silver compound such as silver oxide; a chromic acid compound, e.g. potassium chromate, chromic acid-sulfuric acid complex or chromic acid-pyridine complex, or a cerium compound such as ammonium cerium nitrate (CAN); a reagent used for DMSO oxidation (a complex of dimethyl sulfoxide and dicyclohexylcarbodiimide, oxalyl chloride, acetic anhydride or phosphorus pentoxide or a complex of pyridine-sulfuric anhydride); a succinimide such as N-bromosuccinimide; or a quinone compound such as 2,3-dichloro-5,6-dicyano-p-benzoquinone (DDQ), preferably the inorganic metal oxidants or the reagents used for DMSO oxidation, more preferably the inorganic metal oxidants (particularly the chromic acid-pyridine complex).

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; ketones such as acetone; esters such as methyl acetate or ethyl acetate; nitrites such as acetonitrile; amides such as dimethylformamide, dimethylacetamide or hexamethylphosphoric triamide; sulfoxides such as dimethyl sulfoxide; or an aqueous mixture of the above solvent, preferably the halogenated hydrocarbons, ethers, ketones, nitrites, amides or sulfoxides, more preferably the halogenated hydrocarbons (particularly methylene chloride).

The reaction temperature may be varied depending on the nature of the starting material and reagent, and is usually from 0° C. to 100° C., preferably from 20° C. to 50° C.

The reaction time may be varied depending on the nature of the starting material, reagent and reaction temperature, and is usually from 30 minutes to 48 hours, preferably from 1 to 30 hours.

After the completion of the reaction, the target compound of this step is isolated from the reaction mixture according to a conventional method. For example, the target compound is obtained by filtering off the oxidant, removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (f):

The reaction in which a carboxyl group is esterified is carried out according to a conventional method in organic chemistry. For example, the reaction is carried out by (1) reaction with an esterifying agent in an inert solvent,
(2) reaction with an active esterifying agent in an inert solvent to prepare an active ester and then reaction of the active ester with alcohol in an inert solvent, or (3) reaction with a halogenating agent in an inert solvent to prepare an acid halide and then reaction of the acid halide with alcohol.

The esterifying agent used in reaction (f1) is not particularly limited so long as it is usually used in organic chemistry, and may be, for example, a diazoalkane or trialkylsilyldiazoalkane, preferably a $C_1$–$C_6$ diazoalkane such as diazomethane, diazoethane, diazopropane, diazobutane, diazopentane or diazohexane; or trimethylsilyldiazomethane, more preferably a $C_1$–$C_4$ diazoalkane or trimethylsilyldiazomethane, particularly preferably diazomethane.

The solvent used in the reaction with the diazo $C_1$–$C_6$ alkane is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; esters such as methyl acetate or ethyl acetate; or a mixture of the above-mentioned solvents, preferably the halogenated hydrocarbons, ethers, esters or the mixture of the above-mentioned solvents, more preferably the ethers (particularly diethyl ether), esters (particularly the ethyl acetate) or a mixture of the above-mentioned solvents.

The solvent used in the reaction with the trimethylsilyldiazomethane is not particularly limited so long as it does not interfere with the reaction and can dissolve a certain amount of the starting material. Examples of suitable solvents may be alcohols such as methanol, ethanol, propanol, isopropanol, butanol, isobutanol, t-butanol, pentanol or hexanol; or a mixture of the solvent selected from the group consisting of aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; and esters such as methyl acetate or ethyl acetate and the above-mentioned alcohols, preferably the alcohols (particularly methanol), and a mixture of aromatic hydrocarbons (particularly benzene) and the alcohols (particularly methanol).

The reaction temperature may be varied depending on the nature of the starting material and reagent, and is usually from –10° C. to 100° C., preferably from 10° C. to 50° C.

The reaction time may be varied depending on the nature of the starting material and reagent and reaction temperature, and is usually from 10 minutes to 10 hours, preferably from 15 minutes to 2 hours.

After the completion of the reaction, the target compound of this step is isolated from the reaction mixture according to a conventional method. For example, after the reaction, the target compound is obtained by removing the solvent by evaporation. The target compound thus obtained can be further purified, if necessary, by a conventional method, for example, recrystallization, reprecipitation or chromatography.

The active esterifying agent used in reaction (f2) is not particularly limited so long as it is generally used in the technology of organic chemistry, and may be, for example, an N-hydroxy compound such as ethyl chloroformate, N-hydroxysuccinimide, 1-hydroxybenzotriazole or N-hydroxy-5-norbomene-2,3-dicarboximide; or a disulfide compound such as dipyridyldisulfide.

The esterification reaction is preferably carried out in the presence of a condensing agent such as dicyclohexylcarbodiimide, carbonyldiimidazole or triphenylphosphine.

The solvent used in both reactions is not particularly limited so long as it does not interfere with the reaction and can dissolve a certain amount of the starting material. Examples of suitable solvents may be halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; amides such as formamide, dimethylformamide, dimethylacetamide or hexamethylphosphoric triamide; or nitriles such as acetonitrile, preferably the ethers (particularly tetrahydrofuran) or amides (particularly dimethylformamide).

The reaction temperature may be varied depending on the nature of the starting materials and reagents, and is usually from –70° C. to 150° C. (preferably from –10° C. to 100° C.) in the active esterification reaction and from –20° C. to 100° C. (preferably from 0° C. to 50° C.) in the reaction of the active ester compound with alcohols.

The reaction time may be varied depending on the nature of the starting materials, reagents and reaction temperatures, and is usually from 30 minutes to 80 hours (preferably from 1 to 48 hours) in both reactions.

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

The halogenating agent used in reaction (f3) is not particularly limited so long as it is generally used in the technology of organic chemistry, and may be, for example, oxalyl chloride, thionyl chloride, phosphorus oxychloride or phosphorus pentachloride, preferably thionyl chloride.

The solvent used in both reactions is not particularly limited so long as it does not interfere with the reaction and can dissolve a certain amount of the starting material. Examples of suitable solvents may be aromatic hydrocarbons such as benzene, toluene or xylene; halogenated hydrocarbons such as methylene chloride, chloroform, carbon tetrachloride, dichloroethane, chlorobenzene or dichlorobenzene; and ethers such as diethyl ether, diisopropyl ether, tetrahydrofuran, dioxane, dimethoxyethane or diethylene glycol dimethyl ether, preferably the ethers (particularly tetrahydrofuran).

The reaction temperature varies depending on the starting materials and reagents, and is usually from –70° C. to 150° C. (preferably from –10° C. to 100° C.) in the halogenation reaction and from –20° C. to 100° C. (preferably from 0° C. to 50° C.) in the reaction of an acid halide with alcohol.

The time required for both reactions vary depending on the nature of the starting materials and reagents and reaction temperatures, and is usually from 30 minutes to 80 hours (preferably from 1 to 48 hours).

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (g):

The reaction in which an alkoxycarbonyl group is converted to a carbamoyl group in reaction (g) is carried out according to a conventional method in organic chemistry. For example, the reaction is carried out by reacting the alkoxycarbonyl group with ammonia gas or conc. ammonia water in an inert solvent.

The solvent to be employed here is not particularly limited so long as it does not interfere with the reaction and can dissolve a certain amount of the starting material. Examples of suitable solvents may be aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; alcohols such as methanol, ethanol, propanol, isopropanol, butanol or isobutanol; diamines such as N,N,N',N'-tetramethylethylenediamine; amides such as formamide, dimethylformamide, dimethylacetamide, hexamethylphosphoric triamide or hexamethylphosphorous triamide; or sulfoxides such as dimethyl sulfoxide or sulfolane, preferably the ethers or alcohols, more preferably the ethers (particularly tetrahydrofuran).

The reaction temperature may be varied depending on the nature of the starting material and reagent, and is usually from −10° C. to 100° C., preferably from 0° C. to 50° C.

The reaction time may be varied depending on the nature of the starting material, reagent and reaction temperature, and is usually from 10 minutes to 10 hours, preferably from 30 minutes to 3 hours.

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (h):

The reaction in which a carboxyl group is converted to a carbamoyl group is carried out according to a conventional method in organic chemistry. For example, the reaction is carried out by condensing the carboxyl group with ammonia in an inert solvent according to a conventional method in a peptide synthesis method, for example, an azide method, an active ester method, a mixed acid anhydride method or a condensation method (preferably the mixed acid anhydride method).

In the above-mentioned method, the azide method is carried out by reacting an amino acid hydrazide, which is obtained by reacting with hydrazine in an inert solvent (for example, an amide such as formamide, dimethylformamide, dimethylacetamide or hexamethylphosphoric triamide, preferably dimethylformamide) at from −10° C. to 100° C. (preferably from 0° C. to 50° C.), with a nitrite compound to afford an azide compound and then treating it with ammonia.

The nitrite compound to be employed here may be, for example, an alkali metal nitrite such as sodium nitrite or an alkyl nitrite such as isoamyl nitrite.

The reaction is preferably carried out in an inert solvent, and the solvent to be employed here may be, for example, an amide such as formamide, dimethylformamide, dimethylacetamide or hexamethylphosphoric triamide; a sulfoxide such as dimethyl sulfoxide or sulfolane; or a pyrrolidone such as NNmethylpyrrolidone, preferably the amides (particularly dimethylformamide).

Further, the two steps of the present reaction (azidation and the reaction with ammonia) are usually carried out in one reaction solution.

The reaction temperature may be varied depending on the nature of the starting materials and reagents, and is usually from −70° C. to 50° C. (preferably from −50° C. to 0° C.) in the step of azidation and usually from −70° C. to 50° C. (preferably from −10° C. to 10° C.) in the reaction with ammonia.

The time required for the reaction varies depending on the nature of the starting material, reagent and reaction temperature. It is usually from 5 minutes to 3 hours (preferably from 10 minutes to one hour) in the step of azidation. It is from 5 hours to 7 days (preferably 10 hours to 5 days) in the reaction with ammonia.

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

The active ester method is carried out by reacting with a reagent to prepare an active ester in an inert solvent and then reacting the active ester with ammonia in an inert solvent.

The solvent used in both reactions is not particularly limited so long as it does not interfere with the reaction and can dissolve a certain amount of the starting material, and may be, for example, a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; an amide such as formamide, dimethylformamide, dimethylacetamide or hexamethylphosphoric triamide; or a nitrile such as acetonitrile, preferably the ethers (particularly tetrahydrofuran) or the amides (particularly dimethylformamide).

The reagent to prepare an active ester employed here may be, for example, an N-hydroxy compound such as N-hydroxysuccinimide, 1-hydroxybenzotriazole or N-hydroxy-5-norbornene-2,3-dicarboxyimide; or a disulfide compound such as dipyridyldisulfide. The active esterification reaction is preferably carried out in the presence of a condensing agent such as dicyclohexylcarbodiimide, carbonyldiimidazole or triphenylphosphine.

The reaction temperatures may be varied depending on the nature of the starting materials and reagent, and are usually from −70° C. to 150° C. (preferably from −10° C. to 100° C.) in the active esterification reaction and from −20° C. to 100° C. (preferably from 0° C. to 50° C.) in the reaction of the active ester compound with ammonia.

The times required for the both reactions may be varied depending on the nature of the starting materials, reagents and reaction temperatures, and are usually from 30 minutes to 80 hours (preferably from 1 to 48 hours).

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

The mixed acid anhydride method is carried out by reacting with a reagent to prepare a mixed acid anhydride in the presence of a base in an inert solvent and then reacting the mixed acid anhydride with ammonia in an inert solvent.

The solvent used in the reaction for preparing the mixed acid anhydride is not particularly limited so long as it does not interfere with the reaction and can dissolve a certain amount of the starting material, and may be, for example, a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; or an amide such as formamide, dimethylformamide, dimethylacetamide or hexamethylphosphoric triamide, preferably the ethers (particularly tetrahydrofuran).

Examples of reagents to prepare mixed acid anhydrides may be, for example, $C_1$–$C_4$ alkyl haloformates such as ethyl chloroformate or isobutyl chloroformate; $C_1$–$C_5$ alkanoyl halide such as pivaloyl chloride or $C_1$–$C_4$ alkyl; or di-$C_6$–$C_{14}$ arylcyanophosphoric acid such as diethylcyanophosphoric acid or diphenylcyanophosphoric acid, preferably the $C_1$–$C_4$ alkyl haloformate (particularly isobutyl chloroformate).

The base employed here may be, for example, an alkali metal carbonate such as sodium carbonate, potassium carbonate or lithium carbonate; or an organic amine such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane (DABCO) or 1,8-diazabicyclo[5.4.0]undec-7-ene (DBU), preferably the organic amines particularly triethylamine).

The reaction temperature in the reaction for preparing the mixed acid anhydride may be varied depending on the nature of the starting material and reagent, and is usually from −50° C. to 100° C. (preferably from −10° C. to 50° C.).

The reaction time in the reaction for preparing the mixed acid anhydride may be varied depending on the nature of the starting material, reagent and reaction temperature, and is usually from 5 minutes to 20 hours (preferably from 10 minutes to 10 hours).

The solvent used in the reaction of the mixed acid anhydride with ammonia is not particularly limited so long as it does not interfere with the reaction and can dissolve a certain amount of the starting material, and may be, for example, an ether such as diethyl ether, diisopropyl ether, tetrahydrofuran, dioxane, dimethoxyethane or diethylene glycol dimethyl ether; or an amide such as formamide, dimethylformamide, dimethylacetamide or hexamethylphosphoric triamide, preferably the ethers (particularly tetrahydrofuran).

The reaction temperature in the reaction of the mixed acid anhydride with ammonia may be varied depending on the nature of the starting material and reagent, and is usually from −30° C. to 100° C. (preferably from 0° C. to 80° C.).

The reaction time in the reaction of the mixed acid anhydride with ammonia may be varied depending on the nature of the starting material, reagent and reaction temperature, and is usually from 5 minutes to 24 hours (preferably from 10 minutes to 5 hours).

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

The condensation method is carried out by directly reacting a carboxyl group with ammonia in the presence of a condensing agent in an inert solvent.

The condensing agent employed here may be, for example, dicyclohexylcarbodiimide, carbonyldiimidazole or 1-methyl-2-chloro-pyridiniumiodotriethylamine, preferably dicyclohexylcarbodiimide.

The present reaction can be carried out under similar conditions to those described in the preparation of active ester.

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (i):

The reaction in which a carbamoyl group is converted to a cyano group is carried out according to a conventional method in organic chemistry. For example, the reaction is carried out by reacting a carbamoyl group with a dehydrating agent in an inert solvent.

The solvent to be employed here is not particularly limited so long as it does not interfere with the reaction and can dissolve a certain amount of the starting material, and may be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; an ester such as methyl acetate or ethyl acetate; a ketone such as acetone; an amide such as formamide, dimethylformamide, dimethylacetamide, hexamethylphosphoric triamide or hexamethylphosphorous triamide; or a sulfoxide such as dimethyl sulfoxide or sulfolane, preferably the ethers, amides, or sulfoxides, more preferably the amides (particularly dimethylformamide).

The dehydrating agent employed here may be, for example, phosphorus oxychloride, trifluoroacetic anhydride, methanesulfonyl chloride, paratoluenesulfonyl chloride or phosphorus pentoxide, preferably phosphorus oxychloride.

The reaction temperature may be varied depending on the nature of the starting material and reagent, and is usually from −30° C. to 100° C., preferably from 0° C. to 50° C.

The reaction time may be varied depending on the nature of the starting material, reagent and the reaction temperature, and is usually from 5 minutes to 10 hours, preferably from 10 minutes to 3 hours.

After completion of the reaction, the target compound of this reaction is isolated from the reaction mixture according to a conventional method. For example, the target compound is obtained by removing the solvent by evaporation, or adding water to the reaction mixture, adding a hydrophobic solvent (for example, benzene, ether, ethyl acetate, etc.) to the resulting mixture to extract the desired compound, washing the organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (j):

The reaction in which the alkoxy group on an aromatic ring is converted to a hydroxyl group is carried out according to a conventional method in organic chemistry. For example, the reaction is carried out by reacting the alkoxy group with aluminum chloride in an inert solvent.

The solvent employed here is not particularly limited so long as it does not interfere with the reaction and can dissolve a certain amount of the starting material, and may be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; or an ester such as methyl acetate or ethyl acetate, preferably the halogenated hydrocarbons (particularly methylene chloride).

The reaction temperature may be varied depending on the nature of the starting material and reagent, and is usually from −10° C. to 100° C., preferably from 10° C. to 50° C.

The reaction time may be varied depending on the nature of the starting material, reagent and reaction temperature, and is usually from 1 to 72 hours, preferably from 2 to 30 hours.

After completion of the reaction, the target compound of this reaction is isolated from the reaction mixture according to a conventional method. For example, the target compound is obtained by removing the solvent by evaporation, adding water to the reaction mixture, neutralizing it, if desired, adding a hydrophobic solvent (for example, benzene, ether, ethyl acetate, etc.) to the resulting mixture to extract the desired compound, washing the organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (k):

The reaction in which a hydroxyl group or an amino group is acylated is carried out according to a conventional method in organic chemistry. For example, the reaction is carried out by reacting a hydroxyl group or amino group with an acylating agent (preferably alkanoyl halide, a mixed acid anhydride of formic acid and acetic acid, alkanecarboxylic acid anhydride, arylcarbonyl halide or arylcarboxylic acid anhydride) in the presence or absence of a base (preferably in the presence of a base), in an inert solvent.

The alkanoyl halide employed here may be, for example, a straight or branched alkanoyl halide having from 2 to 6 carbon atoms such as acetyl chloride, propionyl chloride, butyryl chloride, butyryl bromide, isobutyryl chloride, valeryl chloride, pivaloyl chloride or hexanoyl chloride, preferably a $C_2$–$C_4$ alkanoyl chloride, more preferably acetyl chloride.

The alkanecarboxylic acid anhydride employed here may be, for example, a straight or branched alkanecarboxylic acid anhydride having from 4 to 12 carbon atoms such as acetic anhydride, propionic anhydride, butanoic anhydride, valeric anhydride, pivalic anhydride, pentanoic anhydride or hexanoic anhydride, preferably a $C_4$–$C_8$ alkanecarboxylic acid anhydride, more preferably acetic anhydride.

The arylcarbonyl halide employed here may be, for example, a $C_6$–C 10 arylcarboxylic acid halide such as benzoyl chloride, benzoyl bromide, fluorobenzoyl chloride, chlorobenzoyl chloride, dichlorobenzoyl chloride, toluoyl chloride, anisoyl chloride, indenoyl chloride, indenoyl bromide, naphthoyl chloride, naphthoyl bromide, phenanthrenoyl chloride or anthracenoyl chloride, preferably benzoyl chloride.

The arylcarboxylic acid anhydride employed here may be, for example, a $C_6$–$C_{10}$ arylcarboxylic acid anhydride such as benzoic anhydride, fluorobenzoic anhydride, chlorobenzoic anhydride, methylbenzoic anhydride, methoxybenzoic anhydride, indenylcarboxylic anhydride or naphthylcarboxylic anhydride, preferably benzoic anhydride.

The base employed here may be, for example, an alkali metal carbonate such as sodium carbonate, potassium carbonate or lithium carbonate; or an organic amine such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo-[2.2.2] octane (DABCO) or 1,8-diazabicyclo[5.4.0]undec-7-ene (DBU), preferably the organic amines (particularly triethylamine, diisopropylethylamine, pyridine or 4-(N,N-dimethylamino)pyridine).

The solvent employed here is not particularly limited so long as it does not interfere with the reaction and can dissolve a certain amount of the starting material, and may be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a ketone such as acetone and methyl ethyl ketone; or an amide such as formamide, dimethylformamide, dimethylacetamide or hexamethylphosphoric triamide, preferably the ethers (particularly tetrahydrofuran).

The reaction temperature may be varied depending on the nature of the starting material and the reagent, and is usually from −50° C. to 100° C. (preferably from 0° C. to 50° C.).

The reaction time may be varied depending on the nature of the starting material, reagent and reaction temperature, and is usually from 5 minutes to 20 hours (preferably from 10 minutes to 10 hours).

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (l):

The reaction in which a hydroxyl group or amino group is aralkylated is carried out according to a conventional method in organic chemistry. For example, the reaction is carried out by reacting a hydroxyl group or amino group with an aralkyl halide in the presence or absence of a base (preferably in the presence of a base) in an inert solvent.

The $C_6$–$C_{48}$ aralkyl halide to be employed here may be, for example, a $C_6$–$C_{48}$ aralkyl halide which has from 1 to 3 substituents which may be the same as or different from each other and selected from the group consisting of halogen, $C_1$–$C_6$ alkyl and $C_1$–$C_6$ alkoxy such as benzyl chloride, benzyl bromide, 4-chlorobenzyl chloride, 4-chlorobenzyl bromide, 4-bromobenzyl chloride, 4-bromobenzyl bromide, 2,4-difluorobenzyl chloride, 2,4-dichlorobenzyl chloride, 2,4-dichlorobenzyl bromide, 4-methoxybenzyl chloride, 4-methoxybenzyl bromide, trityl chloride, trityl bromide, dimethoxytrityl chloride or α-naphthyldiphenylmethyl chloride, preferably benzyl chloride or benzyl bromide which may have from 1 to 3 substituents which may be the same as or different from each other and selected from the group consisting of halogen, $C_1$–$C_4$ alkyl and $C_1$–$C_4$ alkoxy, more preferably benzyl chloride or benzyl bromide.

The base employed here may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]-undec-7-ene (DBU); an alkyllithium such as methyllithium, ethyllithium or butyllithium; or a lithium alkylamide such as lithium diisopropylamide or lithium dicyclohexylamide, preferably the alkali metal carbonates, alkali metal hydrides or organic amines, more preferably the alkali metal carbonates (particularly sodium carbonate or potassium carbonate) or alkali metal hydrides (particularly sodium hydride).

The solvent employed here is not particularly limited so long as it does not interfere with the reaction and can dissolve a certain amount of the starting material, and may be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a ketone such as acetone or methyl ethyl ketone; or an amide such as formamide, dimethylformamide, dimethylacetamide or hexamethylphosphoric triamide, preferably the amides (particularly dimethylformamide).

The reaction temperature may be varied depending on the nature of the starting material and reagent, and is usually from −50° C. to 100° C. (preferably from 0° C. to 50° C.).

The reaction time may be varied depending on the nature of the starting material, reagent and reaction temperature, and is usually from 5 minutes to 24 hours (preferably from 10 minutes to 5 hours).

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, neutralizing it, if desired, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (m):

The reaction in which a nitro group is converted to an amino group is carried out according to a conventional method in organic chemistry. For example, the reaction is carried out by reacting a nitro group with zinc in the presence of acetic acid in an inert solvent.

The solvent employed here is not particularly limited so long as it does not interfere with the reaction and can dissolve a certain amount of the starting material, and may be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; an alcohol such as methanol, ethanol, propanol, isopropanol, butanol or isobutanol; a diamine such as N,N,N',N'-tetramethylethylenediamine; an amide such as formamide, dimethylformamide, dimethylacetamide, hexamethylphosphoric triamide or hexamethylphosphorous triamide; a sulfoxide such as dimethyl sulfoxide or sulfolane; water or an aqueous mixture of the above-mentioned solvent, preferably water.

The reaction temperature may be varied depending on the nature of the starting material and reagent, and is usually from −10° C. to 100° C., preferably from 0° C. to 5° C.

The reaction time may be varied depending on the nature of the starting material, reagent and reaction temperature, and is usually from 10 minutes to 10 hours, preferably from 30 minutes to 3 hours.

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, neutralizing it, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

Reaction (n):

The reaction for removal of the protecting group of the amino group included in $R^3_a$, etc. is carried out under similar conditions to those described in Step A3.

The compound of formula (II) which is a starting material of the present invention is a known compound or can be prepared according to a known method [for example, Chem. Abstr., 74, 125521 (1970), Annual report of Sankyo Research Laboratories, 22, 215 (1970), Agric. Biol. Chem., EN, 50, 1831 (1986), Can. J. Chem., 48, 1371 (1970), Japanese Patent Application (Kokai) No. Sho 59–216881, Japanese Patent Publication (Kokoku) No. Sho 43-14704, etc.]

Further, the compound of formula (IV) or (IVa) is a known compound or can be prepared according to a known method [for example, Synthesis, 366 (1990), J. Med. Chem., 34, 1258 (1991), etc.]

Furthermore, the compound (II) which is a starting material of the present invention is a known compound or can be prepared according to a known method. The compound of the general formula (VI), (X) or (XIII) can be prepared by reacting according to the methods described below.

Method D

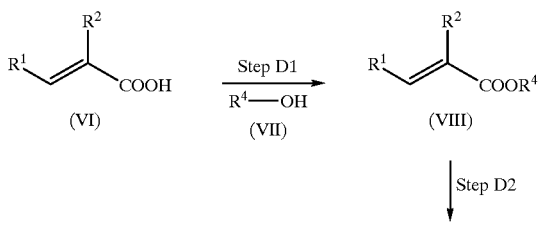

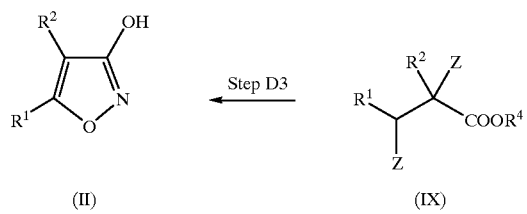

Method E

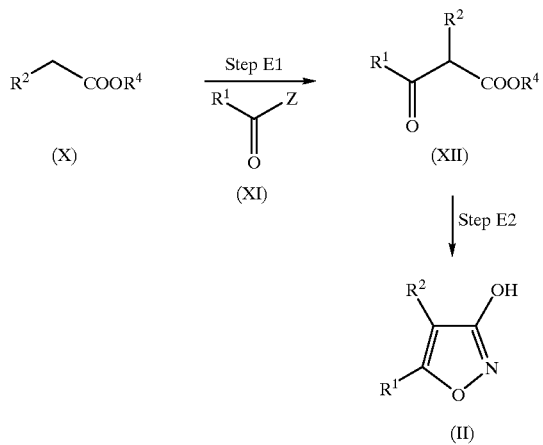

Method F

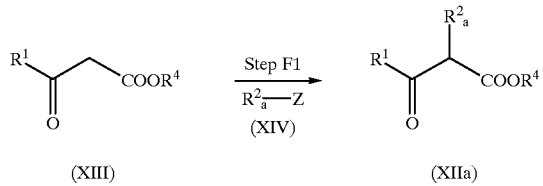

Wherein $R^1$, $R^2$ and Z have the same meanings as defined above, $R^2_a$ represents a specific substituent group in $R^2$ (the substituent group consists of a halogen atom, $C_1$–$C_6$ alkyl, $C_1$–$C_6$ alkyl substituted with halogen or $C_1$–$C_6$ alkoxy, $C_2$–$C_6$ alkenyl, $C_2$–$C_6$ alkynyl, $C_3$ $C_{10}$ cycloalkyl, $C_3$–$C_{10}$ cycloalkenyl, $C_2$–$C_6$ alkanoyl and $C_1$–$C_6$ alkoxycarbonyl groups), and $R^4$ represents a $C_1$–$C_6$ alkyl group.

The alkyl group in $R^4$ may be, for example, a straight or branched alkyl group having from 1 to 6 carbon atoms such as the methyl, ethyl, propyl, isopropyl, butyl, isobutyl, s-butyl, t-butyl, pentyl, isopentyl, 2-methylbutyl, neopentyl, 1-ethylpropyl, hexyl, 4methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl groups, preferably the $C_1$–$C_4$ alkyl group, more preferably the methyl or ethyl groups.

Method D is a process for preparing the compound (II) which is a starting material in Process A or Process B.

In step D1 the compound of formula (VIII) is prepared
(a) by reacting the compound of general formula (VI) in an inert solvent with a reagent to prepare an active ester, followed by reacting the active ester with the compound of formula (VII) in an inert solvent, (b) by reacting the compound of general formula (VI) with a halogenating agent in an inert solvent, followed by reacting the halogenated compound with the compound (VII), or (c) by reacting the compound of formula (VI) with the compound of formula (VII) in the presence of an acid in an inert solvent.

Step D1(a) and Step D1(b) are carried out under similar conditions to those described in reaction (f2) and reaction (f3) in Step C1, respectively.

The acid used in Step D1(c) is not particularly limited so long as it is conventionally used in the technology of organic chemistry, and may be a mineral acid such as hydrofluoric acid, hydrochloric acid, hydrobromic acid, hydroiodic acid, nitric acid, perchloric acid, sulfuric acid or phosphoric acid; a sulfonic acid such as methanesulfonic acid, trifluoromethanesulfonic acid, ethanesulfonic acid, benzenesulfonic acid or p-toluenesulfonic acid; or a carboxylic acid such as fumaric acid, succinic acid, citric acid, tartaric acid, oxalic acid or maleic acid; preferably the mineral acids (particularly sulfuric acid).

The solvent employed here is not particularly limited so long as it does not interfere with the reaction and can dissolve a certain amount of the starting material, and may be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a ketone such as acetone or methyl ethyl ketone; an alcohol such as methanol, ethanol, propanol, isopropanol, butanol or isobutanol; or an amide such as formamide, dimethylformamide, dimethylacetamide or hexamethylphosphoric triamide, preferably the alcohols (particularly methanol or ethanol).

The reaction temperature may be varied depending on the nature of the starting material and reagent, and is usually from −50° C. to 150° C. (preferably from 20° C. to 100° C.).

The reaction time may be varied depending on the nature of the starting material, reagent and reaction temperature, and is usually from 5 minutes to 24 hours (preferably from 10 minutes to 5 hours).

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

In step D2 the compound of formula (IX) is prepared by reacting the compound (VIII) with a halogen molecule in an inert solvent.

The halogen molecule employed here may be, for example, a chlorine molecule or a bromine molecule, preferably the bromine molecule.

The solvent employed here is not particularly limited so long as it does not interfere with the reaction and can dissolve a certain amount of the starting material, and may be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a ketone such as acetone and methyl ethyl ketone; an alcohol such as methanol, ethanol, propanol, isopropanol, butanol or isobutanol; or an amide such as formamide, dimethylformamide, dimethylacetamide or hexamethylphosphoric triamide, preferably the halogenated hydrocarbons (particularly chloroform or carbon tetrachloride).

The reaction temperature may be varied depending on the nature of the starting material and reagent, and is usually from −50° C. to 100° C. (preferably from 0° C. to 50° C.).

The reaction time may be varied depending on the nature of the starting material, reagent and reaction temperature, and is usually from 5 minutes to 12 hours (preferably from 10 minutes to 5 hours).

After completion of the reaction, the target compound of this reaction is isolated from the reaction mixture according to a conventional method. For example, after the reaction, the target compound is obtained by removing the solvent by evaporation, or adding water to the residue obtained by removing the solvent by evaporation, adding a hydrophobic solvent (for example, benzene, ether, ethyl acetate, etc.) to the resulting mixture to extract the desired compound, washing the extracted organic layer with water, drying it over anhydrous magnesium sulfate and removing the solvent by evaporation. The target compound thus obtained can be further purified, if necessary, by a conventional method, for example, recrystallization, reprecipitation or chromatography.

In step D3 the compound of formula (II) is prepared by reacting the compound of formula (IX) with hydroxylamine or a mineral acid salt of hydroxylamine (preferably the mineral acid salt of hydroxylamine) in the presence or absence of a base (preferably in the presence of a base) in an inert solvent.

The mineral acid salt of hydroxylamine employed here may be, for example, hydroxylamine hydrofluoride, hydroxylamine hydrochloride, hydroxylamine hydrobromide, hydroxylamine hydroiodide, hydroxylamine nitric acid salt, hydroxylamine perchloric acid salt, hydroxylamine sulfuric acid salt or hydroxylamine phosphoric acid salt, preferably hydroxylamine hydrochloride.

Method E is an alternative method for preparing the compound (II) which is a starting material in Process A or Process B.

In step E1 the compound of formula (XII) is prepared by reacting the compound of formula (X) with the compound of formula (XI) in the presence of a base in an inert solvent.

The solvent employed here is not particularly limited so long as it does not interfere with the reaction and can dissolve a certain amount of the starting material, and may be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; or a sulfoxide such as dimethyl sulfoxide or sulfolane, preferably the aromatic hydrocarbons, halogenated hydrocarbons or ethers, more preferably the aromatic hydrocarbons (particularly benzene) or ethers (particularly tetrahydrofuran and dioxane).

The base employed here may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; a mercaptan alkali metal such as methylmercaptan sodium or ethylmercaptan sodium; an organic amine such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane (DABCO) or 1,8-diazabicyclo[5.4.0]undec-7-ene (DBU); an alkyllithium such as methyllithium, ethyllithium or butyllithium; or a lithium alkylamide such as lithium diisopropylamide or lithium dicyclohexylamide, preferably the lithium alkylamides (particularly lithium diisopropylamide) or organic amines (particularly 1,8-diazabicyclo[5.4.0]undec-7-ene (DBU)).

The reaction temperature may be varied depending on the nature of the starting material and reagent, and is usually from −100° C. to 100° C., preferably from −70° C. to 50° C.

The reaction time may be varied depending on the nature of the starting material, reagent and reaction temperature, and is usually from 5 minutes to 48 hours, preferably from 10 minutes to 24 hours.

After the completion of the reaction, the target compound of this step is isolated from the reaction mixture according to a conventional method. For example, the target compound is obtained by removing the solvent by evaporation, adding water to the reaction mixture, making the reaction mixture weakly acidic, adding a hydrophobic solvent (for example, benzene, ether, ethyl acetate, etc.) to the resulting mixture to extract the desired compound, washing the organic layer with water, drying it over anhydrous magnesium sulfate and removing the solvent by evaporation. The target compound thus obtained can be further purified, if necessary, by a conventional method, for example, recrystallization, reprecipitation or chromatography.

In step E2 the compound of formula (II) is prepared by reacting the compound of formula (XII) with hydroxylamine or a mineral acid salt of hydroxylamine (preferably the mineral acid salt of hydroxylamine) in the presence or absence of a base (preferably in the presence of a base) in an inert solvent, and is carried out under similar conditions to those described in Step D3.

Method F is a process for preparing the compound (XIIa) in which $R^2$ is a halogen atom, $C_1$–$C_6$ alkyl, $C_1$–$C_6$ alkyl substituted with halogen or $C_1$–$C_6$ alkoxy, $C_2$–$C_6$ alkenyl, $C_2$–$C_6$ alkynyl, $C_3$–$C_{10}$ cycloalkyl, $C_3$–$C_{10}$ cycloalkenyl, $C_2$–$C_6$ alkanoyl or $C_1$–$C_6$ alkoxycarbonyl in the intermediate (XII) of Method E.

In step F1 the compound of formula (XIIa) is prepared by reacting the compound of formula (XIII) with the compound of formula (XIV) in the presence of a base in an inert solvent, and is carried out under similar conditions to those described in Step E1.

The isoxazole derivative (I) of the present invention has excellent type A-monoamine oxidase inhibiting activities and is weakly toxic. Therefore, it is useful as an agent for treating or preventing (particularly an agent for treating) nervous diseases including depression, Parkinson's disease, Alzheimer's dementia (cognitive disorder owing to Alzheimer's disease) or cerebrovascular dementia (cognitive disorder owing to cerebrovascular dementia), (particularly for depression).

BEST MODE FOR CARRYING OUT THE INVENTION

In the following, the present invention will be described in more detail by way of Examples, Reference examples, Test example and Preparation examples, but the present invention is not limited thereto.

EXAMPLE 1

3-(2-Aminoethoxy)-5-phenylisoxazole hydrochloride (Compound list No. 1)

(a) 3-(2-(N-tert-Butoxycarbonylamino)ethoxy)-5-phenylisoxazole

Triphenylphosphine (0.87 g) was dissolved in tetrahydrofuran (10 ml), and diethyl azodicarboxylate (0.57 g) was added dropwise to the solution under ice-cooling with stirring, and the mixture was stirred at the same temperature for 10 minutes. 3-Hydroxy-5-phenylisoxazole (0.48 g) and 2-(N-tert-butoxycarbonylamino)ethanol (0.48 g) were added to the reaction mixture, and the resulting mixture was stirred under ice-cooling for 10 minutes and at room temperature for 24 hours. The solvent was evaporated under reduced pressure and the residue was purified by silica gel column chromatography (eluent: cyclohexane/ethyl acetate=4/1) and was crystallized from isopropyl ether to obtain the title compound (0.63 g, 69%) as colorless crystals.

m.p.: 125–126° C.;

IR spectrum (KBr)$v_{max}$ cm$^{-1}$: 3322, 1721, 1710, 1619; NMR spectrum (CDCl$_3$) δ ppm: 1.46(9H, s), 3.56(2H, q, J=5.1 Hz), 4.35(2H, t, J=5.1 Hz), 4.94(1H, brs), 6.14(1H, s), 7.43–7.51(3H, m), 7.71–7.74(2H, m).

(b) 3-(2-Aminoethoxy)-5-phenylisoxazole hydrochloride

A solution of 4N hydrochloric acid/1,4-dioxane (4.0 ml) was added to 3-(2-(N-tert-butoxycarbonylamino)ethoxy)-5-phenylisoxazole (0.50 g), and the mixture was stirred at room temperature for 15 minutes. The precipitate was separated from the mixture by filtration and washed with ethyl acetate to obtain the title compound (0.39 g, 99%) as colorless crystals.

m.p.: 215–218° C. (decomposed); IR spectrum (KBr)$v_{max}$ cm$^{-1}$: 3132, 2963, 2810, 2756, 1620, 1597, 1579; NMR spectrum (DMSO-d$_6$) δ ppm: 3.26(2H, t, J=5.1 Hz), 4.45 (2H, t, J=5.1 Hz), 6.85(1H, s), 7.51–7.57(3H, m), 7.84–7.87 (2H, m), 8.25(3H, brs).

EXAMPLE 2

3-(2-Aminoethoxy)-4-chloro-5-phenylisoxazole hydrochloride (Compound list No.: 5)

(a) 3-(2-(N-tert-Butoxycarbonylamino)ethoxy)-4-chloro-5-phenylisoxazole

4-Chloro-3-hydroxy-5-phenylisoxazole (0.58 g) and 2-(N-tert-butoxycarbonylamino)ethanol (0.48 g) were subjected to reaction and post-treatment in a similar manner to that described in Example 1 (a) to obtain the title compound (0.73 g, 72%) as colorless crystals.

m.p.: 115–116° C.; IR spectrum (KBr)$v_{max}$ cm$^{-1}$: 3346, 1720, 1709, 1616; NMR spectrum (CDCl$_3$) δ ppm: 1.46(9H, s), 3.61(2H, q, J=5.1 Hz), 4.42(2H, t, J=5.1 Hz), 4.97(1 H, brs), 7.46–7.53(3H, m), 7.94–8.00(2H, m).

(b) 3-(2-Aminoethoxy)-4-chloro-5-phenylisoxazole hydrochloride 3-(2-(N-tert-Butoxycarbonylamino)ethoxy)-4-chloro-5-phenylisoxazole (0.54 g) was subjected to reaction and post-treatment in a similar manner to that described in Example 1(b) to obtain the title compound (0.41 g, 93%) as colorless crystals.

m.p.: 204–207° C. (decomposed); IR spectrum (KBr)$v_{max}$ cm$^{-1}$: 2971, 2905, 2848, 2775, 1606, 1575, 1534; NMR spectrum (DMSO-d$_6$) δ ppm: 3.31(2H, t, J=5.1 Hz), 4.56 (2H, t, J=5.1 Hz), 7.59–7.67(3H, m), 7.92–7.97(2H, m), 8.27(3H, brs).

EXAMPLE 3

3-(2-Aminoethoxy)-5-(4-chlorophenyl)isoxazole hydrochloride (Compound list No.: 143)

(a) 3-(2-(N-tert-Butoxycarbonylamino)ethoxy)-5-(4-chlorophenyl)isoxazol 5-(4-Chlorophenyl)-3-hydroxyaminoisoxazole (0.58 g) and 2-(N-tert-butoxycarbonylamino)ethanol (0.48 g) were subjected to reaction and post-treatment in a similar manner to that described in Example 1(a) to obtain the title compound (0.69 g, 68%) as colorless crystals.

m.p.: 128–129° C.; IR spectrum (KBr)$v_{max}$ cm$^{-1}$: 3378, 1683, 1622; NMR spectrum (CDCl$_3$) δ ppm: 1.46(9H, s), 3.56(2H, q, J=5.1 Hz), 4.35(2H, t, J=5.1 Hz), 4.93(1H, brs), 6.14(1H, s), 7.43(2H, d, J=8.7 Hz), 7.66(2H, d, J=8.7 Hz).

(b) 3-(2-Aminoethoxy)-5-(4-chlorophenyl)isoxazole hydrochloride 3-(2-(N-tert-butoxycarbonylamino)ethoxy)-5-(4-chlorophenyl)isoxazole (0.54 g) was subjected to reaction and post-treatment in a similar manner to that described in Example 1(b) to obtain the title compound (0.43 g, 98%) as colorless crystals.

m.p.: 218–223° C. (decomposed); IR spectrum (KBr)$v_{max}$ cm$^{-1}$: 3135, 2998, 2809, 1618, 1603, 1594, 1575, 1567; NMR spectrum (DMSO-d$_6$) δ ppm: 3.26(2H, t, J=5.1 Hz), 4.45(2H, t, J=5.1 Hz), 6.91(1H, s), 7.63(2H, d, J=8.7 Hz), 7.89(2H, d, J=8.7 Hz), 8.25(3, brs).

EXAMPLE 4

3-(2-Aminoethoxy)-4-isopropyl-5-phenylisoxazole hydrochloride (Compound list No.: 9)

(a) 3-(2-(N-tert-Butoxycarbonylamino)ethoxy-4-isopropyl-5-phenylisoxazole

3-Hydroxy-4-isopropyl-5-phenylisoxazole (0.50 g) and 2-(N-tert-butoxycarbonylamino)ethanol (0.40 g) were subjected to reaction and post-treatment in a similar manner to that described in Example 1(a) to obtain the title compound (0.60 g, 69%) as colorless crystals.

m.p.: 98–99° C.; IR spectrum (KBr)$v_{max}$ cm$^{-1}$: 3386, 1686, 1642; NMR spectrum (CDCl$_3$) δ ppm: 1.29(6H, d, J=6.8), 1.46(9H, s), 3.06(1H, q, J=6.8), 3.60(2H, q, J=5.1 Hz), 4.38(2H, t, J=5.1 Hz), 4.85(1H, brs), 7.42–7.50(3H, m), 7.55–7.60(2H, m).

(b) 3-(2-Aminoethoxy)-4-isopropyl-5-phenylisoxazole hydrochloride 3-(2-(N-tert-Butoxycarbonylamino)ethoxy)-4-isopropyl-5-phenylisoxazole (0.50 g) was subjected to reaction and post-treatment in a similar manner to that described in Example 1(b) to obtain the title compound (0.39 g, 95%) as colorless crystals.

m.p.: 202–210° C. (decomposed); IR spectrum (KBr)$v_{max}$ cm$^{-1}$: 2975, 2939, 1642, 1599, 1575; NMR spectrum (DMSO-d$_6$) δ ppm: 1.26(6H, d, J=6.8 Hz), 3.04(1H, q, J=6.8 Hz), 3.28(2H, t, J=5.1 Hz), 4.46(2H, t, J=5.1 Hz), 7.50–7.64 (5H, m), 8.26(3H, brs).

EXAMPLE 5

3-(2-Aminoethoxy)-5-(2-thienyl)isoxazole hydrochloride (Compound list No.: 535)

(a) 3-(2-(-tert-Butoxycarbonylamino)ethoxy)-5-(2-thienyl)isoxazole

3-Hydroxy-5-(2-thienyl)isoxazole (0.42 g) and 2-(N-tert-butoxycarbonylamino)ethanol (0.40 g) were subjected to reaction and post-treatment in a similar manner to that described in Example 1(a) to obtain the title compound (0.63 g, 82%) as colorless crystals.

m.p.: 129–130° C. (decomposed); IR spectrum (KBr)$v_{max}$ cm$^{-1}$: 3323, 1708, 1694, 1618; NMR spectrum (CDCl$_3$) δ ppm: 1.46(9H, s), 3.56(2H, q, J=5.1 Hz), 4.34(2H, t, J=5.1 Hz), 4.93(1H, brs), 6.05(1H, s), 7.11(1H, dd, J=5.1 Hz, J=3.7 Hz), 7.43–7.48(2H, m).

(b) 3-(2-Aminoethoxy)-5-(2-thienyl)isoxazole hydrochloride 3-(2-(N-tert-Butoxycarbonylamino)ethoxy)-5-(2-thienyl)isoxazole (0.05 g) was subjected to reaction and post-treatment in a similar manner to that described in Example 1(b) to be obtain the title compound (0.37g, 95%) as colorless crystals.

m.p.: 278–283° C. (decomposed); IR spectrum (KBr)$v_{max}$ cm$^{-1}$: 3108, 3086, 2993, 2978, 2913, 1613, 1596; NMR spectrum (DMSO-d$_6$) δ ppm: 3.25(2H, t, J=5.1 Hz), 4.44 (2H, t, J=5.1 Hz), 6.69(1H, s), 7.25(1H, dd, J=5.5 Hz, J=3.7 Hz), 7.71(1H, d, J=3.7 Hz), 7.84(1H, d, J=5.5 Hz), 8.25(3H, brs).

EXAMPLE 6

3-(2-Aminoethoxy)-4-chloro-5-(2-thienyl)isoxazole hydrochloride (Compound list No.: 539)

(a) 3-(2-(N-tert-Butoxycarbonylamino)ethoxy)-5-(2-thienyl)isoxazole

4-Chloro-3-hydroxy-5-(2-thienyl)isoxazole (0.50 g) and 2-(N-tert-butoxycarbonylamino)ethanol (0.40 g) were subjected to reaction and post-treatment in a similar manner to that described in Example 1(a) to obtain the title compound (0.57 g, 66%) as colorless crystals.

m.p.: 94–95° C.; IR spectrum (KBr)$v_{max}$ cm$^{-1}$: 3342, 1718, 1708, 1622; NMR spectrum (CDCl$_3$) δ ppm: 1.46(9H, s), 3.60(2H, q, J=5.1 Hz), 4.40(2h, t, J=5.1 Hz), 4.96(1H, brs), 7.19(1H, dd, J=5.2 Hz, J=3.6 Hz), 7.56(1H, d, J=5.2 Hz), 7.74(1H, d, J=3.6 Hz).

(b) 3-(2-Aminoethoxy)-4-chloro-5-(2-thienyl)isoxazole hydrochloride 3-(2-(N-tert-Butoxycarbonylamino)ethoxy)4-chloro-5-(2-thienyl)-isoxazole (0.40 g) was subjected to reaction and post-treatment in a similar manner to that described in Example 1(b) to obtain the title compound (0.31 g, 95%) as colorless crystals.

m.p.: 278–283° C. (decomposed); IR spectrum (KBr)$v_{max}$ cm$^{-1}$: 3109, 2960, 2897, 1626, 1596, 1579; NMR spectrum (DMSO-d$_6$) δ ppm: 3.30(2H, t, J=5.1 Hz), 4.54(2H, t, J=5.1 Hz), 7.34(1H, dd, J=5.1 Hz, J=3.6 Hz), 7.83(1H, d, J=3.6 Hz), 8.01(1H, d, J=5.1 Hz), 8.26(3H, brs).

EXAMPLE 7

3-(2-Aminoethoxy)-5-(3-pyridyl)isoxazole hydrochloride (Compound list No.: 1056)

(a) 3-(2-(N-tert-Butoxycarbonylamino)ethoxy)-5-(3-pyridyl)isoxazole

3-Hydroxy-5-(3-pyridyl)isoxazole (0.41 g) and 2-(N-tert-butoxycarbonylamino)ethanol (0.40 g) were subjected to reaction and post-treatment in a similar manner to that described in Example 1(a) to obtain the title compound (0.50 g, 65%) as colorless crystals.

m.p.: 97–98° C.; IR spectrum (KBr) $v_{max}$ cm$^{-1}$: 3249, 3145, 1712, 1626; NMR spectrum (CDCl$_3$) δ ppm: 1.46(9H, s), 3.57(2H, q, J=5.1 Hz), 4.37(2H, t, J=5.1 Hz), 4.94(1H, brs), 6.25(1H, s), 7.42(1H, dd, J=8.0 Hz, J=4.9 Hz), 8.04 (1H, d, J=8.0 Hz), 8.64(1H, d, J=4.9 Hz), 8.97(1H, s).

(b) 3-(2-Aminoethoxy)-5-(3-pyridyl)isoxazole dihydrochloride 3-(2-(N-tert-Butoxycarbonylamino)ethoxy)-5-(3-pyridyl) isoxazole (0.48 g) was subjected to reaction and post-treatment in a similar manner to that described in Example 1(b) to obtain the title compound (0.41 g, 92%) as colorless crystals.

m.p.: 222–227° C.; IR spectrum (KBr)$v_{max}$ cm$^{-1}$: 3096, 3068, 3043, 2967, 2886, 2813, 1641, 1597, 1539; NMR spectrum (DMSO-d$_6$) δ ppm: 3.26(2H, q, J=5.1 Hz), 4.48 (2H, t, J=5.1 Hz), 7.11(1H, s), 7.77(1H, dd, J=8.0 Hz, J=5.1 Hz), 8.38(3H, brs), 8.46(1H, d, J=8.0 Hz), 8.79(1H, d, J=5.1 Hz), 9.21(1H, s).

EXAMPLE 8

3-(2-Aminoethoxy)-4-chloro-5-(3-pyridyl)isoxazole hydrochloride (Compound list No.: 1061)

(a) 3-(2-(N-tert-Butoxycarbonylamino)ethoxy)-4-chloro-5-(3-pyridyl)isoxazole

4-Chloro-3-hydroxy-5-(3-pyridyl)isoxazole (0.49 g) and 2-(N-tert-butoxycarbonylamino)ethanol (0.40 g) were subjected to reaction and post-treatment in a similar manner to that described in Example 1(a) to obtain the title compound (0.54 g, 63%) as colorless crystals.

m.p.: 76–77° C.; IR spectrum (KBr)$v_{max}$ cm$^{-1}$: 3353, 3248, 1754, 1721, 1709, 1616; NMR spectrum (CDCl$_3$) δ ppm: 1.47(9H, s), 3.62(2H, q, J=5.1 Hz), 4.43(2H, t, J=5.1 Hz), 4.97(1H, brs), 7.45(1H, dd, J=8.0 Hz, J=5.1 Hz), 8.24(1H, ddd, J=8.0 Hz, J=2.0 Hz, J=1.5 Hz), 8.72(1H, dd, J=5.1 Hz, J=1.5 Hz), 9.24(1H, d, J=2.0 Hz).

(b) 3-(2-Aminoethoxy)-4-chloro-5-(3-pyridyl)isoxazole dihydrochloride 3-(2-(N-tert-Butoxycarbonylamino)ethoxy)-4-chloro-5-(3-pyridyl)-isoxazole (0.40 g) was subjected to reaction and post-treatment in a similar manner to that described in Example 1(b) to obtain the title compound (0.35 g, 96%) as colorless crystals.

m.p.: 205–210° C. (decomposed); IR spectrum (KBr)$v_{max}$ cm$^{-1}$: 3103, 3053, 2937, 2899, 2875, 2823, 2800, 1634, 1607, 1590, 1541; NMR spectrum (DMSO-d$_6$) δ ppm: 3.31(2H, q, J=5.1 Hz), 4.59(2H, t, J=5.1 Hz), 7.74(1H, dd, J=8.0 Hz, J=5.1 Hz), 8.40(1H, ddd, J=8.0 Hz, J=2.0 Hz, J=1.5 Hz), 8.40(3H, brs), 8.82(1H, dd, J=5.1 Hz, J=1.5 Hz), 9.15(1H, d, J=2.0 Hz).

EXAMPLE 9

3-(2-Aminoethoxy)-5-(2-methoxyphenyl)isoxazole hydrochloride (Compound list No.: 357)

(a) 3-(2-(N-tert-Butoxycarbonylamino)ethoxy)-5-(2-methoxyphenyl)isoxazole

Triphenylphosphine (0.45 g) was dissolved in tetrahydrofuran (5 ml), and diethyl azodicarboxylate (0.27 ml) was added dropwise to the solution under ice-cooling with stirring, and the resulting mixture was stirred at the same temperature for 30 minutes. Then, 2-(N-tert-butoxycarbonylamino)ethanol (0.20 g) and 3-hydroxy-5-(2-methoxyphenyl)isoxazole (0.22 g) were added to the reaction mixture, followed by stirring of the resulting mixture under ice-cooling for 10 minutes and at room temperature for 24 hours. The solvent was evaporated under reduced pressure and the residue was purified by silica gel column chromatography (eluent: hexane/ethyl acetate=4/1) to obtain the title compound (0.33 g, 86%) as colorless crystals.

m.p.: 131–133° C.; IR spectrum (KBr)$v_{max}$ cm$^{-1}$: 3309, 1712, 1620; NMR spectrum (CDCl$_3$) δ ppm: 1.46(9H, s), 3.57(2H, q, J=5.2 Hz), 3.95(3H, s), 4.36(2H, t, J=5.2 Hz), 4.96(1H, brs), 6.43(1H, s), 7.00(1H, d, J=7.8 Hz), 7.06(1H, t, J=7.8 Hz), 7.41(1H, ddd, J=7.8 Hz, J=7.8 Hz, J=1.7 Hz), 7.91(1H, dd, J=7.8 Hz, J=1.7 Hz).

(b) 3-(2-Aminoethoxy)-5-(2-methoxyphenyl)isoxazole hydrochloride 3-(2-(N-tert-Butoxycarbonylamino)ethoxy)-5-(2-methoxyphenyl)isoxazole (0.31 g) was dissolved in a solution of 4N hydrochloric acid/1,4-dioxane (2.3 ml), and the solution was stirred at room temperature for 30 minutes. The solvent was evaporated under reduced pressure and the residue was recrystallized from a mixture of ethanol and isopropanol to obtain the title compound (0.21 g, 84%) as colorless crystals.

m.p.: 160–162° C. (decomposed); IR spectrum (KBr)$v_{max}$ cm$^{-1}$: 3000, 2959, 2837, 1621, 1614; NMR spectrum (DMSO-d$_6$) δ ppm: 3.25(2H, t, J=5.1 Hz), 3.94(3H, s), 4.45(2H, t, J=5.1 Hz), 6.56(1H, s), 7.11(1H, t, J=7.8 Hz), 7.23(1H, d, J=7.8 Hz), 7.52(1H, ddd, J=7.8 Hz, J=7.8 Hz, J=1.7 Hz), 7.81(1H, dd, J=7.8 Hz, J=1.7 Hz), 8.25(3H, brs).

EXAMPLE 10

3-(2-Aminoethoxy)-5-(3-methoxyphenyl)isoxazole hydrochloride (Compound list No.: 363)

(a) 3-(2-(N-tert-Butoxycarbonylamino)ethoxy)-5-(3-methoxyphenyl)isoxazole

3-Hydroxy-5-(3-methoxyphenyl)isoxazole (0.22 g) and 2-(N-tert-butoxycarbonylamino)ethanol (0.20 g) were subjected to reaction and post-treatment in a similar manner to that described in Example 9(a) to obtain the title compound (0.31 g, 82%) as a colorless powder.

m.p.: 89–90° C.; IR spectrum (KBr)$v_{max}$ cm$^{-1}$: 3312, 1710; NMR spectrum (CDCl$_3$) δ ppm: 1.46(9H, s), 3.56(2H, q, J=5.2 Hz), 3.86(3H, s), 4.35(2H, t, J=5.2 Hz), 4.93(1H, brs), 6.13(1H, s), 6.96–7.00(1H, m), 7.26–7.42(3H, m).

(b) 3-(2-Aminoethoxy)-5-(3-methoxyphenyl)isoxazole hydrochloride 3-(2-(N-tert-Butoxycarbonylamino)ethoxy)-5-(3-methoxyphenyl)-isoxazole (0.29 g) was allowed to react in a similar manner to that described in Example 9(b) and the reaction product was recrystallized from a mixture of ethanol and isopropanol to obtain the title compound (0.19 g, 83%) as colorless crystals.

m.p.: 180–182° C. (decomposed); IR spectrum (KBr)$v_{max}$ cm$^{-1}$: 2995, 2976, 2914, 1591; NMR spectrum (DMSO-d$_6$) δ ppm: 3.26(2H, t, J=5.1 Hz), 3.84(3H, s), 4.45(2H, t, J=5.1 Hz), 6.88(1H, s), 7.09–7.11(1H, m), 7.38–7.48(3H, m), 8.28(3H, brs).

EXAMPLE 11

3-(2-Aminoethoxy)-5-(4-methoxyphenyl)isoxazole hydrochloride (Compound list No.: 350)

(a) 3-(2-(N-tert-Butoxycarbonylamino)ethoxy)-5-(4-methoxyphenyl)isoxazole

3-Hydroxy-5-(4-methoxyphenyl)isoxazole (0.22 g) and 2-(N-tert-butoxycarbonylamino)ethanol (0.20 g) were subjected to reaction and post-treatment in a similar manner to that described in Example 9(a) to obtain the title compound (0.32 g, 84%) as a colorless powder.

m.p.: 117–118° C.; IR spectrum (KBr)$v_{max}$ cm$^{-1}$: 3344, 1719, 1623; NMR spectrum (CDCl$_3$) δ ppm: 1.46(9H, s), 3.56(2H, q, J=5.2 Hz), 3.86(3H, s), 4.34(2H, t, J=5.2 Hz), 4.95(1H, brs), 6.02(1H, s), 6.96(2H, d, J=8.9 Hz), 7.66(2H, d, J=8.9 Hz).

(b) 3-(2-Aminoethoxy)-5-(4-methoxyphenyl)isoxazole hydrochloride 3-2-(N-tert-Butoxycarbonylamino)ethoxy)-5-(4-methoxyphenyl)-isoxazole (0.30 g) was reacted in a similar manner to that described in Example 9(b) and the reaction product was recrystallized from a mixture of ethanol and isopropanol to obtain the title compound (0.17 g, 71%) as colorless crystals.

m.p.: 190–193° C.(decomposed); IR spectrum (KBr)$v_{max}$ cm$^{-1}$: 2990, 2969, 2950, 2900, 1617; NMR spectrum (DMSO-d$_6$) δ ppm: 3.25(2H, t, J=5.1 Hz), 3.83(3H, s), 4.43(2H, t, J=5.1 Hz), 6.69(1H, s), 7.09(2H, d, J=8.9 Hz), 7.79(2H, d, J=8.9 Hz), 8.25(3H, brs).

EXAMPLE 12

3-(2-Aminoethoxy)-5-(2-chlorophenyl)isoxazole hydrochloride (Compound list No.: 111)

(a) 3-(2-(N-tert-Butoxycarbonylamino)ethoxy)-5-(2-chlorophenyl)isoxazole 5-(2-Chlorophenyl)-3-hydroxy-isoxazole (0.23 g) and 2-(N-tert-butoxycarbonylamino)ethanol (0.20 g) were subjected to reaction and post-treatment in a similar manner to that described in Example 9(a) to obtain the title compound (0.35 g, 88%) as a colorless powder.

m.p.: 125–127° C.; IR spectrum (KBr)$v_{max}$ cm$^{-1}$: 3333, 1710, 1697, 1618; NMR spectrum (CDCl$_3$) δ ppm: 1.46(9H, s), 3.57(2H, q, J=5.2 Hz), 4.37(2H, t, J=5.2 Hz), 4.96(1H, brs), 6.59(1H, s), 7.33–7.43(2H, m), 7.46–7.54(1H, m), 7.87–7.94(1 H, m).

(b) 3-(2-Aminoethoxy)-5-(2-chlorophenyl)isoxazole hydrochloride 3-(2-(N-tert-Butoxycarbonylamino)ethoxy)-5-(2-chlorophenyl)isoxazole (0.33 g) was reacted in a similar manner to that described in Example 9(b) and the reaction product was recrystallized from isopropanol to obtain the title compound (0.20 g, 74%) as colorless crystals.

m.p.: 141–144° C. (decomposed); IR spectrum (KBr)$v_{max}$ cm$^{-1}$: 3003, 2965, 1610; NMR spectrum (DMSO-d$_6$) δ ppm: 3.278(2H, t, J=5.1 Hz), 4.48(2H, t, J=5.1 Hz), 6.80(1H, s), 7.52–7.60(2H, m), 7.68(1H, dd, J=7.5 Hz, J=1.9 Hz), 7.87 (1H, dd, J=7.5 Hz, J=1.9 Hz), 8.27(3H, brs).

EXAMPLE 13

3-(2-Aminoethoxy)-5-(3-chlorophenyl)isoxazole hydrochloride (Compound list No.: 125)

(a) 3-(2-(N-tert-Butoxycarbonylamino)ethoxy)-5-(3-chlorophenyl)isoxazole 5-(3-Chlorophenyl)-3-hydroxyisoxazole (0.23 g) and 2-(N-tert-butoxycarbonylamino)ethanol (0.20 g) were subjected to reaction and post-treatment in a similar manner to that described in Example 9(a) to obtain the title compound (0.34 g, 85%) as a colorless powder.

m.p.: 117–119° C.; IR spectrun (KBr)$v_{max}$ cm$^{-1}$: 3385, 1685; NMR spectrum (CDCl$_3$) δ ppm: 1.46(9H, s), 3.57(2H, q, J=5.2 Hz), 4.36(2H, t, J=5.2 Hz), 4.93(1H, brs), 6.16(1H, s), 7.36–7.44(2H, m), 7.57–7.67(1H, m), 7.70(1H, s).

(b) 3-(2-Aminoethoxy)-5-(3-chlorophenyl)isoxazole hydrochloride 3-(2-(N-tert-Butoxycarbonylamino)ethoxy)-5-(3-chlorophenyl)isoxazole (0.33 g) was reacted in a similar manner to that described in Example 9(b) and the reaction product was recrystallized from a mixture of ethanol and isopropanol to obtain the title compound (0.21 g, 78%) as colorless crystals.

m.p.: 204–208° C. (decomposed); IR spectrum (KBr)$v_{max}$ cm$^{-1}$: 2996, 2980, 2920, 1619; NMR spectrum (DMSO-d$_6$) δ ppm: 3.26(2H, t, J=5.1 Hz), 4.45(2H, t, J=5.1 Hz), 6.98 (1H, s), 7.56–7.63(2H, m), 7.80–7.84(1H, m), 7.96(1H, s), 8.22(3H, brs).

EXAMPLE 14

3-(2-Aminoethoxy)-4-methyl-5-phenylisoxazole hydrochloride (Compound list No.: 6)

(a) 3-(2-(N-tert-Butoxycarbonylamino)ethoxy)-4-methyl-5-phenylisoxazole 3-(2-(N-tert-Butoxycarbonylamino)ethoxy)-5-phenylisoxazole (0.30 g) was dissolved in tetrahydrofuran (10 ml), and a solution of n-butyllithium/n-hexane (1.56M, 1.4 ml) was added dropwise thereto at −70° C. under a nitrogen atmosphere, followed by stirring of the resulting mixture for 10 minutes. Then, methyl iodide (0.09 ml) was added dropwise to the reaction mixture, and the resulting mixture was stirred for 10 minutes. After the temperature of the reaction mixture was raised to 0° C., the reaction mixture was poured into ice-cold water, and an aqueous potassium dihydrogenphosphate solution was added to the mixture to adjust the pH to a value of 6. Then, the mixture was extracted with ethyl acetate and the organic layer was washed with a saturated aqueous NaCl solution, followed by drying over anhydrous magnesium sulfate. After filtration, the solvent was evaporated under reduced pressure. The residue was purified by silica gel column chromatography (eluent: hexane/ethyl acetate=4/1) to obtain the title compound (0.29 g, 94%) as a colorless powder.

m.p.: 118–120° C.; IR spectrum (KBr)$v_{max}$ cm$^{-1}$: 3334, 2974, 1719, 1708; NMR spectrum (CDCl$_3$) δ ppm: 1.46(9H, s), 2.12(3H, s), 3.59(2H, q, J=5.1 Hz), 4.38(2H, t, J=5.1 Hz), 4.94(1H, brs), 7.40–7.53(3H, m), 7.69(2H, d, J=7.9 Hz).

(b) 3-(2-Aminoethoxy)-4-methyl-5-phenylisoxazole hydrochloride 3-(2-(N-tert-Butoxycarbonylamino)ethoxy)-4-methyl-5-phenylisoxazole (0.29 g) was allowed to react in a similar manner to that described in Example 9(b) and the reaction product was recrystallized from a mixture of methanol and ethanol to obtain the title compound (0.1 8g, 78%) as colorless crystals.

m.p.: 245–250° C. (decomposed); IR spectrum (KBr)$v_{max}$ cm$^{-1}$: 3003, 2892, 1516; NMR spectrum (DMSO-d$_6$) δ ppm: 2.13(3H, s), 3.28(2H, t, J=5.1 Hz), 4.46(2H, t, J=5.1 Hz), 7.50–7.59(3H, m), 7.73(2H, d, J=7.2 Hz), 8.21(3H, brs).

EXAMPLE 15

3-(2-Aminoethoxy)-4-ethyl-5-phenylisoxazole hydrochloride (Compound list No.: 7)

(a) 3-(2-(N-tert-Butoxycarbonylamino)ethoxy)-4-ethyl-5-phenylisoxazole 3-(2-(N-tert-Butoxycarbonylamino)ethoxy)-5-phenylisoxazole (0.3 g) and ethyl iodide (0.12 ml) were subjected to reaction and post-treatment in a similar manner to that described in Example 14(a) to obtain the title compound (0.24 g, 73%) as a colorless oil.

IR spectrum (CHCl$_3$)$v_{max}$ cm$^{-1}$: 3460,2980, 1713; NMR spectrum (CDCl$_3$) δ ppm: 1.21(3H, t, J=7.5 Hz), 1.46(9H, s), 2.56(2H, q, J=7.5 Hz), 3.59(2H, q, J=5.2 Hz), 4.38(2H, t, J=5.2 Hz), 4.90(1H, brs), 7.37–7.51(3H, m), 7.64–7.68(2H, m).

(b) 3-(2-Aminoethoxy)-4-ethyl-5-phenylisoxazole hydrochloride 3-(2-(N-tert-Butoxycarbonylamino)ethoxy)-4-ethyl-5-phenylisoxazole (0.21 g) was subjected to reaction and post-treatment in a similar manner to that described in Example 9(b) to obtain the title compound (0.12 g, 71%) as colorless crystals.

m.p.: 210–215° C. (decomposed); IR spectrum (KBr)$v_{max}$ cm$^{-1}$: 2968, 2886, 1518; NMR spectrum (DMSO-d$_6$) δ ppm: 1.15(3H, t, J=7.5 Hz), 2.58(2H, q, J=7.5 Hz), 3.29(2H, t, J=5.1 Hz), 4.46(2H, t, J=5.1 Hz), 7.51–7.59(3H, m), 7.67–7.70(2H, m), 8.25(3H, brs).

EXAMPLE 16

3-(2-Aminoethoxy)-5-phenyl-4-propylisoxazole hydrochloride (Compound list No.: 8)

(a) 3-(2-(N-tert-Butoxycarbonylamino)ethoxy)-5-phenyl-4-propylisoxazole 3-(2-(N-tert-Butoxycarbonylamino)ethoxy)-5-phenylisoxazole (0.3 g) and propyl iodide (0.29 ml) were subjected to reaction and post-treatment in a similar manner to that described in Example 14(a) to obtain the title compound (0.22 g, 65%) as a colorless oil.

IR spectrum (CHCl$_3$)$v_{max}$ cm$^{-1}$: 3460, 2966, 1713; NMR spectrum (CDCl$_3$) δ ppm: 0.97(3H, t, J=7.4 Hz), 1.46(9H, s), 1.56–1.69(2H, m), 2.51(2H, t, J=7.6 Hz), 3.58(2H, q, J=5.2 Hz), 4.37(2H, t, J=5.2 Hz), 4.90(1H, brs), 7.43–7.53(3H, m), 7.65–7.68(2H, m).

(b) 3-(2-Aminoethoxy)-5-phenyl-4-propylisoxazole hydrochloride 3-(2-(N-tert-Butoxycarbonylamino)ethoxy)-5-phenyl-4-propylisoxazole (0.18 g) was subjected to reaction and post-treatment in a similar manner to that described in Example 9(b) to obtain the title compound (0.10 g, 71%) as colorless crystals.

m.p.: 119–121° C. (decomposed); IR spectrum (KBr)$v_{max}$ cm$^{-1}$: 2960, 2933, 2872, 1518; NMR spectrum (DMSO-d$_6$) δ ppm: 0.91(3H, t, J=7.3 Hz), 1.51–1.61(2H, m), 2.54(2H, t, J=7.7 Hz), 3.28(2H, t, J=5.1 Hz), 4.45(2H, t, J=5.1 Hz), 7.50–7.59(3H, m), 7.68–7.70(2H, m), 8.20(3H, brs).

EXAMPLE 17

3-(2-Aminoethoxy-4-butyl-5-phenylisoxazole hydrochloride (Compound list No.: 10)

(a) 3-(2-(N-tert-Butoxycarbonylamino)ethoxy)-4-butyl-5-phenylisoxazole 3-(2-(N-tert-Butoxycarbonylamino)ethoxy)-5-phenylisoxazole (0.3 g) and butyl iodide (0.17 ml) were subjected to reaction and post-treatment in a similar manner to that described in Example 14(a) to obtain the title compound (0.23 g, 66%) as a colorless oil.

IR spectrum (CHCl$_3$)$v_{max}$ cm$^{-1}$: 3460, 2962, 1713; NMR spectrum (CDCl$_3$) δ ppm: 0.93(3H, t, J=7.3 Hz), 1.31–1.63 (4H, m), 1.46(9H, s), 2.53(2H, t, J=7.6 Hz), 3.58(2H, q, J=5.3 Hz), 4.38(2H, t, J=5.3 Hz), 4.90(1H, brs), 7.42–7.51 (3H, m), 7.65–7.68(2H, m).

(b) 3-(2-Aminoethoxy)-4-butyl-5-phenylisoxazole hydrochloride 3-(2-(N-tert-Butoxycarbonylamino)ethoxy)-4-butyl-5-phenylisoxazole (0.20 g) was subjected to reaction and post-treatment in a similar manner to that described in Example 9(b) to obtain the title compound (0.12 g, 75%) as colorless crystals.

m.p.: 104–106° C.; IR spectrum (KBr)$v_{max}$ cm$^{-1}$: 3006, 2963, 2951, 2931, 2869, 1516; NMR spectrum (DMSO-d$_6$) δ ppm: 0.87(3H, t, J=7.3 Hz), 1.27–1.37(2H, m), 1.47–1.55 (2H, m), 2.57(2H, t, J=7.7 Hz), 3.28(2H, t, J=5.1 Hz), 4.46(2H, t, J=5.1 Hz), 7.51–7.59(3H, m), 7.68–7.70(2H, m), 8.23(3H, brs).

EXAMPLE 18

3-(2-Aminoethoxy)-4-hexyl-5-phenylisoxazole hydrochloride (Compound list No.: 1388)

(a) 3-(2-(N-tert-Butoxycarbonylamino)ethoxy-4-hexyl-5-phenylisoxazole 3-(2-(N-tert-Butoxycarbonylamino)ethoxy)-5-phenylisoxazole (0.4 g) and hexyl iodide (0.23 ml) were subjected to reaction and post-treatment in a similar manner to that described in Example 14(a) to obtain the title compound (0.31 g, 61%) as a colorless powder.

IR spectrum (KBr)$v_{max}$ cm$^{-1}$: 3387, 2936, 1715; NMR spectrum (CDCl$_3$) δ ppm: 0.88(3H, t, J=6.6 Hz), 1.23–1.42 (6H, m), 1.46(9H, s), 1.53–1.70(2H, m), 2.52(2H, t, J=7.7 Hz), 3.58(2H, q, J=5.1 Hz), 4.37(2H, t, J=5.1 Hz), 4.90(1H, brs), 7.40–7.51(3H, m), 7.65–7.68(2H, m).

(b) 3-(2-Aminoethoxy)-4-hexyl-5-phenylisoxazole hydrochloride 3-(2-(N-tert-Butoxycarbonylamino)ethoxy)-4-hexyl-5-phenylisoxazole (0.2 g) was subjected to reaction and post-treatment in a similar manner to that described in Example 9(b) to obtain the title compound (0.13 g, 81%) as colorless crystals.

m.p.: 99–101° C.; IR spectrum (KBr)$v_{max}$ cm$^{-1}$: 2954, 2930, 1515; NMR spectrum (DMSO-d$_6$) δ ppm: 0.83(3H, t, J=6.9 Hz), 1.18–1.32(6H, m), 1.48–1.55(2H, m), 2.56(2H, t, J=7.7 Hz), 3.28(2H, t, J=5.1 Hz), 4.45(2H, t, J=5.1 Hz), 7.50–7.59(3H, m), 7.67–7.69(2H, m), 8.16(3H, brs).

EXAMPLE 19

3-(2-Aminoethoxy)-4-carboxy-5-phenylisoxazole hydrochloride (Compound list No.: 1408)

(a) 3-(2-(N-tert-Butoxycarbonylamino)ethoxy)-4-carboxy-5-phenylisoxazole 3-(2-(N-tert-Butoxycarbonylamino)ethoxy)-5-phenylisoxazole (2.00 g) was dissolved in tetrahydrofuran (20 ml), and butyllithium (1.56M hexane solution, 9.3 ml) was added dropwise thereto at −70° C. under a nitrogen atmosphere, and the resulting mixture was stirred for 10 minutes. Then, carbon dioxide gas was bubbled into the reaction mixture for 10 minutes and the temperature of the reaction mixture was raised to 0° C. The reaction mixture was poured into ice-cold water and the pH of the mixture was adjusted to a value of 6 with an aqueous potassium dihydrogenphosphate solution, followed by extraction with ethyl acetate. The organic layer was washed with a saturated aqueous NaCl solution and dried over anhydrous magnesium sulfate. After filtration, the solvent was evaporated under reduced pressure. The residue was washed with ether to obtain the title compound (2.18 g, 95%) as a colorless powder.

IR spectrum (KBr) $v_{max}$ cm$^{-1}$: 2982, 1706; NMR spectrum (DMSO-d$_6$) δ ppm: 1.38(9H, s), 3.38(2H, q, J=5.7 Hz), 4.29(2H, t, J=5.7 Hz), 7.01(1H, brs), 7.51–7.62(3H, m), 7.84–7.91(2H, m).

(b) 3-(2-Aminoethoxy)-4-carboxy-5-phenylisoxazole hydrochloride 3-(2-(N-tert-butoxycarbonylamino)ethoxy)-4-carboxy-5-phenylisoxazole (0.12 g) was subjected to reaction and post-treatment in a similar manner to that described in Example 9(b) to obtain the title compound (0.06 g, 60%) as colorless crystals.

m.p.: 180–183° C. (decomposed); IR spectrum (KBr) $v_{max}$ cm$^{-1}$: 3149, 2873, 2820, 1755, 1709; NMR spectrum (DMSO-d$_6$) δ ppm: 3.30(2H, t, J=5.3 Hz), 4.54(2H, t, J=5.3 Hz), 7.54–7.65(3H, m), 7.85–7.87(2H, m), 8.22(3H, brs).

EXAMPLE 20

3-(2-Aminoethoxy)-4-carbamoyl-5-phenylisoxazole hydrochloride (Compound list No.: 1414)

(a) 3-(2-(N-tert-Butoxycarbonylamino)ethoxy)-4-carbamoyl-5-phenylisoxazole 3-(2-(N-tert-Butoxycarbonylamino)ethoxy)-4-carboxy-5-phenylisoxazole (0.6 g) was dissolved in tetrahydrofuran (6 ml) and carbonyldiimidazole (0.31 g) was added thereto under ice-cooling with stirring, followed by stirring of the mixture at room temperature for 30 minutes. Aqueous ammonia (1 ml) was added dropwise to the reaction mixture and the mixture was stirred at room temperature for one hour. The reaction mixture was poured into ice-cold water and extracted with ethyl acetate. The organic layer was washed with a saturated aqueous NaCl solution and dried using anhydrous magnesium sulfate. After filtration, the solvent was evaporated under reduced pressure to obtain the title compound (0.60 g, quantitative) as a colorless powder.

IR spectrum (KBr) $v_{max}$ cm$^{-1}$: 3439, 3371, 3149, 1694, 1680; NMR spectrum (DMSO-d$_6$) δ ppm: 1.39(9H, s), 3.39(2H, q, J=5.0 Hz), 4.30(2H, t, J=5.0 Hz), 7.38(1H, brs), 7.51–7.57(3H, m), 7.71(1H, brs), 7.91–7.94(2H, m).

(b) 3-(2-Aminoethoxy)-4-carbamoyl-5-phenylisoxazole hydrochloride 3-(2-(N-tert-Butoxycarbonylamino)ethoxy)-4-carbamoyl-5-phenylisoxazole (0.22 g) was subjected to reaction and post-treatment in a similar manner to that described in Example 9(b) to obtain the title compound (0.13 g, 72%) as colorless crystals.

m.p.: 225–230° C. (decomposed); IR spectrum (KBr) $v_{max}$ cm$^{-1}$: 3407, 3213, 2963, 2878, 1662; NMR spectrum (DMSO-d$_6$) δ ppm: 3.32(2H, t, J=4.9 Hz), 4.54(2H, t, J=4.9 Hz), 7.52–7.60(4H, m), 7.77(1H, brs), 7.92–7.94(2H, m), 8.29(3H, brs).

EXAMPLE 21

3-(2-Aminoethoxy)-4-cyano-5-phenylisoxazole hydrochloride (Compound list No.: 1406)

(a) 3-(2-(N-tert-Butoxycarbonylamino)ethoxy)-4-cyano-5-phenylisoxazole 3-(2-(N-tert-Butoxycarbonylamino)ethoxy)-4-carbamoyl-5-phenylisoxazole (0.38 g) was dissolved in dimethylformamide (4 ml), and phosphorus oxychloride (0.11 ml) was added dropwise thereto at 5° C. under a nitrogen atmosphere, followed by stirring of the mixture at room temperature for 30 minutes. The reaction mixture was poured into ice-cold water and extracted with ethyl acetate. The organic layer was washed with a saturated aqueous NaCl solution and dried over anhydrous magnesium sulfate. After filtration, the solvent was evaporated under reduced pressure. The residue was purified by silica gel column chromatography (eluent: hexane/ethyl acetate=3/1) to obtain the title compound (0.28 g, 78%) as a colorless solid.

IR spectrum (KBr) $v_{max}$ cm$^{-1}$: 3384, 2237, 1690, 1680; NMR spectrum (CDCl$_3$) δ ppm: 1.47(9H, s), 3.61(2H, q, J=5.2 Hz), 4.43(2H, t, J=5.2 Hz), 4.97(1H, brs), 7.52–7.64 (3H, m), 8.01–8.05(2H, m).

(b) 3-(2-Aminoethoxy)-4-cyano-5-phenylisoxazole hydrochloride 3-(2-(N-tert-Butoxycarbonylamino)ethoxy)-4-cyano-5-phenylisoxazole (0.25 g) was subjected to reaction and post-treatment in a similar manner to that described in Example 9(b) to obtain the title compound (0.13 g, 65%) as colorless crystals.

m.p.: 200–205° C. (decomposed); IR spectrum (KBr) $v_{max}$ cm$^{-1}$: 2967, 2236, 1611; NMR spectrum (DMSO-d$_6$) δ ppm: 3.32(2H, t, J=5.1 Hz), 4.60(2H, t, J=5.1 Hz), 7.68–7.76 (3H, m), 7.98–8.01(2H, m), 8.29(3H, brs).

EXAMPLE 22

3-(2-Aminoethoxy)-4-methoxycarbonyl-5-phenylisoxazole hydrochloride (Compound list No.: 1412)

(a) 3-(2-(N-tert-Butoxycarbonylamino)ethoxy)-4-methoxycarbonyl-5-phenylisoxazole 3-(2-(N-tert-Butoxycarbonylamino)ethoxy)-4-carboxy-5-phenylisoxazole (0.2 g) was dissolved in a mixture of methanol and benzene (1:5, 10 ml), and trimethylsilyldiazomethane (0.6 ml, 2.0M hexane solution) was added dropwise thereto under ice-cooling, followed by stirring of the mixture at room temperature for 30 minutes. The reaction mixture was poured into an ice-cold water and extracted with ethyl acetate. The organic layer was washed with a saturated aqueous NaCl solution and dried over anhydrous magnesium sulfate. After filtration, the solvent was evaporated under reduced pressure. The residue was purified by silica gel column chromatography (eluent: hexane/ethyl acetate=3/1) to obtain the title compound (0.17 g, 81%) as a colorless solid.

IR spectrum (KBr) $v_{max}$ cm$^{-1}$: 3355, 1725, 1691; NMR spectrum (CDCl$_3$) δ ppm: 1.46(9H, s), 3.62(2H, q, J=5.1 Hz), 3.85(3H, s), 4.43(3H, t, J=5.1 Hz), 5.03(1H, brs), 7.46–7.54(3H, m), 7.87–7.91(2H, m).

(b) 3-(2-Aminoethoxy)-4-methoxycarbonyl-5-phenylisoxazole hydrochloride 3-(2-(N-tert-Butoxycarbonylamino)ethoxy)-4-methoxycarbonyl-5-phenylisoxazole (0.16 g) was subjected to reaction and post-treatment in a similar manner to that described in Example 9(b) to obtain the title compound (0.08 g, 62%) as colorless crystals.

m.p.: 195–198° C. (decomposed); IR spectrum (KBr) $v_{max}$ cm$^{-1}$: 3148, 2870, 2848, 2821, 1708; NMR spectrum (DMSO-d$_6$) δ ppm: 3.30(2H, t, J=5.2 Hz), 3.77(3H, s), 4.54(2H, t, J=5.2 Hz), 7.56–7.66(3H, m), 7.85–7.87(2H, m), 8.24(3H, brs).

EXAMPLE 23

3-(2-Aminoethoxy)-4-methylaminocarbonyl-5-phenylisoxazole hydrochloride (Compound list No.: 1416)

(a) 3-(2-(N-tert-Butoxycarbonylamino)ethoxy)-4-methylaminocarbonyl-5-phenylisoxazole 3-(2-(N-tert-Butoxycarbonylamino)ethoxy)-4-carboxy-5-phenylisoxazole (0.2 g) and methylamine (30% methanol solution, 0.12 ml) were subjected to reaction and post-treatment in a similar manner to that described in Example 20(a) to obtain the title compound (0.18 g, 87%) as a colorless powder.

IR spectrum (KBr) $v_{max}$ cm$^{-1}$: 3405, 3369, 1677; NMR spectrum (CDCl$_3$) δ ppm: 1.45(9H, s), 2.97(3H, d, J=5.0 Hz), 3.64(2H, q, J=5.1 Hz), 4.44(2H, t, J=5.1 Hz), 4.90(1H, brs), 7.30(1H, brs), 7.46–7.50(3H, m), 8.05–8.09(2H, m).

(b) 3-(2-Aminoethoxy)-4-methylaminocarbonyl-5-phenylisoxazole hydrochloride 3-(2-(N-tert-Butoxycarbonylamino)ethoxy)-4-methylaminocarbonyl-5-phenylisoxazole (0.17 g) was subjected to reaction and post-treatment in a similar manner to that described in Example 14(a) to obtain the title compound (0.08 g, 57%) as colorless crystals.

m.p.: 223–226° C. (decomposed); IR spectrum (KBr) $v_{max}$ cm$^{-1}$: 3102, 2935, 2879, 1646; NMR spectrum (DMSO-d$_6$) δ ppm: 2.78(3H, d, J=4.4 Hz), 3.32(2H, t, J=4.8

Hz), 4.53(2H, t, J=4.8 Hz), 7.51–7.60(3H, m), 7.89–7.92 (2H, m), 8.18(1H, d, J=4.4 Hz), 8.31(3H, brs).

EXAMPLE 24

3-(2-Aminoethoxy)-5-(4-chlorophenyl)-4-methylisoxazole hydrochloride (Compound list No.: 148)

(a) 3-(2-(N-tert-Butoxycarbonylamino)ethoxy)-5-(4-chlorophenyl)-4-methylisoxazole 3-(2-(N-tert-Butoxycarbonylamino)ethoxy)-5-(4-chlorophenyl)isoxazole (0.25 g) and methyl iodide (0.06 ml) were subjected to reaction and post-treatment in a similar manner to that described in Example 14(a) to obtain the title compound (0.23 g, 89%) as a colorless powder.

IR spectrum (KBr) $v_{max}$ cm$^{-1}$: 3344, 2980, 1682; NMR spectrum (CDCl$_3$) δ ppm: 1.46(9H, s), 2.10(3H, s), 3.58(2H, q, J=5.2 Hz), 4.37(2H, t, J=5.2 Hz), 4.90(1H, brs), 7.45(2H, d, J=8.6 Hz), 7.63(2H, d, J=8.6 Hz).

(b) 3-(2-Aminoethoxy)-5-(4-chlorophenyl)-4-methylisoxazole hydrochloride 3-(2-(N-tert-Butoxycarbonylamino)ethoxy)-5-(4-chlorophenyl)-4-methylisoxazole (0.22 g) was subjected to reaction and post-treatment in a similar manner to that described in Example 9(b) to obtain the title compound (0.09 g, 50%) as colorless crystals.

m.p.: 248–253° C. (decomposed); IR spectrum (KBr) $v_{max}$ cm$^{-1}$: 3020, 2991, 2884, 1513; NMR spectrum (DMSO-d$_6$) δ ppm: 2.12(3H, s), 3.27(2H, t, J=5.1 Hz), 4.45(2H, t, J=5.1 Hz), 7.63(2H, d, J=8.6 Hz), 7.75(2H, d, J=8.6 Hz), 8.23(3H, brs).

EXAMPLE 25

3-(2-Aminoethoxy)-5-(4-chlorophenyl)-4-ethylisoxazole hydrochloride (Compound list No.: 149)

(a) 3-(2-(N-tert-Butoxycarbonylamino)ethoxy)-5-(4-chlorophenyl)-4-ethylisoxazole 3-(2-(N-tert-Butoxycarbonylamino)ethoxy)-5-(4-chlorophenyl)isoxazole (0.4 g) and ethyl iodide (0.11 ml) were subjected to reaction and post-treatment in a similar manner to that described in Example 14(a) to obtain the title compound (0.26 g, 61%) as a colorless oil.

IR spectrum (CHCl$_3$) $v_{max}$ cm$^{-1}$: 3460, 2980, 1713; NMR spectrum (CDCl$_3$) δ ppm: 1.20(3H, t, J=7.4 Hz), 1.46(9H, s), 2.54(2H, q, J=7.4 Hz), 3.59(2H, q, J=5.2 Hz), 4.37(2H, t, J=5.2 Hz), 4.90(1H, brs), 7.45(2H, d, J=8.5 Hz), 7.59(2H, d, J=8.5 Hz).

(b) 3-(2-Aminoethoxy)-5-(4-chlorophenyl)-4-ethylisoxazole hydrochloride 3-(2-(N-tert-Butoxycarbonylamino)ethoxy)-5-(4-chlorophenyl)-4-ethylisoxazole (0.22 g) was subjected to reaction and post-treatment in a similar manner to that described in Example 9(b) to obtain the title compound (0.13 g, 72%) as colorless crystals.

m.p.: 217–220° C. (decomposed); IR spectrum (KBr) $v_{max}$ cm$^{-1}$: 2972, 2892, 1515; NMR spectrum (DMSO-d$_6$) δ ppm: 1.14(3H, t, J=7.5 Hz), 2.58(2H, q, J=7.5 Hz), 3.28(2H, t, J=5.2 Hz), 4.46(2H, t, J=5.2 Hz), 7.64(2H, d, J=8.6 Hz), 7.71(2H, d, J=8.6 Hz), 8.20(3H, brs).

EXAMPLE 26

3-(2-Aminoethoxy)-5-(4-chlorophenyl)-4-propylisoxazole hydrochloride (Compound list No.: 150)

(a) 3-(2-(N-tert-Butoxycarbonylamino)ethoxy)-5-(4-chlorophenyl)-4-propylisoxazole 3-(2-(N-tert-Butoxycarbonylamino)ethoxy)-5-(4-chlorophenyl)isoxazole (0.4 g) and propyl iodide (0.14 ml) were subjected to reaction and post-treatment in a similar manner to that described in Example 14(a) to obtain the title compound (0.21 g, 47%) as a colorless powder.

IR spectrum (KBr) $v_{max}$ cm$^{-1}$: 3392, 2963, 1685; NMR spectrum (CDCl$_3$) δ ppm: 0.96(3H, t, J=7.4 Hz), 1.46(9H, s), 1.57–1.69(2H, m), 2.49(2H, t, J=7.6 Hz), 3.58(2H, q, J=5.2 Hz), 4.37(2H, t, J=5.2 Hz), 4.87(1H, brs), 7.45(2H, d, J=8.6 Hz), 7.60(2H, d, J=8.6 Hz).

(b) 3-(2-Aminoethoxy)-5-(4-chlorophenyl)-4-propylisoxazole hydrochloride 3-(2-(N-tert-Butoxycarbonylamino)ethoxy)-5-(4-chlorophenyl)-4-propylisoxazole (0.19 g) was subjected to reaction and post-treatment in a similar manner to that described in Example 9(b) to obtain the title compound (0.13 g, 81%) as colorless crystals.

m.p.: 146–149° C. (decomposed); IR spectrum (KBr) $v_{max}$ cm$^{-1}$: 2958, 2871, 2829, 1516; NMR spectrum (DMSO-d$_6$) δ ppm: 0.90(3H, t, J=7.3 Hz), 1.50–1.59(2H, m), 2.54(2H, t, J=7.3 Hz), 3.28(2H, t, J=5.2 Hz), 4.45(2H, t, J=5.2 Hz), 7.63(2H, d, J=8.7 Hz), 7.72(2H, d, J=8.7 Hz), 8.21(3H, brs).

EXAMPLE 27

3-(2-Aminoethoxy)-5-(4-methylphenyl)isoxazole hydrochloride (Compound list No.: 260)

(a) 3-(2-(N-tert-Butoxycarbonylamino)ethoxy)-5-(4-methylphenyl)isoxazole

3-Hydroxy-5-(4-methylphenyl)isoxazole (1.5 g) and 2-(N-tert-butoxycarbonylamino)ethanol (1.5 g) were subjected to reaction and post-treatment in a similar manner to that described in Example 9(a) to obtain the title compound (2.2 g, 82%) as a colorless powder.

IR spectrum (KBr) $v_{max}$ cm$^{-1}$: 3375, 3356, 3332, 1719, 1684; NMR spectrum (CDCl$_3$) δ ppm: 1.46(9H, s), 2.40(3H, s), 3.56(2H, q, J=5.1 Hz), 4.35(2H, t, J=5.1 Hz), 4.94(1H, brs), 6.09(1 H, s), 7.26(2H, d, J=8.1 Hz), 7.61(2H, d, J=8.1 Hz).

(b) 3-(2-Aminoethoxy)-5-(4-methylphenyl)isoxazole hydrochloride 3-(2-(N-tert-Butoxycarbonylamino)ethoxy)-5-(4-methylphenyl)isoxazole (0.3 g) was subjected to reaction and post-treatment in a similar manner to that described in Example 9(b) to obtain the title compound (0.16 g, 67%) as colorless crystals.

m.p.: 215–220° C. (decomposed); IR spectrum (KBr) $v_{max}$ cm$^{-1}$: 2993, 2979, 1622; NMR spectrum (DMSO-d$_6$) δ ppm: 2.37(3H, s), 3.25(2H, t, J=5.0 Hz), 4.44(2H, t, J=5.0 Hz), 6.76(1H, s), 7.35(2H, d, J=8.1 Hz), 7.74(2H, d, J=8.1 Hz), 8.26(3H, brs).

EXAMPLE 28

3-(2-Aminoethoxy)-5-(4-trifluoromethylphenyl) isoxazole hydrochloride (Compound list No.: 332)

(a) 3-(2-(N-tert-Butoxycarbonylamino)ethoxy)-5-(4-trifluoromethylphenyl)isoxazole 3-Hydroxy-5-(4-trifluoromethylphenyl)isoxazole (0.2 g) and 2-(N-tert-butoxycarbonylamino)ethanol (0.15 g) were subjected to reaction and post-treatment in a similar manner to that described in Example 9(a) to obtain the title compound (0.26 g, 81%) as a colorless powder.

IR spectrum (KBr) $v_{max}$ cm$^{-1}$: 3376, 1679, 1608; NMR spectrum (CDCl$_3$) δ ppm: 1.46(9H, s), 3.58(2H, q, J=5.1 Hz), 4.37(2H, t, J=5.1 Hz), 4.92(1H, brs), 6.25(1H, s), 7.72(2H, d, J=8.2 Hz), 7.84(2H, d, J=8.2 Hz).

(b) 3-(2-Aminoethoxy)-5-(4-trifluoromethylphenyl) isoxazole hydrochloride 3-(2-(N-tert-Butoxycarbonylamino)ethoxy)-5-(4-trifluoromethylphenyl)-isoxazole (0.24 g) was subjected to reaction and post-treatment in a similar manner to that described in Example 9(b) to obtain the title compound (0.14 g, 70%) as colorless crystals.

m.p.: 226–232° C. (decomposed); IR spectrum (KBr) $v_{max}$ cm$^{-1}$: 2993, 2965, 2914, 1608; NMR spectrum (DMSO-d$_6$) δ ppm: 3.27(2H, t, J=5.1 Hz), 4.47(2H, t, J=5.1 Hz), 7.07(1H, s), 7.93(2H, d, J=8.3 Hz), 8.09(2H, d, J=8.3 Hz), 8.26(3H, brs).

EXAMPLE 29

3-(2-Aminoethoxy)-5-(4-fluorophenyl)isoxazole hydrochloride (Compound list No.: 66)

(a) 3-(2-(N-tert-Butoxycarbonylamino)ethoxy)-5-(4-fluorophenyl)isoxazole 5-(4-Fluorophenyl)-3-hydroxyisoxazole (0.06 g) and 2-(N-tert-butoxycarbonylamino)ethanol (0.06 g) were subjected to reaction and post-treatment in a similar manner to that described in Example 9(a) to obtain the title compound (0.08 g, 74%) as a colorless powder.

IR spectrum (KBr) $v_{max}$ cm$^{-1}$: 3375, 1682; NMR spectrum (CDCl$_3$) δ ppm: 1.46(9H, s), 3.56(2H, q, J=5.1 Hz), 4.35(2H, t, J=5.1 Hz), 4.93(1H, brs), 6.09(1H, s), 7.15(2H, t, J=8.6 Hz), 7.71(2H, dd, J=8.6 Hz, J=5.3 Hz).

(b) 3-(2-Aminoethoxy)-5-(4-fluorophenyl)isoxazole hydrochloride 3-(2-(N-tert-Butoxycarbonylamino)ethoxy)-5-(4-fluorophenyl)isoxazole (0.05 g) was subjected to reaction and post-treatment in a similar manner to that described in Example 9(b) to obtain the title compound (0.02 g, 56%) as colorless crystals.

m.p.: 232–238° C. (decomposed); IR spectrum (KBr) $v_{max}$ cm$^{-1}$: 2993, 2978, 2911, 1621; NMR spectrum (DMSO-d$_6$) δ ppm: 3.26(2H, t, J=5.0 Hz), 4.44(2H, t, J=5.0 Hz), 6.84(1H, s), 7.40(2H, t, J=8.8 Hz), 7.93(2H, dd, J=8.8 Hz, J=5.3 Hz), 8.25(3H, brs).

EXAMPLE 30

3-(2-Aminoethoxy)-5-(1-naphthyl)isoxazole hydrochloride (Compound list No.: 475)

(a) 3-(2-(N-tert-Butoxycarbonylamino)ethoxy)-5-(1-naphthyl)isoxazole

3-Hydroxy-5-(1-naphthyl)isoxazole (0.20 g) and 2-(N-tert-butoxycarbonylamino)ethanol (0.17 g) were subjected to reaction and post-treatment in a similar manner to that described in Example 9(a) to obtain the title compound (0.30 g, 89%) as a colorless powder.

IR spectrum (KBr) $v_{max}$ cm$^{-1}$: 3318, 1712; NMR spectrum (CDCl$_3$) δ ppm: 1.47(9H, s), 3.61(2H, q, J=5.3 Hz), 4.42(2H, t, J=5.3 Hz), 4.97(1H, brs), 6.25(1H, s), 7.52–7.61 (3H, m), 7.77–7.79(1H, m), 7.90–7.99(2H, m), 8.27–8.31 (1 H, m).

(b) 3-(2-Aminoethoxy)-5-(1-naphthyl)isoxazole hydrochloride 3-(2-(N-tert-Butoxycarbonylamino)ethoxy)-5-(1-naphthyl)isoxazole (0.28 g) was subjected to reaction and post-treatment in a similar manner to that described in Example 9(b) to obtain the title compound (0.18 g, 78%) as colorless crystals.

m.p.: 201–205° C. (decomposed); IR spectrum (KBr) $v_{max}$ cm$^{-1}$: 3002, 2968, 2913, 1602; NMR spectrum (DMSO-d$_6$) δ ppm: 3.31(2H, t, J=5.1 Hz), 4.52(2H, t, J=5.1 Hz), 6.83(1H, s), 7.63–7.70(3H, m), 7.87–7.89(1H, m), 8.07–8.25(3H, m), 8.30(3H, brs).

EXAMPLE 31

3-(2-Aminoethoxy)-4-bromo-5-phenylisoxazole hydrochloride (Compound list No.: 1357)

(a) 4-Bromo-3-(2-(N-tert-butoxycarbonylamino)ethoxy)-5-phenylisoxazole

4-Bromo-3-hydroxy-5-phenylisoxazole (0.2 g) and 2-(N-tert-butoxycarbonylamino)ethanol (0.15 g) were subjected to reaction and post-treatment in a similar manner to that described in Example 9(a) to obtain the title compound (0.26 g, 81%) as a colorless powder.

IR spectrum (KBr) $v_{max}$ cm$^{-1}$: 3352, 2976, 1719, 1709; NMR spectrum (CDCl$_3$) δ ppm: 1.47(9H, s), 3.61(2H, q, J=5.1 Hz), 4.41(2H, t, J=5.1 Hz), 4.97(1H, brs), 7.47–7.55 (3H, m), 7.98–8.04(2H, m).

(b) 3-(2-Aminoethoxy)-4-bromo-5-phenylisoxazole hydrochloride

4-Bromo-3-(2-(N-tert-butoxycarbonylamino)ethoxy)-5-phenylisoxazole (0.24 g) was subjected to reaction and post-treatment in a similar manner to that described in Example 9(b) to obtain the title compound (0.13 g, 65%) as colorless crystals.

m.p.: 192–198° C. (decomposed); IR spectrum (KBr) $v_{max}$ cm$^{-1}$: 2991, 2921, 2894, 1614, 1594, 1574; NMR spectrum (DMSO-d$_6$) δ ppm: 3.32(2H, t, J=5.1 Hz), 4.54 (2H, t, J=5.1 Hz), 7.60–7.66(3H, m), 7.95–7.98(2H, m), 8.19(3H, brs).

EXAMPLE 32

3-(2-Aminoethoxy)-4-iodo-5-phenylisoxazole hydrochloride (Compound list No.: 1359)

(a) 3-(2-(N-tert-Butoxycarbonylamino)ethoxy)-4-iodo-5-phenylisoxazole

3-Hydroxy-4-iodo-5-phenylisoxazole (0.2 g) and 2-(N-tert-butoxycarbonylamino)ethanol (0.12 g) were subjected to reaction and post-treatment in a similar manner to that described in Example 9(a) to obtain the title compound (0.22 g, 73%) as a colorless powder.

IR spectrum (KBr) $v_{max}$ cm$^{-1}$: 3328, 2977, 1696; NMR spectrum (CDCl$_3$) δ ppm: 1.47(9H, s), 3.61(2H, q, J=5.2 Hz), 4.41(2H, t, J=5.2 Hz), 4.97(1H, brs), 7.47–7.55(3H, m), 7.99–8.06(2H, m).

(b) 3-(2-Aminoethoxy)-4-iodo-5-phenylisoxazole hydrochloride 3-(2-(N-tert-Butoxycarbonylamino)ethoxy)-4-iodo-5-phenylisoxazole (0.20 g) was subjected to reaction and post-treatment in a similar manner to that described in Example 9(b) to obtain the title compound (0.12 g, 71%) as colorless crystals.

m.p.: 201–206° C. (decomposed); IR spectrum (KBr) $v_{max}$ cm$^{-1}$: 2961, 2912, 1591; NMR spectrum (DMSO-d$_6$) δ ppm: 3.30(2H, t, J=5.3 Hz), 4.51(2H, t, J=5.3 Hz), 7.58–7.64 (3H, m), 7.96–8.01(2H, m), 8.22(3H, brs).

EXAMPLE 33

3-(2-Aminoethoxy)-5-(4-isopropylphenyl)isoxazole hydrochloride (Compound list No.: 1618)

(a) 3-(2-(N-tert-Butoxycarbonylamino)ethoxy)-5-(4-isopropylphenyl)isoxazole

3-Hydroxy-5-(4-isopropylphenyl)isoxazole (0.2 g) and 2-(N-tert-butoxycarbonylamino)ethanol (0.17 g) were subjected to reaction and post-treatment in a similar manner to that described in Example 9(a) to obtain the title compound (0.26 g, 77%) as a colorless powder.

IR spectrum (KBr) $v_{max}$ cm$^{-1}$: 3326, 2973, 1713, 1697, 1623; NMR spectrum (CDCl$_3$) δ ppm: 1.27(6H, d, J=6.9 Hz), 1.46(9H, s), 2.95(1H, qq, J=6.9 Hz, J=6.9 Hz), 3.56(2H, q, J=5.1 Hz), 4.35(2H, t, J=5.1 Hz), 4.94(1H, brs), 6.09(1H, s), 7.31(2H, d, J=8.3 Hz), 7.65(2H, d, J=8.3 Hz).

(b) 3-(2-Aminoethoxy)-5-(4-isopropylphenyl)isoxazole hydrochloride 3-(2-(N-tert-Butoxycarbonylamino)ethoxy)-5-(4-isopropylphenyl)-isoxazole (0.25 g) was subjected to reaction and post-treatment in a similar manner to that described in Example 9(b) to obtain the title compound (0.11 g, 55%) as colorless crystals.

m.p.: 162–166° C. (decomposed);

IR spectrum (KBr) $v_{max}$ cm$^{-1}$: 3000, 2959, 2924, 1623, 1604; NMR spectrum (DMSO-d$_6$) δ ppm: 1.23(6H, d, J=6.9 Hz), 2.96(1H, qq, J=6.9 Hz, J=6.9 Hz), 3.26(2H, t, J=5.1 Hz), 4.44(2H, t, J=5.1 Hz), 6.77(1H, s), 7.41(2H, d, J=8.2 Hz), 7.77(2H, d, J=8.2 Hz), 8.20(3H, brs).

EXAMPLE 34

3-(2-Aminoethoxy)-5-(2-methylphenyl)isoxazole hydrochloride (Compound list No.: 224)

(a) 3-(2-(N-tert-Butoxycarbonylamino)ethoxy)-5-(2-methylphenyl)isoxazole

3-Hydroxy-5-(2-methylphenyl)isoxazole (0.2 g) and 2-(N-tert-butoxycarbonylamino)ethanol (0.2 g) were subjected to reaction and post-treatment in a similar manner to that described in Example 9(a) to obtain the title compound (0.31 g, 86%) as a colorless powder.

IR spectrum (KBr) $v_{max}$ cm$^{-1}$: 3315, 1710, 1619; NMR spectrum (CDCl$_3$) δ ppm: 1.46(9H, s), 2.49(3H, s), 3.57(2H, q, J=5.2 Hz), 4.37(2H, t, J=5.2 Hz), 4.95(1H, brs), 6.06(1H, s), 7.19–7.39(3H, m), 7.65–7.69(1H, m).

(b) 3-(2-Aminoethoxy)-5-(2-methylphenyl)isoxazole hydrochloride 3-(2-(N-tert-Butoxycarbonylamino)ethoxy)-5-(2-methylphenyl)isoxazole (0.30 g) was subjected to reaction and post-treatment in a similar manner to that described in Example 9(b) to obtain the title compound (0.18 g, 75%) as colorless crystals.

m.p.: 165–167° C.; IR spectrum (KBr) $v_{max}$ cm$^{-1}$: 2996, 2976, 2911, 1613; NMR spectrum (DMSO-d$_6$) δ ppm: 2.46(3H, s), 3.26(2H, t, J=5.2 Hz), 4.46(2H, t, J=5.2 Hz), 6.59(1H, s), 7.34–7.46(3H, m), 7.67–7.69(1H, m), 8.21(3H, brs).

EXAMPLE 35

3-(2-Aminoethoxy)-5-(4-phenylphenyl)isoxazole hydrochloride (Compound list No.: 368)

(a) 3-(2-(N-tert-Butoxycarbonylamino)ethoxy)-5-(4-phenylphenyl)isoxazole

3-Hydroxy-5-(4-phenylphenyl)isoxazole (0.2 g) and 2-(N-tert-butoxycarbonylamino)ethanol (0.15 g) were subjected to reaction and post-treatment in a similar manner to that described in Example 9(a) to obtain the title compound (0.22 g, 69%) as a colorless powder.

IR spectrum (KBr) $v_{max}$ cm$^{-1}$: 3345, 1694; NMR spectrum (CDCl$_3$) δ ppm: 1.46(9H, s), 3.58(2H, q, J=5.1 Hz), 4.37(2H, t, J=5.1 Hz), 4.95(1H, brs), 6.18(1H, s), 7.37–7.51(3H, m), 7.61–7.70(4H, m), 7.79–7.82(2H, m).

(b) 3-(2-Aminoethoxy)-5-(4-phenylphenyl)isoxazole hydrochloride 3-(2-(N-tert-Butoxycarbonylamino)ethoxy)-5-(4-phenylphenyl)isoxazole (0.2 g) was subjected to reaction and post-treatment in a similar manner to that described in Example 9(b) to obtain the title compound (0.1 g, 63%) as colorless crystals.

m.p.: 212–218° C. (decomposed); IR spectrum (KBr) $v_{max}$ cm$^{-1}$: 2996, 2966, 2909, 1619, 1602; NMR spectrum (DMSO-d$_6$) δ ppm: 3.27(2H, t, J=5.1 Hz), 4.46(2H, t, J=5.1 Hz), 6.90(1H, s), 7.41–7.55(3H, m), 7.74–7.76(2H, m), 7.84–7.87(2H, m), 7.94–7.96(2H, m), 8.18(3H, brs).

EXAMPLE 36

3-(2-Aminoethoxy)-5-(4-phenoxyphenyl)isoxazole hydrochloride (Compound list No.: 1632)

(a) 3-(2-(N-tert-Butoxycarbonylamino)ethoxy)-5-(4-phenoxyphenyl)isoxazole

3-Hydroxy-5-(4-phenoxyphenyl)isoxazole (0.2 g) and 2-(N-tert-butoxycarbonylamino)ethanol (0.14 g) were subjected to reaction and post-treatment in a similar manner to that described in Example 9(a) to obtain the title compound (0.23 g, 74%) as a colorless powder.

IR spectrum (KBr) $v_{max}$ cm$^{-1}$: 3331, 1720; NMR spectrum (CDCl$_3$) δ ppm: 1.46(9H, s), 3.56(2H, q, J=5.2 Hz), 4.34(2H, t, J=5.2 Hz), 4.95(1H, brs), 6.06(1H, s), 7.02–7.08(4H, m), 7.15–7.20(1H, m), 7.35–7.42(2H, m), 7.65–7.70(2H, m).

(b) 3-(2-Aminoethoxy)-5-(4-phenoxyphenyl)isoxazole hydrochloride 3-(2-(N-tert-Butoxycarbonylamino)ethoxy)-5-(4-phenoxyphenyl)isoxazole (0.18 g) was subjected to reaction and post-treatment in a similar manner to that described in Example 9(b) to obtain the title compound (0.1 g, 67%) as colorless crystals.

m.p.: 207–213° C. (decomposed); IR spectrum (KBr) $v_{max}$ cm$^{-1}$: 3000, 2959, 2909, 1625 NMR spectrum (DMSO-d$_6$) δ ppm: 3.26(2H, t, J=5.1 Hz), 4.43(2H, t, J=5.1 Hz), 6.76(1H, s), 7.10–7.14(4H, m), 7.21–7.25(1H, m), 7.44–7.48(2H, m), 7.85–7.88(2H, m), 8.18(3H, brs).

EXAMPLE 37

3-(2-Aminoethoxy)-5-(2-trifluoromethylphenyl) isoxazole hydrochloride (Compound list No.: 296)

(a) 3-(2-(N-tert-Butoxycarbonylamino)ethoxy)-5-(2-trifluoromethylphenyl)isoxazole 3-Hydroxy-5-(2-trifluoromethylphenyl)isoxazole (0.3 g) and 2-(N-tert-butoxycarbonylamino)ethanol (0.23 g) were subjected to reaction and post-treatment in a similar manner to that described in Example 9(a) to obtain the title compound (0.36 g, 74%) as a colorless oil.

IR spectrum (CHCl$_3$) $v_{max}$ cm$^{-1}$: 3457, 2983, 1712; NMR spectrum (CDCl$_3$) δ ppm: 1.46(9H, s), 3.58(2H, q, J=5.2 Hz), 4.37(2H, t, J=5.2 Hz), 4.96(1H, brs), 6.21(1H, s), 7.56–7.69(2H, m), 7.75–7.82(2H, m).

(b) 3-(2-Aminoethoxy)-5-(2-trifluoromethylphenyl) isoxazole hydrochloride 3-(2-(N-tert-Butoxycarbonylamino)ethoxy)-5-(2-trifluoromethylphenyl)isoxazole (0.35 g) was subjected to reaction and post-treatment in a similar manner to that described in Example 9(b) to obtain the title compound (0.22 g, 76%) as colorless crystals.

m.p.: 118–122° C. (decomposed); IR spectrum (KBr) $v_{max}$ cm$^{-1}$: 2996, 2917, 1622; NMR spectrum (DMSO-d$_6$) δ ppm: 3.28(2H, t, J=5.1 Hz), 4.46(2H, t, J=5.1 Hz), 6.63(1H, s), 7.79–7.89(3H, m), 7.96–7.98(1H, m), 8.22(3H, brs).

EXAMPLE 38

3-(2-Aminoethoxy)-5-(4-hydroxyphenyl)isoxazole hydrochloride (Compound list No.: 1674)

(a) 3-(2-(N-tert-Butoxycarbonylamino)ethoxy)-5-(4-hydroxyphenyl)isoxazole

3-Hydroxy-5-(4-hydroxyphenyl)isoxazole (0.1 g) and 2-(N-tert-butoxycarbonylamino)ethanol (0.1 g) were subjected to reaction and post-treatment in a similar manner to that described in Example 9(a) to obtain the title compound (0.12 g, 67%) as a colorless powder.

IR spectrum (KBr) $v_{max}$ cm$^{-1}$: 3331, 3247, 1698, 1666, 1645, 1619; NMR spectrum (DMSO-d$_6$) δ ppm: 1.38(9H, s), 3.32(2H, q, J=5.6 Hz), 4.17(2H, t, J=5.6 Hz), 6.53(1H, s), 6.87(2H, d, J=8.8 Hz), 7.05(1H, brs), 7.63(2H, d, J=8.8 Hz), 8.98(1H, brs).

(b) 3-(2-Aminoethoxy)-5-(4-hydroxyphenyl)isoxazole hydrochloride 3-(2-(N-tert-Butoxycarbonylamino)ethoxy)-5-(4-hydroxyphenyl)isoxazole (0.12 g) was subjected to reaction and post-treatment in a similar manner to that described in Example 9(b) to obtain the title compound (0.05 g, 56%) as colorless crystals.

m.p.: 240–245° C. (decomposed); IR spectrum (KBr) $v_{max}$ cm$^{-1}$: 3145, 3056, 1620; NMR spectrum (DMSO-d$_6$) δ ppm: 3.24(2H, t, J=5.1 Hz), 4.41(2H, t, J=5.1 Hz), 6.58(1H, s), 6.90(2H, d, J=8.7 Hz), 7.67(2H, d, J=8.7 Hz), 8.13(3H, brs).

EXAMPLE 39

3-(2-Aminoethoxy)-5-(2,4-dichlorophenyl)isoxazole hydrochloride (Compound list No.: 170)

(a) 3-(2-(N-tert-Butoxycarbonylamino)ethoxy)-5-(2,4-dichlorophenyl)isoxazole 5-(2,4-Dichlorophenyl)-3-hydroxyisoxazole (0.2 g) and 2-(N-tert-butoxycarbonylamino)ethanol (0.17 g) were subjected to reaction and post-treatment in a similar manner to that described in Example 9(a) to obtain the title compound (0.26 g, 81%) as a colorless powder.

IR spectrum (KBr) $v_{max}$ cm$^{-1}$: 3386, 1681, 1606; NMR spectrum (CDCl$_3$) δ ppm: 1.46(9H, s), 3.57(2H, q, J=5.2 Hz), 4.37(2H, t, J=5.2 Hz), 4.94(1H, brs), 6.58(1H, s), 7.38(1H, dd, J=8.5 Hz, J=2.1 Hz), 7.53(1H, d, J=2.1 Hz), 7.85(1H, d, J=8.5 Hz).

(b) 3-(2-Aminoethoxy)-5-(2,4-dichlorophenyl)isoxazole hydrochloride 3-(2-(N-tert-Butoxycarbonylamino)ethoxy)-5-(2,4-dichlorophenyl)isoxazole (0.24 g) was subjected to reaction and post-treatment in a similar manner to that described in Example 9(b) to obtain the title compound (0.12 g, 60%) as colorless crystals.

m.p.: 192–195° C. (decomposed); IR spectrum (KBr) $v_{max}$ cm$^{-1}$: 3069, 3005, 2967, 1611; NMR spectrum (DMSO-d$_6$) δ ppm: 3.27(2H, t, J=5.1 Hz), 4.47(2H, t, J=5.1 Hz), 6.84(1H, s), 7.64(1H, dd, J=8.7 Hz, J=2.1 Hz), 7.89(1H, d, J=2.1 Hz), 7.90(1H, d, J=8.7 Hz), 8.20(3H, brs).

EXAMPLE 40

3-(2-Aminoethoxy)-5-(3,4-dichlorophenyl)isoxazole hydrochloride (Compound list No.: 1604)

(a) 3-(2-(N-tert-Butoxycarbonylamino)ethoxy)-5-(3,4-dichlorophenyl)isoxazole 5-(3,4-Dichlorophenyl)-3-hydroxyisoxazole (0.3 g) and 2-(N-tert-butoxycarbonylamino)ethanol (0.23 g) were subjected to reaction and post-treatment in a similar manner to that described in Example 9(a) to obtain the title compound (0.41 g, 85%) as a colorless powder.

IR spectrum (KBr) $v_{max}$ cm$^{-1}$: 3369, 1687; NMR spectrum (CDCl$_3$) δ ppm: 1.46(9H, s), 3.56(2H, q, J=5.1 Hz), 4.35(2H, t, J=5.1 Hz), 4.91(1H, brs), 6.16(1H, s), 7.54(2H, s), 7.80(1H, s).

(b) 3-(2-Aminoethoxy)-5-(3,4-dichlorophenyl)isoxazole hydrochloride 3-(2-(N-tert-Butoxycarbonylamino)ethoxy)-5-(3,4-dichlorophenyl)isoxazole (0.4 g) was subjected to reaction and post-treatment in a similar manner to that described in Example 9(b) to obtain the title compound (0.22 g, 67%) as colorless crystals.

m.p.: 202–210° C. (decomposed); IR spectrum (KBr) $v_{max}$ cm$^{-1}$: 2993, 2977, 2915, 1617; NMR spectrum (DMSO-d$_6$) δ ppm: 3.26 (2H, t, J=5.1 Hz), 4.45 (2H, t, J=5.1 Hz), 7.02 (1H, s), 7.84 (1H, d, J=8.9 Hz), 7.85 (1H, d, J=8.9 Hz), 8.17 (4H, brs).

EXAMPLE 41

3-(2-Aminoethoxy)-5-(2,3-dichlorophenyl)isoxazole hydrochloride (Compound list No.: 1526)

(a) 3-(2-(N-tert-Butoxycarbonylamino)ethoxy)-5-(2,3-dichlorophenyl)isoxazole 5-(2,3-Dichlorophenyl)-3-hydroxyisoxazole (0.3 g) and 2-(N-tert-butoxycarbonylamino)ethanol (0.23 g) were subjected to reaction and post-treatment in a similar manner to that described in Example 9(a) to obtain the title compound (0.37 g, 77%) as a colorless powder.

IR spectrum (KBr) $v_{max}$ cm$^{-1}$: 3381, 1688, 1607; NMR spectrum (CDCl$_3$) δ ppm: 1.46 (9H, s), 3.58 (2H, q, J=5.1 Hz), 4.37 (2H, t, J=5.1 Hz), 4.95 (1H, brs), 6.60 (1H, s), 7.34 (1H, t, J=7.9 Hz), 7.58 (1H, dd, J=7.9 Hz, J=1.4 Hz), 7.81 (1H, dd, J=7.9 Hz, J=1.4 Hz).

(b) 3-(2-Aminoethoxy)-5-(2,3-dichlorophenyl)isoxazole hydrochloride 3-(2-(N-tert-Butoxycarbonylamino)ethoxy)-5-(2,3-dichlorophenyl)isoxazole (0.36 g) was subjected to reaction and post-treatment in a similar manner to that described in Example 9(b) to obtain the title compound (0.20 g, 67%) as colorless crystals.

m.p.: 183–186° C. (decomposed); IR spectrum (KBr) $v_{max}$ cm$^{-1}$: 3010, 2979, 2908, 1604; NMR spectrum (DMSO-d$_6$) δ ppm: 3.27 (2H, t, J=5.1 Hz), 4.48 (2H, t, J=5.1 Hz), 6.87 (1H, s), 7.57 (1H, t, J=7.8 Hz), 7.82–7.87 (2H, m), 8.19 (3H, brs).

EXAMPLE 42

3-(2-Aminoethoxy)-5-(2,6-dichlorophenyl)isoxazole hydrochloride (Compound list No.: 188)

(a) 3-(2-(N-tert-Butoxycarbonylamino)ethoxy)-5-(2,6-dichlorophenyl)isoxazole 5-(2,6-Dichlorophenyl)-3-hydroxyisoxazole (0.3 g) and 2-(N-tert-butoxycarbonylamino)ethanol (0.23 g) were subjected to reaction and post-treatment in a similar manner to that described in Example 9(a) to obtain the title compound (0.31 g, 65%) as a colorless powder.

IR spectrum (KBr) $v_{max}$ cm$^{-1}$: 3358, 1703, 1626; NMR spectrum (CDCl$_3$) δ ppm: 1.46 (9H, s), 3.58 (2H, q, J=5.1 Hz), 4.39 (2H, t, J=5.1 Hz), 4.96 (1H, brs), 6.11 (1H, s), 7.32–7.44 (3H, m).

(b) 3-(2-Aminoethoxy)-5-(2.6-dichlorophenyl)isoxazole hydrochloride 3-(2-(N-tert-Butoxycarbonylamino)ethoxy)-5-(2,6-dichlorophenyl)isoxazole (0.16 g) was subjected to reaction and post-treatment in a similar manner to that described in Example 9(b) to obtain the title compound (0.07 g, 54%) as colorless crystals.

m.p.: 148–151° C. (decomposed); IR spectrum (KBr) $v_{max}$ cm$^{-1}$: 3005, 2966, 2935, 1631; NMR spectrum (DMSO-d$_6$) δ ppm: 3.27 (2H, t, J=5.0 Hz), 4.47 (2H, t, J=5.0 Hz), 6.69 (1H, s), 7.61–7.71 (3H, m), 8.15 (3H, brs).

EXAMPLE 43

3-(2-Aminoethoxy)-5-(2,4-difluorophenyl)isoxazole hydrochloride (Compound list No.: 93)

(a) 3-(2-(N-tert-Butoxycarbonylamino)ethoxy)-5-(2,4-difluorophenyl)isoxazole 5-(2,4-difluorophenyl)-3-hydroxyisoxazole (0.3 g) and 2-(N-tert-butoxycarbonylamino)ethanol (0.27 g) were subjected to reaction and post-treatment in a similar manner to that described in Example 9(a) to obtain the title compound (0.44 g, 85%) as a colorless powder.

IR spectrum (KBr) $v_{max}$ cm$^{-1}$: 3382, 1694; NMR spectrum (CDCl$_3$) δ ppm: 1.46 (9H, s), 3.57 (2H, q, J=5.1 Hz), 4.36 (2H, t, J=5.1 Hz), 4.93 (1H, brs), 6.30 (1H, s), 6.90–7.05 (2H, m), 7.85–7.94 (1H, m).

(b) 3-(2-Aminoethoxy)-5-(2,4-difluorophenyl)isoxazole hydrochloride 3-(2-(N-tert-Butoxycarbonylamino)ethoxy)-5-(2,4-difluorophenyl)isoxazole (0.42 g) was subjected to reaction and post-treatment in a similar manner to that described in Example 9(b) to obtain the title compound (0.32 g, 94%) as colorless crystals.

m.p.: 226–232° C. (decomposed); IR spectrum (KBr) $v_{max}$ cm$^{-1}$: 2997, 2980, 2922, 1626; NMR spectrum (DMSO-d$_6$) δ ppm: 3.26 (2H, t, J=5.1 Hz), 4.47 (2H, t, J=5.1 Hz), 6.63 (1H, s), 7.29–7.34 (1H, m), 7.53–7.59 (1H, m), 7.94–8.00 (1H, m), 8.21 (3H, brs).

EXAMPLE 44

3-(2-Aminoethoxy)-4-(1-chloroethyl)-5-phenylisoxazole hydrochloride (Compound list No.: 1390)

(a) 3-(2-(N-tert-Butoxycarbonylamino)ethoxy)-4-(1-hydroxyethyl)-5-phenylisoxazole 3-(2-(N-tert-Butoxycarbonylamino)ethoxy)-5-phenylisoxazole (0.8 g) was dissolved in tetrahydrofuran (16 ml), and butyllithium (1.6M hexane solution, 3.7 ml) was added dropwise thereto at -70° C. under a nitrogen atmosphere, and the mixture was stirred for 10 minutes. After acetaldehyde (0.22 ml) was added dropwise to the reaction mixture, the resulting mixture was stirred for 10 minutes and the temperature of the mixture was raised to 0° C. The mixture was then poured into ice-cold water and the pH of the mixture was adjusted to a value of 6 with an aqueous potassium dihydrogenphosphate solution. After the reaction mixture was extracted with ethyl acetate and the organic layer was washed with a saturated aqueous NaCl solution, the solvent was evaporated under reduced pressure. The residue was purified by silica gel column chromatography (eluent: hexane/ethyl acetate=2/1) to obtain the title compound (0.90 g, 98%) as a colorless oil.

IR spectrum (CHCl$_3$) $v_{max}$ cm$^{-1}$: 3602, 3459, 2982, 2936, 1712; NMR spectrum (CDCl$_3$) δ ppm: 1.45 (9H, s), 1.60 (3H, d, J=6.7 Hz), 2.64 (1H, brs), 3.58 (2H, q, J=5.0 Hz), 4.39 (2H, t, J=5.0 Hz), 4.90–5.10 (2H, m), 7.45–7.50 (3H, m), 7.64–7.69 (2H, m).

(b) 3-(2-Aminoethoxy)-4-(1-chloroethyl -5-phenylisoxazole hydrochloride 3-(2-(N-tert-Butoxycarbonylamino)ethoxy)-4-(1-hydroxyethyl)-5-phenylisoxazole (0.2 g) was subjected to reaction and post-treatment in a similar manner to that described in Example 1(b) to obtain the title compound (0.13 g, 75%) as colorless crystals.

m.p.: 200–204° C. (decomposed); IR spectrum (KBr) $v_{max}$ cm$^{-1}$: 2975, 1640; NMR spectrum (DMSO-d$_6$) δ ppm: 1.86 (3H, d, J=7.0 Hz), 3.27 (2H, t, J=5.2 Hz), 4.52 (2H, t, J=5.2 Hz), 5.46 (1H, q, J=7.0 Hz), 7.60–7.68 (3H, m), 7.71–7.77 (2H, m), 8.20 (3H, brs).

EXAMPLE 45

4-Acetyl-3-(2-aminoethoxy)-5-phenylisoxazole hydrochloride (Compound list No.: 1410)

(a) 4-Acetyl-3-(2-(N-tert-butoxycarbonylamino)ethoxy)-5-phenylisoxazole 3-(2-(N-tert-Butoxycarbonylamino)ethoxy)-4-(1-hydroxyethyl)-5-phenylisoxazole (0.3 g) was dissolved in methylene chloride (3 ml), and pyridinium dichromate (0.49 g) was added thereto at room temperature, followed by stirring of the resulting mixture at the same temperature for 24 hours. After the reaction, insolubles were filtered and the solvent of the filtrate was evaporated under reduced pressure. The residue was purified by silica gel column chromatography (eluent: hexane/ethyl acetate=2/1) to obtain the title compound (0.26 g, 87%) as a colorless powder.

IR spectrum (KBr) $v_{max}$ cm$^{-1}$: 3359,1685; NMR spectrum (CDCl$_3$) δ ppm: 1.47 (9H, s), 2.51 (3H, s), 3.65 (2H, q, J=5.2 Hz), 4.48 (2H, t, J=5.2 Hz), 4.87 (1H, brs), 7.40–7.63 (3H, m), 7.93–7.96 (2H, m).

(b) 4-Acetyl-3-(2-aminoethoxy)-5-phenylisoxazole hydrochloride

4-Acetyl-3-(2-(N-tert-butoxycarbonylamino)ethoxy)-5-phenylisoxazole (0.2 g) was subjected to reaction and post-treatment in a similar manner to that described in Example 9(b) to obtain the title compound (0.12 g, 75%) as colorless crystals.

m.p.: 150–152° C. (decomposed); IR spectrum (KBr) $v_{max}$ cm$^{-1}$: 3006, 2909, 1682; NMR spectrum (DMSO-d$_6$) δ ppm: 2.52 (3H, s), 3.35 (2H, t, J=5.0 Hz), 4.59 (2H, t, J=5.0 Hz), 7.54–7.64 (3H, m), 7.85–7.88 (2H, m), 8.30 (3H, brs).

EXAMPLE 46

3-(2-Aminoethoxy)-4-isopropenyl-5-phenylisoxazole hydrochloride (Compound list No.: 1394)

(a) 3-(2-(N-tert-Butoxycarbonylamino)ethoxy)-4-(1-hydroxyisopropyl)-5-phenylisoxazole 3-(2-(N-tert-Butoxycarbonylamino)ethoxy)-5-phenylisoxazole (0.8 g) was dissolved in tetrahydrofuran (16 ml), butyllithium (1.6M hexane solution, 3.7 ml) was added dropwise thereto at -70° C. under a nitrogen atmosphere, and the resulting mixture was stirred at the same temperature for 10 minutes. After acetone (0.3 ml) was added dropwise to the reaction mixture and the mixture was stirred for 10 minutes, the temperature of the mixture was raised to 0° C. The reaction mixture was poured into ice-cold water and the pH of the mixture was adjusted to a value of 6 with an aqueous potassium dihydrogenphosphate solution. The mixture was extracted with ethyl acetate and the organic layer was washed with a saturated aqueous NaCl solution, followed by evaporation of the solvent under reduced pressure. The residue was purified by silica gel column chromatography (eluent: hexane/ethyl acetate=3/1) to obtain the title compound (0.42 g, 44%) as a colorless oil.

IR spectrum (CHCl$_3$) $v_{max}$ cm$^{-1}$: 3460, 2982, 2936, 1713; NMR spectrum (CDCl$_3$) δ ppm: 1.46 (9H, s), 1.50 (6H, s), 2.52 (1H, brs), 3.60 (2H, q, J=5.3 Hz), 4.41 (2H, t, J=5.3 Hz), 4.87 (1H, brs), 7.41–7.49 (3H, m), 7.52–7.56 (2H, m).

(b) 3-(2-Aminoethoxy)-4-isopropenyl-5-phenylisoxazole hydrochloride 3-(2-(N-tert-Butoxycarbonylamino)ethoxy)-4-(1-hydroxyisopropyl)-5-phenylisoxazole (0.13 g) was dissolved in a 4N hydrochloric acid/1,4-dioxane solution (10 ml), and the solution was stirred at 100° C. for one hour. After the reaction, the reaction mixture was left to be cooled, followed by evaporation of the solvent under reduced pressure. The residue was washed with ethyl acetate to obtain the title compound (0.10 g, 83%) as colorless crystals.

m.p.: 130–133° C. (decomposed); IR spectrum (KBr) $v_{max}$ cm$^{-1}$: 2974, 1591, 1572; NMR spectrum (DMSO-d$_6$) δ ppm: 1.95 (3H, s), 3.28 (2H, t, J=5.2 Hz), 4.48 (2H, t, J=5.2 Hz), 5.23 (1H, s), 5.33 (1H, s), 7.53–7.58 (3H, m), 7.62–7.71 (2H, m), 8.20 (3H, brs).

EXAMPLE 47

3-(2-Aminoethoxy)-5-(4-nitrophenyl)isoxazole hydrochloride (Compound list No.: 1660)

(a) 3-(2-(N-tert-Butoxycarbonylamino)ethoxy-5-(4-nitrophenyl)isoxazole

3-Hydroxy-5-(4-nitrophenyl)isoxazole (0.64 g) and 2-(N-tert-butoxycarbonylamino)ethanol (0.55 g) were subjected to reaction and post-treatment in a similar manner to that described in Example 9(a) to obtain the title compound (0.86 g, 80%) as a colorless powder.

IR spectrum (KBr) $v_{max}$ cm$^{-1}$: 3385, 1681; NMR spectrum (CDCl$_3$) δ ppm: 1.46 (9H, s), 3.57 (2H, q, J=5.2 Hz), 4.38 (2H, t, J=5.2 Hz), 4.90 (1H, brs), 6.33 (1H, s), 7.90 (2H, d, J=8.6 Hz), 8.33 (2H, d, J=8.6 Hz).

(b) 3-(2-Aminoethoxy)-5-(4-nitrophenyl)isoxazole hydrochloride 3-(2-(N-tert-Butoxycarbonylamino)ethoxy-5-(4-nitrophenyl)isoxazole (0.28 g) was subjected to reaction and post-treatment in a similar manner to that described in Example 9(b) to obtain the title compound (0.12 g, 52%) as colorless crystals.

m.p.: 216–220° C. (decomposed); IR spectrum (KBr) $v_{max}$ cm$^{-1}$: 2994, 2977, 2913, 1620, 1608; NMR spectrum (DMSO-d$_6$) δ ppm: 3.28 (2H, t, J=5.1 Hz), 4.47 (2H, t, J=5.1 Hz), 7.16 (1H, s), 8.15 (2H, d, J=8.9 Hz), 8.22 (3H, brs), 8.39 (2H, d, J=8.9 Hz).

EXAMPLE 48

3-(2-Aminoethoxy)-5-(4-aminophenyl)isoxazole dihydrochloride (Compound list No.: 1702)

(a) 5-(4-Aminophenyl)-3-(2-(N-tert-butoxycarbonylamino)ethoxy)isoxazole 3-(2-(N-tert-butoxycarbonylamino)ethoxy)-5-(4-nitrophenyl)isoxazole (0.55 g) was dissolved in a mixture of acetic acid and water (9:1, 5.5 ml), and zinc powder (0.55 g) was added thereto at room temperature, followed by stirring of the resulting mixture at the same temperature for 2 hours. After the reaction, zinc powder was filtered off and the filtrate was extracted with ethyl acetate. The organic layer was washed with a saturated aqueous NaCl solution and dried over anhydrous magnesium sulfate. After filtration, the solvent was evaporated under reduced pressure. The residue was purified by silica gel column chromatography (eluent: hexane/ethyl acetate=2/1) to obtain the title compound (0.45 g, 90%) as a colorless powder.

IR spectrum (KBr) $v_{max}$ cm$^{-1}$: 3391, 3378, 3300, 1712, 1615; NMR spectrum (CDCl$_3$) δ ppm: 1.46 (9H, s), 3.55 (2H, q, J=5.1 Hz), 4.00 (2H, brs), 4.33 (2H, t, J=5.1 Hz), 4.96 (1H, brs), 5.94 (1H, s), 6.70 (2H, d, J=8.7 Hz), 7.52 (2H, d, J=8.7 Hz).

(b) 3-(2-Aminoethoxy)-5-(4-aminophenyl)isoxazole dihydrochloride 5-(4-Aminophenyl)-3-(2-(N-tert-butoxycarbonylamino)ethoxy)isoxazole (0.25 g) was subjected to reaction and post-treatment in a similar manner to that described in Example 9(b) to obtain the title compound (0.15 g, 65%) as colorless crystals.

m.p.: 242–248° C. (decomposed); IR spectrum (KBr) $v_{max}$ cm$^{-1}$: 3039,2939,2584, 1625, 1597; NMR spectrum (DMSO-d$_6$) δ ppm: 3.25 (2H, t, J=5.0 Hz), 4.21 (2H, brs), 4.42 (2H, t, J=5.0 Hz), 6.56 (1H, s), 6.94 (2H, d, J=8.3 Hz), 7.65 (2H, d, J=8.3 Hz), 8.25 (3H, brs).

EXAMPLE 49

3-(2-Aminoethoxy)-5-(4-benzoylaminophenyl) isoxazole hydrochloride (Compound list No.: 1716)

(a) 5-(4-Benzoylaminophenyl)-3-(2-(N-tert-butoxycarbonylamino)ethoxy)isoxazole 5-(4-Aminophenyl)-3-(2-(N-tert-butoxycarbonylamino) ethoxy)isoxazole (0.1 g) was dissolved in tetrahydrofuran (I ml), and triethylamine (0.05 ml) and benzoyl chloride (0.04 ml) were successively added dropwise thereto at 5° C. under a nitrogen atmosphere, followed by stirring of the resulting mixture at room temperature for 30 minutes. The reaction mixture was poured into ice-cold water and extracted with ethyl acetate. The organic layer was washed with a saturated aqueous NaCl solution and dried over anhydrous magnesium sulfate. After filtration, the solvent was evaporated under reduced pressure. The residue was purified by silica gel column chromatography (eluent: hexane/ethyl acetate= 3/1) to obtain the title compound (0.08 g, 62%) as a colorless powder.

IR spectrum (KBr) $v_{max}$ cm$^{-1}$: 3375, 1712; NMR spectrum (CDCl$_3$) δ ppm: 1.46 (9H, s), 3.57 (2H, q, J=5.1 Hz), 4.35 (2H, t, J=5.1 Hz), 4.96 (1H, brs), 6.12 (1H, s), 7.52–7.61 (3H, m), 7.72–7.80 (4H, m), 7.87–7.95 (3H, m).

(b) 3-(2-Aminoethoxy)-5-(4-benzoylaminophenyl) isoxazole hydrochloride 5-(4-Benzoylaminophenyl)-3-(2-(N-tert-butoxycarbonylamino)ethoxy)isoxazole (0.07 g) was subjected to reaction and post-treatment in a similar manner to that described in Example 9(b) to obtain the title compound (0.04 g, 68%) as colorless crystals.

m.p.: 242–248° C. (decomposed); IR spectrum (KBr) $v_{max}$ cm-$^1$: 3322, 2959, 2910, 1645, 1621; NMR spectrum (DMSO-d$_6$) δ ppm: 3.26 (2H, t, J=5.1 Hz), 4.44 (2H, t, J=5.1 Hz), 6.75 (1H, s), 7.53–7.65 (3H, m), 7.83–8.00 (6H, m), 8.20 (3H, brs), 10.55 (1H, s).

EXAMPLE 50

3-(2-Aminoethoxy-5-(2,4-dichloro-3-methylphenyl) isoxazole hydrochloride (Compound list No.: 1576)

(a) 3-(2-(N-tert-Butoxycarbonylamino)ethoxy)-5-(2,4-dichloro-3-methylphenyl)isoxazole 3-(2-(N-tert-Butoxycarbonylamino)ethoxy)-5-(2,4-dichlorophenyl)isoxazole (0.3 g) and methyl iodide (0.08 ml) were subjected to reaction and post-treatment in a similar manner to that described in Example 14(a) to obtain the title compound (0.14 g, 45%) as a colorless powder.

IR spectrum (KBr) $v_{max}$ cm$^{-1}$: 3342, 1710; NMR spectrum (CDCl$_3$) δ ppm: 1.46 (9H, s), 2.56 (3H, s), 3.58 (2H, q, J=5.1 Hz), 4.38 (2H, t, J=5.1 Hz), 4.95 (1H, brs), 6.54 (1H, s), 7.39 (1H, d, J=8.5 Hz), 7.76 (1H, d, J=8.5 Hz).

(b) 3-(2-Aminoethoxy)-5-(2,4-dichloro-3-methylphenyl)isoxazole hydrochloride 3-(2-(N-tert-Butoxycarbonylamino)ethoxy)-5-(2,4-dichloro-3-methylphenyl)isoxazole (0.13 g) was subjected to reaction and post-treatment in a similar manner to that described in Example 9(b) to obtain the title compound (0.06 g, 55%) as colorless crystals.

m.p.: 197–200° C. (decomposed); IR spectrum (KBr) $v_{max}$ cm$^{-1}$: 3130, 2969, 2897, 1607; NMR spectrum (DMSO-d$_6$) δ ppm: 2.52 (3H, s), 3.27 (2H, t, J=5.1 Hz), 4.47 (2H, t, J=5.1 Hz), 6.82 (1H, s), 7.65 (1H, d, J=8.5 Hz), 7.71 (1H, d, J=8.5 Hz), 8.17 (3H, brs).

EXAMPLE 51

3-(2-Aminoethoxy)-5-(2,4-dichloro-3-ethylphenyl)isoxazole hydrochloride (Compound list No.: 1590)

(a) 3-(2-N-tert-Butoxycarbonylamino)ethoxy)-5-(2,4-dichloro-3-ethylphenyl)isoxazole 3-(2-(N-tert-Butoxycarbonylamino)ethoxy)-5-(2,4-dichlorophenyl)isoxazole (0.3 g) and ethyl iodide (0.1 ml) were subjected to reaction and post-treatment in a similar manner to that described in Example 14(a) to obtain the title compound (0.25 g, 78%) as a colorless powder.

IR spectrum (KBr) $v_{max}$ cm$^{-1}$: 3342, 1702; NMR spectrum (CDCl$_3$) δ ppm: 1.21 (3H, t, J=7.5 Hz), 1.46 (9H, s), 3.05 (2H, q, J=7.5 Hz), 3.57 (2H, q, J=5.1 Hz), 4.36 (2H, t, J=5.1 Hz), 4.94 (1H, brs), 6.54 (1H, s), 7.40 (1H, d, J=8.5 Hz), 7.65 (1H, d, J=8.5 Hz).

(b) 3-(2-Aminoethoxy)-5-(2,4-dichloro-3-ethylphenyl)isoxazole hydrochloride 3-(2-(N-tert-Butoxycarbonylamino)ethoxy)-5-(2,4-dichloro-3-ethylphenyl)isoxazole (0.23 g) was subjected to reaction and post-treatment in a similar manner to that described in Example 9(b) to obtain the title compound (0.14 g, 74%) as colorless crystals.

m.p.: 173–176° C. (decomposed); IR spectrum (KBr) $v_{max}$ cm$^{-1}$: 2970, 2935, 2876, 1608; NMR spectrum (DMSO-d$_6$) δ ppm: 1.16 (3H, t, J=7.4 Hz), 3.00 (2H, q, J=7.4 Hz), 3.27 (2H, t, J=5.1 Hz), 4.47 (2H, t, J=5.1 Hz), 6.82 (1H, s), 7.65 (1H, d, J=8.4 Hz), 7.70 (1H, d, J=8.4 Hz), 8.21 (3H, brs).

EXAMPLE 52

5-(4-Acetoxyphenyl)-3-(2-aminoethoxy)isoxazole hydrochloride (Compound list No.: 1688)

(a) 5-(4-Acetoxyphenyl)-3-(2-(N-tert-butoxycarbonylamino)ethoxy)isoxazole 3-(2-(N-tert-Butoxycarbonylamino)ethoxy)-5-(4-hydroxyphenyl)isoxazole (0.15 g) was dissolved in tetrahydrofuran (1.5 ml), and triethylamine (0.07 ml) and acetyl chloride (0.04 ml) were added dropwise thereto at 5° C. under a nitrogen atmosphere, followed by stirring of the resulting mixture at room temperature for 30 minutes. The reaction mixture was poured into ice-cold water and extracted with ethyl acetate. The organic layer was washed with a saturated aqueous NaCl solution and dried over anhydrous magnesium sulfate. After filtration, the solvent was evaporated under reduced pressure. The residue was purified by silica gel column chromatography (eluent: hexane/ethyl acetate=2/1) to obtain the title compound (0.12 g, 71%) as a colorless powder.

IR spectrum (KBr) $v_{max}$ cm$^{-1}$: 3345, 1696; NMR spectrum (CDCl$_3$) δ ppm: 1.46 (9H, s), 2.33 (3H, s), 3.56 (2H, q, J=5.2 Hz), 4.35 (2H, t, J=5.2 Hz), 4.94 (1H, brs), 6.12 (1H, s), 7.20 (2H, d, J=8.8 Hz), 7.74 (2H, d, J=8.8 Hz).

(b) 5-(4-Acetoxyphenyl)-3-(2-aminoethoxy)isoxazole hydrochloride 5-(4-Acetoxyphenyl)-3-(2-(N-tert-butoxycarbonylamino)ethoxy)isoxazole (0.1 g) was subjected to reaction and post-treatment in a similar manner to that described in Example 9(b) to obtain the title compound (0.05 g, 63%) as colorless crystals.

m.p.: 202–212° C. (decomposed); IR spectrum (KBr) $v_{max}$ cm$^{-1}$: 2996, 2977, 2912, 1755, 1621; NMR spectrum (DMSO-d$_6$) δ ppm: 2.30 (3H, s), 3.26 (2H, t, J=5.1 Hz), 4.45 (2H, t, J=5.1 Hz), 6.84 (1H, s), 7.32 (2H, d, J=8.6 Hz), 7.91 (2H, d, J=8.6 Hz), 8.22 (3H, brs).

EXAMPLE 53

3-(2-Aminoethoxy)-5-(4-benzyloxyphenyl)isoxazole hydrochloride (Compound list No.: 1646)

(a) 5-(4-Benzyloxyphenyl)-3-(2-(N-tert-butoxycarbonylamino)ethoxy)isoxazole 3-(2-(N-tert-Butoxycarbonylamino)ethoxy)-5-(4-hydroxyphenyl)isoxazole (0.2 g) was dissolved in dimethylformamide (2 ml), and 55% sodium hydride (oil, 0.03 g) was added thereto at 5° C. under a nitrogen atmosphere, followed by stirring of the resulting mixture at the same temperature for 10 minutes. Then, benzyl bromide (0.08 ml) was added dropwise thereto and the mixture was stirred at room temperature for 30 minutes. The reaction mixture was poured into ice-cold water and extracted with ethyl acetate. The organic layer was washed with a saturated aqueous NaCl solution and dried over anhydrous magnesium sulfate. After filtration, the solvent was evaporated under reduced pressure. The residue was purified by silica gel column chromatography (eluent: hexane/ethyl acetate=3/1) to obtain the title compound (0.14 g, 54%) as a colorless powder.

IR spectrum (KBr) $v_{max}$ cm$^{-1}$: 3338, 1698; NMR spectrum (CDCl$_3$) δ ppm: 1.46 (9H, s), 3.56 (2H, q, J=5.0 Hz), 4.34 (2H, t, J=5.0 Hz), 4.94 (1H, brs), 5.12 (2H, s), 6.02 (1H, s), 7.04 (2H, d, J=8.7 Hz), 7.28–7.47 (5H, m), 7.66 (2H, d, J=8.7 Hz).

(b) 3-(2-Aminoethoxy)-5-(4-benzyloxyphenyl)isoxazole hydrochloride 5-(4-Benzyloxyphenyl)-3-(2-(N-tert-butoxycarbonylamino)ethoxy)isoxazole (0.13 g) was subjected to reaction and post-treatment in a similar manner to that described in Example 9(b) to obtain the title compound (0.07 g, 64%) as colorless crystals.

m.p.: 205–210° C. (decomposed); IR spectrum (KBr) $v_{max}$ cm$^{-1}$: 2997, 2966, 2912, 1621, 1604; NMR spectrum (DMSO-d$_6$) δ ppm: 3.25 (2H, t, J=5.1 Hz), 4.43 (2H, t, J=5.1 Hz), 5.19 (2H, s), 6.69 (1H, s), 7.17 (2H, d, J=9.0 Hz), 7.33–7.48 (5H, m), 7.79 (2H, d, J=9.0 Hz), 8.21 (3H, brs).

EXAMPLE 54

3-(2-Aminoethoxy-5-(2-furyl)-4-isopropylisoxazole hydrochloride (Compound list No.: 510)

(a) 3-(2-(N-tert-Butoxycarbonylamino)ethoxy)-5-(2-furyl)-4-isopropylisoxazole 5-(2-Furyl)-3-hydroxy-4-isopropylisoxazole (0.2 g) and 2-(N-tert-butoxycarbonylamino)ethanol (0.18 g) were subjected to reaction and post-treatment in a similar manner to that described in Example 9(a) to obtain the title compound (0.29 g, 83%) as a colorless powder.

IR spectrum (KBr) $v_{max}$ cm$^{-1}$: 3317, 2985, 1690; NMR spectrum (CDCl$_3$) δ ppm: 1.28 (6H, d, J=7.2 Hz), 1.46 (9H, s), 3.33 (1H, qq, J=7.2 Hz, J=7.2 Hz), 3.58 (2H, q, J=5.1 Hz), 4.35 (2H, t, J=5.1 Hz), 4.84 (1H, brs), 6.52 (1H, dd, J=3.4 Hz, J=1.8 Hz), 6.80 (1H, d, J=3.4 Hz), 7.55 (1H, d, J=1.8 Hz).

(b) 3-(2-Aminoethoxy)-5-(2-furyl)-4-isopropylisoxazole hydrochloride 3-(2-(N-tert-Butoxycarbonylamino)ethoxy)-5-(2-furyl)-4-isopropylisoxazole (0.27 g) was subjected to reaction and post-treatment in a similar manner to that described in Example 1 (b) to obtain the title compound (0.17 g, 77%) as colorless crystals.

m.p.: 137–139° C.; IR spectrum (KBr) $v_{max}$ cm$^{-1}$: 2972, 2898, 1560, 1513; NMR spectrum (DMSO-d$_6$) δ ppm: 1.26 (6H, d, J=7.0 Hz), 3.24 (1H, qq, J=7.0 Hz, J=7.0 Hz), 3.28 (2H, t, J=5.2 Hz), 4.44 (2H, t, J=5.2 Hz), 6.73 (1H, dd, J=3.4 Hz, J=1.8 Hz), 7.01 (1H, d, J=3.4 Hz), 7.97 (1H, d, J=1.8 Hz), 8.21 (3H, brs).

EXAMPLE 55

3-(2-Aminoethoxy)-4-(tert-butyl)-5-phenylisoxazole hydrochloride (Compound list No.: 13)

(a) 3-(2-(N-tert-Butoxycarbonylamino)ethoxy)-4-(tert-butyl)-5-phenylisoxazole 4-(tert-Butyl)-3-hydroxy-5-phenylisoxazole (0.15 g) and 2-(N-tert-butoxycarbonylamino)ethanol (0.12 g) were subjected to reaction and post-treatment in a similar manner to that described in Example 9(a) to obtain the title compound (0.16 g, 64%) as a colorless powder.

IR spectrum (KBr) $v_{max}$ cm$^{-1}$: 3374, 2974, 1683; NMR spectrum (CDCl$_3$) δ ppm: 1.18 (9H, s), 1.46 (9H, s), 3.60 (2H, q, J=5.2 Hz), 4.38 (2H, t, J=5.2 Hz), 4.85 (1H, brs), 7.36–7.55 (5H, m).

(b) 3-(2-Aminoethoxy)-4-(tert-butyl)-5-phenylisoxazole hydrochloride 3-(2-(N-tert-Butoxycarbonylamino)ethoxy)-4-(tert-butyl)-5-phenylisoxazole (0.14 g) was subjected to reaction and post-treatment in a similar manner to that described in Example 1(b) to obtain the title compound (0.09 g, 82%) as colorless crystals.

m.p.: 230–234° C. (decomposed); IR spectrum (KBr) $v_{max}$ cm$^{-1}$: 2961, 2910, 2890, 1516; NMR spectrum (DMSO-d$_6$) δ ppm: 1.16 (9H, s), 3.30 (2H, t, J=5.3 Hz), 4.46 (2H, t, J=5.3 Hz), 7.44–7.57 (5H, m), 8.20 (3H, brs).

EXAMPLE 56

3-(2-Aminoethoxy)-4-cyclopropyl-5-phenylisoxazole hydrochloride (Compound list No.: 1400)

(a) 3-(2-(N-tert-butoxycarbonylamino)ethoxy)-4-cyclopropyl-5-phenylisoxazole

4-Cyclopropyl-3-hydroxy-5-phenylisoxazole (0.2 g) and 2-(N-tert-butoxycarbonylamino)ethanol (0.18 g) were subjected to reaction and post-treatment in a similar manner to that described in Example 9(a) to obtain the title compound (0.25 g, 74%) as a colorless powder.

IR spectrum (KBr) $v_{max}$ cm$^{-1}$: 3369, 1692, 1536, 1520; NMR spectrum (CDCl$_3$) δ ppm: 0.66–0.75 (2H, m), 0.88–0.95 (2H, m), 1.46 (9H, s), 1.67–1.73 (1H, m), 3.58 (2H, q, J=5.1 Hz), 4.35 (2H, t, J=5.1 Hz), 4.90 (1H, brs), 7.40–7.51 (3H, m), 7.84–7.87 (2H, m).

(b) 3-(2-Aminoethoxy)-4-cyclopropyl-5-phenylisoxazole hydrochloride 3-(2-(N-tert-Butoxycarbonylamino)ethoxy)-4-cyclopropyl-5-phenylisoxazole (0.15 g) was subjected to reaction and post-treatment in a similar manner to that described in Example 1(b) to obtain the title compound (0.06 g, 49%) as colorless crystals.

m.p.: 180–182° C.; IR spectrum (KBr) $v_{max}$ cm$^{-1}$: 2919, 2851, 1713, 1519; NMR spectrum (DMSO-d$_6$) δ ppm: 0.68–0.76 (2H, m), 0.83–0.92 (2H, m), 1.71– 1.78 (1H, m), 3.27 (2H, t, J=5.2 Hz), 4.44 (2H, t, J=5.2 Hz), 7.51–7.60 (3H, m), 7.83–7.86 (2H, m), 8.20 (3H, brs).

EXAMPLE 57

3-(2-Aminoethoxy)-5-(2,4-dichlorophenyl)-4-isopropylisoxazole hydrochloride (Compound list No.: 176)

(a) 3-(2-(N-tert-Butoxycarbonylamino)ethoxy)-5-(2,4-dichlorophenyl)-4-isopropylisoxazole 5-(2,4-Dichlorophenyl)-3-hydroxy-4-isopropylisoxazole (0.06 g) and 2-(N-tert-butoxycarbonylamino)ethanol (0.04 g) were subjected to reaction and post-treatment in a similar manner to that described in Example 9(a) to obtain the title compound (0.078 g, 86%) as a colorless oil.

IR spectrum (CHCl$_3$) $v_{max}$ cm$^{-1}$: 3460, 2975, 2936, 1713; NMR spectrum (CDCl$_3$) δ ppm: 1.18 (6H, d, J=7.0 Hz), 1.46 (9H, s), 2.69 (1H, qq, J=7.0 Hz, J=7.0 Hz), 3.59 (2H, q, J=5.2 Hz), 4.38 (2H, t, J=5.2 Hz), 4.85 (1H, brs), 7.30 (1H, d, J=8.3 Hz), 7.35 (1H, dd, J=8.3 Hz, J=1.9 Hz), 7.52 (1H, d, J=1.9 Hz).

(b) 3-(2-Aminoethoxy)-5-(2,4-dichlorophenyl-4-isopropylisoxazole hydrochloride 3-(2-(N-tert-Butoxycarbonylamino)ethoxy)-5-(2,4-dichlorophenyl)-4-isopropylisoxazole (0.07 g) was subjected to reaction and post-treatment in a similar manner to that described in Example 1(b) to obtain the title compound (0.04 g, 68%) as colorless crystals.

m.p.: 171–173° C.; IR spectrum (KBr) $v_{max}$ cm$^{-1}$: 2968, 2934, 2875, 1514; NMR spectrum (DMSO-d$_6$) δ ppm: 1.13 (6H, d, J=7.0 Hz), 2.69 (1H, qq, J=7.0 Hz, J=7.0 Hz), 3.29 (2H, t, J=5.3 Hz), 4.46 (2H, t, J=5.3 Hz), 7.56 (1H, d, J=8.5 Hz), 7.62 (1H, dd, J=8.5 Hz, J=2.0 Hz), 7.89 (1H, d, J=2.0 Hz), 8.18 (3H, brs).

EXAMPLE 58

3-(2-Aminoethoxy)-5-(2-chlorophenyl)-4-isopropylisoxazole hydrochloride (Compound list No.: 117)

(a) 3-(2-(N-tert-Butoxycarbonylamino)ethoxy)-5-(2-chlorophenyl)-4-isopropylisoxazole 5-(2-Chlorophenyl)-3-hydroxy-4-isopropylisoxazole (0.13 g) and 2-(N-tert-butoxycarbonylamino)ethanol (0.1 g) were subjected to reaction and post-treatment in a similar manner to that described in Example 9(a) to obtain the title compound (0.15 g, 72%) as a colorless powder.

IR spectrum (KBr) $v_{max}$ cm$^{-1}$: 3382, 2974, 1691; NMR spectrum (CDCl$_3$) δ ppm: 1.18 (6H, d, J=6.9 Hz), 1.46 (9H, s), 2.71 (1H, qq, J=6.9 Hz, J=6.9 Hz), 3.60 (2H, q, J=5.2 Hz), 4.39 (2H, t, J=5.2 Hz), 4.87 (1H, brs), 7.34–7.51 (4H, m).

(b) 3-(2-Aminoethoxy)-5-(2-chlorophenyl)-4-isopropylisoxazole hydrochloride 3-(2-(N-tert-Butoxycarbonylamino)ethoxy)-5-(2-chlorophenyl)-4-isopropylisoxazole (0.13 g) was subjected to reaction and post-treatment in a similar manner to that described in Example 1(b) to obtain the title compound (0.08 g, 73%) as colorless crystals.

m.p.: 143–145° C.;
IR spectrum (KBr) $v_{max}$ cm$^{-1}$: 2970, 2937, 2896, 2879, 1513; NMR spectrum (DMSO-d$_6$) δ ppm: 1.13 (6H, d, J=7.0 Hz), 2.69 (1H, qq, J=7.0 Hz, J=7.0 Hz), 3.29 (2H, t, J=5.2 Hz), 4.47 (2H, t, J=5.2 Hz), 7.50–7.68 (4H, m), 8.24 (3H, brs).

EXAMPLE 59

3-(2-Aminoethoxy)-5-(4-chlorophenyl)-4-isopropylisoxazole hydrochloride (Compound list No.: 151)

(a) 3-(2-(N-tert-Butoxycarbonylamino)ethoxy)-5-(4-chlorophenyl-4-isopropylisoxazole 5-(4-Chlorophenyl)-3-hydroxy-4-isopropylisoxazole (0.15 g) and 2 -(N-tert-butoxycarbonylamino)ethanol (0.11 g) were subjected to reaction and post-treatment in a similar manner to that described in Example 9(a) to obtain the title compound (0.19 g, 79%) as a colorless powder.

IR spectrum (KBr) $v_{max}$ cm$^{-1}$: 3382, 2966, 1685; NMR spectrum (CDCl$_3$) δ ppm: 1.29 (6H, d, J=7.0 Hz), 1.46 (9H, s), 3.03 (1H, qq, J=7.0 Hz, J=7.0 Hz), 3.59 (2H, q, J=5.1 Hz), 4.36 (2H, t, J=5.1 Hz), 7.44 (2H, d, J=8.7 Hz), 7.52 (2H, d, J=8.7 Hz).

(b) 3-(2-Aminoethoxy)-5-(4-chlorophenyl)-4-isopropylisoxazole hydrochloride 3-(2-(N-tert-Butoxycarbonylamino)ethoxy)-5-(4-chlorophenyl)-4-isopropylisoxazole (0.18 g) was subjected to reaction and post-treatment in a similar manner to that described in Example 1(b) to obtain the title compound (0.12 g, 80%) as colorless crystals.

m.p.: 224–227° C.; IR spectrum (KBr) $v_{max}$ cm$^{-1}$: 2971, 2919, 2851, 1639; NMR spectrum (DMSO-d$_6$) δ ppm: 1.26 (6H, d, J=7.0 Hz), 3.02 (1H, qq, J=7.0 Hz, J=7.0 Hz), 3.28 (2H, t, J=5.3 Hz), 4.45 (2H, t, J=5.3 Hz), 7.62 (2H, d, J=9.0 Hz), 7.63 (2H, d, J=9.0 Hz), 8.18 (3H, brs).

EXAMPLE 60

4-Allyl-3-(2-aminoethoxy)-5-phenylisoxazole hydrochloride (Compound list No.: 1392)

(a) 4-Allyl-3-(2-(N-tert-butoxycarbonylamino)ethoxy)-5-phenylisoxazole

4-Allyl-3-hydroxy-5-phenylisoxazole (1.00 g) and 2-(N-tert-butoxycarbonylamino)ethanol (0.96 g) were subjected to reaction and post-treatment in a similar manner to that described in Example 1(a) to obtain the title compound (1.57 g, 91%) as colorless crystals.

m.p.: 78–79° C.; IR spectrum (KBr) $v_{max}$ cm$^{-1}$: 3327, 1708, 1644, 1526, 1518; NMR spectrum (CDCl$_3$) δ ppm: 1.46 (9H, s), 3.27–3.29 (2H, m), 3.57 (2H, q, J=5.1 Hz), 4.38 (2H, t, J=5.1 Hz), 4.90 (1H, brs), 5.05–5.15 (2H, m), 5.91–6.01 (1H, m), 7.41–7.49 (3H, m), 7.63–7.68 (2H, m).

(b) 4-Allyl-3-(2-aminoethoxy)-5-phenylisoxazole hydrochloride

4-Allyl-3-(2-(N-tert-butoxycarbonylamino)ethoxy)-5-phenylisoxazole (200 mg) was subjected to reaction and post-treatment in a similar manner to that described in Example 1(b) to obtain the title compound (160 mg, 98%) as colorless crystals.

m.p.: 95–96° C.; IR spectrum (KBr) $v_{max}$ cm$^{-1}$: 2967, 2912, 2885, 2817, 2694, 1643, 1601, 1577, 1514, 1495; NMR spectrum (DMSO-d$_6$) δ ppm: 3.25–3.30 (2H, m), 3.35 (2H, t, J=5.1 Hz), 4.46 (2H, t, J=5.1 Hz), 5.03–5.09 (2H, m), 5.91–6.00 (1H, m), 7.52–7.58 (3H, m), 7.67–7.70 (2H, m), 8.20 (3H, brs).

EXAMPLE 61

3-(2-Aminoethoxy)-5-phenyl-4-propargylisoxazole hydrochloride (Compound list No.: 1398)

(a) 3-(2-(N-tert-Butoxycarbonylamino)ethoxy)-5-phenyl-4-propargylisoxazole

3-Hydroxy-5-phenyl-4-propargylisoxazole (1.00 g) and 2-(N-tert-butoxycarbonylamino)ethanol (0.96 g) were subjected to reaction and post-treatment in a similar manner to that described in Example 1(a) to obtain the title compound (1.44 g, 84%) as a colorless oil.

IR spectrum (KBr) $v_{max}$ cm$^{-1}$: 3352, 3302, 1711, 1643, 1600, 1577, 1520, 1499; NMR spectrum (CDCl$_3$) δ ppm: 1.46 (9H, s), 2.09 (1H, t, J=2.8 Hz), 3.43 (2H, d, J=2.8 Hz), 3.60 (2H, q, J=5.1 Hz), 4.41 (2H, t, J=5.1 Hz), 5.02 (1H, brs), 7.45–7.55 (3H, m), 7.74–7.76 (2H, m).

(b) 3-(2-Aminoethoxy)-5-phenyl-4-propargylisoxazole hydrochloride 3-(2-(N-tert-Butoxycarbonylamino)ethoxy)-5-phenyl-4-propargylisoxazole (200 mg) was subjected to reaction and post-treatment in a similar manner to that described in Example 1(b) to obtain the title compound (152 mg, 94%) as colorless crystals.

m.p.: 210–212° C. (decomposed); IR spectrum (KBr) $v_{max}$ cm$^{-1}$: 3258, 2959, 2899, 2830, 1632, 1601, 1577, 1523; NMR spectrum (DMSO-d$_6$) δ ppm: 2.97 (1H, t, J=2.8 Hz), 3.30 (1H, t, J=5.1 Hz), 3.59 (2H, d, J=2.8 Hz), 4.47 (2H, t, J=5.1 Hz), 7.56–7.62 (3H, m), 7.79–7.82 (2H, m), 8.13 (3H, brs).

EXAMPLE 62

3-(2-Aminoethoxy)-4-isobutyl-5-phenylisoxazole hydrochloride (Compound list No.: 11)

(a) 3-(2-(N-tert-Butoxycarbonylamino)ethoxy)-4-isobutyl-5-phenylisoxazole

3-Hydroxy-4-isobutyl-5-phenylisoxazole (217 mg) and 2-(N-tert-butoxycarbonylamino)ethanol (193 mg) were subjected to reaction and post-treatment in a similar manner to that described in Example 1(a) to obtain the title compound (303 mg, 84%) as colorless crystals.

m.p.: 80–81° C.;

IR spectrum (KBr) $v_{max}$ cm$^{-1}$: 3377, 1683, 1637, 1516, 1498; NMR spectrum (CDCl$_3$) δ ppm: 0.93 (6H, d, J=6.8 Hz), 1.46 (9H, s), 1.89–1.96 (1H, m), 2.42 (2H, d, J=7.3 Hz), 3.58 (2H, q, J=5.1 Hz), 4.37 (2H, t, J=5.1 Hz), 4.88 (1H, brs), 7.40–7.49 (3H, m), 7.66–7.70 (2H, m).

(b) 3-(2-Aminoethoxy)-4-isobutyl-5-phenylisoxazole hydrochloride 3-(2-(N-tert-Butoxycarbonylamino)ethoxy)-4-isobutyl-5-phenylisoxazole (200 mg) was subjected to reaction and post-treatment in a similar manner to that described in Example 1(b) to obtain the title compound (160 mg, 98%) as colorless crystals.

m.p.: 202–210° C. (decomposed); IR spectrum (KBr) $v_{max}$ cm$^{-1}$: 3005, 2957, 2869, 1629, 1601, 1576, 1514, 1495; NMR spectrum (DMSO-d$_6$) δ ppm: 0.86 (6H, d, J=6.8 Hz), 2.47 (2H, d, J=7.3 Hz), 3.27 (2H, t, J=5.1 Hz), 4.45 (2H, t, J=5.1 Hz), 7.49–7.58 (3H, m), 7.70–7.74 (2H, m), 8.19 (3H, brs).

EXAMPLE 63

3-(2-Aminoethoxy)-4-cyclopentyl-5-phenylisoxazole hydrochloride (Compound list No.: 1402)

(a) 3-(2-(N-tert-Butoxycarbonylamino)ethoxy)-4-cyclopentyl-5-phenylisoxazole

3-Hydroxy-4-cyclopentyl-5-phenylisoxazole (229 mg) and 2-(N-tert-butoxycarbonylamino)ethanol (193 mg) were subjected to reaction and post-treatment in a similar manner to that described in Example I (a) to obtain the title compound (308 mg, 83%) as colorless crystals.

m.p.: 112–113° C.; IR spectrum (KBr) $v_{max}$ cm$^{-1}$: 3391, 1691, 1655, 1643, 1531, 1515; NMR spectrum (CDCl$_3$) δ ppm: 1.46 (9H, s), 1.56–1.67 (2H, m), 1.71–1.92 (6H, m), 3.03–3.12 (1H, m), 3.58 (2H, q, J=5.1 Hz), 4.38 (2H, t, J=5.1 Hz), 4.82 (1H, brs), 7.41–7.49 (3H, m), 7.55–7.61 (2H, m).

(b) 3-(2-Aminoethoxy-4-cyclopentyl-5-phenylisoxazole hydrochloride 3-(2-(N-tert-Butoxycarbonylamino)ethoxy)-4-cyclopentyl-5-phenylisoxazole (200 mg) was subjected to reaction and post-treatment in a similar manner to that described in Example 1(b) to obtain the title compound (161 mg, 97%) as colorless crystals.

m.p.: 197–199° C.; IR spectrum (KBr) $v_{max}$ cm$^{-1}$: 2954, 2869, 1637, 1599, 1576, 1511, 1490; NMR spectrum (DMSO-d$_6$) δ ppm: 1.57–1.63 (2H, m), 1.72–1.91 (6H, m), 2.98–3.07 (1H, m), 3.27 (2H, t, J=5.1 Hz), 4.45 (2H, t, J=5.1 Hz), 7.51–7.61 (5H, m), 8.07 (3H, brs).

EXAMPLE 64

3-(2-Aminoethoxy)-4-(2-cyclopentenyl)-5-phenylisoxazole hydrochloride (Compound list No.: 1404)

(a) 3-(2-(N-tert-Butoxycarbonylamino)ethoxy)-4-(2-cyclopentenyl)-5-phenylisoxazole 3-Hydroxy-4-(2-cyclopentenyl)-5-phenylisoxazole (227 mg) and 2-(N-tert-butoxycarbonylamino)ethanol (193 mg) were subjected to reaction and post-treatment in a similar manner to that described in Example 1(a) to obtain the title compound (295 mg, 80%) as colorless crystals.

m.p.: 81–82° C.; IR spectrum (KBr) $v_{max}$ cm$^{-1}$: 3394, 1690, 1636, 1515, 1495; NMR spectrum (CDCl$_3$) δ ppm: 1.46 (9H, s), 1.88–1.98 (1H, m), 2.24–2.34 (1H, m), 2.39–2.49 (1H, m), 2.52–2.61 (1H, m), 3.47–3.59 (2H, m), 4.01–4.06 (1H, m), 4.30–4.36 (2H, m), 4.86 (1H, brs), 5.63–5.67 (1H, m), 5.89–5.92 (1H, m), 7.42–7.49 (3H, m), 7.60–7.63 (2H, m).

(b) 3-(2-Aminoethoxy)-4-(2-cyclopentenyl)-5-phenylisoxazole hydrochloride 3-(2-(N-tert-Butoxycarbonylamino)ethoxy)-4-(2-cyclopentenyl)-5-phenylisoxazole (200 mg) was subjected to reaction and post-treatment in a similar manner to that described in Example 1(b) to obtain the title compound (156 mg, 94%) as colorless crystals.

m.p.: 157–160° C. (decomposed); IR spectrum (KBr) $v_{max}$ cm$^{-1}$: 3051, 2954, 2901, 2852, 1635, 1599, 1575, 1516, 1492; NMR spectrum (DMSO-d$_6$) δ ppm: 1.79–1.99 (1H, m), 2.21–2.41 (2H, m), 2.44–2.53 (1H, m), 3.25 (2H, brs), 3.95–4.02 (1H, m), 4.38–4.48 (2H, m), 5.56–5.71 (1H, m), 5.85–5.89 (1H, m), 7.51–7.57 (3H, m), 7.59–7.63 (2H, m), 8.12 (3H, brs).

EXAMPLE 65

3-(2-Aminoethoxy)-4-pentyl-5-phenylisoxazole hydrochloride (Compound list No.: 1386)

(a) 3-(2-(N-tert-Butoxycarbonylamino)ethoxy)-4-pentyl-5-phenylisoxazole

3-Hydroxy-4-pentyl-5-phenylisoxazole (231 mg) and 2-(N-tert-butoxycarbonylamino)ethanol (193 mg) were subjected to reaction and post-treatment in a similar manner to that described in Example 1(a) to obtain the title compound (305 mg, 82%) as a colorless oil.

IR spectrum (KBr) $v_{max}$ cm$^{-1}$: 3461, 1713, 1640, 1510, 1496; NMR spectrum (CDCl$_3$) δ ppm: 0.89 (3H, t, J=7.0 Hz), 1.26–1.38 (2H, m), 1.46 (9H, s), 1.49–1.61 (2H, m), 2.52 (2H, t, J=7.7 Hz), 3.59 (2H, q, J=5.1 Hz), 4.37 (2H, t, J=5.1 Hz), 4.89 (1H, brs), 7.40–7.49 (3H, m), 7.64–7.69 (2H, m).

(b) 3-(2-Aminoethoxy)-4-pentyl-5-phenylisoxazole hydrochloride 3-(2-(N-tert-Butoxycarbonylamino)ethoxy)-4-pentyl-5-phenylisoxazole (100 mg) was subjected to reaction and post-treatment in a similar manner to that described in Example 1(b) to obtain the title compound (80 mg, 95%) as colorless crystals.

m.p.: 107–109° C.; IR spectrum (KBr) $v_{max}$ cm$^{-1}$: 3008, 2955, 2930, 2869, 1641, 1601, 1576, 1566, 1516, 1496; NMR spectrum (DMSO-d$_6$) δ ppm: 0.83 (3H, t, J=7.0 Hz), 1.25–1.30 (4H, m), 1.48–1.56 (2H, m), 2.55 (2H, t, J=7.7 Hz), 3.28 (2H, t, J=5.1 Hz), 4.45 (2H, t, J=5.1 Hz), 7.51–7.59 (3H, m), 7.66–7.69 (2H, m), 8.10 (3H, brs).

EXAMPLE 66

3-(2-Aminoethoxy)4-(2-butenyl)-5-phenylisoxazole hydrochloride (Compound list No.: 1396)

(a) 3-(2-(N-tert-Butoxycarbonylamino)ethoxy)-4-(2-butenyl)-5-phenylisoxazole

3-Hydroxy-4-(2-butenyl)-5-phenylisoxazole (215 mg) and 2-(N-tert-butoxycarbonylamino)ethanol (193 mg) were subjected to reaction and post-treatment in a similar manner to that described in Example 1(a) to obtain the title compound (292 mg, 82%) as colorless crystals.

m.p.: 62–63° C.; IR spectrum (KBr) $v_{max}$ cm$^{-1}$: 3378, 1682, 1634, 1514, 1497; NMR spectrum (CDCl$_3$) δ ppm: 1.46 (9H, s), 1.68–1.74 (3H, m), 3.19–3.21 (2H, m), 3.57 (2H, q, J=5.1 Hz), 4.37 (2H, t, J=5.1 Hz), 4.89 (1H, brs), 5.46–5.60 (2H, m), 7.40–7.52 (3H, m), 7.64–7.68 (2H, m).

(b) 3-(2-Aminoethoxy)-4-(2-butenyl)-5-phenylisoxazole hydrochloride 3-(2-(N-tert-Butoxycarbonylamino)ethoxy)-4-(2-butenyl)-5-phenylisoxazole (200 mg) was subjected to reaction and post-treatment in a similar manner to that described in Example 1(b) to obtain the title compound (162 mg, 98%) as colorless crystals.

m.p.: 123–125° C.; IR spectrum (KBr) $v_{max}$ cm$^{-1}$: 3028, 2961, 2934, 2916, 2855, 1641, 1601, 1577, 1570, 1515, 1494; NMR spectrum (DMSO-d$_6$) δ ppm: 1.60–1.70 (3H, m), 3.26–3.28 (2H, m), 3.33 (2H, t, J=5.1 Hz), 4.45 (2H, t, J=5.1 Hz), 5.43–5.59 (2H, m), 7.50–7.58 (3H, m), 7.65–7.70 (2H, m), 8.10 (3H, brs).

EXAMPLE 67

3-(2-Aminoethoxy)-4-isopropyl-5-(2-thienyl)isoxazole hydrochloride (Compound list No.: 543)

(a) 3-(2-(N-tert-Butoxycarbonylamino)ethoxy)-4-isopropyl-5-(2-thienyl)isoxazole

3-Hydroxy-4-isopropyl-5-(2-thienyl)isoxazole (209 mg) and 2-(N-tert-butoxycarbonylamino)ethanol (193 mg) were subjected to reaction and post-treatment in a similar manner to that described in Example 1(a) to obtain the title compound (301 mg, 86%) as colorless crystals.

m.p.: 94–95° C.; IR spectrum (KBr) $v_{max}$ cm$^{-1}$: 3325, 1711, 1693, 1635, 1542, 1528, 1508; NMR spectrum (CDCl$_3$) δ ppm: 1.29 (6H, d, J=7.1 Hz), 1.46 (9H, s), 3.19 (1H, m), 3.58 (2H, q, J=5.1 Hz), 4.36 (2H, t, J=5.1 Hz), 4.83 (1H, brs), 7.14 (1H, dd, J=5.3 Hz, J=3.7 Hz), 7.42 (1H, dd, J=3.4 Hz, J=1.4 Hz), 7.46 (1H, d, J=5.3 Hz).

(b) 3-(2-Aminoethoxy)-4-isopropyl-5-(2-thienyl)isoxazole hydrochloride 3-(2-(N-tert-Butoxycarbonylamino)ethoxy)-4-isopropyl-5-(2-thienyl)isoxazole (200 mg) was subjected to reaction and post-treatment in a similar manner to that described in Example 1(b) to obtain the title compound (150 mg, 93%) as colorless crystals.

m.p.: 192–194° C. (decomposed); IR spectrum (KBr) $v_{max}$ cm$^{-1}$: 3105, 3087, 2973, 1644, 1579, 1527, 1498; NMR spectrum (DMSO-d$_6$) δ ppm: 1.27 (6H, d, J=7.2 Hz), 3.16 (1H, m), 3.28 (2H, t, J=5.1 Hz), 4.44 (2H, t, J=5.1 Hz), 7.26

(1H, dd, J=5.2 Hz, J=1.4 Hz), 7.54 (1H, dd, J=4.7 Hz, J=1.0 Hz), 7.87 (1H, d, J=5.2 Hz), 8.13 (3H, brs).

EXAMPLE 68

3-(2-Aminoethoxy)-4-fluoro-5-phenylisoxazole hydrochloride (Compound list No.: 4)

(a) 3-Methoxymethoxy-5-phenylisoxazole

3-Hydroxy-5-phenylisoxazole (8.05 g) was dissolved in dimethylformamide (80 ml), and sodium methoxide (28% methanol solution, 3.24 g) was added dropwise thereto, followed by stirring of the resulting mixture at room temperature for one hour. While the reaction mixture was cooled to 5° C., chloromethyl methyl ether (4.83 g) was added thereto, followed by stirring of the resulting mixture at the same temperature for one hour. The reaction mixture was poured into ice-cold water (200 ml) and extracted with ether (200 ml×2), and the organic layer was dried over anhydrous magnesium sulfate. After filtration, the solvent was evaporated under reduced pressure. The residue was purified by silica gel column chromatography (eluent: hexane/ethyl acetate=4/1) to obtain the title compound (6.30 g, 61%) as a colorless oil.

IR spectrum (KBr) $v_{max}$ cm$^{-1}$: 1621, 1596, 1577, 1512; NMR spectrum (CDCl$_3$) δ ppm: 3.58 (3H, s), 5.37 (2H, s), 7.40–7.48 (3H, m), 7.71–7.95 (2H, m).

(b) 4-Fluoro-3-methoxymethoxy-5-phenylisoxazole

3-Methoxymethoxy-5-phenylisoxazole (2.05 g) was dissolved in anhydrous tetrahydrofuran (30 ml), and the solution was cooled to −78° C. Butyllithium (1.68M hexane solution, 7.1 ml) was added dropwise thereto, and the resulting mixture was stirred at the same temperature for 15 minutes. Then, N-fluorobenzenesulfonimide (3.15 g) was added to the reaction mixture, followed by stirring of the resulting mixture at the same temperature for 15 minutes. The cooling bath was removed and the temperature of the resulting mixture was raised to room temperature. The reaction mixture was poured into ice-cold water (200 ml) and extracted with ether (200 ml×2). The organic layer was dried over anhydrous magnesium sulfate. After filtration, the solvent was evaporated under reduced pressure. The residue was purified by silica gel column chromatography (eluent: hexane/ethyl acetate=4/1) to obtain the title compound (1.78 g, 80%) as a colorless oil.

IR spectrum (KBr) $v_{max}$ cm$^{-1}$: 1672, 1545; NMR spectrum (CDCl$_3$) δ ppm: 3.62 (3H, s), 5.45 (2H, s), 7.43–7.52 (3H, m), 7.70–7.80 (2H, m).

(c) 4-Fluoro-3-hydroxy-5-phenylisoxazole

4-Fluoro-3-methoxymethoxy-5-phenylisoxazole (0.44 g) was dissolved in a solution of 4N hydrochloric acid/dioxane (5.0 ml), and the solution was stirred at room temperature for one hour. After the reaction, the solvent was evaporated under reduced pressure and the crystal thus obtained was washed with dichloromethane (10 ml) to obtain the title compound (0.30 g, 83%) as colorless crystals.

IR spectrum (KBr) $v_{max}$ cm$^{-1}$: 3059, 3014, 2995, 2919, 2851, 2822, 2747, 2645, 2565, 1674, 1582, 1527; NMR spectrum (DMSO-d$_6$) δ ppm: 7.51–7.61 (3H, m), 7.73–7.74 (2H, m), 12.6 (1H, brs).

s (d) 3-(2-(N-tert-Butoxycarbonylamino)ethoxy)-4-fluoro-5-phenylisoxazole

4-Fluoro-3-hydroxy-5-phenylisoxazole (100 mg) and 2-(N-tert-butoxycarbonylamino)ethanol (108 mg) were subjected to reaction and post-treatment in a similar manner to that described in Example 1(a) to obtain the title compound (132 mg, 73%) as colorless crystals.

m.p.: 103–104° C.; IR spectrum (KBr) $v_{max}$ cm$^{-1}$: 3325, 1718, 1667, 1549, 1532; NMR spectrum (CDCl$_3$) δ ppm: 1.46 (9H, s), 3.60 (2H, q, J=5.1 Hz), 4.41 (2H, t, J=5.1 Hz), 4.97 (1H, brs), 7.41–7.52 (3H, m), 7.76–7.79 (2H, m).

(e) 3-(2-Aminoethoxy)-4-fluoro-5-phenylisoxazole hydrochloride 3-(2-(N-tert-Butoxycarbonylamino)ethoxy)-4-fluoro-5-phenylisoxazole (110 mg) was subjected to reaction and post-treatment in a similar manner to that described in Example 1(b) to obtain the title compound (82 mg, 93%) as colorless crystals.

m.p.: 207–211° C. (decomposed); IR spectrum (KBr) $v_{max}$ cm$^{-1}$: 2999, 2965, 2909, 2845, 1665, 1602, 1581, 1555, 1532; NMR spectrum (DMSO-d$_6$) δ ppm: 3.32 (2H, t, J=5.1 Hz), 4.55 (2H, t, J=5.1 Hz), 7.55–7.64 (3H, m), 7.75–7.78 (2H, m), 8.17 (3H, brs).

EXAMPLE 69

3-(2-Dimethylaminoethoxy)-5-phenylisoxazole hydrochloride (Compound list No.: 27)

(a) 3-(2-Bromoethoxy)-5-phenylisoxazole

Triphenylphosphine (15.7 g) was dissolved in toluene (200 ml), and the solution was cooled to 5° C. Diethyldiazodicarboxylate (10.4 g) was added to the solution, and the resulting mixture was stirred at the same temperature for 10 minutes. Then, 3-hydroxy-5-phenylisoxazole (8.0 g) and 2-bromoethanol (7.5 g) were added in this order to the reaction mixture, followed by stirring of the resulting mixture at room temperature for 10 minutes and further at room temperature for 2 hours. Insolubles were filtered off from the mixture, and the solvent was evaporated under reduced pressure. The residue was purified by silica gel column chromatography (eluent: hexane/ethyl acetate=4/1) to obtain the title compound (12.1 g, 90%) as colorless crystals.

IR spectrum (KBr) $v_{max}$ cm$^{-1}$: 3148, 1623, 1597, 1576, 1510; NMR spectrum (CDCl$_3$) δ ppm: 3.71 (2H, t, J=5.9 Hz), 4.62 (2H, t, J=5.9 Hz), 6.19 (1H, s), 7.42–7.49 (3H, m), 7.70–7.77 (2H, m).

(b) 3-(2-Dimethylaminoethoxy)-5-phenylisoxazole

After dimethylamine hydrochloride (815 mg) was dissolved in methanol (50 ml), 3-(2-bromoethoxy)-5-phenylisoxazole (268 mg) and triethylamine (2.8 ml) were added thereto, followed by reflux of the resulting mixture for 8 hours. After the reaction, the solvent was evaporated under reduced pressure. The residue was dissolved in ether (20 ml), and the solution was washed with a diluted aqueous NaCl solution (20 ml), followed by drying of the organic layer over anhydrous magnesium sulfate. After filtration, the solvent was evaporated under reduced pressure. The residue was purified by silica gel column chromatography (eluent: ethyl acetate) to obtain the title compound (146 mg, 63%) as colorless crystals.

m.p.:28–29° C.; IR spectrum (KBr) $v_{max}$ cm$^{-1}$: 2980, 2951, 1625, 1597, 1577, 1514; NMR spectrum (CDCl$_3$) δ ppm: 2.34 (6H, s), 2.75 (2H, t, J=5.4 Hz), 4.40 (2H, t, J=5.4 Hz), 6.18 (1H, s), 7.40–7.48 (3H, m), 7.69–7.73 (2H, m).

(c) 3-(2-Dimethylaminoethoxy)-5-phenylisoxazole hydrochloride 3-(2-Dimethylaminoethoxy)-5-phenylisoxazole (130 mg) was dissolved in dioxane (1.0 ml), and a solution of 4N hydrochloric acid/dioxane (0.2 ml) was added thereto, and the resulting mixture was allowed to stand at room temperature for 15 minutes. The solvent was evaporated under reduced pressure and the residue was washed with ethyl acetate (5 ml) to obtain the title compound (148 mg, 98%) as colorless crystals.

m.p.: 163–164° C. (decomposed); IR spectrum (KBr) $v_{max}$ cm$^{-1}$: 3133, 1624, 1597, 1577, 1513; NMR spectrum (DMSO-d$_6$) δ ppm: 2.84 (6H, s), 3.55 (2H, t, J=5.0 Hz), 4.61

(2H, t, J=5.0 Hz), 7.50–7.58 (3H, m), 7.81–7.87 (2H, m), 10.31 (1H, brs).

EXAMPLE 70

5-Phenyl-3-(2-(1-piperidyl)ethoxy)isoxazole hydrochloride (Compound list No.: 28)

(a) 5-Phenyl-3-(2-(1-piperidyl)ethoxy)isoxazole 3-(2-Bromoethoxy)-5-phenylisoxazole (268 mg) was dissolved in methanol (1.0 ml), and piperidine (426 mg) was added thereto, followed by reflux of the resulting mixture for 3 hours. After the reaction mixture was added to ice-cold water (20 ml) and extracted with ether (20 ml×2), the organic layer was dried over anhydrous magnesium sulfate. After filtration, the solvent was evaporated under reduced pressure. The residue was purified by silica gel column chromatography (eluent: ethyl acetate) to obtain the title compound (251 mg, 92%) as colorless crystals.

m.p.: 75–76° C.; IR spectrum (KBr) $v_{max}$ cm$^{-1}$: 3149, 1625, 1598, 1577, 1513; NMR spectrum (CDCl$_3$) δ ppm: 1.42–1.48 (2H, m), 1.54–1.67 (4H, m), 2.50 (4H, brs), 2.79 (2H, t, J=5.8 Hz), 4.42 (2H, t, J=5.8 Hz), 6.16 (1H, s), 7.41–7.48 (3H, m), 7.69–7.75 (2H, m).

(b) 5-Phenyl-3-(2-(1-piperidyl)ethoxy)isoxazole hydrochloride

5-Phenyl-3-(2-piperidylethoxy)isoxazole (200 mg) was subjected to reaction and post-treatment in a similar manner to that described in Example 1(b) to obtain the title compound (181 mg, 80%) as colorless crystals.

m.p.: 190–192° C. (decomposed); IR spectrum (KBr) $v_{max}$ cm$^{-1}$: 2950, 2938, 1620, 1595, 1576, 1511; NMR spectrum (DMSO-d$_6$) δ ppm: 1.32–1.44 (2H, m), 1.68–1.86 (4H, m), 2.95–3.04 (2H, m), 3.45–3.58 (4H, m), 4.64 (2H, t, J=4.7 Hz), 6.87 (1H, s), 7.50–7.58 (3H, m), 7.81–7.85 (2H, m), 9.94–10.05 (1H, brs).

EXAMPLE 71

5-Phenyl-3-(2-(1-pyrrolidinyl)ethoxy)isoxazole hydrochloride (Compound list No.: 1350)

(a) 5-Phenyl-3-(2-(1-pyrrolidinyl)ethoxy)isoxazole

Pyrrolidine (710 mg) was added to 3-(2-bromoethoxy)-5-phenylisoxazole (268 mg), and the mixture was stirred at 100° C. for one hour. After ice-cold water (20 ml) was added to the reaction mixture and the mixture was extracted with ether (20 ml×2), the organic layer was dried over anhydrous magnesium sulfate. After filtration, the solvent was evaporated under reduced pressure. The residue was purified by silica gel column chromatography (eluent: ethyl acetate) to obtain the title compound (211 mg, 82%) as colorless crystals.

m.p.: 61–62° C.; IR spectrum (KBr) $v_{max}$ cm$^{-1}$: 1623, 1596, 1575, 1509; NMR spectrum (CDCl$_3$) δ ppm: 1.77–1.87 (4H, m), 2.57–2.65 (4H, m), 2.92 (2H, t, J=5.5 Hz), 4.43 (2H, t, J=5.5 Hz), 6.18 (1H, s), 7.40–7.48 (3H, m), 7.69–7.75 (2H, m).

(b) 5-Phenyl-3-(2-(1-pyrrolidinyl)ethoxy)isoxazole hydrochloride

5-Phenyl-3-(2-(1-pyrrolidinyl)ethoxy)isoxazole (200 mg) was subjected to reaction and post-treatment in a similar manner to that described in Example 1(b) to obtain the title compound (211 mg, 93%) as colorless crystals.

m.p.: 182–184° C. (decomposed); IR spectrum (KBr) $v_{max}$ cm$^{-1}$: 2982, 2950, 2884, 2848, 2671, 2653, 2607, 2560, 2480, 1619, 1595, 1576, 1511; NMR spectrum (DMSO-d$_6$) δ ppm: 1.83–2.08 (4H, m), 3.01–3.21 (2H, m), 3.50–3.68 (4H, m), 4.60 (2H, t, J=5.1 Hz), 6.87 (1H, s), 7.50–7.58 (3H, m), 7.81–7.87 (2H, m), 10.63 (1H, brs).

EXAMPLE 72

3-(2-(4-Morpholinyl)ethoxy)-5-phenylisoxazole hydrochloride (Compound list No.: 29)

(a) 3-(2-(4-Morpholinyl)ethoxy)-5-phenylisoxazole

Morpholine (871 mg) was added to 3-(2-bromoethoxy)-5-phenylisoxazole (268 mg), and the mixture was stirred at 100° C. for one hour. After ice-cold water (20 ml) was added to the reaction mixture and the resulting mixture was extracted with ether (20 ml×2), the organic layer was dried over anhydrous magnesium sulfate. After filtration, the solvent was evaporated under reduced pressure. The residue was purified by silica gel column chromatography (eluent: ethyl acetate) to obtain the title compound (250 mg, 91%) as colorless crystals.

m.p.: 66–67° C.; IR spectrum (KBr) $v_{max}$ cm$^{-1}$: 3152, 1623, 1596, 1575, 1512; NMR spectrum (CDCl$_3$) δ ppm: 2.57 (2H, t, J=5.4 Hz), 2.82 (2H, t, J=5.4 Hz), 3.75 (2H, t, J=5.5 Hz), 4.44 (2H, t, J=5.5 Hz), 6.17 (1H, s), 7.41–7.50 (3H, m), 7.69–7.76 (2H, m).

(b) 3-(2-(4-Morpholinyl)ethoxy)-5-phenylisoxazole hydrochloride 3-(2-(4-Morpholinyl)ethoxy)-5-phenylisoxazole (200 mg) was subjected to reaction and post-treatment in a similar manner to that described in Example 1(b) to obtain the title compound (202 mg, 89%) as colorless crystals.

m.p.: 180–182° C. (decomposed); IR spectrum (KBr) $v_{max}$ cm$^{-1}$: 2981, 2925, 2897, 2878, 2683, 2646, 2584, 2512, 2469, 2429, 1620, 1595, 1576, 1512; NMR spectrum (DMSO-d$_6$) δ ppm: 3.10–3.25 (2H, m), 3.40–3.55 (2H, m), 3.55–3.65 (2H, m), 3.70–3.85 (2H, m), 3.90–4.05 (2H, m), 4.67 (2H, brs), 6.86 (1H, s), 7.50–7.58 (3H, m), 7.81–7.87 (2H, m), 10.96 (1H, brs).

EXAMPLE 73

5-Phenyl-3-(2-(1-piperazinyl)ethoxy)isoxazole dihydrochloride (Compound list No.: 1351)

(a) 3-(2-(4-N-tert-Butoxycarbonyl-1-piperazinyl)ethoxy)-5-phenylisoxazole 3-(2-Bromoethoxy)-5-phenylisoxazole (268 mg) was dissolved in methanol (1.0 ml), and piperazine (861 mg) was added thereto, followed by reflux of the resulting mixture for 3 hours. After the reaction mixture was added to a diluted aqueous NaCl solution (40 ml) and extracted with dichloromethane (40 ml×2), the organic layer was dried over anhydrous magnesium sulfate. After filtration, the solvent was evaporated under reduced pressure. The residue was dissolved in dichloromethane (5 ml), and di-tert-butyl dicarbonate (1.09 g) was added to the mixture, followed by stirring of the resulting mixture at room temperature for 30 minutes. After the reaction, the solvent was evaporated under reduced pressure and the residue was purified by silica gel column chromatography (eluent: hexane/ethyl acetate=2/1) to obtain the title compound (310 mg, 83%) as colorless crystals.

m.p.: 110–111° C.; IR spectrum (KBr) $v_{max}$ cm$^{-1}$: 3146, 1696, 1626, 1598, 1577, 1514; NMR spectrum (CDCl$_3$) δ ppm: 1.46 (9H, s), 2.51 (2H, t, J=5.0 Hz), 2.83 (2H, t, J=5.5 Hz), 3.47 (2H, t, J=5.0 Hz), 4.43 (2H, t, J=5.5 Hz), 6.16 (1H, s), 7.41–7.49 (3H, m), 7.69–7.75 (2H, m).

(b) 5-Phenyl-3-(2-(1-piperazinyl)ethoxy)isoxazole dihydrochloride 3-(2-(4-tert-Butoxycarbonyl-1-piperazinyl)ethoxy)-5-phenylisoxazole (250 mg) was subjected to reaction and post-treatment in a similar manner to that described in Example 1(b) to obtain the title compound (222 mg, 95%) as colorless crystals.

m.p.: 216–222° C. (decomposed); IR spectrum (KBr) $v_{max}$ cm$^{-1}$: 3443, 3189, 3123, 3001, 2972, 2950, 2915, 2771, 2715, 2623, 2527, 2422, 1704, 1648, 1621, 1596, 1578, 1565, 1514; NMR spectrum (DMSO-d$_6$) δ ppm: 3.00–3.85 (I OH, brs), 4.64 (2H, brs), 6.86 (1H, s), 7.50–7.57 (3H, m), 7.82–7.85 (2H, m), 9.10–9.80 (1H, brs).

EXAMPLE 74

3-(2-N-Methylaminoethoxy)-5-phenylisoxazole hydrochloride (Compound list No.: 25)

(a) 3-(2-(4-N-tert-Butoxycarbonyl-N-methylamino) ethoxy)-5-phenylisoxazole 3-(2-(N-tert-Butoxycarbonylamino)ethoxy)-5-phenylisoxazole (304 mg) was dissolved in dimethylformamide (3 ml), and sodium hydride [>55% (oily), 52 mg] was added thereto, followed by stirring of the resulting mixture at room temperature for one hour. The reaction mixture was cooled to 5° C., and methyl iodide (220 mg) was added thereto, followed by stirring of the resulting mixture at the same temperature for 15 minutes and further at room temperature for one hour. At the end of this time, the reaction mixture was added to ice-cold water (20 ml) and extracted with ether (20mlx2), the organic layer was dried over anhydrous magnesium sulfate. After filtration, the solvent was evaporated under reduced pressure. The residue was purified by silica gel column chromatography (eluent: hexane/ethyl acetate=4/1) to obtain the title compound (296 mg, 93%) as colorless crystals.

m.p.: 72–73° C.; IR spectrum (KBr) $v_{max}$ cm$^{-1}$: 3125, 1680, 1626, 1596, 1578, 1514; NMR spectrum (CDCl$_3$) δ ppm: 1.49 (9H, s), 2.97 (3H, s), 3.64 (2H, brs), 4.41 (2H, brs), 6.14 (1H, s), 7.41–7.52 (3H, m), 7.69–7.75 (2H, m).

(b) 3-(2-Methylaminoethoxy)-5-phenylisoxazole hydrochloride 3-(2-(N-tert-Butoxycarbonyl-N-methylamino)ethoxy)-5-phenylisoxazole (250 mg) was subjected to reaction and post-treatment in a similar manner to that described in Example 1(b) to obtain the title compound (197 mg, 99%) as colorless crystals.

m.p.: 219–221° C. (decomposed); IR spectrum (KBr) $v_{max}$ cm$^{-1}$: 3134, 3022, 2981, 2954, 2883, 2869, 2843, 2803, 2785, 2734, 1621, 1597, 1578, 1516; NMR spectrum (DMSO-d$_6$) δ ppm: 2.62 (3H, s), 3.37 (2H, t, J=5.1 Hz), 4.50 (1H, t, J=5.1 Hz), 6.85 (1H, s), 7.50–7.58 (3H, m), 7.82–7.88 (2H, m), 8.79 (2H, brs).

EXAMPLE 75

3-(2-Acetylaminoethoxy)-5-phenylisoxazole (Compound list No.: 1347)

3-(2-Aminoethoxy)-5-phenylisoxazole hydrochloride (240 mg) was suspended in anhydrous tetrahydrofuran (5 ml), and the suspension was cooled to 5° C. Acetyl chloride (94 mg) and triethylamine (243 mg) were added thereto, and the resulting mixture was stirred at the same temperature for 30 minutes. At the end of this time, the reaction mixture was added to ice-cold water (40 ml) and extracted with ethyl acetate (40 mlx2). Then, the organic layer was dried over anhydrous magnesium sulfate. After filtration, the solvent was evaporated under reduced pressure. The crystals thus obtained were recrystallized from ethyl acetate to obtain the title compound (225 mg, 91%) as colorless crystals.

m.p.: 144–145° C.; IR spectrum (KBr) $v_{max}$ cm$^{-1}$: 3316, 1641, 1624, 1597, 1578, 1547, 1509; NMR spectrum (CDCl$_3$) δ ppm: 2.03(3H, s), 3.70 (2H, q, J=5.1 Hz), 4.39 (2H, q, J=5.1 Hz), 6.16 (1H, brs), 6.26 (1H, s), 7.41–7.49 (3H, m), 7.70–7.75 (2H, m).

EXAMPLE 76

3-(2-Benzoylaminoethoxy)-5-phenylisoxazole (Compound list No.: 1349)

3-(2-Aminoethoxy)-5-phenylisoxazole hydrochloride (240 mg) was suspended in anhydrous tetrahydrofuran (5 ml), and the suspension was cooled to 5° C. Benzoyl chloride (168 mg) and triethylamine (243 mg) were added thereto, followed by stirring of the resulting mixture at the same temperature for 30 minutes. At the end of this time, the reaction mixture was added to ice-cold water (40 ml) and extracted with ethyl acetate (40 mlx2). Then, the organic layer was dried over anhydrous magnesium sulfate. After filtration, the solvent was evaporated under reduced pressure. The residue was recrystallized from ethyl acetate to obtain the title compound (276 mg, 90%) as colorless crystals.

m.p.: 129–130° C.; IR spectrum (KBr) $v_{max}$ cm$^{-1}$: 3359, 1641, 1626, 1597, 1578, 1534, 1518; NMR spectrum (CDCl$_3$) δ ppm: 3.92 (2H, q, J=5.1 Hz), 4.52 (2H, q, J=5.1 Hz), 6.17 (1H, s), 6.74 (1H, brs), 7.42–7.53 (6H, m), 7.71–7.74 (2H, m), 7.79–7.88 (2H, m).

EXAMPLE 77

3-(2-Methoxycarbonylaminoethoxy)-5-phenylisoxazole (Compound list No.: 1348)

3-(2-Aminoethoxy)-5-phenylisoxazole hydrochloride (240 mg) was suspended in anhydrous tetrahydrofuran (5 ml), and the suspension was cooled to 5° C. Then, methyl chloroformate (113 mg) and triethylamine (243 mg) were added thereto, and the resulting mixture was stirred at the same temperature for 30 minutes. At the end of this time, the reaction mixture was added to ice-cold water (40 ml) and extracted with ethyl acetate (40 mlx2). Then, the organic layer was dried over anhydrous magnesium sulfate. After filtration, the solvent was evaporated under reduced pressure. The crystals thus obtained were recrystallized from a mixture of ethyl acetate and ether to obtain the title compound (233 mg, 89%) as colorless crystals.

m.p.: 95–96° C.; IR spectrum (KBr) $v_{max}$ cm$^{-1}$: 3293, 1729, 1624, 1596, 1577, 1552, 1516; NMR spectrum (CDCl$_3$) δ ppm: 3.63 (2H, q, J=5.1 Hz), 3.70 (3H, s), 4.37 (2H, q, J=5.1 Hz), 5.11 (1H, brs), 6.14 (1H, s), 7.40–7.49 (3H, m), 7.69–7.75 (2H, m).

EXAMPLE 78

3-(2-Aminoethylthio)-5-phenylisoxazole hydrochloride (Compound list No.: 15)

(a) 3-(2-(N-tert-Butoxycarbonylamino)ethylthio)-5-phenylisoxazole 2-(N-tert-Butoxycarbonylamino)ethanethiol (300 mg) was dissolved in dimethylformamide (3.0 ml), and the mixture was cooled to 5° C., followed by addition of sodium hydride [>55% (oil), 73 mg]. The resulting mixture was stirred at the same temperature for 30 minutes. Then, 3-chloro-5-phenylisoxazole (300 mg) was added to the reaction mixture, followed by stirring of the mixture at the same temperature for 30 minutes and further at room temperature for 3 days. At the end of this time, the reaction mixture was added to ice-cold water (40 ml) and extracted with ethyl acetate (40 mlx2), and the organic layer was dried over anhydrous magnesium sulfate. After filtration, the solvent was evaporated under reduced pressure. The residue was purified by silica gel column chromatography (eluent:

hexane/ethyl acetate=4/1) to obtain the title compound (130 mg, 24%) as colorless crystals.

m.p.: 87–88° C.; IR spectrum (KBr) $v_{max}$ cm$^{-1}$: 3376, 1682, 1613, 1572, 1521, 1494; NMR spectrum (CDCl$_3$) δ ppm: 1.44 (9H, s), 3.27 (2H, t, J=6.3 Hz), 3.53 (2H, q, J=6.3 Hz), 5.01 (1H, brs), 6.44 (1H, s), 7.42–7.50 (3H, m), 7.71–7.76 (2H, m).

(b) 3-(2-Aminoethylthio)-5-phenylisoxazole hydrochloride 3-(2-(N-tert-Butoxycarbonylamino)ethylthio)-5-phenylisoxazole (64 mg) was subjected to reaction and post-treatment in a similar manner to that described in Example 1 (b) to obtain the title compound (40 mg, 78%) as colorless crystals.

m.p.: 196–198° C. (decomposed); IR spectrum (KBr) $v_{max}$ cm$^{-1}$: 3141,2988, 2951,2923, 1609, 1590, 1569, 1492; NMR spectrum (DMSO-d$_6$) δ ppm: 3.18 (2H, t, J=7.2 Hz), 3.36 (2H, t, J=7.2 Hz), 7.23 (1H, s), 7.53–7.59 (3H, m), 7.83–7.97 (2H, m), 7.97 (3H, brs).

EXAMPLE 79

3-(2-Aminoethoxy)-4-isopropyl-5-(3-pyridyl) isoxazole dihydrochloride (Compound list No.: 1065)

(a) 3-(2-(N-tert-Butoxycarbonylamino)ethoxy)-4-isopropyl-5-(3-pyridyl)isoxazole

3-Hydroxy-4-isopropyl-5-(3-pyridyl)isoxazole (0.12 g) and 2-(N-tert-butoxycarbonylamino)ethanol (0.09 g) were subjected to reaction and post-treatment in a similar manner to that described in Example 9(a) to obtain the title compound (0.14 g, 74%) as a colorless powder.

IR spectrum (KBr) $v_{max}$ cm$^{-1}$: 3323, 3247, 2979, 1753, 1690; NMR spectrum (CDCl$_3$) δ ppm: 1.31 (6H, d, J=6.8 Hz), 1.46 (9H, s), 3.06 (1H, qq, J=6.8 Hz, J=6.8 Hz), 3.60 (2H, q, J=5.2 Hz), 4.39 (2H, t, J=5.2 Hz), 4.84 (1H, brs), 7.43 (1H, dd, J=8.0 Hz, J=4.7 Hz), 7.90 (1H, ddd, J=8.0 Hz, J=2.0 Hz, J=1.4 Hz), 8.69 (1H, dd, J=4.7 Hz, J=1.4 Hz), 8.83 (1H, d, J=2.0 Hz).

(b) 3-(2-Aminoethoxy)-4-isopropyl-5-(3-pyridyl)isoxazole dihydrochloride 3-(2-(N-tert-Butoxycarbonylamino)ethoxy)-4-isopropyl-5-(3-pyridyl)isoxazole (0.13 g) was subjected to reaction and post-treatment in a similar manner to that described in Example 9(b) to obtain the title compound (0.07 g, 64%) as colorless crystals.

m.p.: 193–197° C. (decomposed); IR spectrum (KBr) $v_{max}$ cm$^{-1}$: 3049, 2963, 2874, 1549; NMR spectrum (DMSO-d$_6$) δ ppm: 1.27 (6H, d, J=7.0 Hz), 3.03 (1H, qq, J=7.0 Hz, J=7.0 Hz), 3.29 (2H, t, J=5.4 Hz), 4.48 (2H, t, J=5.4 Hz), 7.68 (1H, dd, J=8.0 Hz, J=5.0 Hz), 8.12 (1H, ddd, J=8.0 Hz, J=2.0 Hz, J=1.4 Hz), 8.28 (3H, brs), 8.78 (1H, dd, J=5.0 Hz, J=1.4 Hz), 8.85 (1H, d, J=2.0 Hz).

EXAMPLE 80

3-(2-Aminoethoxy)-4-(1-chloropropyl)-5-phenylisoxazole hydrochloride (Compound list No.: 1802)

(a) 3-(2-(N-tert-Butoxycarbonylamino)ethoxy)-4-(1-hydroxypropyl-5-phenylisoxazole 3-(2-(N-tert-Butoxycarbonylamino)ethoxy)-5-phenylisoxazole (0.2 g), butyllithium (1.6M hexane solution, 0.9 ml) and propionaldehyde (0.06 ml) were subjected to reaction and post-treatment in a similar manner to that described in Example 44(a) to obtain the title compound (0.14 g, 58%) as a colorless oil.

IR spectrum (CHCl$_3$) $v_{max}$ cm$^{-1}$: 3602, 3459, 2980, 2937, 1712; NMR spectrum (CDCl$_3$) δ ppm: 0.95 (3H, t, J=7.4 Hz), 1.45 (9H, s), 1.83–2.08 (2H, m), 2.51 (1H, brs), 3.57 (2H, q, J=5.2 Hz), 4.39 (2H, t, J=5.2 Hz), 4.68 (1H, t, J=7.2 Hz), 4.94 (1H, brs), 7.43–7.52 (3H, m), 7.64–7.75 (2H, m).

(b) 3-(2-Aminoethoxy-4-(1-chloropropyl)-5-phenylisoxazole hydrochloride 3-(2-(N-tert-Butoxycarbonylamino)ethoxy)-4-(1-hydroxypropyl)-5-phenylisoxazole (0.13 g) was subjected to reaction and post-treatment in a similar manner to that described in Example 1(b) to obtain the title compound (0.10 g, 91%) as colorless crystals.

m.p.: 122–124° C.; IR spectrum (KBr) $v_{max}$ cm$^{-1}$: 2974, 2936, 2878, 1631, 1600, 1577; NMR spectrum (DMSO-d$_6$) δ ppm: 0.94 (3H, t, J=7.3 Hz), 2.11–2.28 (2H, m), 3.31 (2H, t, J=5.1 Hz), 4.50 (2H, t, J=5.1 Hz), 5.14 (1H, t, J=6.5 Hz), 7.61–7.65 (3H, m), 7.72–7.75 (2H, m).

EXAMPLE 81

3-(2-Aminoethoxy)-4-(1-chloroisobutyl)-5-phenylisoxazole hydrochloride (Compound list No.: 1804)

(a) 3-(2-(N-tert-Butoxycarbonylamino)ethoxy)-4-(1-hydroxyisobutyl)-5-phenylisoxazole 3-(2-(N-tert-Butoxycarbonylamino)ethoxy)-5-phenylisoxazole (0.2 g), butyllithium (1.6M hexane solution, 0.9 ml) and isobutylaldehyde (0.07 ml) were subjected to reaction and post-treatment in a similar manner to that described in Example 44(a) to obtain the title compound (0.21 g, 84%) as a colorless oil.

IR spectrum (CHCl$_3$) $v_{max}$ cm$^{-1}$: 3606,3459, 2981,2937, 1712, 1637; NMR spectrum (CDCl$_3$) δ ppm: 0.79 (3H, d, J=6.6 Hz), 1.11 (3H, d, J=6.6 Hz), 1.45 (9H, s), 2.16–2.29 (1H, m), 2.56 (1H, brs), 3.58 (2H, q, J=5.1 Hz), 4.30–4.48 (3H, m), 4.94 (1H, brs), 7.46–7.51 (3H, m), 7.70–7.74 (2H, m).

(b) 3-(2-Aminoethoxy)-4-(1-chloroisobutyl)-5-phenylisoxazole hydrochloride 3-(2-(N-tert-Butoxycarbonylamino)ethoxy)-4-(1-hydroxyisobutyl)-5-phenylisoxazole (0.20 g) was subjected to reaction and post-treatment in a similar manner to that described in Example 1 (b) to obtain the title compound (0.11 g, 65%) as colorless crystals.

m.p.: 165–167° C.; IR spectrum (KBr) $v_{max}$ cm$^{-1}$: 2967, 2902, 2870, 1636, 1600; NMR spectrum (DMSO-d$_6$) δ ppm: 0.78 (3H, d, J=6.6 Hz), 1.15 (3H, d, J=6.6 Hz), 2.53–2.63 (1H, m), 3.30 (2H, t, J=5.2 Hz), 4.50 (2H, t, J=5.2 Hz), 4.85 (1H, d, J=10.7 Hz), 7.60–7.65 (3H, m), 7.71–7.75 (2H, m), 8.25 (3H, brs).

EXAMPLE 82

3-(2-Aminoethoxy)-4-(1-chloroisopentyl)-5-phenylisoxazole hydrochloride (Compound list No.: 1806)

(a) 3-(2-(N-tert-Butoxycarbonylamino)ethoxy)-4-(1-hydroxyisopentyl)-5-phenylisoxazole 3-(2-(N-tert-Butoxycarbonylamino)ethoxy)-5-phenylisoxazole (0.2 g), butyllithium (1.6M hexane solution, 0.9 ml) and isovaleraldehyde (0.09 ml) were subjected to reaction and post-treatment in a similar manner to that described in Example 44(a) to obtain the title compound (0.2 g, 77%) as a colorless oil.

IR spectrum (CHCl$_3$) $v_{max}$ cm$^{-1}$: 3601, 3459, 2981, 2961, 2936, 1712, 1639; NMR spectrum (CDCl$_3$) δ ppm: 0.87 (3H, d, J=6.3 Hz), 0.92 (3H, d, J=6.3 Hz), 1.45 (9H, s), 1.63–1.78 (2H, m), 1.83–1.98 (1H, m), 3.58 (2H, q, J=5.2 Hz), 4.40 (2H, t, J=5.2 Hz), 4.75–5.00 (2H, m), 7.44–7.50 (3H, m), 7.66–7.71 (2H, m).

(b) 3-(2-Aminoethoxy)-4-(1-chloroisopentyl)-5-phenylisoxazole hydrochloride 3-(2-(N-tert-Butoxycarbonylamino)ethoxy)-4-(1-hydroxyisopentyl)-5-phenylisoxazole (0.19 g) was subjected to reaction and post-treatment in a similar manner to that described in Example 1(b) to obtain the title compound (0.11 g, 69%) as colorless crystals.

m.p.: 134–136° C.; IR spectrum (KBr) $v_{max}$ cm$^{-1}$: 2961, 2905, 2873, 1630; NMR spectrum (DMSO-d$_6$) δ ppm: 0.79 (3H, d, J=6.6 Hz), 0.82 (3H, d, J=6.6 Hz), 1.57 (1H, qq, J=6.6 Hz, J=6.6 Hz), 2.00–2.12 (2H, m), 3.31 (2H, t, J=5.4 Hz), 4.51 (2H, t, J=5.4 Hz), 5.21 (1H, t, J=8.0 Hz), 7.62–7.65 (3H, m), 7.69–7.72 (2H, m), 8.22 (3H, brs).

EXAMPLE 83

3-(2-Aminoethoxy)-5-(2,4-difluorophenyl)-4-isopropylisoxazole hydrochloride (Compound list No.: 99)

(a) 3-(2-(N-tert-Butoxycarbonylamino)ethoxy)-5-(2,4-difluorophenyl)-4-isopropylisoxazole 5-(2,4-Difluorophenyl)-3-hydroxy-4-isopropylisoxazole (0.2 g) and 2-(N-tert-butoxycarbonylamino)ethanol (0.16 g) were subjected to reaction and post-treatment in a similar manner to that described in Example 1(a) to obtain the title compound (0.25 g, 78%) as a colorless powder.

IR spectrum (KBr) $v_{max}$ cm$^{-1}$: 3400, 2980, 2936, 1683; NMR spectrum (CDCl$_3$) δ ppm: 1.22 (6H, d, J=6.9 Hz), 1.46 (9H, s), 2.78 (1H, qq, J=6.9 Hz, J=6.9 Hz), 3.59 (2H, q, J=5.2 Hz), 4.38 (2H, t, J=5.2 Hz), 4.86 (1H, brs), 6.90–7.03 (2H, m), 7.42–7.50 (1H, m).

(b) 3-(2-Aminoethoxy)-5-(2,4-difluorophenyl)-4-isopropylisoxazole hydrochloride 3-(2-(N-tert-Butoxycarbonylamino)ethoxy)-5-(2,4-difluorophenyl)-4-isopropylisoxazole (0.24 g) was subjected to reaction and post-treatment in a similar manner to that described in Example 1(b) to obtain the title compound (0.17 g, 85%) as colorless crystals.

m.p.: 177–179° C.; IR spectrum (KBr) $v_{max}$ cm$^{-1}$: 2973, 2936, 1642, 1614, 1590; NMR spectrum (DMSO-d$_6$) δ ppm: 1.18 (6H, d, J=6.9 Hz), 2.76 (1H, qq, J=6.9 Hz, J=6.9 Hz), 3.29 (2H, t, J=5.3 Hz), 4.46 (2H, t, J=5.3 Hz), 7.28–7.33 (1H, m), 7.50–7.56 (1H, m), 7.60–7.66 (1H, m), 8.12 (3H, brs).

EXAMPLE 84

3-(2-Aminoethoxy)-4-isopropyl-5-(4-methylphenyl) isoxazole hydrochloride (Compound list No.: 266)

(a) 3-(2-(N-tert-Butoxycarbonylamino)ethoxy)-4-isopropyl-5-(4-methylphenyl)isoxazole 3-Hydroxy-4-isopropyl-5-(4-methylphenyl)isoxazole (0.2 g) and 2-(N-tert-butoxycarbonylamino)ethanol (0.16 g) were subjected to reaction and post-treatment in a similar manner to that described in Example 1 (a) to obtain the title compound (0.27 g, 82%) as a colorless powder.

IR spectrum (KBr) $v_{max}$ cm$^{-1}$: 3383, 2965, 1686; NMR spectrum (CDCl$_3$) δ ppm: 1.28 (6H, d, J=7.0 Hz), 1.46 (9H, s), 2.41 (3H, s), 3.06 (1H, qq, J=7.0 Hz, J=7.0 Hz), 3.59 (2H, q, J=5.2 Hz), 4.37 (2H, t, J=5.2 Hz), 4.84 (1H, brs), 7.27 (2H, d, J=8.1 Hz), 7.46 (2H, d, J=8.1 Hz).

(b) 3-(2-Aminoethoxy)-4-isopropyl-5-(4-methylphenyl) isoxazole hydrochloride 3-(2-(N-tert-butoxycarbonylamino)ethoxy)-4-isopropyl-5-(4-methylphenyl)isoxazole (0.25 g) was subjected to reaction and post-treatment in a similar manner to that described in Example 1(b) to obtain the title compound (0.13 g, 65%) as colorless crystals.

m.p.: 208–210° C.;
IR spectrum (KBr) $v_{max}$ cm$^{-1}$: 2971, 2877, 1641, 1522; NMR spectrum (DMSO-d$_6$) δ ppm: 1.25 (6H, d, J=7.0 Hz), 2.38 (3H, s), 3.02 (1H, qq, J=7.0 Hz, J=7.0 Hz), 3.28 (2H, t, J=5.2 Hz), 4.44 (2H, t, J=5.2 Hz), 7.37 (2H, d, J=8.1 Hz), 7.47 (2H, d, J=8.1 Hz), 8.20 (3H, brs).

REFERENCE EXAMPLE 1

4-Chloro-5-(4-chlorophenyl)-3-hydroxyisoxazole (a) 4-Chlorocinnamic acid ethyl ester 4-Chlorocinnamic acid (300 g) was suspended in benzene (1200 ml), and ethanol (340 g) and conc. sulfuric acid (14 ml) were added thereto, followed by reflux of the resulting mixture for 15 hours. After the reaction mixture had been washed successively with a diluted aqueous NaCl solution (500 ml), a saturated aqueous sodium hydrogencarbonate solution (500 ml) and a dilute aqueous NaCl solution (500 ml), the organic layer was dried over anhydrous magnesium sulfate. After filtration, the solvent was evaporated under reduced pressure. The residue was evaporated under reduced pressure to obtain the title compound (334 g, 97%) as a colorless liquid.

b.p.: 147–148° C. (4 mmHg); NMR spectrum (CDCl$_3$) δ ppm: 1.33 (3H, t, J=7.0 Hz), 4.30 (2H, q, J=7.0 Hz), 6.47 (1H, d, J=16.0 Hz), 7.63 (1H, d, J=16.0 Hz), 7.63 (4H, ca.s).

(b) α,β-Dibromo-4-chlorocinnamic acid ethyl ester

4-Chlorocinnamic acid ethyl ester (330 g) was dissolved in carbon tetrachloride (1200 ml), and bromine (251 g) was added dropwise thereto under stirring at room temperature. The resulting mixture was stirred at room temperature for 4 hours and allowed to stand overnight. The solvent was evaporated under reduced pressure to obtain the title compound (572 g, 99%) as colorless crystals.

m.p.: 67–68° C.; NMR spectrum (CDCl$_3$) δ ppm: 1.34 (3H, t, J=7.0 Hz), 4.37 (2H, q, J=7.0 Hz), 4.80 (1H, d, J=12.0 Hz), 5.32 (1H, d, J=12.0 Hz), 7.37 (4H, ca.s).

(c) 5-(4-Chlorophenyl)-3-hydroxyisoxazole

Sodium hydroxide (151 g) was dissolved in methanol (600 ml), and an aqueous hydroxylamine hydrochloride (45 g) solution (50 ml) was added dropwise thereto under stirring at 0° C., and then a solution of α,β-dibromo-4-chlorocinnamic acid ethyl ester (200 g) in dioxane (200 ml) was added dropwise to the mixture. The resulting mixture was stirred at room temperature for 4 hours and further refluxed for 5 hours. The reaction mixture was cooled to 5° C., and the pH of the mixture was adjusted to a value of 2 with conc. hydrochloric acid. Then, the reaction mixture was added to water (5 L). Precipitate was separated from the mixture by filtration and washed with water (2 L) and then with ethanol (1 L) to obtain 90 g of the title compound (85%) as a pale yellow powder.

m.p.: 215–220° C. (decomposed); NMR spectrum (DMF-d$_7$) δ ppm: 6.66 (1H, s), 7.52–8.20 (4H, m), 11.5–12.0 (1H, brs).

(d) 4-Chloro-5-(4-chlorophenyl)-3-hydroxyisoxazole

To a solution of 5-(4-chlorophenyl)-3-hydroxyisoxazole (50.0 g) in dry tetrahydrofuran (300 ml), a solution of sulfuryl chloride (34.5 g) in dry benzene (50 ml) was added dropwise with stirring at 5° C. The resulting mixture was stirred at the same temperature for 30 minutes and then at room temperature for one hour and further refluxed for 3 hours. The solvent of the reaction mixture was evaporated under reduced pressure, and the solid thus obtained was recrystallized from ethanol to obtain the title compound (44.2 g, 76.8%) as colorless needle-like crystals.

m.p.: 235–238° C. (decomposed); NMR spectrum (DMF-d$_7$) δ ppm: 7.60–8.20 (4H, m), 12.6–13.6 (1H, brs).

REFERENCE EXAMPLE 2

3-Hydroxy-5-(2-thienyl)isoxazole

2-Thiophenacrylic acid was subjected to reaction and post-treatment in a similar manner to that described in Reference example 1(a), Reference example 1(b) and Reference example 1(c) to obtain the title compound.

m.p.: 163–165° C.; NMR spectrum (DMSO-$d_6$) δ ppm: 6.38 (1H, s), 7.20–7.25 (1H, m), 7.60–7.80 (2H, m), 11.2–11.6 (1H, brs).

REFERENCE EXAMPLE 3

4-Chloro-3-hydroxy-5-(2-thienyl)isoxazole

3-Hydroxy-5-(2-thienyl)isoxazole was subjected to reaction and post-treatment in a similar manner to that described in Reference example 1(d) to obtain the title compound.

m.p.: 191–194° C.; NMR spectrum (DMF-$d_7$) δ ppm: 7.21–7.45 (1H, m), 7.70–8.20 (2H, m), 10.0–13.0 (1H, brs).

REFERENCE EXAMPLE 4

3-Hydroxy-5-(3-pyridyl)isoxazole

3-Pyridineacrylic acid was subjected to reaction and post-treatment in a similar manner to that described in Reference example 1(a), Reference example 1(b) and Reference example 1(c) to obtain the title compound.

m.p.: 212–214° C. (decomposed); NMR spectrum (DMF-$d_7$) δ ppm: 6.76 (1H, s), 7.40–7.80 (1H, m), 8.10–8.50 (1H, m), 8.66–9.00 (1H, m), 9.05–9.33 (1H, m).

REFERENCE EXAMPLE 5

4-Chloro-3-hydroxy-5-(2-pyridyl)isoxazole

3-Hydroxy-5-(2-pyridyl)isoxazole was subjected to reaction and post-treatment in a similar manner to that described in Reference example 1(d) to obtain the title compound.

REFERENCE EXAMPLE 6

3-Hydroxy-4-isopropyl-5-phenylisoxazole

Ethyl benzoylacetate was subjected to reaction and post-treatment in a similar manner to that described in Agric. Biol. Chem., EN. 50, 1831 (1986) to obtain the title compound.

m.p.: 203–205° C.; NMR spectrum (DMSO-$d_6$) δ ppm: 1.24 (6H, d, J=7.1 Hz), 3.01 (1H, q, J=7.1 Hz), 7.47–7.61 (5H, m), 11.2–11.6 (1H, brs).

REFERENCE EXAMPLE 7

2-(N-tert-Butoxycarbonylamino)ethanol

2-Aminoethanol (6.1 g) was dissolved in a mixture of tetrahydrofuran and water (1:1, 100 ml), and di-tert-butyl dicarbonate (21.8 g) was added dropwise thereto under ice-cooling with stirring, followed by stirring of the resulting mixture at the same temperature for one hour and further at room temperature for 5 hours. After ethyl acetate (200 ml) was added to the reaction mixture and the mixture was washed with water, the organic layer was dried over anhydrous magnesium sulfate. After filtration, the solvent was evaporated under reduced pressure to obtain the title compound (15.3 g, 95%) as a colorless oil.

Rf value: 0.35 (Developing solvent: cyclohexane/ethyl acetate=1/1) NMR spectrum (CDCl$_3$) δ ppm: 1.45 (9H, s), 2.35–2.50 (1H, brs), 3.29 (2H, q, J=5.3 Hz), 3.71 (2H, q, J=5.3 Hz), 4.85–5.05 (1H, brs).

REFERENCE EXAMPLE 8

4-(tert-Butyl)-3-hydroxy-5-phenylisoxazole (a) 2-Benzoyl-3,3-dimethylbutyric acid ethyl ester Diisopropylamine (5.6 ml) was dissolved in tetrahydrofuran (56 ml), butyllithium (1.6M hexane solution, 25 ml) was added dropwise thereto at 5° C. with stirring under a nitrogen atmosphere, and the resulting mixture was stirred for 15 minutes. The reaction mixture was cooled to −70° C., and 3,3-dimethylbutyric acid ethyl ester (6.7 ml) was added dropwise thereto, followed by stirring of the resulting mixture for 10 minutes. Then, benzoyl chloride (2.3 ml) was added dropwise to the reaction mixture and the resulting mixture was stirred at the same temperature for 10 minutes. After the reaction, a saturated aqueous ammonium chloride solution was added to the reaction mixture, and the mixture was extracted with ethyl acetate. The organic layer was washed with a saturated aqueous NaCl solution and dried over anhydrous magnesium sulfate. After filtration, the solvent was evaporated under reduced pressure. The residue was purified by silica gel column chromatography (eluent: hexane/ethyl acetate=20/1) to obtain the title compound (4.5 g, 91%) as a colorless oil.

(b) 4-(tert-Butyl)-3-hydroxy-5-phenylisoxazole

2-Benzoyl-3,3-dimethylbutyric acid ethyl ester (2.0 g) was dissolved in methanol (20 ml), and sodium methoxide (28% methanol solution, 1.6 ml) was added dropwise thereto at 5° C. under a nitrogen atmosphere, followed by stirring of the resulting mixture for 10 minutes. The reaction mixture was cooled to −30° C., and a suspension of hydroxylamine hydrochloride (1.1 g) and sodium methoxide (28% methanol solution, 6.2 ml) in methanol (10 ml) was added dropwise to the reaction mixture. The resulting mixture was stirred at the same temperature for 30 minutes, and 6N hydrochloric acid (14 ml) was added to the reaction mixture, followed by stirring of the resulting mixture at 80° C. for one hour. After the reaction, the solvent was evaporated under reduced pressure. After the residue was poured into ice-cold water and extracted with ethyl acetate, the organic layer was washed with a saturated aqueous NaCl solution and dried over anhydrous magnesium sulfate. After filtration, the solvent was evaporated under reduced pressure. The residue was crystallized from isopropyl ether to obtain the title compound (0.35 g, 20%) as colorless crystals.

IR spectrum (KBr) ν$_{max}$ cm$^{-1}$: 3027, 2993, 2960, 2936, 2869, 2790, 2697, 2623, 2574, 1644, 1600; NMR spectrum (CDCl$_3$) δ ppm: 1.22 (9H, s), 7.39–7.50 (5H, m).

REFERENCE EXAMPLE 9

5-(4-Chlorophenyl)-3-hydroxy-4-isopropylisoxazole (a) 2-(4-Chlorobenzoyl)isovaleric acid ethyl ester 4-Chlorobenzoyl chloride (2.5 ml) and isovaleric acid ethyl ester (1.5 ml) were subjected to reaction and post-treatment in a similar manner to that described in Reference example 8(a) to obtain the title compound (2.2 g, 82%) as a colorless oil.

(b) 5-(4-Chlorophenyl-3-hydroxy-4-isopropylisoxazole 2-(4-Chlorobenzoyl)isovaleric acid ethyl ester (2.1 g), hydroxylamine hydrochloride (1.1 g) and sodium methoxide (28% methanol solution, 7.5 ml) were subjected to reaction and post-treatment in a similar manner to that described in Reference example 8(b) to obtain the title compound (1.3 g, 71%) as colorless crystals.

IR spectrum (KBr) ν$_{max}$ cm$^{-1}$: 3065, 3018, 2970, 2935, 2875, 2820, 2768, 2695, 2609, 1646; NMR spectrum (CDCl$_3$) δ ppm: 1.35 (6H, d, J=7.0 Hz), 3.06 (1H, qq, J=7.0 Hz, J=7.0 Hz), 7.46 (2H, d, J=8.6 Hz), 7.54 (2H, d, J=8.6 Hz).

REFERENCE EXAMPLE 10

5-(2.4-Difluorophenyl)-3-hydroxyisoxazole (a) 2.4-Difluorocinnamic acid ethyl ester 2,4-Difluorocinnamic acid (10.1 g) was dissolved in ethanol (100 ml), and conc. sulfuric acid (1 ml) was added thereto, and the resulting mixture was refluxed for 3 hours. The solvent was evaporated under reduced pressure and the residue was poured into ice-cold water and extracted with ethyl acetate. The extract was washed successively with 5% aqueous sodium hydrogencarbonate and a saturated aqueous NaCl solution, and the organic layer was dried over anhydrous magnesium sulfate. After filtration, the solvent was evaporated under reduced pressure to obtain the title compound (11.2 g, 97%) as a colorless oil.

(b) α,β-Dibromo-2,4-difluorocinnamic acid ethyl ester 2,4-Difluorocinnamic acid ethyl ester (11.2 g) was dissolved in carbon tetrachloride (110 ml), and bromine (2.7 ml) was added dropwise thereto at room temperature with stirring, followed by stirring of the mixture at room temperature for 3 hours. After the reaction, the solvent was evaporated under reduced pressure to obtain the title compound (19.6 g, quantitative) as a colorless powder.

(c) 5-(2,4-Difluorophenyl)-3-hydroxyisoxazole

Sodium hydroxide (10.9 g) was dissolved in methanol (110 ml), and a solution of hydroxylamine hydrochloride (4.2 g) in water (10 ml) was added dropwise thereto at 5° C. with stirring. A solution of α,β-dibromo-2,4-difluorocinnamic acid ethyl ester (19.6 g) in tetrahydrofuran (20 ml) was added dropwise to the mixture, and the resulting mixture was stirred at room temperature for 2 hours, followed by reflux for 5 hours. The solvent was evaporated under reduced pressure and the residue was poured into ice-cold water. The pH of the reaction mixture was adjusted to a value of 2 with conc. hydrochloric acid, and the reaction mixture was extracted with ethyl acetate. The extract was washed with a saturated aqueous NaCl solution, and the organic layer was dried over anhydrous magnesium sulfate. After filtration, the solvent was evaporated under reduced pressure. The residue was purified by silica gel column chromatography (eluent: cyclohexane/ethyl acetate=1/1) to obtain the title compound (8.2 g, 79%) as colorless crystals.

IR spectrum (KBr) v$_{max}$ cm$^{-1}$: 3170, 3090, 3028, 2848, 2806, 2689, 2655, 2603, 1630; NMR spectrum (DMSO-d$_6$) δ ppm: 6.38 (1H, s), 7.25–7.32 (1H, m), 7.47–7.56 (1H, m), 7.89–7.99 (1H, m), 11.62 (1H, brs).

REFERENCE EXAMPLE 11

3-Hydroxy-5-(2-trifluoromethylphenyl)isoxazole (a) 2-Trifluoromethylcinnamic acid ethyl ester 2-Trifluoromethylcinnamic acid (10.1 g), conc. sulfuric acid (1 ml) and ethanol (100 ml) were subjected to reaction and post-treatment in a similar manner to that described in Reference example 10(a) to obtain the title compound (10.8 g, 95%) as a colorless oil.

(b) α,β-Dibromo-2-trifluoromethylcinnamic acid ethyl ester

2-Trifluoromethylcinnamic acid ethyl ester (10.8 g) and bromine (2.3 ml) were subjected to reaction and post-treatment in a similar manner to that described in Reference example 10(b) to obtain the title compound (17.9 g, quantitative) as a colorless powder.

(c) 3-Hydroxy-5-(2-trifluoromethylphenyl)isoxazole

α,β-Dibromo-2-trifluoromethylcinnamic acid ethyl ester (17.9 g), hydroxylamine hydrochloride (3.8 g) and sodium hydroxide (9.1 g) were subjected to reaction and post-treatment in a similar manner to that described in Reference example 10(c) to obtain the title compound (7.6 g, 76%) as colorless crystals.

IR spectrum (KBr) v$_{max}$ cm$^{-1}$: 3176, 3096, 3022, 2950, 2836, 2796, 2669, 1620, 1600; NMR spectrum (DMSO-d$_6$) δ ppm: 6.34 (1H, s), 7.73–7.87 (3H, m), 7.92–7.95 (1H, m), 11.58 (1H, brs).

REFERENCE EXAMPLE 12

3-Hydroxy-5-(4-trifluoromethylphenyl)isoxazole (a) Ethyl 4-trifluoromethylcinnamate 4-Trifluoromethylcinnamic acid (10.2 g), conc. sulfuric acid (1 ml) and ethanol (100 ml) were subjected to reaction and post-treatment in a similar manner to that described in Reference example 10(a) to obtain the title compound (10.9 g, 95%) as a colorless oil.

(b) α,β-Dibromo-4-trifluoromethylcinnamic acid ethyl ester

4-Trifluoromethylcinnamic acid ethyl ester (10.8 g) and bromine (2.4 ml) were subjected to reaction and post-treatment in a similar manner to that described in Reference example 10(b) to obtain the title compound (17.9 g, quantitative) as a colorless powder.

(c) 3-Hydroxy-5-(4-trifluoromethylphenyl)isoxazole

α,β-Dibromo-4-trifluoromethylcinnamic acid ethyl ester (17.9 g), hydroxylamine hydrochloride (3.8 g) and sodium hydroxide (9.1 g) were subjected to reaction and post-treatment in a similar manner to that described in Reference example 10(c) to obtain the title compound (8.3 g, 83%) as colorless crystals.

IR spectrum (KBr) v$_{max}$ cm$^{-1}$: 3154, 3018, 2987, 2838, 2788, 2673, 2637, 2607, 2547, 1631, 1614; NMR spectrum (DMSO-d$_6$) δ ppm: 6.77 (1H, s), 7.88 (2H, d, J=8.4 Hz), 8.03 (2H, d, J=8.4 Hz), 11.60 (1H, brs).

REFERENCE EXAMPLE 13

3-Hydroxy-5-(4-isopropylphenyl)isoxazole (a) 4-Isopropylcinnamic acid ethyl ester 4-Isopropylcinnamic acid (5.0 g), conc. sulfuric acid (0.5 ml) and ethanol (50 ml) were subjected to reaction and post-treatment in a similar manner to that described in Reference example 10(a) to obtain the title compound (5.5 g, 97%) as a colorless oil.

(b) α,β-Dibromo-4-isopropyicinnamic acid ethyl ester

4-Isopropylcinnamic acid ethyl ester (5.5 g) and bromine (1.3 ml) were subjected to reaction and post-treatment in a similar manner to that described in Reference example 10(b) to obtain the title compound (9.5 g, quantitative) as a colorless powder.

(c) 3-Hydroxy-5-(4-isopropylphenyl)isoxazole

α,β-Dibromo-4-isopropylcinnamic acid ethyl ester (9.5 g), hydroxylamine hydrochloride (2.2 g) and sodium hydroxide (5.2 g) were subjected to reaction and post-treatment in a similar manner to that described in Reference example 10(c) to obtain the title compound (3.6 g, 71%) as colorless crystals.

IR spectrum (KBr) v$_{max}$ cm$^{-1}$: 3013, 2964, 2934, 2893, 2872, 2793, 2665, 2631, 2542, 1624; NMR spectrum (DMSO-d$_6$) δ ppm: 1.22 (6H, d, J=6.9 Hz), 2.94 (1H, qq, J=6.9 Hz, J=6.9 Hz), 6.48 (1H, s), 7.39 (2H, d, J=8.3 Hz), 7.72 (2H, d, J=8.3 Hz).

REFERENCE EXAMPLE 14

3-Hydroxy-5-(4-phenoxyphenyl)isoxazole (a) 4-Phenoxycinnamic acid

4-Phenoxybenzaldehyde (10.0 g) and potassium acetate (9.8 g) were suspended in acetic anhydride (9.5 ml), followed by reflux at 180° C. for 5 hours. After the reaction, the pH of the reaction mixture was adjusted to a value of 2 with hydrochloric acid and the resulting mixture was extracted with ethyl acetate. The extract was washed with a saturated aqueous NaCl solution, and the organic layer was dried over anhydrous magnesium sulfate. After filtration, the solvent was evaporated under reduced pressure. The residue was purified by silica gel column chromatography (eluent: hexane/ethyl acetate=2/1) to obtain the title compound (6.5 g, 54%) as colorless crystals.

(b) 4-Phenoxycinnamic acid ethyl ester

4-Phenoxycinnamic acid (4.0 g), conc. sulfuric acid (0.4 ml) and ethanol (40 ml) were subjected to reaction and post-treatment in a similar manner to that described in Reference example 10(b) to obtain the title compound (4.4 g, 98%) as a colorless oil.

(c) α,β-Dibromo-4-phenoxycinnamic acid ethyl ester

4-Phenoxycinnamic acid ethyl ester (4.4 g), and bromine (0.84 ml) were subjected to reaction and post-treatment in a similar manner to that described in Reference example 10(b) to obtain the title compound (7.0 g, quantitative) as a colorless powder.

(d) 3-Hydroxy-5-(4-phenoxyphenyl)isoxazole

α,β-Dibromo-4-phenoxycinnamic acid ethyl ester (7.0 g), hydroxylamine hydrochloride (1.4 g) and sodium hydroxide (3.3 g) were subjected to reaction and post-treatment in a similar manner to that described in Reference example 10(c) to obtain the title compound (3.4 g, 83%) as colorless crystals.

IR spectrum (KBr) $v_{max}$ cm$^{-1}$: 3147, 3013, 2951,2852, 2785, 2614,2557, 1627; NMR spectrum (DMSO-d$_6$) δ ppm: 6.47 (1H, s), 7.07–7.25 (5H, m), 7.42–7.48 (2H, m), 7.79–7.83 (2H, m), 11.36 (1H, brs).

REFERENCE EXAMPLE 15

3-Hydroxy-5-(1-naphthyl)isoxazole (a) 1-Naphthylacrylic acid

1-Naphthaldehyde (30.5 g), potassium acetate (38.3 g) and acetic anhydride (36.9 ml) were subjected to reaction and post-treatment in a similar manner to that described in Reference example 14(a) to obtain the title compound (22.4 g, 58%) as a colorless powder.

(b) 1-Naphthylacrylic acid ethyl ester

1-Naphthylacrylic acid (9.5 g), conc. sulfuric acid (1 ml) and ethanol (100 ml) were subjected to reaction and post-treatment in a similar manner to that described in Reference example 10(a) to obtain the title compound (10.2 g, 94%) as a colorless oil.

(c) α,β-Dibromo-1-naphthylacrylic acid ethyl ester

1-Naphthylacrylic acid ethyl ester (10.1 g) and bromine (2.5 ml) were subjected to reaction and post-treatment in a similar manner to that described in Reference example 10(b) to obtain the title compound (17.2 g, quantitative) as a colorless powder.

(d) 3-Hydroxy-5-(1-naphthylisoxazole

α,β-Dibromo-1-naphthylacrylic acid ethyl ester (6.0 g), hydroxylamine hydrochloride (1.3 g) and sodium hydroxide (7.2 g) were subjected to reaction and post-treatment in a similar manner to that described in Reference example 10(c) to obtain the title compound (2.6 g, 78%) as colorless crystals.

IR spectrum (KBr) $v_{max}$ cm$^{-1}$: 3136, 3045, 3017, 2790, 2710, 2640, 2569, 1628; NMR spectrum (DMSO-d$_6$) δ ppm: 6.53 (1H, s), 7.61–7.70 (3H, m), 7.84–7.87 (1H, m), 8.03–8.13 (2H, m), 8.22–8.28 (1H, m).

REFERENCE EXAMPLE 16

3-Hydroxy-5-(4-hydroxyphenyl)isoxazole

3-Hydroxy-5-(4-methoxyphenyl)isoxazole (5.0 g) was suspended in dichloromethane (50 ml), and aluminum chloride (7.0 g) was added thereto, followed by reflux of the resulting mixture for 66 hours. At the end of this time, the reaction mixture was poured into ice-cold water, and 6N hydrochloric acid was added thereto, followed by extraction with ethyl acetate. After the extract was washed with a saturated aqueous NaCl solution, the organic layer was dried over anhydrous magnesium sulfate. After filtration, the solvent was evaporated under reduced pressure. The residue was purified by silica gel column chromatography (eluent: cyclohexane/ethyl acetate=2/1) to obtain the title compound (3.8 g, 83%) as colorless crystals.

IR spectrum (KBr) $v_{max}$ cm$^{-1}$: 3140, 3074, 1624, 1588; NMR spectrum (DMSO-d$_6$) δ ppm: 6.24 (1H, s), 6.86 (2H, d, J=8.2 Hz), 7.62 (2H, d, J=8.2 Hz), 10.03 (1H, s), 11.24 (1H, brs).

REFERENCE EXAMPLE 17

5-(2,4-Difluorophenyl)-3-hydroxy-4-isopropylisoxazole (a) 2-(2.4-Difluorobenzoyl)isovaleric acid ethyl ester 2,4-Difluorobenzoyl chloride (4.9 ml) and isovaleric acid ethyl ester (3.0 ml) were subjected to reaction and post-treatment in a similar manner to that described in Reference example 8(a) to obtain the title compound (3.65 g, 68%) as a colorless liquid.

(b) 5-(2.4-Difluorophenyl)-3-hydroxy-4-isopropylisoxazole 2-(2,4-Difluorobenzoyl)isovaleric acid ethyl ester (1.7 g), hydroxylamine hydrochloride (0.9 g) and sodium methoxide (28% methanol solution, 7.5 ml) were subjected to reaction and post-treatment in a similar manner to that described in Reference example 8(b) to obtain the title compound (0.59 g, 39%) as colorless crystals.

IR spectrum (KBr) $v_{max}$ cm$^{-1}$: 3082, 3033, 2980, 2968, 2935, 2913, 2877. 2836, 2795, 2699, 2636, 2604, 1660, 1610; NMR spectrum (DMSO-d$_6$) δ ppm: 1.28 (6H, d, J=7.0 Hz), 2.81 (1H, qq, J=7.0 Hz, J=7.0 Hz), 6.91–7.05 (2H, m), 7.43–7.52 (1H, m).

REFERENCE EXAMPLE 18

4-Cyclopropyl-3-hydroxy-5-phenylisoxazole (a) 2-Benzoyl-2-cyclopropylacetic acid methyl ester Benzoyl chloride (1.0 ml) and 2-cyclopropylacetic acid methyl ester were subjected to reaction and post-treatment in a similar manner to that described in Reference example 8(a) to obtain the title compound (1.05 g, 28%) as a colorless liquid.

(b) 4-Cyclopropyl-3-hydroxy-5-phenylisoxazole

2-Benzoyl-2-cyclopropylacetic acid methyl ester (0.9 g), hydroxylamine hydrochloride (0.6 g) and sodium methoxide (28% methanol solution, 4.0 ml) were subjected to reaction and post-treatment in a similar manner to that described in Reference example 8(b) to obtain the title compound (0.32 g, 39%) as colorless crystals.

IR spectrum (KBr) $v_{max}$ cm$^{-1}$: 3085, 3066, 3012, 2972, 2909, 2851, 2778, 2716, 2652, 2601, 1646; NMR spectrum (CDCl$_3$) δ ppm: 0.79–0.85 (2H, m), 0.91–0.98 (2H, m), 1.67–1.77 (1H, m), 7.43–7.53 (3H, m), 7.86–7.90 (2H, m).

REFERENCE EXAMPLE 19

3-Hydroxy-4-isopropyl-5-(3-pyridyl)isoxazole
(a) 2-Nicotinoylisovaleric acid ethyl ester Nicotinic chloride hydrochloride (0.9 g), isovaleric acid ethyl ester (2.3 ml), diisopropylamine (2.1 ml) and butyl-lithium (1.6M hexane solution, 9.4 ml) were subjected to reaction and post-treatment in a similar manner to that described in Reference example 8(a) to obtain the title compound (0.78 g, 44%) as a colorless liquid.
(b) 3-Hydroxy-4-isopropyl-5-(3-pyridyl)isoxazole 2-Nicotinoylisovaleric acid ethyl ester (0.76 g), hydroxylamine hydrochloride (0.46 g) and sodium methoxide (28% methanol solution, 3.1 ml) were subjected to reaction and post-treatment in a similar manner to that described in Reference example 8(b) to obtain the title compound (0.15 g, 23%) as colorless crystals.

IR spectrum (KBr) v$_{max}$ cm$^{-1}$: 3069, 3035, 2970, 2934, 2876, 2809, 2770, 2709, 2665, 2605, 2576, 2519, 1511; NMR spectrum (CDCl$_3$) δ ppm: 1.38 (6H, d, J=7.0 Hz), 3.10 (1H, qq, J=7.0 Hz, J=7.0 Hz), 7.45 (1H, dd, J=7.9 Hz, J=4.4 Hz), 7.94 (1H, d, J=7.9 Hz), 8.72 (1H, d, J=4.4 Hz), 8.88 (1H, s).

REFERENCE EXAMPLE 20

4-Chloro-3-hydroxy-5-(3-pyridyl)isoxazole

3-Hydroxy-5-(3-pyridyl)isoxazole was subjected to reaction and post-treatment in a similar manner to that described in Reference example 1(d) to obtain the title compound.

m.p.: 220–224° C. (decomposed); NMR spectrum (DMF-d$_7$) δ ppm: 7.60–8.20 (4H, m), 12.6–13.6 (1H, brs).

TEST EXAMPLE 1

Type A-monoamine oxidase inhibitory activity

Type A-monoamine oxidase inhibitory activity was determined according to the method described in *Biochem. Pharmacol.*, 12, 1439 (1963) and *J. Neurochem.*, 35, 109 (1980). To 30 μl of a sample of mouse brain crude mitochondria (30 μg protein) were added 210 μl of a phosphate buffer (pH 7.4) and a test compound (dissolved in a mixture of 10% DMSO and water), and the resulting mixture was preincubated at 38° C. for 20 minutes. Subsequently, $^{14}$C-5-hydroxytryptamine (5-HT, final concentration: 100 μM) was added to the preincubated mixture to effect reaction at 38° C. for 20 minutes. After the reaction had been quenched by adding 2N-hydrochloric acid (200 μl), a $^{14}$C-labelled metabolite obtained by the enzymatic reaction was extracted with a solvent (ethyl acetate: toluene=1: 1), and the $^{14}$C radioactivity was determined using a liquid scintillation counter to obtain the concentration of the compound which decreases the $^{14}$C radioactivity of the control by 50%.

The results of the tests showed that the compounds of Examples 1, 2, 3, 4, 5, 6, 7, 8, 54, 57, 58, 59, 60, 62 and 67 have particularly excellent activities of IC$_{50}$<28 nM.

PREPARATION EXAMPLE 1

Hard capsule preparation 50 mg of the powdery compound of Example 4, 128.7 mg of lactose, 70 mg of cellulose and 1.3 mg of magnesium stearate were mixed and passed through a 60 mesh sieve, and the resulting powder was filled into 250 mg No. 3 gelatin capsules to obtain a capsule preparation.

PREPARATION EXAMPLE 2

Tablet preparation 50 mg of the powdery compound of Example 4, 124 mg of lactose, 25 mg of cellulose and 1 mg of magnesium stearate were mixed and formed into tablets with a tabletting machine to obtain 200 mg tablets. These tablets may be coated with a sugar coating as necessary.

INDUSTRIAL APPLICABILITY

The isoxazole derivatives having general formula (I) of the present invention have excellent type A-monoamine oxidase inhibitory activity and are relatively free from undesirable side effects. Therefore, they are useful as agents for treating or preventing (particularly agents for treating) nervous diseases including depression, Parkinson's disease, Alzheimer's dementia (cognitive disorder owing to Alzheimer's disease) or cerebrovascular dementia (cognitive disorder owing to cerebrovascular dementia), (particularly for depression).

In the case where the compounds (I) or the pharmaceutically acceptable salts thereof of the present invention are used as a therapeutic or preventive agent for a nervous disease, the compounds (I) or the salts thereof as such or a mixture obtained appropriately blending the compound (I) with pharmaceutically acceptable excipients, diluents, etc. can be administered in an oral administration by tablets, capsules, granules, powders or syrups, or in a parenteral administration by injection or suppository, etc.

Such pharmaceutical preparations are prepared by a conventional method using additives such as excipients (for example, sugar derivatives such as lactose, sucrose, glucose, mannitol and sorbitol; starch derivatives such as corn starch, potato starch, a-starch, dextrine and carboxymethyl starch; cellulose derivatives such as crystalline cellulose, low-substituted hydroxypropylcellulose, hydroxypropylmethylcellulose, carmellose, carmellose calcium and internally croscarmellose sodium; acacia; dextran; pullulan; silicate derivatives such as light anhydrous silicic acid, synthetic aluminum silicate or magnesium aluminometasilicate; phosphate salts such as calcium phosphate; carbonate salts such as calcium carbonate; and sulfate salts such as calcium sulfate), binders (for example, the above mentioned excipients; gelatin; polyvinylpyrrolidone; macrogol and the like), decay agents (for example, the above mentioned excipients; croscarmellose sodium, sodium carboxymethyl starch, starch which is chemically modified like crospovidone, cellulose derivatives and the like), lubricants (for example, talc; stearic acid; metal stearates such as calcium stearate and magnesium stearate; colloidal silica; beegum; waxes such as spermaceti; boric acid; glycol; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acids such as silicic acid anhydride and silicic acid hydrate; and the starch derivatives in the above mentioned excipients), fungicides (for example, p-hydroxybenzoates such as methylparaben and propylparaben; alcohols such as chlorobutanol, benzyl alcohol and phenylethyl alcohol; benzalkonium chloride; phenols such as phenol and cresol; thimerosal; acetic acid anhydride; and sorbic acid), taste or odor-masking agents (for example, generally used sweeteners, acidulants and flavors and the like), diluents, and solvents for injection (for example, water, ethanol, glycerine and the like).

The dose used differs depending on the symptoms and age of the patient. For example, in the case of oral

What is claimed is:

1. Isoxazole compound of formula (I):

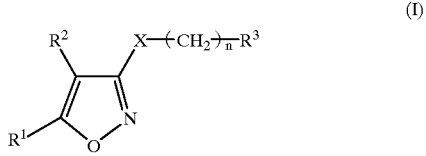

wherein

R$^1$ represents a C$_6$–C$_{14}$ aryl group unsubstituted or substituted with from 1 to 3 substituents which may be the same as or different from each other and selected from the following substituent group, or a 5- or 6-membered aromatic heterocyclic group unsubstituted or substituted with from 1 to 3 substituents and having one or two hetero atoms which are the same as or different from each other and selected from the group consisting of nitrogen, oxygen and sulfur atoms (the substituent group is a halogen; a C$_1$–C$_6$ alkyl; a C$_1$–C$_6$ alkyl substituted with a halogen or a C$_1$–C$_6$ alkoxy; a C$_1$–C$_6$ alkoxy; a C$_6$–C$_{14}$ aryl, a C$_7$–C$_{18}$ aralkyl, a C$_6$–C$_{14}$ aryloxy or a C$_7$–C$_{18}$ aralkyloxy unsubstituted or substituted with from 1 to 3 substituents which are the same as or different from each other and selected from a halogen, a C$_1$–C$_6$ alkyl or a C$_1$–C$_6$ alkoxy; a cyano; a nitro; a hydroxyl; a C$_1$–C$_7$ alkanoyl; a C$_1$–C$_7$ alkanoyloxy; a C$_2$–C$_7$ alkoxycarbonyl; amino; a carbamoyl; a mono(C$_1$–C$_6$ alkyl)carbamoyl; a di(C$_1$–C$_6$ alkyl)carbamoyl or a mono C$_7$–C$_{15}$ arylcarbonylamino unsubstituted or substituted with 1 to 3 substituents selected from a halogen, a C$_1$–C$_6$ alkyl or a C$_1$–C$_6$ alkoxy), R$^2$ represents a hydrogen; a halogen; a C$_1$–C$_6$ alkyl substituted with a halogen or a C$_1$–C$_6$ alkoxy; a C$_2$–C$_6$ alkenyl; a C$_2$–C$_6$ alkynyl; a C$_3$–C$_{10}$ cycloalkyl; a C$_3$–C$_{10}$ cycloalkenyl; a C$_1$–C$_6$ alkoxy; a cyano; a carboxyl; a C$_1$–C$_7$ alkanoyl; a C$_2$–C$_7$ alkoxycarbonyl; a carbamoyl; a mono (C$_1$–C$_6$ alkyl)carbamoyl or a di(C$_1$–C$_6$ alkyl)carbamoyl group, R$^3$ represents amino; a mono C$_1$–C$_6$ alkylamino; a di(C$_1$–C$_6$ alkyl)amino; a mono C$_1$–C$_7$ alkanoylamino; a mono-C$_2$–C$_7$ alkoxycarbonylamino; a mono C$_7$–C$_{15}$ arylcarbonylamino unsubstituted or substituted with from 1 to 3 substituents which are the same as or different from each other and selected from a halogen, a C$_1$–C$_6$ alkyl or a C$_1$–C$_6$ alkoxy; or a 5- or 6-membered saturated heterocyclic group (attached thorough a ring nitrogen atom), which contains one nitrogen atom and or further contains another nitrogen atom or an oxygen atom, X represents an oxygen atom or a sulfur atom, and n represents an integer of 2 to 6, or pharmaceutically acceptable salts thereof.

2. The isoxazole compounds of claim 1, wherein R$^1$ is a C$_6$–C$_{14}$ aryl group unsubstituted or substituted with from 1 to 3 substituents which are the same as or different from each other and are selected from the following substituent group, or a 5- or 6-membered aromatic heterocyclic group unsubstituted or substituted with from 1 to 3 substituents and having one or two hetero atoms which are the same as or different from each other and selected from the group consisting of nitrogen, oxygen and sulfur atoms (the substituent group is a halogen; a C$_1$–C$_6$ alkyl; a C$_1$–C$_6$ alkyl substituted with a halogen or a C$_1$–C$_6$ alkoxy; a C$_1$–C$_6$ alkoxy; a C$_6$–C$_{14}$ aryl unsubstituted or substituted with from 1 to 3 substituents which are the same as or different from each other and selected from a halogen, a C$_1$–C$_6$ alkyl or a C$_1$–C$_6$ alkoxy; a benzyl, a fluorobenzyl, a chlorobenzyl, a difluorobenzyl, a dichlorobenzyl, a methylbenzyl, a dimethylbenzyl, a methoxybenzyl; a phenoxy, a 4-fluorophenoxy, a 4-chlorophenoxy, a 2,4-dichlorophenoxy, a 4-methylphenoxy, a 4-methoxyphenoxy; a benzyloxy, a 4-fluorobenzyloxy, a 4-chlorobenzyloxy, a 2,4-difluorobenzyloxy, a 2,4-dichlorobenzyloxy, a 4-methylbenzyloxy, a 2,4-dimethylbenzyloxy, a 4-methoxybenzyloxy; a cyano; a nitro; a hydroxyl; an acetoxy; a C$_2$–C$_7$ alkoxycarbonyl; an amino; a carbamoyl; a mono(C$_1$–C$_6$ alkyl)carbamoyl; a di(C$_1$–C$_6$ alkyl)carbamoyl; a benzoylamino, a 4-fluorobenzoylamino, a chlorobenzoylamino, a 2,4-dichlorobenzoylamino, a 4-toluoylamino and a 4-anisoylamino group), or pharmaceutically acceptable salts thereof.

3. The isoxazole compound of claim 1, wherein R$^1$ is a C$_6$–C$_{14}$ aryl group unsubstituted or substituted with from 1 to 3 substituents which are the same as or different from each other and selected from the following substituent group, or a 5- or 6-membered aromatic heterocyclic group unsubstituted or substituted with from 1 to 3 substituents and having one or two hetero atoms which are the same as or different from each other and selected from the group consisting of nitrogen, oxygen and sulfur atoms (the substituent group is a halogen; a C$_1$–C$_6$ alkyl; a C$_1$–C$_6$ alkyl substituted with a halogen or a C$_1$–C$_6$ alkoxy; a C$_1$–C$_6$ alkoxy; a C$_6$–C$_{14}$ aryl unsubstituted or substituted with from 1 to 3 substituents which are the same as or different from each other and selected from a halogen, a C$_1$–C$_6$ alkyl or a C$_1$–C$_6$ alkoxy; a cyano; a C$_2$–C$_7$ alkoxycarbonyl; a carbamoyl; a mono-(C$_1$–C$_6$ alkyl)carbamoyl; and a di(C$_1$–C$_6$ alkyl)carbamoyl group), or pharmaceutically acceptable salts thereof.

4. The isoxazole compound of claim 1, wherein R$^1$ is a C$_6$–C$_{14}$ aryl group unsubstituted or substituted with from 1 to 3 substituents which are the same as or different from each other and selected from the following substituent group, or a 5- or 6-membered aromatic heterocyclic group unsubstituted or substituted with one or two substituents and having one or two hetero atoms which are the same as or different from each other and selected from the group consisting of nitrogen, oxygen and sulfur atoms (the substituent group is a halogen, a C$_1$–C$_4$ alkyl, a fluoromethyl, a difluoromethyl, a trifluoromethyl, a 2-fluoroethyl, a 2,2,2-trifluoroethyl, a methoxymethyl, a methoxyethyl, a C$_1$–C$_4$ alkoxy, a phenyl, a 4-fluorophenyl, a 4-chlorophenyl, a 2,4-dichlorophenyl, a 4-methylphenyl, a 4-methoxyphenyl, a cyano, a methoxycarbonyl, an ethoxycarbonyl, a carbamoyl, a methylcarbamoyl, an ethylcarbamoyl, an N,N-dimethylcarbamoyl and an N,N-diethylcarbamoyl group), or pharmaceutically acceptable salts thereof.

5. The isoxazole compound of claim 1, wherein R$^1$ is a phenyl group unsubstituted or substituted with from 1 to 3 substituents which are the same as or different from each other and selected from the following substituent group, or a furyl, a thienyl or a pyridyl group unsubstituted or substituted with one or two substituents (the substituent group is a halogen, a methyl, an ethyl, a trifluoromethyl, a methoxy, a phenyl, a cyano, a methoxycarbonyl, a carbamoyl, a methylcarbamoyl, an ethylcarbamoyl and an N,N-dimethylcarbamoyl group), or pharmaceutically acceptable salts thereof.

6. The isoxazole compound of claim 1, wherein $R^1$ is a phenyl group unsubstituted or substituted with one or two substituents which are the same as or different from each other and selected from the following substituent group, or a furyl, a thienyl or a pyridyl group unsubstituted or substituted with one substituent (the substituent group is a fluorine, a chlorine, a methyl, an ethyl, a trifluoromethyl and a methoxy group), or pharmaceutically acceptable salts thereof.

7. The isoxazole compound of claim 1, wherein $R^1$ is a phenyl, a fluorophenyl, a chlorophenyl, a difluorophenyl, a dichlorophenyl, a methylphenyl, a 2-furyl, a 3-furyl, a 2-thienyl or a 3-thienyl group, or pharmaceutically acceptable salts thereof.

8. The isoxazole compound of claim 1, wherein $R^1$ is a phenyl, a 2-chlorophenyl, a 4-chlorophenyl, a 2,4-difluorophenyl, a 2,4-dichlorophenyl, a 2-furyl or a 2-thienyl group, or pharmaceutically acceptable salts thereof.

9. The isoxazole compound of claim 1, wherein $R^2$ is a hydrogen, a halogen, a $C_1$–$C_6$ alkyl, a fluoromethyl, a difluoromethyl, a trifluoromethyl, a 2-fluoroethyl, a 1-chloroethyl, a 2-chloroethyl, a 2,2,2-trifluoroethyl, a methoxymethyl, a methoxyethyl, a $C_2$–$C_6$ alkenyl, a $C_2$–$C_6$ alkynyl, a cyclopropyl, a cyclopentyl, a cyclohexyl, a 2-cyclopentenyl, a 3-cyclopentenyl, a 2-cyclohexenyl, a 3-cyclohexenyl, a methoxy, an ethoxy, a cyano, a carboxyl, a formyl, an acetyl, a methoxycarbonyl, an ethoxycarbonyl, a carbamoyl, a methylcarbamoyl, an ethylcarbamoyl or an N,N-dimethylcarbamoyl group, or pharmaceutically acceptable salts thereof.

10. The isoxazole compound of claim 1, wherein $R^2$ is a hydrogen, a halogen, a $C_1$–$C_6$ alkyl, a $C_2$–$C_6$ alkenyl or a $C_2$–$C_6$ alkynyl group, or pharmaceutically acceptable salts thereof.

11. The isoxazole compound of claim 1, wherein $R^2$ is a hydrogen, a halogen, a $C_1$–$C_4$ alkyl, an allyl, an isopropenyl, a 2-butenyl or a propargyl group, or pharmaceutically acceptable salts thereof.

12. The isoxazole compound of claim 1, wherein $R^2$ is a hydrogen, a chlorine, an ethyl, a propyl, an isopropyl, an isobutyl or a t-butyl group, or pharmaceutically acceptable salts thereof.

13. The isoxazole compound of claim 1, wherein $R^2$ is a hydrogen or an isopropyl group, or pharmaceutically acceptable salts thereof.

14. The isoxazole compound of claim 1, wherein $R^2$ is amino, a mono $C_1$–$C_6$ alkylamino, a di($C_1$–$C_6$ alkyl)amino or a 5- or 6-membered saturated heterocyclic group (attached thorough a ring nitrogen atom) having one nitrogen atom or further containing another nitrogen atom or an oxygen atom, or pharmaceutically acceptable salts thereof.

15. The isoxazole compound of claim 1, wherein $R^3$ is amino, a methylamino, an ethylamino, an N,N-dimethylamino, a piperidyl or a morpholinyl group, or pharmaceutically acceptable salts thereof.

16. The isoxazole compound of claim 1, wherein $R^3$ is the amino group, or pharmaceutically acceptable salts thereof.

17. The isoxazole compound of claim 1, wherein X is an oxygen atom, or pharmaceutically acceptable salts thereof.

18. The isoxazole compound of claim 1, wherein n is 2, or pharmaceutically acceptable salts thereof.

19. The isoxazole compound of claim 1, wherein $R^1$ is a $C_6$–$C_{14}$ aryl group unsubstituted or substituted with from 1 to 3 substituents which are the same as or different from each other and selected from the following substituent group, or a 5- or 6-membered aromatic heterocyclic group unsubstituted or substituted with from 1 to 3 substituents and having one or two hetero atoms which are the same as or different from each other and selected from the group consisting of nitrogen, oxygen and sulfur atoms (the substituent group is a halogen; a $C_1$–$C_6$ alkyl; a $C_1$–$C_6$ alkyl substituted with a halogen or a $C_1$–$C_6$ alkoxy; a $C_1$–$C_6$ alkoxy; a $C_6$–$C_{14}$ aryl unsubstituted or substituted with from 1 to 3 substituents which are the same as or different from each other and selected from a halogen, a $C_1$–$C_6$ alkyl or a $C_1$–$C_6$ alkoxy; a cyano; a $C_2$–$C_7$ alkoxycarbonyl; a carbamoyl; a mono-($C_1$–$C_6$ alkyl)carbamoyl; and a di($C_1$–$C_6$ alkyl)carbamoyl group), $R^2$ is a hydrogen, a halogen, a $C_1$–$C_6$ alkyl, a $C_2$–$C_6$ alkenyl or a $C_2$–$C_6$ alkynyl group, and $R^3$ is amino, a mono $C_1$–$C_6$ alkylamino, a di($C_1$–$C_6$ alkyl)amino group or a 5- or 6-membered saturated heterocyclic group (provided that the group attached thorough a ring nitrogen atom) which contains one nitrogen atom or further containing another nitrogen or an oxygen atom, or pharmaceutically acceptable salts thereof.

20. The isoxazole compound of claim 1, wherein $R^1$ is a $C_6$–$C_{14}$ aryl group unsubstituted or substituted with from 1 to 3 substituents which are the same as or different from each other and selected from the following substituent group, or a 5- or 6-membered aromatic heterocyclic group unsubstituted or substituted with from 1 to 3 substituents and having one or two hetero atoms which are the same as or different from each other and selected from the group consisting of nitrogen, oxygen and sulfur atoms (the substituent group is a halogen; a $C_1$–$C_6$ alkyl; a $C_1$–$C_6$ alkyl substituted with a halogen or a $C_1$–$C_6$ alkoxy; a $C_1$–$C_6$ alkoxy; a $C_6$–$C_{14}$ aryl unsubstituted or substituted with from 1 to 3 substituents which are the same as or different from each other and selected from a halogen, a $C_1$–$C_6$ alkyl or a $C_1$–$C_6$ alkoxy; a cyano; a $C_2$–$C_7$ alkoxycarbonyl; a carbamoyl; a mono ($C_1$–$C_6$ alkyl)carbamoyl; and a di($C_1$–$C_6$ alkyl)carbamoyl group), $R^2$ is a hydrogen, a halogen, a $C_1$–$C_6$ alkyl, a $C_2$–$C_6$ an alkenyl or a $C_2$–$C_6$ alkynyl group, $R^3$ is the amino group, X is a oxygen atom, and n is 2, or pharmaceutically acceptable salts thereof.

21. The isoxazole compound of claim 1, wherein $R^1$ is a $C_6$–$C_{14}$ aryl group unsubstituted or substituted with from 1 to 3 substituents which are the same as or different from each other and selected from the following substituent group, or a 5- or 6-membered aromatic heterocyclic group unsubstituted or substituted with one or two substituents and having one or two hetero atoms which are the same as or different from each other and selected from the group consisting of nitrogen, oxygen and sulfur atoms (the substituent group is a halogen, a $C_1$–$C_4$ alkyl, a fluoromethyl, a difluoromethyl, a trifluoromethyl, a 2-fluoroethyl, a 2,2,2-trifluoroethyl, a methoxymethyl, a methoxyethyl, a $C_1$–$C_4$ alkoxy, a phenyl, a 4-fluorophenyl, a 4-chlorophenyl, a 2,4-dichlorophenyl, a 4-methylphenyl, a 4-methoxyphenyl, a cyano, a methoxycarbonyl, an ethoxycarbonyl, a carbamoyl, a methylcarbamoyl, an ethylcarbamoyl, an N,N-dimethylcarbamoyl and an N,N-diethylcarbamoyl group), $R^2$ is a hydrogen, a halogen, a $C_1$–$C_4$ alkyl, an allyl, an isopropenyl, a 2-butenyl or a propargyl group, R³ is the amino group, X is an oxygen atom, and n is 2, or pharmaceutically acceptable salts thereof.

22. The isoxazole compound of claim 1, wherein R¹ is a phenyl group unsubstituted or substituted with from 1 to 3 substituents which are the same as or different from each other and selected from the following substituent group, or a furyl, a thienyl or a pyridyl group unsubstituted or substituted with one or two substituents (the substituent group is a halogen, a methyl, an ethyl, a trifluoromethyl, a methoxy, a phenyl, a cyano, a methoxycarbonyl, a carbamoyl, a methylcarbamoyl, an ethylcarbamoyl and an N,N-dimethylcarbamoyl group), R² is a hydrogen, a halogen, a C₁–C₄ alkyl, an allyl, an isopropenyl, a 2-butenyl or a propargyl group, R³ is the amino group, X is an oxygen atom, and n is 2, or pharmaceutically acceptable salts thereof.

23. The isoxazole compound of claim 1, wherein R¹ is a phenyl group unsubstituted or substituted with one or two substituents which are the same as or different from each other and selected from the following substituent group, or a furyl, a thienyl or a pyridyl group unsubstituted or substituted with one substituent (the substituent group is a fluorine, a chlorine, a methyl, an ethyl, a trifluoromethyl and a methoxy group), R² is a hydrogen, a chlorine, an ethyl, a propyl, an isopropyl, an isobutyl or a t-butyl group, R³ is the amino group, X is an oxygen atom, and n is 2, or pharmaceutically acceptable salts thereof.

24. The isoxazole compound of claim 1, wherein R¹ is a fluorophenyl, a chlorophenyl, a difluorophenyl, a dichlorophenyl, a methylphenyl, a 2-furyl, a 3-furyl, a 2-thienyl or a 3-thienyl group, R² is a hydrogen, a chlorine, an ethyl, a propyl, an isopropyl, an isobutyl or a t-butyl group, R³ is the amino group, X is an oxygen atom, and n is 2, or pharmaceutically acceptable salts thereof.

25. The isoxazole compound of claim 1, wherein R¹ is a phenyl, a 2-chlorophenyl, a 4-chlorophenyl, a 2,4-difluorophenyl, a 2,4-dichlorophenyl, a 2-furyl or a 2-thienyl group, R² is a hydrogen atom or a propyl group, R³ is the amino group, X is an oxygen atom, and n is 2, or pharmaceutically acceptable salts thereof.

26. The isoxazole compound of claim 1 selected from the group consisting of 3-(2-aminoethoxy)-5-phenylisoxazole, 3-(2-aminoethoxy)-4-chloro-5-phenylisoxazole, 3-(2-aminoethoxy)-4-ethyl-5-phenylisoxazole, 3-(2-aminoethoxy)-5-phenyl-4-propylisoxazole, 3-(2-aminoethoxy)-4-isopropyl-5-phenylisoxazole, 3-(2-aminoethoxy)-4-isobutyl-5-phenylisoxazole, 3-(2-aminoethoxy)-5-(2-chlorophenyl)-4-isopropylisoxazole, 3-(2-aminoethoxy)-5-(4-chlorophenyl)isoxazole, 3-(2-aminoethoxy)-5-(4-chlorophenyl)-4-isopropylisoxazole, 3-(2-aminoethoxy)-5-(2,4-dichlorophenyl)-4-isopropylisoxazole, 3-(2-aminoethoxy)-5-(2-furyl)-4-isopropylisoxazole, 3-(2-aminoethoxy)-5-(2-thienyl)isoxazole, 3-(2-aminoethoxy)-4-chloro-5-(2-thienyl)isoxazole, 3-(2-aminoethoxy)-4-isopropyl-5-(2-thienyl)isoxazole, and 4-allyl-3-(2-aminoethoxy)-5-phenylisoxazole, and pharmaceutically acceptable salts thereof.

27. The isoxazole compound of claim 1 selected from the group consisting of 3-(2-aminoethoxy)-5-phenylisoxazole, and pharmaceutically acceptable salts thereof.

28. The isoxazole compound of claim 1 selected from the group consisting of 3-(2-aminoethoxy)-4-chloro-5-phenylisoxazole, and pharmaceutically acceptable salts thereof.

29. The isoxazole compound of claim 1 selected from the group consisting of 3-(2-aminoethoxy)-4-ethyl-5-phenylisoxazole, and pharmaceutically acceptable salts thereof.

30. The isoxazole compound of claim 1 selected from the group consisting of 3-(2-aminoethoxy)-5-phenyl-4-propylisoxazole, and pharmaceutically salts thereof.

31. The isoxazole compound of claim 1 selected from the group consisting of 3-(2-aminoethoxy)-4-isopropyl-5-phenylisoxazole, and pharmaceutically acceptable salts thereof.

32. The isoxazole compound of claim 1 selected from the group consisting of 3-(2-aminoethoxy)-4-isobutyl-5-phenylisoxazole, and pharmaceutically acceptable salts thereof.

33. The isoxazole compound of claim 1 selected from the group consisting of 3-(2-aminoethoxy)-5-(2-chlorophenyl)-4-isopropylisoxazole, and pharmaceutically acceptable salts thereof.

34. The isoxazole compound of claim 1 selected from the group consisting of 3-(2-aminoethoxy)-5-(4-chlorophenyl)isoxazole, and pharmaceutically acceptable salts thereof.

35. The isoxazole compound of claim 1 selected from the group consisting of 3-(2-aminoethoxy)-5-(4-chlorophenyl)-4-isopropylisoxazole, and pharmaceutically acceptable salts thereof.

36. The isoxazole compound of claim 1 selected from the group consisting of 3-(2-aminoethoxy)-5-(2,4-dichlorophenyl)-4-isopropylisoxazole, and pharmaceutically acceptable salts thereof.

37. The isoxazole compound of claim 1 selected from the group consisting of 3-(2-aminoethoxy)-5-(2-furyl)-4-isopropylisoxazole, and pharmaceutically acceptable salts thereof.

38. The isoxazole compound of claim 1 selected from the group sonsisting of 3-(2-aminoethoxy)-5-(2-thienyl)isoxazole, and pharmaceutically acceptable salts thereof.

39. The isoxazole compound of claim 1 selected from the group consisting of 3-(2-aminoethoxy)-4-chloro-5-(2-thienyl)isoxazole, and pharmaceutically acceptable salts thereof.

40. The isoxazole compound of claim 1 selected from the group consisting of 3-(2-aminoethoxy)-4-isopropyl-5-(2-thienyl)isoxazole, and pharmaceutically acceptable salts thereof.

41. The isoxazole compound of claim 1 selected from the group consisting of
4-allyl-3-(2-aminoethoxy)-5-phenylisoxazole, and pharmaceutically acceptable salts thereof.

42. A pharmaceutical composition having type A-monoamine oxidase inhibitory activity comprising (i) an effective amount of an isoxazole compound or a pharmaceutically acceptable salt thereof as defined in any one of claims 1 to 25 and (ii) a pharmaceutically acceptable carrier.

43. A method for the prophylaxis or treatment of nervous diseases in humans comprising administering an effective amount of an isoxazole compound or a pharmaceutically acceptable salt thereof as defined in any one of claims 1 to 25.

* * * * *